United States Patent
Diehen et al.

(10) Patent No.: US 10,344,290 B2
(45) Date of Patent: Jul. 9, 2019

(54) REGULATORY SEQUENCES FOR MODULATING TRANSGENE EXPRESSION IN PLANTS

(71) Applicants: PIONEER HI-BRED INTERNATIONAL, INC., Johnston, IA (US); E I DU PONT DE NEMOURS AND COMPANY, Wilmington, DE (US)

(72) Inventors: Scott Diehen, West Des Moines, IA (US); Ajit Nott, Secunderabad (IN); David A. Selinger, Johnston, IA (US); Carl Simmons, Des Moines, IA (US); Priyanka Bhyri, Secunderabad (IN); Venkata S. Tavva, Hyderabad (IN)

(73) Assignees: E I DU PONT DE NEMOURS AND COMPANY, Wilmington, DE (US); PIONEER HI-BRED INTERNATIONAL, INC. IA (US)

( * ) Notice: Subject to any disclaimer, the term of this patent is extended or adjusted under 35 U.S.C. 154(b) by 0 days.

(21) Appl. No.: 15/660,390

(22) Filed: Jul. 26, 2017

(65) Prior Publication Data
US 2017/0335337 A1    Nov. 23, 2017

Related U.S. Application Data

(63) Continuation of application No. 14/660,076, filed on Mar. 17, 2015, now abandoned, which is a continuation of application No. 13/701,848, filed as application No. PCT/US2011/039691 on Jun. 9, 2011, now abandoned.

(60) Provisional application No. 61/372,515, filed on Aug. 11, 2010.

(30) Foreign Application Priority Data

Jun. 9, 2010   (IN) .......................... 1340/DEL/2010

(51) Int. Cl.
C12N 15/82        (2006.01)
(52) U.S. Cl.
CPC ................ *C12N 15/8216* (2013.01)

(58) Field of Classification Search
None
See application file for complete search history.

(56) References Cited

U.S. PATENT DOCUMENTS

2007/0204367 A1*  8/2007  Flasinski ............ C12N 15/8216
                                                                800/278

FOREIGN PATENT DOCUMENTS

EP        1 817 419 B1       8/2007
WO      1993019189 A1       9/1993

OTHER PUBLICATIONS

Rose (2008) Curr Top Microbiol Innnnunol 326:277-90.*
Gallegos & Rose (2015) Plant Sci 237:8-15.*
Rose, Curr Top Microbiol Immunol, 326:277-90 (2008).
Crane, Phil Trans Biol Sci 359(1444): 735-37 (2004).
Narsai et al., Plant Cell, 19:3418-36 (2007).
Clancy et al. "Maize Shrunken-1 intron and exon regions increase gene expression in maize protoplasts." Plant Science. (1994) 98:151-161.
Luehrsen, Kenneth R. & Virginia Walbot. "Intron enhancement of gene expression and the splicing efficiency of introns in maize cells." Molecular and General Genetics. (1991) 225:81-93.
Maas et al. "The combination of a novel stimulatory element in the first exon of the maize Shrunken-1 gene with the following intron 1 enhances reporter expression up to 1000-fold." Plant Molecular Biology. (1991) 16:199-207.
Database Accession No. AC202950.
International Search Report and Written Opinion for International Application PCT/US2011/039691.

* cited by examiner

*Primary Examiner* — Russell T Boggs

(57) ABSTRACT

The invention relates to gene expression regulatory sequences, specifically introns that act as enhancers of gene expression, the promoter and terminator sequences endogenously associated with these introns. Presence of these intronic enhancer sequences in proximity to promoter sequences leads to enhancement of gene expression. Methods of finding such new intronic enhancer sequences and using them to generate transgenic plants are also described.

8 Claims, 13 Drawing Sheets
Specification includes a Sequence Listing.

SEQUENCE LISTING

```
<160> NUMBER OF SEQ ID NOS: 146

<210> SEQ ID NO 1
<211> LENGTH: 978
<212> TYPE: DNA
<213> ORGANISM: zea mays

<400> SEQUENCE: 1
gtgcagcgtg acccggtcgt gcccctctct agagataatg agcattgcat gtctaagtta      60
taaaaaatta ccacatattt tttttgtcac acttgtttga agtgcagttt atctatcttt     120
atacatatat ttaaacttta ctctacgaat aatataatct atagtactac aataatcatca    180 gtgtttttaga gaatcatata aatgaacagt tagacatggt ctaaaggaca attgagtatt    240
ttgacaacag gactctacag ttttatcttt ttagtgtgca tgtgttctcc tttttttttg    300
caaatagctt cacctatata atacttcatc cattttatta gtacatccat ttagggttta    360
gggttaatgg ttttttataga ctaattttttt tagtacatct attttattct attttagcct    420
ctaaattaag aaaactaaaa ctctatttta gttttttttat ttaataattt agatataaaa    480
```

-continued

```
tagaataaaa taaagtgact aaaaattaaa caaataccct ttaagaaatt aaaaaaacta    540
aggaaacatt tttcttgttt cgagtagata atgccagcct gttaaacgcc gtcgacgagt    600
ctaacggaca ccaaccagcg aaccagcagc gtcgcgtcgg gccaagcgaa gcagacggca    660
cggcatctct gtcgctgcct ctggacccct ctcgagagtt ccgctccacc gttggacttg    720
ctccgctgtc ggcatccaga aattgcgtgg cggagcggca gacgtgagcc ggcacggcag    780
gcggcctcct cctcctctca cggcaccggc agctacgggg gattcctttc ccaccgctcc    840
ttcgctttcc cttcctcgcc cgccgtaata aatagacacc ccctccacac cctctttccc    900
caacctcgtg ttgttcggag cgcacacaca caaccagat ctctccccaa atccacccgt     960
cggcacctcc gcttcaag                                                  978

<210> SEQ ID NO 2
<211> LENGTH: 1013
<212> TYPE: DNA
<213> ORGANISM: zea mays

<400> SEQUENCE: 2
gtacgccgct cgtcctcccc ccccccctc tctaccttct ctagatcggc gttccggtcc      60
atgcatggtt agggcccggt agttctactt ctgttcatgt ttgtgttaga tccgtgtttg    120
tgttagatcc gtgctgctag cgttcgtaca cggatgcgac ctgtacgtca gacacgttct    180
gattgctaac ttgccagtgt ttctctttgg ggaatcctgg gatggctcta gccgttccgc    240
agacgggatc gatttcatga ttttttttgt ttcgttgcat agggtttggt ttgccctttt    300
cctttatttc aatatatgcc gtgcacttgt ttgtcgggtc atcttttcat gcttttttt    360 gtcttggttg tgatgatgtg gtctggttgg gcggtcgttc tagatcggag tagaattctg    420
tttcaaacta cctggtggat ttattaattt tggatctgta tgtgtgtgcc atacatattc    480

atagttacga attgaagatg atggatggaa atatcgatct aggataggta tacatgttga    540

tgcgggtttt actgatgcat atacagagat gctttttgtt cgcttggttg tgatgatgtg    600
gtgtggttgg gcggtcgttc attcgttcta gатcggагта gaatactgtt tcaaactacc    660

тggтgтатттт attaattttg gaactgtatg tgtgtgtcat acatcttcat аgттасgагт    720

ттаагатggа тggаааатatc gatctaggat aggtatacat gttgatgtgg gttttactga    780

tgcatataca tgatggcata tgcagcatct att catatgc tctaaccttg agtacctatc    840

тат та та ата асаagтатg тт тт атаатт атттт gатcт тgатат ac тт ggatgatggc    900

atatgcagca gctatatgtg gattttttta gccctgcctt сатacgсатат ttatttgctt    960 ggtactgtt cttttgtcga tgctcaccct gttgttt ggt gtt acttctg cag          1013

<210> SEQ ID NO 3
<211> LENGTH: 16656
<212> TYPE: DNA
<213> ORGANISM: Artificial Sequence
<220> FEATURE:
<223> OTHER INFORMATION: Vector Sequence

<400> SEQUENCE: 3
gtttacccgc aaatatacc tgtcaaacac tgatagttta aactgaaggc gggaaacgac      60 aatctgatca тgаgcggага attaagggag tcacgttatg acccccgccg atgacgcggg    120

ccaagccgtt ttacgtttgg aactgacaga accgcaacgt tgaaggagcc actcagcaag    180
ctggtacgat tgtaatacga ctcactatag ggcgaattga gcgctgttta acgctctttc    240
```

```
aactggaaga gcggttacca gagctggtca cctttgtcca ccaagatgga actgcggcct    300
cgaagcttgg cgcgccgtgc agcgtgaccc ggtcgtgccc ctctctagag ataatgagca    360
ttgcatgtct aagttataaa aaattaccac atatttttt tgtcacactt gtttgaagtg     420
cagtttatct atctttatac atatatttaa actttactct acgaataata taatctatag    480
tactacaata atatcagtgt tttagagaat catataaatg aacagttaga catggtctaa    540
aggacaattg agtattttga caacaggact ctacagtttt atcttttag tgtgcatgtg     600 ttctcctttt tttttgcaaa tagcttcacc tatataatac ttcatccatt ttattagtac    660
atccatttag ggtttagggt taatggtttt tatagactaa ttttttagt acatctattt     720 tattctattt tagcctctaa attaagaaaa ctaaaactct attttagttt ttttatttaa    780
taatttagat ataaaataga ataaaataaa gtgactaaaa attaaacaaa tacccttaa     840 gaaattaaaa aaactaagga acattttc ttgtttcgag tagataatgc cagcctgtta      900
aacgccgtcg acgagtctaa cggacaccaa ccagcgaacc agcagcgtcg cgtcgggcca    960
agcgaagcag acggcacggc atctctgtcg ctgcctctgg accctctcg agagttccgc    1020 tccaccgttg gacttgctcc gctgtcggca tccagaaatt gcgtggcgga gcggcagacg    1080
tgagccggca cggcaggcgg cctcctcctc ctctcacggc accggcagct acggggatt     1140 cctttcccac cgctccttcg ctttcccttc ctcgcccgcc gtaataaata gacacccct     1200 ccacaccctc tttccccaac ctcgtgttgt tcggagcgca cacacacaca accagatctc    1260
ccccaaatcc acccgtcggc acctccgctt caagcgatcg caggtacccg actttaactt    1320
agcctaggat ccacacgaca ccatggtccg tcctgtagaa accccaaccc gtgaaatcaa    1380
aaaactcgac ggcctgtggg cattcagtct ggatcgcgaa aactgtggaa ttgatcagcg    1440
ttggtgggaa agcgcgttac aagaaagccg ggcaattgct gtgccaggca gttttaacga    1500
tcagttcgcc gatgcagata ttcgtaatta tgcgggcaac gtctggtatc agcgcgaagt    1560
ctttataccg aaaggttggg caggccagcg tatcgtgctg cgtttcgatg cggtcactca    1620
ttacggcaaa gtgtgggtca ataatcagga agtgatgag catcagggcg ctatacgcc     1680 atttgaagcc gatgtcacgc cgtatgttat tgccgggaaa agtgtacgta agttctgct     1740 tctacctttg atatatatat aataattatc attaattagt agtaatataa tatttcaaat    1800 attttttca aaataaaaga atgtagtata tagcaattgc ttttctgtag tttataagtg     1860
tgtatatttt aatttataac ttttctaata tatgaccaaa atttgttgat gtgcaggtat    1920
caccgtttgt gtgaacaacg aactgaactg gcagactatc ccgccgggaa tggtgattac    1980
cgacgaaaac ggcaagaaaa agcagtctta cttccatgat ttctttaact atgccggaat    2040
ccatcgcagc gtaatgctct acaccacgcc gaacacctgg gtggacgata tcaccgtggt    2100
gacgcatgtc gcgcaagact gtaaccacgc gtctgttgac tggcaggtgg tggccaatgg    2160
tgatgtcagc gttgaactgc gtgatgcgga tcaacaggtg gttgcaactg acaaggcac     2220 tagcgggact ttgcaagtgg tgaatccgca cctctggcaa ccgggtgaag ttatctcta    2280 tgaactgtgc gtcacagcca aaagccagac agagtgtgat atctacccgc ttcgcgtcgg    2340
catccggtca gtggcagtga agggcgaaca gttcctgatt aaccacaaac cgttctactt    2400
tactggcttt ggtcgtcatg aagatgcgga cttgcgtggc aaaggattcg ataacgtgct    2460
gatggtgcac gaccacgcat taatggactg gattgggggcc aactcctacc gtacctcgca    2520
ttacccttac gctgaagaga tgctcgactg ggcagatgaa catggcatcg tggtgattga    2580
tgaaactgct gctgtcggct ttaacctctc tttaggcatt ggtttcgaag cgggcaacaa    2640
```

```
gccgaaagaa ctgtacagcg aagaggcagt caacggggaa actcagcaag cgcacttaca   2700
ggcgattaaa gagctgatag cgcgtgacaa aaaccaccca agcgtggtga tgtggagtat   2760
tgccaacgaa ccggataccc gtccgcaagg tgcacgggaa tatttcgcgc cactggcgga   2820
agcaacgcgt aaactcgacc cgacgcgtcc gatcacctgc gtcaatgtaa tgttctgcga   2880
cgctcacacc gataccatca gcgatctctt tgatgtgctg tgcctgaacc gttattacgg   2940
atggtatgtc caaagcggcg atttggaaac ggcagagaag gtactggaaa agaacttct   3000 ggcctggcag gagaaactgc atcagccgat tatcatcacc gaatacggcg tggatacgtt   3060
agccgggctg cactcaatgt acaccgacat gtggagtgaa gagtatcagt gtgcatggct   3120
ggatatgtat caccgcgtct ttgatcgcgt cagcgccgtc gtcggtgaac aggtatggaa   3180
tttcgccgat tttgcgacct cgcaaggcat attgcgcgtt ggcggtaaca agaaagggat   3240
cttcactcgc gaccgcaaac cgaagtcggc ggcttttctg ctgcaaaaac gctggactgg   3300
catgaacttc ggtgaaaaac cgcagcaggg aggcaaacaa tgaatcaaca actctcctgg   3360
cgcaccatcg tcggctacag cctcggtgac gtggggcaac ctagacttgt ccatcttctg   3420
gattggccaa cttaattaat gtatgaaata aaaggatgca cacatagtga catgctaatc   3480
actataatgt gggcatcaaa gttgtgtgtt atgtgtaatt actagttatc tgaataaaag   3540
agaaagagat catccatatt tcttatccta aatgaatgtc acgtgtcttt ataattcttt   3600
gatgaaccag atgcatttca ttaaccaaat ccatatacat ataaatatta atcatatata   3660
attaatatca attgggttag caaaacaaat ctagtctagg tgtgttttgc gaattgcggc   3720
cgcgatctga gcttctagag gatccccatc gatgggcccc ggccgaagct tgcatgcctg   3780
cagtgcagcg tgacccggtc gtgcccctct ctagagataa tgagcattgc atgtctaagt   3840
tataaaaaat taccacatat tttttttgtc acacttgttt gaagtgcagt ttatctatct   3900
ttatacatat atttaaactt tactctacga ataatataat ctatagtact acaataaatt   3960 cagtgttttta gagaatcata taaatgaaca gttagacatg gtctaaggga caattgagta   4020
ttttgacaac aggactctac agttttatct ttttagtgtg catgtgttct cctttttttt   4080
tgcaaatagc ttcacctata taatacttca tccatttttat tagtacatcc atttaggtt   4140 tagggttaat ggttttttata gactaatttt tttagtacat ctatttatt ctattttagc   4200 ctctaaatta agaaaactaa aactctattt tagttttttt atttaataat ttagatataa   4260
aatagaataa aataaagtga ctaaaaatta aacaaatacc ctttaagaaa ttaaaaaaac   4320
taaggaaaca ttttttcttgt ttcgagtaga taatgccagc ctgttaaacg ccgtcgacga   4380
gtctaacgga caccaaccag cgaaccagca gcgtcgcgtc gggccaagcg aagcagacgg   4440
cacggcatct ctgtcgctgc ctctggaccc ctctcgagag ttccgctcca ccgttggact   4500
tgctccgctg tcggcatcca gaaattgcgt ggcggagcgg cagacgtgag ccggcacggc   4560
aggcggcctc ctcctcctct cacggcaccg gcagctacgg gggattcctt tcccaccgct   4620
ccttcgcttt cccttcctcg cccgccgtaa taaatagaca cccctccac accctctttc   4680 cccaacctcg tgttgttcgg agcgcacaca cacacaacca gatctccccc aaatccaccc   4740
gtcggcacct ccgcttcaag gtacgccgct cgtcctcccc ccccccctc tctaccttct   4800 ctagatcggc gttccggtcc atgcatggtt agggcccggt agttctactt ctgttcatgt   4860
ttgtgttaga tccgtgtttg tgttagatcc gtgctgctag cgttcgtaca cggatgcgac   4920
ctgtacgtca gacacgttct gattgctaac ttgccagtgt ttctctttgg ggaatcctgg   4980
```

-continued

| | | | | | |
|---|---|---|---|---|---|
| gatggctcta | gccgttccgc | agacgggatc | gatttcatga | ttttttttgt | ttcgttgcat | 5040 |
| agggtttggt | ttgccctttt | cctttatttc | aatatatgcc | gtgcacttgt | ttgtcgggtc | 5100 |
| atcttttcat | gctttttttt | gtcttggttg | tgatgatgtg | gtctggttgg | gcggtcgttc | 5160 |
| tagatcggag | tagaattctg | tttcaaacta | cctggtggat | ttattaattt | tggatctgta | 5220 |
| tgtgtgtgcc | atacatattc | atagttacga | attgaagatg | atggatggaa | atatcgatct | 5280 |
| aggataggta | tacatgttga | tgcgggtttt | actgatgcat | atacagagat | gcttttttgtt | 5340 |
| cgcttggttg | tgatgatgtg | gtgtggttgg | gcggtcgttc | attcgttcta | gatcggagta | 5400 |
| gaatactgtt | tcaaactacc | tggtgtattt | attaattttg | gaactgtatg | tgtgtgtcat | 5460 |
| acatcttcat | agttacgagt | ttaagatgga | tggaaatatc | gatctaggat | aggtatacat | 5520 |
| gttgatgtgg | gttttactga | tgcatataca | tgatggcata | tgcagcatct | attcatatgc | 5580 |
| tctaaccttg | agtacctatc | tattataata | aacaagtatg | ttttataatt | attttgatct | 5640 |
| tgatatactt | ggatgatggc | atatgcagca | gctatatgtg | gattttttta | gccctgcctt | 5700 |
| catacgctat | ttatttgctt | ggtactgttt | cttttgtcga | tgctcaccct | gttgtttggt | 5760 |
| gttacttctg | caggtcgact | ttaacttagc | ctaggatcca | cacgacacca | tgtcccccga | 5820 |
| gcgccgcccc | gtcgagatcc | gcccggccac | cgccgccgac | atggccgccg | tgtgcgacat | 5880 |
| cgtgaaccac | tacatcgaga | cctccaccgt | gaacttccgc | accgagccgc | agaccccgca | 5940 |
| ggagtggatc | gacgacctgg | agcgcctcca | ggaccgctac | ccgtggctcg | tggccgaggt | 6000 |
| ggagggcgtg | gtggccggca | tcgcctacgc | cggcccgtgg | aaggcccgca | acgcctacga | 6060 |
| ctggaccgtg | gagtccaccg | tgtacgtgtc | ccaccgccac | cagcgcctcg | gcctcggctc | 6120 |
| caccctctac | acccacctcc | tcaagagcat | ggaggcccag | ggcttcaagt | ccgtggtggc | 6180 |
| cgtgatcggc | ctcccgaacg | acccgtccgt | gcgcctccac | gaggccctcg | gctacaccgc | 6240 |
| ccgcggcacc | ctccgcgccg | ccggctacaa | gcacggcggc | tggcacgacg | tcggcttctg | 6300 |
| gcagcgcgac | ttcgagctgc | cggccccgcc | gcgcccggtg | cgcccggtga | cgcagatctg | 6360 |
| agtcgaaacc | tagacttgtc | catcttctgg | attggccaac | ttaattaatg | tatgaaataa | 6420 |
| aaggatgcac | acatagtgac | atgctaatca | ctataatgtg | ggcatcaaag | ttgtgtgtta | 6480 |
| tgtgtaatta | ctagttatct | gaataaaaga | gaaagagatc | atccatattt | cttatcctaa | 6540 |
| atgaatgtca | cgtgtcttta | taattctttg | atgaaccaga | tgcatttcat | taaccaaatc | 6600 |
| catatacata | taaatattaa | tcatatataa | ttaatatcaa | ttgggttagc | aaaacaaatc | 6660 |
| tagtctaggt | gtgttttgcg | aatgcggccg | ccaccgcggt | ggagctcagg | cctccaattc | 6720 |
| gtcaacttcg | tccacagaca | tcaacatctt | atcgtccttt | gaagataaga | taataatgtt | 6780 |
| gaagataaga | gtgggagccc | ccactaaaac | attgctttgt | caaaagctaa | aaagatgat | 6840 |
| gcccgacagc | cacttgtgtg | aagcatgaga | agccggtccc | tccactaaga | aaattagtga | 6900 |
| agcatcttcc | agtggtccct | ccactcacag | ctcaatcagt | gagcaacagg | acgaaggaaa | 6960 |
| tgacgtaagc | catgacgtct | aatcccaact | tcgtccacag | acatcaacat | cttatcgtcc | 7020 |
| tttgaagata | agataataat | gttgaagata | agagtgggag | ccaccactaa | acattgctt | 7080 |
| tgtcaaaagc | taaaaagat | gatgcccgac | agccacttgt | gtgaagcatg | agaagccggt | 7140 |
| ccctccacta | agaaaattag | tgaagcatct | tccagtggtc | cctccactca | cagctcaatc | 7200 |
| agtgagcaac | aggacgaagg | aaatgacgta | agccatgacg | tctaatccca | caagaatttc | 7260 |
| cttatataag | gaacacaaat | cagaaggaag | agatcaatcg | aaatcaaaat | cggaatcgaa | 7320 |
| atcaaaatcg | gaatcgaaat | ctctcatcta | acgtacgacc | atgacttcga | aagtttatga | 7380 |

```
tccagaacaa aggaaacgga tgataactgg tccgcagtgg tgggccagat gtaaacaaat    7440
gaatgttctt gattcattta ttaattatta tgattcagaa aaacatgcag aaaatgctgt    7500
tattttttta catggtaacg cggcctcttc ttatttatgg cgacatgttg tgccacatat    7560
tgagccagta gcgcggtgta ttataccaga ccttattggt atgggcaaat caggcaaatc    7620
tggtaatggt tcttataggt tacttgatca ttacaaatat cttactgcat ggtttgaact    7680
tcttaattta ccaagaagaa tcattttgt cggccatgat gggggtgctt gtttggcatt    7740
tcattatagc tatgagcatc aagataagat caaagcaata gttcacgctg aaagtgtagt    7800
agatgtgatt gaatcatggg atgaatggcc tgatattgaa aagatattg cgttgatcaa    7860 atctgaagaa ggagaaaaaa tggttttgga gaataacttc ttcgtggaaa ccatgttgcc    7920
atcaaaaatc atgagaaagt tagaaccaga agaatttgca gcatatcttg aaccattcaa    7980
agagaaaggt gaagttcgtc gtccaacatt atcatggcct cgtgaaatcc cgttagtaaa    8040
aggtggtaaa cctgacgttg tacaaattgt taggaattat aatgcttatc tacgtgcaag    8100
tgatgattta ccaaaaatgt ttattgaatc ggacccagga ttcttttcca atgctattgt    8160
tgaaggtgcc aagaagtttc ctaatactga atttgtcaaa gtaaaaggtc ttcattttc    8220 gcaagaagat gcacctgatg aaatgggaaa atatatcaaa tcgttcgttg agcgagttct    8280
caaaaatgaa caatgaccgt taacctagac ttgtccatct tctggattgg ccaacttaat    8340
taatgtatga ataaaagga tgcacacata gtgacatgct aatcactata atgtgggcat    8400
caaagttgtg tgttatgtgt aattactagt tatctgaata aaagagaaag agatcatcca    8460
tatttcttat cctaaatgaa tgtcacgtgt ctttataatt ctttgatgaa ccagatgcat    8520
ttcattaacc aaatccatat acatataaat attaatcata tataattaat atcaattggg    8580
ttagcaaaac aaatctagtc taggtgtgtt ttgcgagctc gaattcattc cgattaatcg    8640
tggcctcttg ctcttcagga tgaagagcta tgtttaaacg tgcaagcgct actagacaat    8700
tcagtacatt aaaaacgtcc gcaatgtgtt attaagttgt ctaagcgtca atttgtttac    8760
accacaatat atcctgccac cagccagcca acagctcccc gaccggcagc tcggcacaaa    8820
atcaccactc gatacaggca gcccatcagt ccgggacggc gtcagcggga gagccgttgt    8880
aaggcggcag actttgctca tgttaccgat gctattcgga agaacggcaa ctaagctgcc    8940
gggtttgaaa cacggatgat ctcgcggagg gtagcatgtt gattgtaacg atgacagagc    9000
gttgctgcct gtgatcaaat atcatctccc tcgcagagat ccgaattatc agccttctta    9060
ttcatttctc gcttaaccgt gacaggctgt cgatcttgag aactatgccg acataatagg    9120
aaatcgctgg ataaagccgc tgaggaagct gagtggcgct atttctttag aagtgaacgt    9180
tgacgatcgt cgggcccagg tagaatccgc ctgagtcgca agggtgactt cgcctatatt    9240
ggacgacggc gcgcagaggg cgacctcttt ttgggttacg attgtaggat tatcactaaa    9300
acaatacatg aacatattca aatggcaatc tctctaaggc attggaaata aatacaaata    9360
acagttgggt ggagtttttc gacctgaggg cgttaacctt ctgttaacct aaaagctctt    9420
gcccaaacag cagaatcggc gctaattgcc agcggcggaa cttttccagt ttcgcgaaaa    9480
atatcgccac tggcaaggaa tgggtttgag atggcgaagt ctgtcctaaa agcagcgcct    9540
gtagttgtag ggttgacggc cttgatggag cgtcatgccg atgccctctc gagccaactt    9600
caagcacatc atcttaaggt tttcccgccg cattccgaga agggcattcg aacattcggg    9660
ccatcggagg cgtccaagct gctcggcgtt ggcgagtcat atttacggca gaccgcgtct    9720
```

```
gagatgccag agttgaatgt tagcatgagc ccgggtggca ggcgaatgtt ctcaattgaa      9780
gatatccatg tgattcggaa gtatatggat caggtcggcc gcgggaaccg gcgctacctg      9840
ccacatcgtc gaggcggcga gcagcttcag gttatctctg tgatgaattt caaaggtggg      9900
tcgggtaaga ccaccaccgc cgcgcatctg gcgcagtacc tcgctatgcg cggatatcga      9960
gtcttggcca ttgatctcga tcctcaagcg agcctttctg cactctttgg gagccaaccg     10020
gagacggacg ttggcccgaa cgaaacgctc tacggcgcta aaggtatga tgatgagcag     10080 gtggcaatcg aacgagtcgt ccgagggact tacattcccg acctccacct gattcctggt     10140
aaccttgagc tgatggagtt tgaacacgat acgccacgcg cgctgatgaa ccgcaaagag     10200
ggcgacacgc tcttttatgg tcgcatcagc caagtaattg aagatatcgc ggataactat     10260
gacgtcgtgg tcatcgactg ccctccccag cttgggtatc tcacgctatc cgcattgact     10320
gcggcgacgt ccattcttgt cacggtccat ccgcagatgc tggatgtgat gtcgatgaac     10380
cagtttctgg caatgacatc gaaccttttg cgtgaaatcg agaatgctgg cgccaagttc     10440
aagtttaatt ggatgcgcta tctgataacc cgtttcgaac cgagcgacgg accacagaac     10500
caaatggtag gttatctgcg gtcgattttt ggcgaaaatg tcctcaattt tccgatgctt     10560
aaaaccaccg cggtttcgga cgctggcctg acaaaccaga ctctattcga agtggagcgt     10620
ggcctgttca cgcgctcgac ctatgatcga gccttggagg cgatgaacgc cgtcaacgac     10680
gagatcgaaa cactgatcaa aaaagcatgg ggtaggccca catgagccgg aagcacatcc     10740
ttggcgtctc aactgacgcc cctgagacgt cgcccgccga caataggacg gcaaagaacc     10800
gctccatgcc gctcctcggc gtaacaagga aggagcgcga tccggcaacg aagctcacag     10860
cgaacattgg taacgcactg cgagagcaaa acgatcgtct tagccgtgcc gaagagatcg     10920
agcggcgtct cgctgaaggt caggcagtga tagagttgga tgcctcgtca atagaaccgt     10980
ctttcgtgca ggatcgtatg cgaggggaca ttgacgggct ccttacttcg atccgggaac     11040
aaggacagca agtcccaatc cttgtgcgac cgcatccgag ccagccgggc cgatatcagg     11100
ttgccttcgg ccaccgccgg ctacgcgccg tttcagaact cggacttccg gtcagagcgg     11160
tcgttcgcga actgacggac gagcaagtgg tcgtagcaca gggtcaggaa acaatgagc     11220 gcgaagatct taccttcatc gaaaaggcgc gcttcgcaca tcgcctgaac aggcagttttt    11280 ctcgagagat tgtcatcgcc gcgatgtcga tcgacaagag caattgtcc aagatgcttc      11340 tgctcgttga cgccctcccc tctgaactga ccgatgctat tggtgccgct cctggtgttg    11400 gacgccgag ttggcaacaa cttgccgagc tgattgagaa agtttcttca ccggccgacg     11460
tggctaaata tgctatgtcg gaggaagttc aagcgctgcc atcggcagaa cgattcaagg    11520
cggtgatcgc tagtctgaag cccagtcggg ttgcgcgtgg acttcccgag gtcatggcca    11580
ccccagacgg caccagaatt gcacaggtga cgcagagcaa ggccaaactg gaaatcacga    11640
ttgacaggaa ggcgacgccc gatttttgcga ccttcgtgct cgatcatgtg ccagcgctgt    11700
atcaagcgta ccacgctgag aaccaacgga aacggggaga gtaaaccgca aaagaaaaga    11760 gcccccctcaa cgtcgccgtc gcggaagccc ttctgtctct ctagcgcgaa cagaatcgca    11820
tttcctcgaa tcctcgtcaa gagttttag cgccgttttg gtgagctgat ttcctttgcc     11880
tgctgaaagg tgaaagatga tgcagacagg aagtgtaacg acgccattcg ggcggcggcc    11940
aatgacgctt gcgcttgtgc ggcgccagac ggcgctggcc gatatcaaac aaggcaagac    12000
agcggacaag tggaaggtct ttagagacgc gtccgcggct atggaactac ttggaatcca    12060
gtccaacagt cttgccgtcc ttgatgcgct attgagcttt caccccggaaa cggagttgcg    12120
```

```
tcaggaggca cagctgatcg tcttcccgtc gaatgctcag cttgcccttc gggcgcatgg   12180
gatggctggc gcgactttgc gtaggcacat cgccatgctc gtggagtcag gcttgatcgt   12240
ccggaaggat agcgccaacg gaaagcgtta cgctcgtaag gatggcgctg gtcagatcga   12300
gcgcgcgttt ggcttcgatt tgtctccgct tctcgcgcgg tccgaagagc tagcgatgat   12360
ggcacagcag gtgatggccg atcgagcagc attcaggatg ccaaagaaa gtctgacgat    12420 ttgccgacgg gacgttcgga agctaattac ggcagctatg gaagagggag cggagggcga   12480
ctggcaagct gtcgaggaag tctatgtgga acttgtgggt agaattccac gcgccccgac   12540
gcttgctgat gtagagtcaa ttctcgaaga gatgtggatg ctccaggaag agataatcaa   12600
ccggttggaa attagagaca attcagaaaa taatagcacc aatgctgccc agagcgagca   12660
gcacatacag aattcaaaac ccgaatccgt taatgaactt gaacctcgct ctgaaaagga   12720
gcagggcgct aagccgagtg aaatagaccg ggcaaggagc gagccgataa agcgttccc   12780 cctcgggatc atcctgaaag catgcccgac cattggcaat tatgggccga gcggtgcggt   12840
tgctagctgg cgtgacctca tgtcggctgc ggtggtggtt cggtctatgc tgggggtcag   12900
cccgtcggct taccaagacg cgtgtgaggc aatgggaccg gagaatgcgg cagcagcgat   12960
ggcgtgcatt ttggagcgag cgaacttcat caattcgccc gggggctatc tccgagatct   13020
gacacggcgg agcgagcttg ggaagttttc acttggcccg atgataatgg cgctcttgaa   13080
ggctagcggg caggggacgt tgcggtttgg ctagaattag cgagtatgga gcaggatggt   13140
ctgtggtcag ctgaccacag acctaatagg ttgaaaacat gagcgttttt tggatgatcg   13200
acagaccatc cgattcccgg agtaccaagc gtgctctgat gggagcgata acattactca   13260
acaagcacga aggcccccatg ccgatcgttg atcgtgaagg agagcctgct ctacatgcgg   13320
cggtattttg ccggccgagg catgtagtcg cggagcactg cctatttact gccctaggca   13380
caaacgttga ctcttggatc gagctggcag acaaagcaat aacccacaca gaggacgatt   13440
aatggctgac gaagagatcc agaatccgcc ggacggtact gctgctgccg aagttgagcc   13500
ggctgctcct agaggtagaa gagcaaagaa agcaccagcc gaaacagccc gcacgggatc   13560
gttcaaatcc gtgaagccga aaaccccgcg cctcagcaac cgagaaaaac tggagaagat   13620
cggtcaaatc gaagctcagg tcgctggcgg cgcaaccttg aaggacgccg ttaagatcgt   13680 gggtattttcc gttcagacct attatcaatg gaagagagct gcggttcaac ctgtctcaca   13740
gaatccggcc gtgtctgttt cagttgacga tgaactcggc gagttcatcc aactcgagga   13800
ggaaaatatg catggcatgc ccgttccata cagaagctgg gcgaacaaac gatgctcgcc   13860
ttccagaaaa ccgaggatgc gaaccacttc atccggggtc agcaccaccg gcaagcgccg   13920
cgacggccga ggtcttccga tctcctgaag ccagggcaga tccgtgcaca gcaccttgcc   13980
gtagaagaac agcaaggccg ccaatgcctg acgatgcgtg gagaccgaaa ccttgcgctc   14040
gttcgccagc caggacagaa atgcctcgac ttcgctgctg cccaaggttg ccgggtgacg   14100
cacaccgtgg aaacggatga aggcacgaac ccagtggaca taagcctgtt cggttcgtaa   14160
gctgtaatgc aagtagcgta tgcgctcacg caactggtcc agaaccttga ccgaacgcag   14220
cggtggtaac ggcgcagtgg cggttttcat ggcttgttat gactgttttt ttggggtaca   14280
gtctatgcct cggcatcca agcagcaagc gcgttacgcc gtgggtcgat gtttgatgtt    14340
atggagcagc aacgatgtta cgcagcaggg cagtcgccct aaaacaaagt taaacatcat   14400
gagggaagcg gtgatcgccg aagtatcgac tcaactatca gaggtagttg gcgtcatcga   14460
```

```
gcgccatctc gaaccgacgt tgctggccgt acatttgtac ggctccgcag tggatggcgg    14520
cctgaagcca cacagtgata ttgatttgct ggttacggtg accgtaaggc ttgatgaaac    14580
aacgcggcga gctttgatca cgacctttt ggaaacttcg gcttcccctg agagagcga     14640
gattctccgc gctgtagaag tcaccattgt tgtgcacgac gacatcattc cgtggcgtta    14700
tccagctaag cgcgaactgc aatttggaga atggcagcgc aatgacattc ttgcaggtat    14760
cttcgagcca gccacgatcg acattgatct ggctatcttg ctgacaaaag caagagaaca    14820
tagcgttgcc ttggtaggtc cagcggcgga ggaactcttt gatccggttc ctgaacagga    14880
tctatttgag gcgctaaatg aaaccttaac gctatggaac tcgccgcccg actgggctgg    14940
cgatgagcga aatgtagtgc ttacgttgtc ccgcatttgg tacagcgcag taaccggcaa    15000
aatcgcgccg aaggatgtcg ctgccgactg ggcaatggag cgcctgccgg cccagtatca    15060
gcccgtcata cttgaagcta gacaggctta tcttggacaa gaagaagatc gcttggcctc    15120
gcgcgcagat cagttggaag aatttgtcca ctacgtgaaa ggcgagatca ccaaggtagt    15180
cggcaaataa tgtctaacaa ttcgttcaag ccgacgccgc ttcgcggcgc ggcttaactc    15240
aagcgttaga tgcactatac gtaaccaact agtgcgctct ccgcttcct cgctcactga    15300
ctcgctgcgc tcggtcgttc ggctgcggcg agcggtatca gctcactcaa aggcggtaat    15360
acggttatcc acagaatcag gggataacgc aggaaagaac atgtgagcaa aaggccagca    15420
aaaggccagg aaccgtaaaa aggccgcgtt gctggcgttt ttccataggc tccgccccc    15480
tgacgagcat cacaaaaatc gacgctcaag tcagaggtgg cgaaacccga caggactata    15540
aagataccag gcgtttcccc ctggaagctc cctcgtgcgc tctcctgttc cgaccctgcc    15600
gcttaccgga tacctgtccg cctttctccc ttcgggaagc gtggcgcttt ctcatagctc    15660
acgctgtagg tatctcagtt cggtgtaggt cgttcgctcc aagctgggct gtgtgcacga    15720
acccccgtt cagcccgacc gctgcgcctt atccggtaac tatcgtcttg agtccaaccc    15780
ggtaagacac gacttatcgc cactggcagc agccactggt aacaggatta gcagagcgag    15840
gtatgtaggc ggtgctacag agttcttgaa gtggtggcct aactacggct acactagaag    15900
gacagtattt ggtatctgcg ctctgctgaa gccagttacc ttcggaaaaa gagttggtag    15960
ctcttgatcc ggcaaacaaa ccaccgctgg tagcggtggt ttttttgttt gcaagcagca    16020
gattacgcgc agaaaaaaag gatctcaaga agatcctttg atcttttcta cggggtctga    16080
cgctcagtgg aacgaaaact cacgttaagg gattttggtc atgagattat caaaaaggat    16140
cttcacctag atccttttaa attaaaaatg aagcgtaccg acgatcttgc tgcgttcgga    16200
tattttcgtg gagttccgc cacagaccg gattgaaggc gagatccagc aactcgcgcc     16260
agatcatcct gtgacggaac tttggcgcgt gatgactggc caggacgtcg gccgaaagag    16320
cgacaagcag atcacgcttt tcgacagcgt cggatttgcg atcgaggatt tttcggcgct    16380
gcgctacgtc cgcgaccgcg ttgagggatc aagccacagc agccactcg accttctagc     16440
cgacccagac gagccaaggg atctttttgg aatgctgctc cgtcgtcagg ctttccgacg    16500
tttgggtggt tgaacagaag tcattatcgc acggaatgcc aagcactccc gaggggaacc    16560
ctgtggttgg catgcacata caaatggacg aacggataaa ccttttcacg ccctttaaa    16620
tatccgatta ttctaataaa cgctctttc tcttag                              16656
```

<210> SEQ ID NO 4
<211> LENGTH: 814
<212> TYPE: DNA
<213> ORGANISM: Zea mays

<400> SEQUENCE: 4

```
gtgagcgctt acacctctcc gttcctcccc gctgccttgc gcgcgcacgc tttcgtgtag      60
atctgggtcg ccgcgtctcc gtctttgttt agccggccgt agagcctccg ctctaggtgc     120
ctcaagctcc tcttcagttc ttctagctcc ggtagggttt ccctttttgcg catagcgggg    180
gcggctgatg cacggttggc tacctcagct attcgtcagg ctactcgtca gtattttcgg     240
cgcactttgc tagcttagat catcgccgtt tgttttgcgc ttcgtccgtc gccgactcga     300
cgaaccggcc aatcaccacc ctcgccgatc cattactctt aaatccggac cacgccatat     360
cggatcgaac caaacgttca cgcgttgtcg actaaagcat tgtgtggttg atttattaat     420
cggctgatgc agtagaaatc ctatagagtg tacatcagtt tctagtttca agcatgtaat     480
tgagcttgtg aggtgcagta ttttgttgat gtacaaggct tagggcattg ttttgctgaa     540
gggcctgtga tcatgtgtaa tctaatgtgg agtattaaac gtgtgtgtag ggttgatgaa     600
attatgctag taatggcttt caagtaacac gttattgtg atctgtgaca tctttaaaca      660
atatgcagtt tgttttcctt aaattcgttg ctgaaattgt gacattggtc atgcttgaga    720
aggaatcatt ccgtgaaatc aggttgcgat gcctatgata cacttgctg gaatctgttg      780
tgcttttctg atcactgttt tttttgcaat ccag                                  814
```

<210> SEQ ID NO 5
<211> LENGTH: 727
<212> TYPE: DNA
<213> ORGANISM: zea mays

<400> SEQUENCE: 5

```
gtagtccttg acgcgttcga gcttgagtag gcgaaggcgg cactttgaga gcggcgccac     60
ggcgaggagc cacgccgccg cctcggagcc cttctgtcgc ttctgcttcc aaccgacacg    120
ggaaggggcg gcgggtggtt cacatttctt ctctttcttc tcgtctccct atttgcggtc    180
gcccgggaga ccgggctgct tgcccatccc gccaggagaa ccatgtccca tctccggcgg    240
ccgtgaatta gggtttggct ttgtgatctg tgtagggatc tagctatatg tgatggtgct    300
tgtctagatc tatgttgtt aagcctggtt cgttgatctg gtgagatggt gcatgatcga    360
ggtttgattg tttaatcta gaatgttgga tagagaatta gaacagggat tagccgaaat    420
tacgcattat tttccatgat ccaatgaagt tagtagttat gtagcataat tgttgttgat     480
ttatgccaat atgtgtgtta gatctgagtg ccctgaaatc gtttaaatgc actggcattc    540
acgatctgta aattttcata ggccaaattc gtgttgcctg tttatgccct tgaagtatgg    600
atatagagtt agtatgttta atgtaaaacg atgtatagta catctattcg tactattatt     660
agatattcaa aaaatgaat acatattagc attagaccct ttgaaccaat tttattttgc     720
tatttag                                                               727
```

<210> SEQ ID NO 6
<211> LENGTH: 834
<212> TYPE: DNA
<213> ORGANISM: Zea mays

<400> SEQUENCE: 6

```
gtacgcccgc tctctcgctc cctctctacc tcctcgactc catctccttg aatttcactc     60
gttactacac cgaccgctac caccgcgct gcgccctgtg ataatcggtg caccgtgcgc     120
cggcggatga ttgtattctt gaatctgcct tgttgatagc tcttggcgcc caccgagtgc    180
```

| | |
|---|---|
| atcaacaaga caacaagaaa ccggtccta tacgaatggt attggctacc gtgttcagtt | 240 |
| cgtccgcgcg gttgttggga aaaaaaaatg gacggtttag ttaggctggt gcgcagccgg | 300 |
| acaggacaaa tacacccgtg cggtggttag gcagcggaga ttgacgcatc attgcgacct | 360 |
| cgcaaatggt ccttgtctcc ctggtggttg tatgctctgt ccaacatcc gttgaggaac | 420 |
| tgcgcttggt gtgtgtggtc cagttcctgc aattagcgtg gttgttgttc gtcgcggcat | 480 |
| cttcgtggga tttggtagat ctgcaagaaa gtgagtgctg cttttcaatg gagttctta | 540 |
| gcaatcagtg agatttggtt tgccataggc cgccttcttt tcctgggtct actgattgag | 600 |
| ccctcccagt cccatgtgct tgccattaag caacttgaca atcaatgaaa aggtgagggg | 660 |
| gtccgaagga gtaattacga agcaaataac ttgactgtgc agatttattg cactgaataa | 720 |
| cagaaatgac acacaaagtg ttttttttta aaaaactt agacagaaaa tcaaaggat | 780 |
| atacctctcc tcttcgtaac atagaattct tatctcataa attcgttcgt gcag | 834 |

<210> SEQ ID NO 7
<211> LENGTH: 982
<212> TYPE: DNA
<213> ORGANISM: Zea mays

<400> SEQUENCE: 7

| | |
|---|---|
| gtaaactcct acgcctccct tcgatgcctc cagcgtctcc ttcccgcgtt ccttagctgt | 60 |
| agttattact gccttgatct gtactccctc cgttttagtt gtcgctggat agtgcaaaat | 120 |
| tgaactatcc agcaacaact aaaaagaaac ggagggagta tctatcttgt tgtaggctct | 180 |
| ctcacttgta gctgcccgaa taccttgact gttcttcacc tcacgttaga aacacaggga | 240 |
| ttccgcatgc ctgttcgtgg tcgctgtgcg cgtgagccta aatttaggcc gcatagagca | 300 |
| tgcggcagct agattgtacc gagcggtgaa actttgccag tgcaaccaag agagggcatg | 360 |
| aggcggcggc acgtccccgc tgcacggctg ctcgtggttg gggcgagatc tcgcgtgatt | 420 |
| gagtctgcga aaagcgcag ctgcgatcta gatcgacgtg gttgctcgtg atctcgtctc | 480 |
| ccatccagat gtggtgaggc agttaggctg agatccggcc ccttgtgcca tgtccgtgtg | 540 |
| gaccgagtca ggctggtgtc gttttatttg tactcgcaaa gtgctgatgc tacgattttt | 600 |
| atttatgttt atgtatagag tgtaaaatac gattttatt tatatttatg tatagaatgt | 660 |
| aaaacacaaa tacatacgtg ttgtgttggg gtggatgcga aattgagttt atagccaaaa | 720 |
| attgggtttt tatttgtaca taattttaaa ttaaatgtga atgagtatga tgatggtgga | 780 |
| aatgaaaact agtgcgtttt atatagtaga gaaaagatag ggagtaggtg ggcttcatcc | 840 |
| agatctttcg gttatgtcgg ggtttgtttg gtcatggcag gcagggccac atgagatttc | 900 |
| tgtacggggt ttgaattgac actgcatcgt cttcgactga cattatgtgc tattgtatct | 960 |
| atgaactgga aaacttttac ag | 982 |

<210> SEQ ID NO 8
<211> LENGTH: 856
<212> TYPE: DNA
<213> ORGANISM: Zea mays

<400> SEQUENCE: 8

| | |
|---|---|
| gtaaggttcc cttccctcct cccctcacac ccctgttcgt gttccttcgg atcggatctc | 60 |
| agtggtgatg ttagacgtcc gcggctgcct acgtagtggc attgccgccc gaaaggtttg | 120 |
| tttaggtggg gtagatccga aacaggccgg atctggacca tgtccgcggc ggggcggcgg | 180 |
| gacttgatcg cgtagctgtc gtgtgcattt ctccctacca gtggcggaat cggcgatgtg | 240 |

```
gacctaaggg ctaaggctta tctgctgcct tgaccatttc gtcgctgaca aaaacaaagt      300
gacaatcatg ccgttctctg tttgtttatc tggatcgtta ttacgctgtg aatcctgcga      360
tatgtggcta agtgattttt cttcttttc tggggcagt ttagcctttg acccagtcct       420
aggtgtggtc actaggactg tgtagcatga tgagtgaggt tgcagcaggc tgattgctag      480
tggacgtttt tttccccaat tgttaggtt ttcacgctcc aggttgtgca agtaattttg      540
ctagtgattg tgtgatccat cttcaacgtt gaaccttgtt tttcccccta aaaccccaa      600 caggaaatct tgccccgact tctattgcaa aaattgtaac gcttagcacc ctgattgact       660
caattcctgt cactaggcat gctcggtcaa aagcagatga tttaccactt agaaactgcc      720
ctgcccctgc tttccacata gcatttcgaa ctttttgact actattgaca ccccccctaac     780 ttgccgaact atttctctct tcagctacta tttacctagt tataattaca taaatgtttg     840
tgtgtatctt gtgcag                                                      856

<210> SEQ ID NO 9
<211> LENGTH: 1020
<212> TYPE: DNA
<213> ORGANISM: zea mays

<400> SEQUENCE: 9
gtaaatctca aatttatcat gtattttcaa atgatataaa attcggatac gaataatttt      60
ttgacatttt ttctctagag agcaaataat acataaaaca aattatacaa aattttattc      120
ttatttataa taatatgttc aataacataa gaaaaaatca gcatcaaatt tcatatatat      180
ctatattaaa atattaaatt tatgctaata atttggatac ccattttatc atcatcttat      240
tccgatatgg tatttcctgc aatcaaacac atgcccaggg aacgctcgca cccgaagatt      300
ggcgtaaccg aaccgatgcg accttggcc cgtttcaaaa tgaaatgggc cggtcaatgc       360
gcggcccatc cggccgatga tatcacgacc cagcgtgcat cctatgaaac ctctgccccg      420
gggctagggt ttcctcccag ccgtcatcgc ttcacgtccg ctacagaccg gcgaggagac      480
gaaaggtaag ccacccactg ccgccgctct cgtttcaccc catttcgtcc ggccgtctaa      540
ttcgttggcc ggcccgttct gttcgtggaa gcgctcggat ctgctctgta tatgcttgtt      600
ctcgttcggt tttgccggtc ggagttgtct cgcgaggcgt agcttgtgcg tcaggctctc      660
ttttgccttg tagatttcct gcatctgctc ttactgatag cttttgctgt taatcttgag      720
agagttatgc cacgagtctc tttgatattc tattggggta atgatatgtg gggatactgt      780
aatgtttctg atattcttgc tatggttggt ttgggcatga agtagaattt gtaatggtgc      840
ttttaggatc ctgttttgg tgctaactct gtcaacacta gactgagaat tgttgttaac       900
aagtagcttt catgttgcac gacaagatcc ttctgtgttt cattccagtt ctcatgattt      960
tatttctttt ttgcatcttc atccgcctga cataatggtc tttatctact tgcaattcag     1020

<210> SEQ ID NO 10
<211> LENGTH: 841
<212> TYPE: DNA
<213> ORGANISM: zea mays

<400> SEQUENCE: 10
gtatacaacc gacctcgtct ccccgatttt ctcaactacg tagtgtatgt acgcatcggt       60
aggtagatgg gaatttcggg ccactggttt gggggggttta atttgcgcta tcgtttcggt    120
ttgcctgtgg tttcggaggt agatttgggt cgcaggtagg ttgtcgcttg gatctgggag     180
```
aggcgaggag ctaaattcgc atagcttgta ataactcacc ccggttgcta tgaaaagccg      240
taggccgtag ctgctgctgc tgctgtaatt tactacttat tttcttctaa tatagggat       300 tcccttcctg caactttttt ttaaatacgg ttcttggtta ctggctggct tagtgcagtg      360
ggaccttgtt gccatgaatg attgttgcgc aatttagtag atcattagat tagcacgacg      420
tacctaatca tgggtcccgt gaattttagc ctagtcccca ttatttgccc cttagtcacg      480
catgtgtttg gtgtacttca aggaatctgt ccatatgcat cggatctatg ggttcggcca      540
tgatgttgac attgaactgt ggccgttcat gttcgacttt accttgcgcc cgagcaaaaa      600
gaaggataaa tcgtgtgtac caatctggct atacggcagc tcgatatgtc tgaatgaaga      660
ttgggagtat tcttctgttt atttatttgt caatttttat tctgaatatt catttgttct      720
ccagtttagt agtgcatcat taacacttca attctaggtc tattgctatg gtatagtagc      780
actctttcaa tctttcatgt gtacagctga tgccttatgt tgatccccett ccttgcttta     840 g                                                                      841

<210> SEQ ID NO 11
<211> LENGTH: 1044
<212> TYPE: DNA
<213> ORGANISM: zea mays

<400> SEQUENCE: 11
gtccgtgccg ggcggcccgg atggacatct atagcccgca ggtcatggat agatagataa       60
tttcgcgtcc gtgataaagc cggactgcta cgtttccgac gggagtaatt atttacacac      120
tcttcagcac caacggcatc tcgtggacgc tggatcccaa taccaaattg ctacaagctc      180
aatgatgtct gggtgggctt ctggcccatt tagaatatca tctctatacg tctttataca      240
gaacgaaaaa aaaacgagcg gccaagatgg tgttggagta tagatcggac ggcaaagccg      300
tgctctccgc cttttaaaag gctgtccgac tcgacccttc tcctctccgt cgcatttccc      360
gtccggtctt tccgttaccc ggcggcttta aaccctagtt cccattccat cttcgtttcc      420
gctccgccgc cgtcgatgga gttctggggt gacctccctt actttctctc tcgcaaactc      480
aattctccgt gatacctgcg cttttcttcgt tttgttgcgg ttcctctgtt tgattttttgg     540 gcgtttagc cttttatttta aggccctggg aatcatgggc atggtttgat tggctactgc      600
tagcacttgt ttgcgaatgt tttagggccc tgtgaatcgt ggctattgtt tggttcgcta      660
ctacttacta ctagggcatc gttgttctac aatcagcagt tatgtggcat tgcctatttg      720
cacagtatgg aaaaaagtag attaaaatgg ttgaaatcat acgtggccgt gtcctgtttc      780
aatagggtct tattatagga cgtgacggtg atgccactga attaggatgt tgttctttt      840 gtaccattgt taaacagcac cagatcattc ttaatgtaac ctacatcaga ttgtttgttt      900
tgttctacta caagtatgtt cagcatggca ggaggaagtg tgctcctaaa tctgttgttt      960
aggcgcattg cgaaatgttt gttctaacag catcaggttt gcattcttaa tttaacctat     1020
cttgtattgc tctgtctttt gcag                                            1044

<210> SEQ ID NO 12
<211> LENGTH: 648
<212> TYPE: DNA
<213> ORGANISM: zea mays

<400> SEQUENCE: 12
gtaagcgacg acaacgagca gtgggcggca ggattgagcc cccccatacc ttctctctct       60
gggtttcgct ctctctcgcg tgctcagaaa gtttcggagg cggcggtttt cgctctctct      120

```
cgagcgctcc gtccaagcgt ttttctttca gaaccagtcc ttttttgattc cagactaaaa    180 tttattgctt ttattattag caataaattt catggttcaa aaatgcgaca gttttttttac    240 ttgaatagag acatttattt taaccaaaga aaaatcatat atatataata aaaacaaatt    300
agtggcatcc atacatatgg atgcccaaac aattatcggt tgaggaagtc aacaggaaag    360
tatcttaaag gttggaaacg tggcaaatcg aggagcatga gctggtaggg cactcgcagt    420
gggtggagcc ggtttgctga cgcggaagga accgaccatt catgactcgc ttggcacgcg    480
gtgaggtgag tgtgagtgtg agtcagcctc tcgatctggg ttgggttttg gtctataaaa    540
taccccggcc tccatctctt ctctgggttg tggttgtggc ctcctatcct tgcacgcaca    600
cgcaaacgca tcccatcctg tcctcgcgtt actactagtt agttagag                648
```

<210> SEQ ID NO 13
<211> LENGTH: 632
<212> TYPE: DNA
<213> ORGANISM: Zea mays

<400> SEQUENCE: 13

```
gtgaggagcc ttctctctct ctctctctct ttctctgtct ctctctcttc ctaacctttc     60
ttcccttcgt cctcgtcccc cacgctctgc tcttgtggaa ttttctatta gcgtctgccg    120
ccatttgttt cggctacttt gtgcgcgcgc aagcgcaaac cacggggggtc tctctcgtgt    180 tcgccattct gccgaatcgc cactgcaagc tcttctaccg ctttctgtgt gctctgacat    240
ctggactccg gagtccggac gtccgcggct ctgtttgctg cgcttgtttt cttttttcca    300
gctatgcttc gtttcttctc gaattccatt ttttttatctc tctttttttcc ctcgtggacg    360 aagcaaagca agcaagacga ccttgcatct gagactctga gactgtactg tttcttttgc    420
cattgggttt tcccctaaga ttcctttttg gctgccaatg ttcagtccga cagcagcacc    480
cgctgcaacc atttcagcac ttcttccgcc tctgtttcca taatatttct tcttttttttt    540 ttccatctct tttttttgt gtgtgctata gcttttgctt gactgaaacg cagcacacac    600
cttacacaac caaacatttt tttttggcgc ag                                   632
```

<210> SEQ ID NO 14
<211> LENGTH: 1405
<212> TYPE: DNA
<213> ORGANISM: zea mays

<400> SEQUENCE: 14

```
gtatatactc tctctctctc atccgcctct tgattcatgc ggcccttgtg atgtgtgtga     60
tcttgttact tggccggctg tggttctttt tgtgtctctt gattcatgcg ggtaggatta    120
atctttgttt aatccgcaaa aaaggccttg attattcgat actatctatc tgtaatccgc    180
aaaaaggcga tgaactttcc atgttctcgg tagtgactgt tctgtatcga ttctgctgtc    240
tcatcaacta gtcgtcggtc gcaaggactc gatcgcacgt ccatttcgac ggtagctaca    300
acaagcattt cctgcagaat aatatctcgg ttttatttct agaaggacgg tcgttgtagt    360
ttatttaaag ggaaaaaaag atcagttgta gtagatatgc gctctagagt ccagaatggc    420
ttaaaggacg atggttacgg atggaaacct tttcctctca tcgcgtgccg atagcgaaac    480
ggaagctttt gtcagtccag ggaggggaaa aaatttcaag gtgttgagca gcccccttcgt    540 tggatatagc agagcaggcg acgtgcaaga caattaaagc aatgcctacg agagcggacc    600
ctgatatttt tgtatgtgtg attgtgatac gtgtctggct ttaggctttg gaccgagaaa    660
```

```
tagctcgctt ttccacaggg gggaaataag gtgccccttg gaaatgacag tcggtattgg      720
gttcagaacc aggctttgag attacaatag agaaactggc agcttgagct gacgtagcgt      780
tttatcagaa gtcgtcaata tcgcctgcta cgtatatctt atagtttaat tgttacttgg      840
gacatcggtc tctagcttgt ctggacaact ggttctcctc ctcctgatcg gatttgattt      900
tttttacgag ccgtcaaatg catggtttgc tataggatat tcatatttca gagacgtcta      960
tcgcttctta gcctaccacc gcaactctgc tgtggaccac cattattatt ggttctcctc     1020
atcgggcttc ggggttcaca gtctgcata ttcttctcta gttttttctt tgctagcttt     1080
caggctgttt tcaatgctac ttcagacaga gacgtcaatt tttgtctgac gcctattgag     1140
gaccgcgggt atagtagggt tttcagatcc agagcactaa accaactact acccggccgc     1200
cgccgccgcc ggtacatgta aaaaaaggct tcgacctgcg agatgaacgc aacgagagc     1260 attcaacaaa ccaaaaccgc ataaccaaaa tgttcagact agcgcgtggt agtagtagta     1320
cttgcagtca tgtcatgcag tttgccacgc cgccgcgtgc acgcagtttg ccacgctagc     1380
taatctgttc tcattccgct cgcag                                           1405

<210> SEQ ID NO 15
<211> LENGTH: 1361
<212> TYPE: DNA
<213> ORGANISM: zea mays

<400> SEQUENCE: 15
gtaagcagga gagagagctc tttgagtttg atcgatcctt aagacaatac tgtagacttg       60
gcacaaccat gccccgtcc atatcccgac cgtccgattg ctgaatccac ccccgcatac      120
ctcatctgcc atccattctc gctcccgccc tcgaccccgc cgccatgcgc gcagccgcct      180
ccgcccaaca accatgcggg atcctcgccc aacagccatg cgcgccgact acgcctccac      240
cagatccagc cttcctatag tcatcctgtc atccaacagg gatcctggcc acatagagtt      300
tcgcccgaat cgatcgccga ttgactccgc tagggttcgg cccgatcgtc gcttcgtcct      360
ctcggctccc gcggggaccc cgccgagatg tctgaccgga gctcgccggc tgcgccgacg      420
ttcttccttt tggcccgcag gccgaggcat gggacgtcac cttcaaggtg aggcatccga      480 tcgattttttc tttctttctt tactacactc ctttgcgata tggggacgac actcggtagt      540
ggcgtgaggt gaggtaaatc gcgttagttt agttgtaggg tttgatcgct tcaggggaga      600
ccaggggttg ggctttccgt gttgaaccgt caatcggacg tagtagtagt gcggattcgg      660
ggtttgatcg atggaaagag gggttgtccg cactcttggt gtggttatag ggttttgcga      720 tttgttttgtc tgtgtaggcc tgtttcgtct cgaggagtag attttcattg ctactaacaa      780
tccctatgtg gtttggtgaa cacgtatttt ggtctgtata tggtttaaac gtgaagacta      840
tggtagtgtg agaccatgat ttggatcctt ttctgtggca ttatagttaa atcgtgagg      900 atgcacctat atctatcttt tagcgcttag ggtattgtta tagacgagat ccctctcttg      960
ggctctaaaa atagcaagaa aaagacatct tttgggcaag ttaacgtcct gtattattct     1020
gaacgagata tgtttacttt cttataagtt tgatgtttg gtctggaata tggttgcgtt     1080
catcttccaa ttagtgtgtt tgcagtatgt gttggtgtag tttctctgtg gcatttttgt     1140
ggccacagaa atgatagatt ttaagaaagg tttaggtaga agggtaccttt aagtgttgtc     1200 cagtacaaag taacaatttg tagcacttgt ttctttttctt ttgtttgact atatgaaatt     1260
tcggccatgt aattgtttca aaataataag atcgaatagt gttgcacact acttcccagt     1320
cctatgtata cttataagat ttttcctctt tgatatttca g                         1361
```

```
<210> SEQ ID NO 16
<211> LENGTH: 703
<212> TYPE: DNA
<213> ORGANISM: zea mays

<400> SEQUENCE: 16
gtgagatttc gagagattcg tccgtaccag ggcttggatc tacgctccgg ccaccttcag      60
gcttcggttc gccgcccacc aaccgagcct aggagtccgc cattcattca aacgccctcg     120
acggcgactg cgcatcggtt cagatccagg cgtcctttca ccggcagctc cgcctcccat     180
gcaatcttgc tcgttgttgt tgtcccctcc ctggactcgg gtgtactgga agtccatgcg     240
gataaaagaa actcttttgt tggtatggac gccataatgc gttttgttgc ggaatttttt     300
tgcggcttgg cgtgctgtca ataccggttt agttttccaa ttttttttgca gggttcaacc    360
aaacctcctg ctgacagacc cttctctgtt cagtttgctt acccaactga cttttttttc     420
ttgttcatat tctagttgga tgctgagtgg catgccggtc gatatttggg aaagcagatt     480
tttatgttgg caagtgtgag tgcgagttct ttgctgaaac tttaagcttc acctgagatc     540
tgatattgtc ggtgccaaat tgctgtacat ttgactattt gaggacacgt tcttaggtaa     600
atcattggaa gacatatttc acttcgcgta ggacacgtac ttctccaaga tgatgccttc     660
acctgtctca aacctttgtg attttatat actcgcttgg cag                         703

<210> SEQ ID NO 17
<211> LENGTH: 1341
<212> TYPE: DNA
<213> ORGANISM: zea mays

<400> SEQUENCE: 17
gtgaggccgc gaccaagaag gcgtaggcgg cggcgctggc cgtggcgggg cggtggcacg      60
atacgctggc cggctgggcg acgccgtagc ctgtaggtct ctctcgcagg aaaaagtttc     120
tgtgttccaa tggaagtaag atacaaccgt tggattctaa tggaagtaag atcgaacggt     180
tgtgatagat acaaacgaaa ctgaagatct tttatagtat acatagatag atcgacttaa     240
gcaaaaaaat cttaggcccc gtttgtttcg ttggattgaa ttccattttg ataattataa     300
tttagtcaaa actaattaag tttatatatt tatatatacg atatatttgt atattatcct     360
aaatcatacg agagagatag ttatatacta tatttatgtt atagcgaaac aaatagatga     420
gtgtgctata agttgtacat cggaaaaata gcatgtaaat ctatagaatc aatttccatc     480
tctcacccca ttaatttgag ataggcttat atgataactt tggaaagttg tggaatgtca     540
cattcttta aaaaaataga ctattttatt agtaagattc aaatttctcg aaataaaaga     600
aaacaaacga gacctaaag ataatgttcc tataacaatc taataacaac tcaaagagta      660
agaaataaaa aaagtaacgg cgtgtttggt ttgcaggttg gactgcttct ggagtcatcc     720
ggacctatgt ccgagcctac attatcattt ggtttgaatc gcggaacgat gtcgtccgtc     780
actgcgttgt tctaataata tactaacaca tggaattagc tcacttcgca agaaagtgca     840
agaccgcttc gtccggagcc aggccacgat ggatgagtca aaccatcaaa ccaaacacgc     900
tgtaataatt ccgaaaccgc ccgcggagca tcgcagctac tgacaagtgg gttcggaagg     960
ggatcccgtg tcgtgggtcc acacgtcacc gtgtgcggcg tgctctaact gcccgggccc    1020
ggccagtggc gggtaggggg ggagagggac tgagcctgca taaatcgtca gcgaataggc    1080
cgcccgcacg acttctcttc ccaattccca tagatcgatc gccgaccct cgagcaacgc     1140
```

```
gatcgcccgc cgacccgacg gcggcatgga caccgagtac gtcgaccacc ccgcccgtcg    1200
ccgccgcgat cagacggcgc atctctttt cgcacgcggg ggcctttttc ctttctctat    1260
cccccatctt tgtcgatttc ttttatttt cttccccct tgaggatgat gatgatcgcc    1320
tcgggccgtc ggctcctgca g                                             1341

<210> SEQ ID NO 18
<211> LENGTH: 1125
<212> TYPE: DNA
<213> ORGANISM: zea mays

<400> SEQUENCE: 18
gtactaataa actgatgatt cattcattca tggcacggcc taccaatgca aataaatcta     60
tctcacgcta tgagaagaaa accgagagag agagagagag agagagagag ggcttgcctt    120
cccggccggc cgttagtgct caattgggca cgcgattacc gaggcaagca gaggcctcgg    180
gtcgggtggg gcttgtttga cggggacggc agatccacgt ctctgtcacg tgactccagg    240
cggtggtcgc ttgctccatg tgccgcgtcg catcccgatc tctggctgtg gttgcctggc    300
tggcaagggc caaccgcccg tcgtcagcga tgaggatgct tgtagtgtcg tgtcgacttt    360
tgcaaaaaca acgtgcccag ccctgggttt gtgcgccgcc gcaccagcca aaacaaagac    420
gaaaccgaaa gactcgtcaa aaggcaaaac caagtgagga aagacaactg accatagcaa    480
aaaacacaac tttgctagtt ggtttccacg tatctttgcc gcatgaactg gtcccggccg    540
tcacgtttgc ttatagttcc accacaataa tagtcgaccc gtggtcccgt tggttttgat    600
tgagagtaga gagcatccac cggacagtta aaagtgtgtt tcattgtttt ttcccctaat    660
aatctagtac ttattctcta cgtccacata atttagtcgt tttgggttta ttctaaatta    720
aactatttta attttaatca acaatatata taattaaatt attttaaact taaaagaatt    780
atatattatg atagtttaat tcatgataaa tttagtaaaa ttacttttgt attgtaaaac    840
cttataaaag gttcgatata tatataactg gtcaaaattg atagggaacg acttagaaca    900
aacttaaaat aactaaatta aactaaatta tatggacgaa ggggtaggta cctactccac    960
agtacttaat ttcctctagt agttaaccga aacacggtag atactgaatg aatgtgttgc   1020
aagaaacata ctgatctgtc tacttttgct tctcccctct tcgcctcttc aataattcgg   1080
tgtgcaaaga tgttgagaag agaaccgtga ataccgattt tgcag                   1125

<210> SEQ ID NO 19
<211> LENGTH: 894
<212> TYPE: DNA
<213> ORGANISM: Zea mays

<400> SEQUENCE: 19
gtgaggcatc cgatcgattt ttctttcttt ctttactaca ctcctttgcg atatggggac     60
gacactcggt agtggcgtga ggtgaggtaa atcgcgttag tttagttgta gggtttgatc    120
gcttcagggg ggaccagggg ttgggctttc cgtgttgaac cgtcaatcgg acgtagtagt    180
agtgcggatt cggggtttga tcgatggaaa gaggggttgt ccgcactctt ggtgtggtta    240
tagggttttg cgatttgttt gtctgtgtag gcctgtttcg tctcgaggag tagattttca    300
ttgctactaa caatccctat gtggtttggt gaacacgtat tttggtctgt atatggttta    360
aacgtgaaga ctatggtagt gtgagaccat gatttggatc cttttctgtg gcattatagt    420
taaaatcgtg aggatgcacc tatatctatc ttttagcgct tagggtattg ttatagacga    480
gatcccctct ttgggctcta aaaatagcaa gaaaaagaca tcttttgggc aagttaatgt    540
```

```
cctgtattat tctgaacgag atatgtttac tttcttataa gtttgatgtt ttggtctgga      600
atatggttgc gttcatcttc caattagtgt gtttgcagta tgtgttggtg tagtttctct      660
gtgggcattt tgtggccaca gaaatgatag attttaagaa aggtttaggc agaagggtac      720
cttaagtgtt gtccagtaca aagtaacaat ttgtagcact tgtttctttt cttttgtttg      780
attatatgaa atttcggcca tgtaattgtt tcaaaataat aagatcgaat agtgttgcac      840
actacttccc agtcctatgt atacttataa gatttttcct ctttgatatt tcag            894
```

<210> SEQ ID NO 20
<211> LENGTH: 33
<212> TYPE: DNA
<213> ORGANISM: Artificial Sequence
<220> FEATURE:
<223> OTHER INFORMATION: intron_TS1 fwd primer

<400> SEQUENCE: 20

```
caagcgatcg caggtgagcg cttacacctc tcc                                    33
```

<210> SEQ ID NO 21
<211> LENGTH: 35
<212> TYPE: DNA
<213> ORGANISM: Artificial Sequence
<220> FEATURE:
<223> OTHER INFORMATION: Intron_TS1 rev primer

<400> SEQUENCE: 21

```
tcgggtacct ggattgcaaa aaaaacagtg atcag                                  35
```

<210> SEQ ID NO 22
<211> LENGTH: 33
<212> TYPE: DNA
<213> ORGANISM: Artificial Sequence
<220> FEATURE:
<223> OTHER INFORMATION: Intron TS4_forward primer

<400> SEQUENCE: 22

```
caagcgatcg caggtagtcc ttgacgcgtt cga                                    33
```

<210> SEQ ID NO 23
<211> LENGTH: 32
<212> TYPE: DNA
<213> ORGANISM: Artificial Sequence
<220> FEATURE:
<223> OTHER INFORMATION: Intron TS4_reverse primer

<400> SEQUENCE: 23

```
tcgggtacct aaatagcaaa ataaaattgg tt                                     32
```

<210> SEQ ID NO 24
<211> LENGTH: 33
<212> TYPE: DNA
<213> ORGANISM: Artificial Sequence
<220> FEATURE:
<223> OTHER INFORMATION: Intron_TS5 forward primer

<400> SEQUENCE: 24

```
caagcgatcg caggtacgcc cgctctctcg ctc                                    33
```

<210> SEQ ID NO 25
<211> LENGTH: 29
<212> TYPE: DNA
<213> ORGANISM: Artificial Sequence
<220> FEATURE:

```
<223> OTHER INFORMATION: Intron_TS5 reverse primer

<400> SEQUENCE: 25
tcgggtacct gcacgaacga atttatgag                                         29

<210> SEQ ID NO 26
<211> LENGTH: 33
<212> TYPE: DNA
<213> ORGANISM: Artificial Sequence
<220> FEATURE:
<223> OTHER INFORMATION: Intron_TS6 forward primer

<400> SEQUENCE: 26
caagcgatcg caggtaaaact cctacgcctc cct                                   33

<210> SEQ ID NO 27
<211> LENGTH: 29
<212> TYPE: DNA
<213> ORGANISM: Artificial Sequence
<220> FEATURE:
<223> OTHER INFORMATION: Intron_TS6 reverse primer

<400> SEQUENCE: 27
tcgggtacct gtaaaagttt tccagttca                                         29

<210> SEQ ID NO 28
<211> LENGTH: 34
<212> TYPE: DNA
<213> ORGANISM: Artificial Sequence
<220> FEATURE:
<223> OTHER INFORMATION: Intron_TS7 forward primer

<400> SEQUENCE: 28
caagcgatcg caggtaaggt tcccttccct cctc                                   34

<210> SEQ ID NO 29
<211> LENGTH: 30
<212> TYPE: DNA
<213> ORGANISM: Artificial Sequence
<220> FEATURE:
<223> OTHER INFORMATION: Intron_TS7 reverse primer

<400> SEQUENCE: 29
tcgggtacct gcacaagata cacacaaaca                                        30

<210> SEQ ID NO 30
<211> LENGTH: 35
<212> TYPE: DNA
<213> ORGANISM: Artificial Sequence
<220> FEATURE:
<223> OTHER INFORMATION: Intron_TS8 forward primer

<400> SEQUENCE: 30
caagcgatcg caggtaaatc tcaaatttat catgt                                  35

<210> SEQ ID NO 31
<211> LENGTH: 33
<212> TYPE: DNA
<213> ORGANISM: Artificial Sequence
<220> FEATURE:
<223> OTHER INFORMATION: Intron_TS8 reverse primer

<400> SEQUENCE: 31
tcgggtacct gaattgcaag tagataaaga cca                                    33
```

<210> SEQ ID NO 32
<211> LENGTH: 33
<212> TYPE: DNA
<213> ORGANISM: Artificial Sequence
<220> FEATURE:
<223> OTHER INFORMATION: Intron_TS10 forward primer

<400> SEQUENCE: 32
caagcgatcg caggtataca accgacctcg tct                33

<210> SEQ ID NO 33
<211> LENGTH: 29
<212> TYPE: DNA
<213> ORGANISM: Artificial Sequence
<220> FEATURE:
<223> OTHER INFORMATION: Intron_TS10 reverse primer

<400> SEQUENCE: 33
tcgggtacct aaagcaagga agggatca                      29

<210> SEQ ID NO 34
<211> LENGTH: 35
<212> TYPE: DNA
<213> ORGANISM: Artificial Sequence
<220> FEATURE:
<223> OTHER INFORMATION: Intron_TS11 forward primer

<400> SEQUENCE: 34
caagcgatcg caggtccgtg ccgggcggcc cggat              35

<210> SEQ ID NO 35
<211> LENGTH: 32
<212> TYPE: DNA
<213> ORGANISM: Artificial Sequence
<220> FEATURE:
<223> OTHER INFORMATION: Intron_TS11 reverse primer

<400> SEQUENCE: 35
tcgggtacct gcaaaagaca gagcaataca ag                 32

<210> SEQ ID NO 36
<211> LENGTH: 33
<212> TYPE: DNA
<213> ORGANISM: Artificial Sequence
<220> FEATURE:
<223> OTHER INFORMATION: Intron_TS12 primer

<400> SEQUENCE: 36
caagcgatcg caggtaagcg acgacaacga gca                33

<210> SEQ ID NO 37
<211> LENGTH: 28
<212> TYPE: DNA
<213> ORGANISM: Artificial Sequence
<220> FEATURE:
<223> OTHER INFORMATION: Intron_TS12 reverse primer

<400> SEQUENCE: 37
tcgggtacct ctaactaact agtagtaa                      28

<210> SEQ ID NO 38
<211> LENGTH: 33
<212> TYPE: DNA
<213> ORGANISM: Artificial Sequence
<220> FEATURE:
<223> OTHER INFORMATION: Intron_TS13 forward primer

```
<400> SEQUENCE: 38
caagcgatcg caggtgagga gccttctctc tct                              33

<210> SEQ ID NO 39
<211> LENGTH: 35
<212> TYPE: DNA
<213> ORGANISM: Artificial Sequence
<220> FEATURE:
<223> OTHER INFORMATION: Intron_TS13 reverse primer

<400> SEQUENCE: 39
tcgggtacct gcgccaaaaa aaaatgtttg gttgt                            35

<210> SEQ ID NO 40
<211> LENGTH: 34
<212> TYPE: DNA
<213> ORGANISM: Artificial Sequence
<220> FEATURE:
<223> OTHER INFORMATION: Intron_TS14 forwrad primer

<400> SEQUENCE: 40
caagcgatcg caggtatata ctctctctct ctca                             34

<210> SEQ ID NO 41
<211> LENGTH: 36
<212> TYPE: DNA
<213> ORGANISM: Artificial Sequence
<220> FEATURE:
<223> OTHER INFORMATION: Intron_TS14 reverse primer

<400> SEQUENCE: 41
tcgggtacct gcgagcggaa tgagaacaga ttagct                           36

<210> SEQ ID NO 42
<211> LENGTH: 43
<212> TYPE: DNA
<213> ORGANISM: Artificial Sequence
<220> FEATURE:
<223> OTHER INFORMATION: Intron_TS15 forward primer

<400> SEQUENCE: 42
cctccgcttc aagcgatcgc aggtaagcag gagagagagc tct                   43

<210> SEQ ID NO 43
<211> LENGTH: 41
<212> TYPE: DNA
<213> ORGANISM: Artificial Sequence
<220> FEATURE:
<223> OTHER INFORMATION: Intron_TS15 reverse primer

<400> SEQUENCE: 43
aggctaagtt aaagtcgggt acctgaaata tcaaagagga a                     41

<210> SEQ ID NO 44
<211> LENGTH: 34
<212> TYPE: DNA
<213> ORGANISM: Artificial Sequence
<220> FEATURE:
<223> OTHER INFORMATION: Intron_TS16 forward primer

<400> SEQUENCE: 44
caagcgatcg caggtgagat ttcgagagat tcgt                             34

<210> SEQ ID NO 45
<211> LENGTH: 34
```

-continued

<212> TYPE: DNA
<213> ORGANISM: Artificial Sequence
<220> FEATURE:
<223> OTHER INFORMATION: Intron_TS16 reverse primer

<400> SEQUENCE: 45
tcgggtacct gccaagcgag tatataaaaa tcac                             34

<210> SEQ ID NO 46
<211> LENGTH: 42
<212> TYPE: DNA
<213> ORGANISM: Artificial Sequence
<220> FEATURE:
<223> OTHER INFORMATION: Intron_TS17 forward primer

<400> SEQUENCE: 46
cctccgcttc aagcgatcgc aggtgaggcc gcgaccaaga ag                    42

<210> SEQ ID NO 47
<211> LENGTH: 43
<212> TYPE: DNA
<213> ORGANISM: Artificial Sequence
<220> FEATURE:
<223> OTHER INFORMATION: Intron_TS17 reverse primer

<400> SEQUENCE: 47
aggctaagtt aaagtcgggt acctgcagga gccgacggcc cga                   43

<210> SEQ ID NO 48
<211> LENGTH: 43
<212> TYPE: DNA
<213> ORGANISM: Artificial Sequence
<220> FEATURE:
<223> OTHER INFORMATION: Intron_TS24 forward primer

<400> SEQUENCE: 48
cctccgcttc aagcgatcgc aggtactaat aaactgatga ttc                   43

<210> SEQ ID NO 49
<211> LENGTH: 44
<212> TYPE: DNA
<213> ORGANISM: Artificial Sequence
<220> FEATURE:
<223> OTHER INFORMATION: Intron_TS24 reverse primer

<400> SEQUENCE: 49
aggctaagtt aaagtcgggt acctgcaaaa tcggtattca cggt                  44

<210> SEQ ID NO 50
<211> LENGTH: 46
<212> TYPE: DNA
<213> ORGANISM: Artificial Sequence
<220> FEATURE:
<223> OTHER INFORMATION: Intron_TS27 forward primer

<400> SEQUENCE: 50
cctccgcttc aagcgatcgc aggtgaggca tccgatcgat ttttct                46

<210> SEQ ID NO 51
<211> LENGTH: 47
<212> TYPE: DNA
<213> ORGANISM: Artificial Sequence
<220> FEATURE:
<223> OTHER INFORMATION: Intron_TS27 reverse primer

<400> SEQUENCE: 51
aggctaagtt aaagtcgggt acctgaaata tcaaagagga aaaatct    47

<210> SEQ ID NO 52
<211> LENGTH: 100
<212> TYPE: DNA
<213> ORGANISM: zea mays

<400> SEQUENCE: 52
gtccgttccc gtcccagatc cgtccatggc ttcgtccaga tctgacctgt cctgacacac    60
cctcacccgg atctgtccct ccttcccctc tcccctgcag    100

<210> SEQ ID NO 53
<211> LENGTH: 147
<212> TYPE: DNA
<213> ORGANISM: zea mays

<400> SEQUENCE: 53
gtctgcttcg tcctcgctag gtttcatttc gcggtctgtt tgtgccgttg gggctagatc    60
cgggtcgtgg ttcaacagat ctgcttcgtt ttggtacaga tctgcgttcg ctcgaatcga    120
gcatgacgtt ttcatgtgat tatgcag    147

<210> SEQ ID NO 54
<211> LENGTH: 82
<212> TYPE: DNA
<213> ORGANISM: zea mays

<400> SEQUENCE: 54
gtgcgtgcat gcgcacgctc tgcttctgcc tccctttccc ttttcctccg aaagaactga    60
aacggaacgc atcttcgctc ag    82

<210> SEQ ID NO 55
<211> LENGTH: 85
<212> TYPE: DNA
<213> ORGANISM: zea mays

<400> SEQUENCE: 55
gtgcgtcact gtccaggtgc ttggcttgga tcagaatatt gttggcggtg acactgtctt    60
ctctcgatcg atcgatcgat gacag    85

<210> SEQ ID NO 56
<211> LENGTH: 107
<212> TYPE: DNA
<213> ORGANISM: zea mays

<400> SEQUENCE: 56
gtcggtttcc aatctgttga ccatggatcc acagatcgga gcagttcttt catagtactc    60
agcgatctgt ttgggtccta aatttccttt ccccggctgt tgtttag    107

<210> SEQ ID NO 57
<211> LENGTH: 604
<212> TYPE: DNA
<213> ORGANISM: zea mays

<400> SEQUENCE: 57
gtatgtttcg tttttatttc cttcgtgtca tatttctggg tgcgagtttt gtgcctagat    60
gattcgtatg tgttcgagtt ggcggtgctc taatctttgt tttaaggttg ttatatggca    120
tgttagtgtc atcaacgatt catgattaat agactcagta gctaccattt catgatttat    180
gcagcgtatc agaggcaaga tataaatctt gggttcaaag ttgcacttga ttagctgata    240

```
ttattttgt attggctagt ccatgttttt ggttggaatt tagtcttgaa tgatagtgtt      300
gcatccggtt tgctctatgt ttaagccgct acacacctgt gaaggcttgt gtgtagtttc      360
tagaatcagt attttgacaa tattcagtc atattgcaat agttgcatgt gctagtgtaa       420
gaattgttct gttcattttt tatacatgct ttgttctctt ttgttttttc atcaatgaaa      480
aaaacataaa agatacagtt tttttatttg tctaaatatg ggtgggttaa cctttcaccc      540
tgctggtcat ggaatatgtg ttttcaatta cttatctgca acttgtggat gcggactctt      600
tcag                                                                   604
```

<210> SEQ ID NO 58
<211> LENGTH: 659
<212> TYPE: DNA
<213> ORGANISM: zea mays

<400> SEQUENCE: 58

```
gtaagtatcg attgctgatt gctgcggatc gcgtaccgtg gtcacgctgc ttagttcagc       60
tctaacaact gatcgctcct cctccactgt taccgattaa tggcttgatc ggtgccgagt      120
ctgttttagg tcgtgcccgg ctctctgctc gggcggcacg tgtggtccgg tgttgcagcg      180
gatgtagaat tttgaccttg ttctctagct gtgaatgaca gtattatagg cacagactta      240
tagattgatg tgcgttttgc gttgaactgc tcatcgaaca gatgctccca attcggtagt      300
ttatggcttg tttggataca tgcgtgaagt tttcagctga taagatttta ggaaatgttg      360
tttttggcat taagtgtttt tataatgtat gggtctaagg gaggcccaga gtgtctacct      420
tccgttattt tgatctctga attgccgcct ttcacacgaa gggcggtcac gcgtgtcacg      480
tgaagggtgg tcacatgatc tgcagcatag cactactaga tgttggacct tagtgtatct      540
atgcacaaat tttctgatta gatacttgct gaaagctatt tcttcttgcg ctatgatgga      600
ccatactagc tattttgtga ttctagcgcc cttacaaaat atttatcact gctttgcag       659
```

<210> SEQ ID NO 59
<211> LENGTH: 9794
<212> TYPE: DNA
<213> ORGANISM: Artificial Sequence
<220> FEATURE:
<223> OTHER INFORMATION: Vector Sequence

<400> SEQUENCE: 59

```
ttcctggcct tttgctggcc ttttgctcac atgttctttc ctgcgttatc ccctgattct       60
gtggataacc gtattaccgc ctttgagtga gctgataccg ctcgccgcag ccgaacgacc      120
gagcgcagcg agtcagtgag cgaggaagcg gaagagcgcc caatacgcaa accgcctctc      180
cccgcgcgtt ggccgattca ttaatgcagc tggcacgaca ggtttcccga ctggaaagcg      240
ggcagtgagc gcaacgcaat taatacgcgt accgctagcc aggaagagtt tgtagaaacg      300
caaaaaggcc atccgtcagg atggccttct gcttagtttg atgcctggca gtttatggcg      360
ggcgtcctgc ccgccaccct ccgggccgtt gcttcacaac gttcaaatcc gctcccggcg      420
gatttgtcct actcaggaga gcgttcaccg acaaacaaca gataaaacga aaggcccagt      480
cttccgactg agcctttcgt tttatttgat gcctggcagt tccctactct cgcgttcatg      540
gagctccaaa taatgatttt attttgactg atagtgacct gttcgttgca acaaattgat      600
aagcaatgct tttttataat gccaactttg tatagaaaag ttgggccgaa ttcgagctcg      660
gtacggccag aatccggtaa gtgactaggg tcacgtgacc ctagtcactt aaattcggcc      720
```

```
agaatggccc ggaccgggtt accaaaaaag cttcggccgg ggccgcactg tcaagctatt    780
attagcttct ttaataagtc caatgtgaac aaaccgtcta gggttagatg gattgctttc    840
acagatttcc ttactggtct aggaatccct gtaaatatag agcacataga tggaaaaaat    900
aaccatctgg ctgatgctct gtccagatta gtaactggtt ttgtttttgc agaaccacaa    960
tgtcaagaca agttccagga cgatttaggg aaattggaag cagctcttca ggagaagaaa   1020
gaggctccgc aagcaatgca cgtagaatat gtctccctgt tgatcagatc agcggaccgc   1080
attacccgct cgctctgctt tatgagggac tcgtctcaca gcagaattta ctcatgcagg   1140
ccaggcaaag aaccaatgaa ggccttaatc tgcgaacaga agtcatgcca atccaaaggc   1200
gacttaggga atacgaggac tgtgcactcc aagagtgcat tcaatcagca agacaactgg   1260
tggccctcca ccagcacaaa ctcgcttaca tcagaagcaa agctacaagg gacaacgcat   1320
atgccgatag gctacccaca tgcaatcggg accacgagca actgtgtgaa gtggtcgagc   1380
tattagaagg aatctcggaa agaatcagcg atacagctgt ctaggacagc tggcttcaat   1440
tatggagcgt gatggacccc cccgcaataa tccaaagttt ggtgtgcttt tagtagtgcg   1500
tctttatgga ccactacttt attgtaataa tcgatgcttt ttgtagtgcg ctcttcgtgc   1560
gctctacttt atgcttttgc ttttgtaagt gcgctgtaag tgcgcctgtc tttcttcaga   1620
tgcttatcct ttaagcatct tttgctttt gcgtggcatc ctttagttca caatttaaag   1680
aatgacgatg gggcccaaga tgtgcacccg gttctctaaa ttgcctatat aaggatatgc   1740
catagccttg tttttgcaag tcaggaatac ctgagcataa cttggctaag caaaagtttg   1800
taagtgttct aagctttcat ttgtaaactt tctgtttggt tttaataaaa tctctcgtca   1860
atcgttgtga acatatattg tttgtttgta ttgttgtatc ttatttgttg tggtgataag   1920
gatcttcgat atcccggact ggcgccaggt ccgccttgtt tctcctctgt ctcttgatct   1980
gactaatctt ggtttatgat tcgttgagta attttgggga aagcttcgtc cacagttttt   2040
ttttcgatga acagtgccgc agtggcgctg atcttgtatg ctatcctgca atcgtggtga   2100
acttatttct tttatatcct tcactcccat gaaaaggcta gtaatctttc tcgatgtaac   2160
atcgtccagc actgctatta ccgtgtggtc catccgacag tctggctgaa cacatcatac   2220
gatattgagc aaagatcgat ctatcttccc tgttctttaa tgaaagacgt cattttcatc   2280
agtatgatct aagaatgttg caacttgcaa ggaggcgttt cttttcttga atttaactaa   2340
ctcgttgagt ggccctgttt tcggacgta aggccttgc tgctccacac atgtccattc   2400
gaatttacc gtgtttagca agggcgaaaa gtttgcatct tgatgattta gcttgactat   2460
gcgattgctt tcctggaccc gtgcagctgg cgccttggga tccatgggca acagcgtgct   2520
caacagcgga cgcaccacca tctgcgacgc ctacaacgtg gccgcgcacg acccgttcag   2580
cttccagcac aagagcctcg acaccgtgca gcgcgagtgg accgagtgga agaagaacaa   2640
ccacagcctc tacctcgacc cgatcgtggg caccgtggcc agcttcctcc tcaagaaggt   2700
gggcagcctc gtgggcaagc gcatcctcag cgagctgcgc aacctcatct cccgagcgg   2760
cagcaccaac ctcatgcagg acatcctccg cgagaccgag cagttcctca ccagcgcct   2820
cgacaccgac accctcgcca gggtgaacgc cgagctgacc ggcctccagg caacgtgga   2880
ggagttcaac cgccaggtgg acaacttcct caacccgaac cgcaacgccg tgccgctcag   2940
catcaccagc agcgtgaaca ccatgcagca gctcttcctc aaccgcctcc cgcagttcca   3000
gatgcagggc taccagctcc tgctcctgcc gctcttcgcc caggccgcca acctccacct   3060
cagcttcatc cgcgacgtga tcctcaacgc cgacgagtgg ggcatcagcg ccgccaccct   3120
```

```
ccgcacctac cgcgactacc tcaagaacta cacccgcgac tacagcaact actgcatcaa   3180
cacctaccag agcgccttca agggcctcaa cacccgcctc cacggcaccc tcgagttccg   3240
cacctacatg ttcctcaacg tcttcgagta cgtgagcatc tggagcctct tcaagtacca   3300
gagcctcctc gtgagcagcg cgccaacct  ctacgccagc ggcagcggcc cgcagcagac   3360
ccagagcttc accagccagg actggccgtt cctctacagc ctcttccagg tgaacagcaa   3420
ctacgtgctc aacggcttca gcggcgccag gctcagcaac accttcccga acatcggcgg   3480
cctcccgggc agcaccacca cccacgccct cctcgcggcc agggtgaact acagcggcgg   3540
catcagcagc ggcgacatcg cgccagccc  gttcaaccag aacttcaact gcagcacctt   3600
cctcccgccg ctcctcaccc cgttcgtgcg cagctggctc gatagcggca gcgaccgcga   3660
gggcgtggcc accgtgacca actggcagac cgagagcttc gagaccacac tcgggctcag   3720
gagcggcgcc ttcaccgccc gcggcaacag caactacttc ccggactact tcatccggaa   3780
catctccggc gttccgttgg tggtccgtaa cgaggatctc aggaggccgc tgcactacaa   3840
cgagatccgc aacatcgctt cgcccagcgg gaccccaggt ggagcacggg cctacatggt   3900
gtccgtgcac aaccggaaga caacatcca  cgcggtccat gagaacggca gcatgatcca   3960
cctggctcct aacgactaca cggggttcac aatctctccg atccatgcta ctcaagtcaa   4020
caaccagacc aggacgttca tctcggagaa gttcggcaac cagggagact ccttgaggtt   4080
cgagcagaac aacacaactg cccgctacac ccttcggggc aacgggaaca gctacaacct   4140
ctacctgcgc gtcagctcca tcggcaactc gacgatcagg gtcacgatca acggaagggt   4200
ctacactgcg accaacgtga acacgacaac taacaacgac ggcgtcaacg acaacggcgc   4260
taggttctcc gacatcaaca tcgggaacgt tgtggcaagc tccaactcgg atgtccctct   4320
tgacatcaac gtcaccttca actctggaac gcagttcgat ctgatgaaca caatgctggt   4380
gccaactaac atcagccctc tgtactgata cgtagttcgc gcctaggttt ttgtgatctg   4440
atgataagtg gttggttcgt gtctcatgca cttgggaggt gatctatttc acctggtgta   4500
gtttgtgttt ccgtcagttg gaaaaactta tccctatcga tttcgttttc attttctgct   4560
tttcttttat gtaccttcgt ttgggcttgt aacgggcctt tgtatttcaa ctctcaataa   4620
taatccaagt gcatgttaaa caatttgtca tctgtttcgg ctttgatata ctactggtga   4680
agatgggccg tactactgca tcacaacgaa aaataataat aagatgaaaa acttgaagtg   4740
gaaaaaaaaa aaaacttgaa tgttcactac tactcattga ccataatgtt taacatacat   4800
agctcaatag tatttttgtg aatatggcaa cacaaacagt ccaaaacaat tgtctcttac   4860
tataccaaac caagggcgcc gcttgtttgc cactctttgt gtgcaatagt gtgattacca   4920
catctccaca ttcaatatat tccctgaatt atctgacgat tttgatggct cactgttttc   4980
ccaagtcttg aattgtcttc tgtgcgccag tcaaatgcat atgtgttgag tttatctttt   5040
aaatatcaag cttttgtttt taacttttgt ttgtaaccaa aaactcacag taggagtttg   5100
atcacataat tttatgtttg cctttgcaat ttctagtgag tctttgatta aaagcttgaa   5160
aagaaaatgc agccaagctt accaagtaag ttatgtgtat taaccagagg aagagagaat   5220
cttgcaaaat ttcaacaaac acaaaaagaa gtattactac gattggtgga gaaagaaaac   5280
gattccaaat cttgaactgt tgttgtaaaa gcatagcaga aagtgggaga caaccgaaat   5340
agaaatgact ataacttaat ttaatgttat cattataatt tcttctagca aatatttaga   5400
aagtaaatat cacatcaacc tttaatgtaa ttaagctttc tcttttttgat tcatgtgaga   5460
```

```
tgaaaagaaa aaaaagaaga gaaaagtgta gaaaacacat catttctaag ctgaaggtac    5520
atagtaccct tgtacttttg gtttcacctg catagagaaa acccacaaga atatgacagt    5580
ctgatttgtc agtctcattc tcaagcaaca tttctctatc cgttactttc atggtgaata    5640
acacaatcca tcatcaatac tttgtgttac tcagaaactg aaagttattc cgagtcttgc    5700
atatctttgg acctactcgt ttttctacca ttattgctga ttgttaagct ctcgctactt    5760
gaatcggcat tgtggagtg ggaaggttca aaaaattgga gttatgacta gttgtctctt    5820
tctatgtacg atggagaaaa tgaataaaca actgagaaaa tggctcttgt ttagttgatg    5880
atgctcttaa gctttccact ggttgccata tatgatttgg gcatttcact ttgatcttaa    5940
tgggccttgt aaagcccaag actcatgatt atctttagtt gatgctctta attaggtgtg    6000
ggcaaataat tcaaactgta tgtacccgac caaaaccaaa gcaaaaataa tcgaaccaaa    6060
ccgaaaattt aaaaataacc gaatgaaaac taaatcctat aactgaaaga actgaaaccg    6120
aatcaaaata tttaatgtaa ccaaaaatat ccgaaatata attatattgt caaaaatatt    6180
aataatttct agattaaata attaaaaata cttaaaaatt tatataaaat agtaaaaata    6240
ctcgaaaata accacaaata ttcaaaaaca accgaaatat cccaaaatat tcaaagcaaa    6300
ataaccgaat ggataccaaa ttttaaaacc gaaaaaactg gaacaaaacc aaaatcgaac    6360
caaaatttca aaaatcgaat aaatactaaa ctttagaaca aaaaaaacg ataaccgaat    6420 gtatacgaac caaagccgaa ttagataacc gaacgtccag gactactctt aatctttccg    6480
ccacttatga tttgggctat tactttgttt ataatgagcc ttttcaagct caagttcatg    6540
attgtccgtg agatgagaaa ctgacttgtt ggattcgaaa ccctagctag tattggttaa    6600
tacttaatac ataaatgacc tgcattgaca tcatcatcca agaaaataaa aattgtatgc    6660
ttgagatatt tagttttcct agctaggttt tcttttatttt agtaccgaat ctttaggtgt    6720
gccacgttaa tttagaccca ttttttcata cttaccaact gagtctagtt taatcatgac    6780
tataatcgta taaatgatt cagtcgacgt cattgcgaac gtatataaaa tcatccaaat    6840
tgacgtcatt ccaaagaggt aagcatgctt atctaagagt ccgagcatac taaacaagac    6900
gacattttat ttgcactcca aatcaaattt tgtattgcct aaagaaaaac aatcaaactc    6960
aagtttctta aaattaattt cattcaaact aatcactttc aatatctcac atattattca    7020
tgccatttct atttgtctaa acatgattta aaaaaaaaag taaaatacaa agattactat    7080
gcaaaaactc tataaaaaaa aattcaaatt tcttatttat ttgtgacatc aaattttcaa    7140 ataattttt ttaattatcg gttgatccgg tcagtcgata aaaacataaa ctttcagcga    7200
ccgttaaaac tttcctacta ccgatttaga gaaaatctta gcttgaaacg taattgtaac    7260
ctgccttcat gcaagtcgca agatatgtca tcctaagttg tatatgtttt ctcaaaagat    7320
gtatttactt gagaaaatac gtttcaacgt tgatggacaa ccaattaaga atcaagcacc    7380
tttcgtaatc aatttaggct tatcgtctaa ggtatactga tttacgacag ttgactagac    7440
ttataaggaa caaaataata gaataatttc gtcaagaaaa attgattttg gactcatact    7500
ttacataata ttttactctt aaatttattt aagtggctcc tcgcatgatc ccaaagagca    7560
agcctagact atatggaaaa gtttctaaac acttcaccta atcatagaga ctaagatggt    7620
aattcgtaaa cgacaaagcc tagtgacact gtccattgta aaattccaca tcatattagt    7680
attaaacata tacatgtagt ttcctgaaca catgtagtat caaacacact tcgtggcttc    7740
ttcctcgaaa cctggtaccc taggcttaag gtttaaacag cccgggcgcg ccgtcccatt    7800
ctggccgaat ttaagtgact agggtcacgt gaccctagtc acttaccgga ttctggccgt    7860
```

```
accgagctcg aattcaaagg tcacccggtc cgggcctaga aggcctaagt gactagggtc    7920
acgtgaccct agtcacttat tcccgggcaa ctttattata caaagttggc attataaaaa    7980
agcattgctt atcaatttgt tgcaacgaac aggtcactat cagtcaaaat aaaatcatta    8040
tttggagctc catgcatggt agcgttatcc cctatagtga gtcgtattac atggtcatag    8100
ctgtttcctg gcagctctgg cccgtgtctc aaaatctctg atgttacatt gcacaagata    8160
aaaatatatc atcatgaaca ataaaactgt ctgcttacat aaacagtaat acaaggggtg    8220
ttatgagcca tattcaacgg gaaacgtcga ggccgcgatt aaattccaac atggatgctg    8280
atttatatgg gtataaatgg gctcgcgata atgtcgggca atcaggtgcg acaatctatc    8340
gcttgtatgg gaagcccgat gcgccagagt tgtttctgaa acatggcaaa ggtagcgttg    8400
ccaatgatgt tacagatgag atggtcagac taaactggct gacggaattt atgcctcttc    8460
cgaccatcaa gcattttatc cgtactcctg atgatgcatg gttactcacc actgcgatcc    8520
ccggaaaaac agcattccag gtattagaag aatatcctga ttcaggtgaa atattgttg     8580 atgcgctggc agtgttcctg cgccggttgc attcgattcc tgtttgtaat tgtccttta    8640 acagcgatcg cgtatttcgt ctcgctcagg cgcaatcacg aatgaataac ggtttggttg    8700
atgcgagtga ttttgatgac gagcgtaatg gctggcctgt tgaacaagtc tggaaagaaa    8760
tgcataaact tttgccattc tcaccggatt cagtcgtcac tcatggtgat ttctcacttg    8820
ataaccttat ttttgacgag gggaaattaa taggttgtat tgatgttgga cgagtcggaa    8880
tcgcagaccg ataccaggat cttgccatcc tatggaactg cctcggtgag ttttctcctt    8940
cattacagaa acggcttttt caaaaatatg gtattgataa tcctgatatg aataaattgc    9000
agtttcattt gatgctcgat gagttttct aatcagaatt ggttaattgg ttgtaacact    9060
ggcagagcat tacgctgact tgacgggacg gcgcaagctc atgaccaaaa tcccttaacg    9120
tgagttacgc gtcgttccac tgagcgtcag accccgtaga aaagatcaaa ggatcttctt    9180
gagatccttt ttttctgcgc gtaatctgct gcttgcaaac aaaaaaacca ccgctaccag    9240
cggtggtttg tttgccggat caagagctac caactctttt tccgaaggta actggcttca    9300
gcagagcgca gataccaaat actgtccttc tagtgtagcc gtagttaggc caccacttca    9360
agaactctgt agcaccgcct acatacctcg ctctgctaat cctgttacca gtggctgctg    9420
ccagtggcga taagtcgtgt cttaccgggt tggactcaag acgatagtta ccggataagg    9480
cgcagcggtc gggctgaacg gggggttcgt gcacacagcc cagcttggag cgaacgacct    9540
acaccgaact gagataccta cagcgtgagc attgagaaag cgccacgctt cccgaaggga    9600
gaaaggcgga caggtatccg gtaagcggca gggtcggaac aggagagcgc acgagggagc    9660
ttccaggggg aaacgcctgg tatctttata gtcctgtcgg gtttcgccac ctctgacttg    9720
agcgtcgatt tttgtgatgc tcgtcagggg ggcggagcct atggaaaaac gccagcaacg    9780
cggccttttt acgg                                                      9794
```

<210> SEQ ID NO 60
<211> LENGTH: 51162
<212> TYPE: DNA
<213> ORGANISM: Artificial Sequence
<220> FEATURE:
<223> OTHER INFORMATION: Vector sequence

<400> SEQUENCE: 60

```
tctagagctc gttcctcgag gaacggtacc tgcggggaag cttacaataa tgtgtgttgt    60
```

| | |
|---|---|
| taagtcttgt tgcctgtcat cgtctgactg actttcgtca taaatcccgg cctccgtaac | 120 |
| ccagctttgg gcaagctcac ggatttgatc cggcggaacg ggaatatcga gatgccgggc | 180 |
| tgaacgctgc agttccagct ttccctttcg ggacaggtac tccagctgat tgattatctg | 240 |
| ctgaagggtc ttggttccac ctcctggcac aatgcgaatg attacttgag cgcgatcggg | 300 |
| catccaattt tctcccgtca ggtgcgtggt caagtgctac aaggcacctt tcagtaacga | 360 |
| gcgaccgtcg atccgtcgcc gggatacgga caaaatggag cgcagtagtc catcgagggc | 420 |
| ggcgaaagcc tcgccaaaag caatacgttc atctcgcaca gcctccagat ccgatcgagg | 480 |
| gtcttcggcg taggcagata gaagcatgga tacattgctt gagagtattc cgatggactg | 540 |
| aagtatggct tccatctttt ctcgtgtgtc tgcatctatt tcgagaaagc ccccgatgcg | 600 |
| gcgcaccgca acgcgaattg ccatactatc cgaaagtccc agcaggcgcg cttgatagga | 660 |
| aaaggtttca tactcggccg atcgcagacg ggcactcacg accttgaacc cttcaacttt | 720 |
| cagggatcga tgctggttga tggtagtctc actcgacgtg gctctggtgt gttttgacat | 780 |
| agcttcctcc aaagaaagcg gaaggtctgg atactccagc acgaaatgtg cccggggtaga | 840 |
| cggatggaag tctagccctg ctcaatatga aatcaacagt acatttacag tcaatactga | 900 |
| atatacttgc tacatttgca attgtcttat aacgaatgtg aaataaaaat agtgtaacaa | 960 |
| cgcttttact catcgataat cacaaaaaca tttatacgaa caaaaataca aatgcactcc | 1020 |
| ggtttcacag gataggcggg atcagaatat gcaacttttg acgttttgtt ctttcaaagg | 1080 |
| gggtgctggc aaaaccaccg cactcatggg cctttgcgct gctttggcaa atgacggtaa | 1140 |
| acgagtggcc ctctttgatg ccgacgaaaa ccggcctctg acgcgatgga gagaaaacgc | 1200 |
| cttacaaagc agtactggga tcctcgctgt gaagtctatt ccgccgacga aatgcccctt | 1260 |
| cttgaagcag cctatgaaaa tgccgagctc gaaggatttg attatgcgtt ggccgatacg | 1320 |
| cgtggcggct cgagcgagct caacaacaca atcatcgcta gctcaaacct gcttctgatc | 1380 |
| cccaccatgc taacgccgct cgacatcgat gaggcactat ctacctaccg ctacgtcatc | 1440 |
| gagctgctgt tgagtgaaaa tttggcaatt cctacagctg ttttgcgcca acgcgtcccg | 1500 |
| gtcggccgat tgacaacatc gcaacgcagg atgtcagaga cgctagagag ccttccagtt | 1560 |
| gtaccgtctc ccatgcatga aagagatgca tttgccgcga tgaaagaacg cggcatgttg | 1620 |
| catcttacat tactaaacac gggaactgat ccgacgatgc gcctcataga gaggaatctt | 1680 |
| cggattgcga tggaggaagt cgtggtcatt tcgaaactga tcagcaaaat cttggaggct | 1740 |
| tgaagatggc aattcgcaag cccgcattgt cggtcggcga agcacggcgg cttgctggtg | 1800 |
| ctcgacccga gatccaccat cccaacccga cacttgttcc ccagaagctg gacctccagc | 1860 |
| acttgcctga aaaagccgac gagaaagacc agcaacgtga gcctctcgtc gccgatcaca | 1920 |
| tttacagtcc cgatcgacaa cttaagctaa ctgtggatgc ccttagtcca cctccgtccc | 1980 |
| cgaaaaagct ccaggttttt ctttcagcgc gaccgcccgc gcctcaagtg tcgaaaacat | 2040 |
| atgacaacct cgttcggcaa tacagtccct cgaagtcgct acaaatgatt ttaaggcgcg | 2100 |
| cgttggacga tttcgaaagc atgctggcag atggatcatt tcgcgtggcc ccgaaaagtt | 2160 |
| atccgatccc ttcaactaca gaaaaatccg ttctcgttca gacctcacgc atgttcccgg | 2220 |
| ttgcgttgct cgaggtcgct cgaagtcatt ttgatccgtt ggggttggag accgctcgag | 2280 |
| ctttcggcca aagctggct accgccgcgc tcgcgtcatt ctttgctgga gagaagccat | 2340 |
| cgagcaattg gtgaagaggg acctatcgga acccctcacc aaatattgag tgtaggtttg | 2400 |
| aggccgctgg ccgcgtcctc agtcacctttt tgagccagat aattaagagc caaatgcaat | 2460 |

```
tggctcaggc tgccatcgtc cccccgtgcg aaacctgcac gtccgcgtca agaaataac    2520 cggcacctct tgctgttttt atcagttgag ggcttgacgg atccgcctca agtttgcggc    2580
gcagccgcaa aatgagaaca tctatactcc tgtcgtaaac ctcctcgtcg cgtactcgac    2640
tggcaatgag aagttgctcg cgcgatagaa cgtcgcgggg tttctctaaa aacgcgagga    2700
gaagattgaa ctcacctgcc gtaagtttca cctcaccgcc agcttcggac atcaagcgac    2760
gttgcctgag attaagtgtc cagtcagtaa aacaaaaaga ccgtcggtct ttggagcgga    2820
caacgttggg gcgcacgcgc aaggcaaccc gaatgcgtgc aagaaactct ctcgtactaa    2880
acggcttagc gataaaatca cttgctccta gctcgagtgc aacaacttta tccgtctcct    2940
caaggcggtc gccactgata attatgattg gaatatcaga cttttgccgcc agatttcgaa    3000 cgatctcaag cccatcttca cgacctaaat ttagatcaac aaccacgaca tcgaccgtcg    3060
cggaagagag tactctagtg aactgggtgc tgtcggctac cgcggtcact ttgaaggcgt    3120
ggatcgtaag gtattcgata ataagatgcc gcatagcgac atcgtcatcg ataagaagaa    3180
cgtgtttcaa cggctcacct ttcaatctaa aatctgaacc cttgttcaca gcgcttgaga    3240
aattttcacg tgaaggatgt acaatcatct ccagctaaat gggcagttcg tcagaattgc    3300
ggctgaccgc ggatgacgaa aatgcgaacc aagtatttca attttatgac aaaagttctc    3360
aatcgttgtt acaagtgaaa cgcttcgagg ttacagctac tattgattaa ggagatcgcc    3420
tatggtctcg ccccggcgtc gtgcgtccgc cgcgagccag atctcgccta cttcataaac    3480
gtcctcatag gcacggaatg gaatgatgac atcgatcgcc gtagagagca tgtcaatcag    3540
tgtgcgatct tccaagctag caccttgggc gctacttttg acaagggaaa acagtttctt    3600
gaatccttgg attggattcg cgccgtgtat tgttgaaatc gatcccggat gtcccgagac    3660
gacttcactc agataagccc atgctgcatc gtcgcgcatc tcgccaagca atatccggtc    3720
cggccgcata cgcagacttg cttggagcaa gtgctcggcg ctcacagcac ccagcccagc    3780
accgttcttg gagtagagta gtctaacatg attatcgtgt ggaatgacga gttcgagcgt    3840
atcttctatg gtgattagcc tttcctgggg ggggatggcg ctgatcaagg tcttgctcat    3900
tgttgtcttg ccgcttccgg tagggccaca tagcaacatc gtcagtcggc tgacgacgca    3960
tgcgtgcaga aacgcttcca aatccccgtt gtcaaaatgc tgaaggatag cttcatcatc    4020
ctgattttgg cgtttccttc gtgtctgcca ctggttccac ctcgaagcat cataacggga    4080
ggagacttct ttaagaccag aaacacgcga gcttggccgt cgaatggtca agctgacggt    4140
gcccgaggga acggtcggcg gcagacagat ttgtagtcgt tcaccaccag gaagttcagt    4200
ggcgcagagg gggttacgtg gtccgacatc ctgctttctc agcgcgcccg ctaaaatagc    4260
gatatcttca agatcatcat aagagacggg caaaggcatc ttggtaaaaa tgccggcttg    4320
gcgcacaaat gcctctccag gtcgattgat cgcaatttct tcagtcttcg ggtcatcgag    4380
ccattccaaa atcggcttca gaagaaagcg tagttgcgga tccacttcca tttacaatgt    4440
atcctatctc taagcggaaa tttgaattca ttaagagcgg cggttcctcc cccgcgtggc    4500
gccgccagtc aggcggagct ggtaaacacc aaagaaatcg aggtcccgtg ctacgaaaat    4560
ggaaacggtg tcaccctgat tcttcttcag ggttggcggg atgttgatgg ttgccttaag    4620
ggctgtctca gttgtctgct caccgttatt ttgaaagctg ttgaagctca tcccgccacc    4680
cgagctgccg gcgtaggtgc tagctgcctg gaaggcgcct tgaacaacac tcaagagcat    4740
agctccgcta aaacgctgcc agaagtggct gtcgaccgag cccggcaatc ctgagcgacc    4800
```

```
gagttcgtcc gcgcttggcg atgttaacga gatcatcgca tggtcaggtg tctcggcgcg    4860
atcccacaac acaaaaacgc gcccatctcc ctgttgcaag ccacgctgta tttcgccaac    4920
aacggtggtg ccacgatcaa gaagcacgat attgttcgtt gttccacgaa tatcctgagg    4980
caagacacac tttacatagc ctgccaaatt tgtgtcgatt gcggtttgca agatgcacgg    5040
aattattgtc ccttgcgtta ccataaaatc ggggtgcggc aagagcgtgg cgctgctggg    5100
ctgcagctcg gtgggtttca tacgtatcga caaatcgttc tcgccggaca cttcgccatt    5160
cggcaaggag ttgtcgtcac gcttgccttc ttgtcttcgg cccgtgtcgc cctgaatggc    5220
gcgtttgctg accccttgat cgccgctgct atatgcaaaa tcggtgtttt cttccggccg    5280
tggctcatgc cgctccggtt cgcccctcgg cggtagagga gcagcaggct gaacagcctc    5340
ttgaaccgct ggaggatccg gcggcacctc aatcggagct ggatgaaatg gcttggtgtt    5400
tgttgcgatc aaagttgacg gcgatgcgtt ctcattcacc ttcttttggc gcccacctag    5460
ccaaatgagg cttaatgata acgcgagaac gacacctccg acgatcaatt tctgagaccc    5520
cgaaagacgc cggcgatgtt tgtcggagac cagggatcca gatgcatcaa cctcatgtgc    5580
cgcttgctga ctatcgttat tcatcccttc gcccccttca ggacgcgttt cacatcgggc    5640
ctcaccgtgc ccgtttgcgg cctttggcca acgggatcgt aagcggtgtt ccagatacat    5700
agtactgtgt ggccatccct cagacgccaa cctcgggaaa ccgaagaaat ctcgacatcg    5760 ctcccttttaa ctgaatagtt ggcaacagct tccttgccat caggattgat ggtgtagatg    5820
gagggtatgc gtacattgcc cggaaagtgg aataccgtcg taaatccatt gtcgaagact    5880
tcgagtggca acagcgaacg atcgccttgg gcgacgtagt gccaattact gtccgccgca    5940
ccaagggctg tgacaggctg atccaataaa ttctcagctt tccgttgata ttgtgcttcc    6000
gcgtgtagtc tgtccacaac agccttctgt tgtgcctccc ttcgccgagc cgccgcatcg    6060
tcggcggggt aggcgaattg gacgctgtaa tagagatcgg gctgctcttt atcgaggtgg    6120
gacagagtct tggaacttat actgaaaaca taacggcgca tcccggagtc gcttgcggtt    6180
agcacgatta ctggctgagg cgtgaggacc tggcttgcct tgaaaaatag ataatttccc    6240
cgcggtaggg ctgctagatc tttgctattt gaaacggcaa ccgctgtcac cgtttcgttc    6300
gtggcgaatg ttacgaccaa agtagctcca accgccgtcg agaggcgcac cacttgatcg    6360
ggattgtaag ccaaataacg catgcgcgga tctagcttgc ccgccattgg agtgtcttca    6420
gcctccgcac cagtcgcagc ggcaaataaa catgctaaaa tgaaaagtgc ttttctgatc    6480
atggttcgct gtggcctacg tttgaaacgg tatcttccga tgtctgatag gaggtgacaa    6540
ccagacctgc cgggttggtt agtctcaatc tgccgggcaa gctggtcacc ttttcgtagc    6600
gaactgtcgc ggtccacgta ctcaccacag gcattttgcc gtcaacgacg agggtccttt    6660
tatagcgaat ttgctgcgtg cttggagtta catcatttga agcgatgtgc tcgacctcca    6720
ccctgccgcg tttgccaaga atgacttgag gcgaactggg attgggatag ttgaagaatt    6780
gctggtaatc ctggcgcact gttggggcac tgaagttcga taccaggtcg taggcgtact    6840
gagcggtgtc ggcatcataa ctctcgcgca ggcgaacgta ctcccacaat gaggcgttaa    6900
cgacggcctc ctcttgagtt gcaggcaatc gcgagacaga cacctcgctg tcaacggtgc    6960
cgtccggccg tatccataga tatacgggca caagcctgct caacggcacc attgtggcta    7020
tagcgaacgc ttgagcaaca tttcccaaaa tcgcgatagc tgcgacagct gcaatgagtt    7080
tggagagacg tcgcgccgat ttcgctcgcg cggtttgaaa ggcttctact tccttatagt    7140
gctcggcaag gctttcgcgc gccactagca tggcatattc aggccccgtc atagcgtcca    7200
```

```
cccgaattgc cgagctgaag atctgacgga gtaggctgcc atcgcccac attcagcggg    7260 aagatcgggc ctttgcagct cgctaatgtg tcgtttgtct ggcagccgct caaagcgaca    7320
actaggcaca gcaggcaata cttcatagaa ttctccattg aggcgaattt ttgcgcgacc    7380
tagcctcgct caacctgagc gaagcgacgg tacaagctgc tggcagattg ggttgcgccg    7440
ctccagtaac tgcctccaat gttgccggcg atcgccggca aagcgacaat gagcgcatcc    7500
cctgtcagaa aaacatatc gagttcgtaa agaccaatga tcttggccgc ggtcgtaccg    7560
gcgaaggtga ttacaccaag cataagggtg agcgcagtcg cttcggttag gatgacgatc    7620
gttgccacga ggtttaagag gagaagcaag agaccgtagg tgataagttg cccgatccac    7680
ttagctgcga tgtcccgcgt gcgatcaaaa atatatccga cgaggatcag aggcccgatc    7740
gcgagaagca ctttcgtgag aattccaacg gcgtcgtaaa ctccgaaggc agaccagagc    7800
gtgccgtaaa ggacccactg tgccccttgg aaagcaagga tgtcctggtc gttcatcgga    7860
ccgatttcgg atgcgatttt ctgaaaaacg gcctgggtca cggcgaacat tgtatccaac    7920
tgtgccggaa cagtctgcag aggcaagccg gttacactaa actgctgaac aaagtttggg    7980
accgtctttt cgaagatgga aaccacatag tcttggtagt tagcctgccc aacaattaga    8040
gcaacaacga tggtgaccgt gatcacccga gtgataccgc tacgggtatc gacttcgccg    8100
cgtatgacta aaataccctg aacaataatc aaagagtga cacaggcgat caatggcgca    8160
ctcaccgcct cctggatagt ctcaagcatc gagtccaagc ctgtcgtgaa ggctacatcg    8220
aagatcgtat gaatggccgt aaacggcgcc ggaatcgtga aattcatcga ttggacctga    8280
acttgactgg tttgtcgcat aatgttggat aaaatgagct cgcattcggc gaggatgcgg    8340
gcggatgaac aaatcgccca gccttagggg agggcaccaa agatgacagc ggtcttttga    8400
tgctccttgc gttgagcggc cgcctcttcc gcctcgtgaa ggccggcctg cgcggtagtc    8460
atcgttaata ggcttgtcgc ctgtacattt tgaatcattg cgtcatggat ctgcttgaga    8520
agcaaaccat tggtcacggt tgcctgcatg atattgcgag atcgggaaag ctgagcagac    8580
gtatcagcat tcgccgtcaa gcgtttgtcc atcgtttcca gattgtcagc cgcaatgcca    8640
gcgctgtttg cggaaccggt gatctgcgat cgcaacaggt ccgcttcagc atcactaccc    8700
acgactgcac gatctgtatc gctggtgatc gcacgtgccg tggtcgacat tggcattcgc    8760
ggcgaaaaca tttcattgtc taggtccttc gtcgaaggat actgattttt ctggttgagc    8820
gaagtcagta gtccagtaac gccgtaggcc gacgtcaaca tcgtaaccat cgctatagtc    8880
tgagtgagat tctccgcagt cgcgagcgca gtcgcgagcg tctcagcctc cgttgccggg    8940
tcgctaacaa caaactgcgc ccgcgcgggc tgaatatata gaaagctgca ggtcaaaact    9000
gttgcaataa gttgcgtcgt cttcatcgtt tcctaccta tcaatcttct gcctcgtggt    9060
gacgggccat gaattcgctg agccagccag atgagttgcc ttcttgtgcc tcgcgtagtc    9120
gagttgcaaa gcgcaccgtg ttggcacgcc ccgaaagcac ggcgacatat tcacgcatat    9180
cccgcagatc aaattcgcag atgacgcttc cactttctcg tttaagaaga aacttacggc    9240
tgccgaccgt catgtcttca cggatcgcct gaaattcctt ttcggtacat ttcagtccat    9300
cgacataagc cgatcgatct gcggttggtg atggatagaa aatcttcgtc atacattgcg    9360
caaccaagct ggctcctagc ggcgattcca gaacatgctc tggttgctgc gttgccagta    9420
ttagcatccc gttgtttttt cgaacggtca ggaggaattt gtcgacgaca gtcgaaaatt    9480
tagggtttaa caaataggcg cgaaactcat cgcagctcat cacaaaacgg cggccgtcga    9540
```

```
tcatggctcc aatccgatgc aggagatatg ctgcagcggg agcgcatact tcctcgtatt   9600
cgagaagatg cgtcatgtcg aagccggtaa tcgacggatc taactttact tcgtcaactt   9660
cgccgtcaaa tgcccagcca agcgcatggc cccggcacca gcgttggagc cgcgctcctg   9720
cgccttcggc gggcccatgc aacaaaaatt cacgtaaccc cgcgattgaa cgcatttgtg   9780
gatcaaacga gagctgacga tggataccac ggaccagacg gcggttctct tccggagaaa   9840
tcccacccccg accatcactc tcgatgagag ccacgatcca ttcgcgcaga aaatcgtgtg   9900
aggctgctgt gttttctagg ccacgcaacg gcgccaaccc gctgggtgtg cctctgtgaa   9960
gtgccaaata tgttcctcct gtggcgcgaa ccagcaattc gccacccccgg tccttgtcaa  10020
agaacacgac cgtacctgca cggtcgacca tgctctgttc gagcatggct agaacaaaca  10080
tcatgagcgt cgtcttaccc ctcccgatag gcccgaatat tgccgtcatg ccaacatcgt  10140
gctcatgcgg gatatagtcg aaaggcgttc cgccattggt acgaaatcgg gcaatcgcgt  10200
tgccccagtg gcctgagctg gcgccctctg gaaagttttc gaaagagaca aaccctgcga  10260
aattgcgtga agtgattgcg ccagggcgtg tgcgccactt aaaattcccc ggcaattggg  10320
accaataggc cgcttccata ccaatacctt cttggacaac cacggcacct gcatccgcca  10380
ttcgtgtccg agcccgcgcg cccctgtccc caagactatt gagatcgtct gcatagacgc  10440
aaaggctcaa atgatgtgag cccataacga attcgttgct cgcaagtgcg tcctcagcct  10500
cggataattt gccgatttga gtcacggctt tatcgccgga actcagcatc tggctcgatt  10560
tgaggctaag tttcgcgtgc gcttgcgggc gagtcaggaa cgaaaaactc tgcgtgagaa  10620
caagtggaaa atcgagggat agcagcgcgt tgagcatgcc cggccgtgtt tttgcagggt  10680
attcgcgaaa cgaatagatg gatccaacgt aactgtcttt tggcgttctg atctcgagtc  10740
ctcgcttgcc gcaaatgact ctgtcggtat aaatcgaagc gccgagtgag ccgctgacga  10800
ccggaaccgg tgtgaaccga ccagtcatga tcaaccgtag cgcttcgcca atttcggtga  10860
agagcacacc ctgcttctcg cggatgccaa gacgatgcag gccatacgct taagagagc   10920
cagcgacaac atgccaaaga tcttccatgt tcctgatctg gcccgtgaga tcgtttttccc 10980
ttttttccgct tagcttggtg aacctcctct ttaccttccc taaagccgcc tgtgggtaga  11040
caatcaacgt aaggaagtgt tcattgcgga ggagttggcc ggagagcacg cgctgttcaa  11100
aagcttcgtt caggctagcg gcgaaaaacac tacggaagtg tcgcggcgcc gatgatggca  11160
cgtcggcatg acgtacgagg tgagcatata ttgacacatg atcatcagcg atattgcgca  11220
acagcgtgtt gaacgcacga caacgcgcat tgcgcatttc agtttcctca agctcgaatg  11280
caacgccatc aattctcgca atggtcatga tcgatccgtc ttcaagaagg acgatatggt  11340
cgctgaggtg gccaatataa gggagataga tctcaccgga tctttcggtc gttccactcg  11400
cgccgagcat cacaccattc ctctccctcg tgggggaacc ctaattggat ttgggctaac  11460
agtagcgccc cccaaactg cactatcaat gcttcttccc gcggtccgca aaatagcag   11520
gacgacgctc gccgcattgt agtctcgctc cacgatgagc cgggctgcaa accataacgg  11580
cacgagaacg acttcgtaga gcgggttctg aacgataacg atgacaaagc cggcgaacat  11640
catgaataac cctgccaatg tcagtggcac cccaagaaac aatgcgggcc gtgtggctgc  11700
gaggtaaagg gtcgattctt ccaaacgatc agccatcaac taccgccagt gagcgtttgg  11760
ccgaggaagc tcgccccaaa catgataaca atgccgccga cgacgccggc aaccagccca  11820
agcgaagccc gcccgaacat ccaggagatc ccgatagcga caatgccgag aacagcgagt  11880
gactggccga acggaccaag gataaacgtg catatattgt taaccattgt ggcggggtca  11940
```

```
gtgccgccac ccgcagattg cgctgcggcg ggtccggatg aggaaatgct ccatgcaatt   12000
gcaccgcaca agcttggggc gcagctcgat atcacgcgca tcatcgcatt cgagagcgag   12060
aggcgattta gatgtaaacg gtatctctca aagcatcgca tcaatgcgca cctccttagt   12120
ataagtcgaa taagacttga ttgtcgtctg cggatttgcc gttgtcctgg tgtggcggtg   12180
gcggagcgat taaaccgcca gcgccatcct cctgcgagcg cgctgatat gaccccaaa    12240 catcccacgt ctcttcggat tttagcgcct cgtgatcgtc ttttggaggc tcgattaacg   12300
cgggcaccag cgattgagca gctgtttcaa cttttcgcac gtagccgttt gcaaaaccgc   12360
cgatgaaatt accggtgttg taagcggaga tcgcccgacg aagcgcaaat tgcttctcgt   12420
caatcgtttc gccgcctgca taacgacttt tcagcatgtt tgcagcggca gataatgatg   12480
tgcacgcctg gagcgcaccg tcaggtgtca gaccgagcat agaaaaattt cgagagttta   12540
tttgcatgag gccaacatcc agcgaatgcc gtgcatcgag acggtgcctg acgacttggg   12600
ttgcttggct gtgatcttgc cagtgaagcg tttcgccggt cgtgttgtca tgaatcgcta   12660
aaggatcaaa gcgactctcc accttagcta tcgccgcaag cgtagatgtc gcaactgatg   12720
gggcacactt gcgagcaaca tggtcaaact cagcagatga gagtggcgtg gcaaggctcg   12780
acgaacagaa ggagaccatc aaggcaagag aaagcgaccc cgatctctta agcatacctt   12840
atctccttag ctcgcaacta acaccgcctc tcccgttgga agaagtgcgt tgttttatgt   12900
tgaagattat cgggagggtc ggttactcga aaattttcaa ttgcttcttt atgatttcaa   12960
ttgaagcgag aaacctcgcc cggcgtcttg gaacgcaaca tggaccgaga accgcgcatc   13020
catgactaag caaccggatc gacctattca ggccgcagtt ggtcaggtca ggctcagaac   13080
gaaaatgctc ggcgaggtta cgctgtctgt aaacccattc gatgaacggg aagcttcctt   13140
ccgattgctc ttggcaggaa tattggccca tgcctgcttg cgctttgcaa atgctcttat   13200
cgcgttggta tcatatgcct tgtccgccag cagaaacgca ctctaagcga ttatttgtaa   13260
aaatgtttcg gtcatgcggc ggtcatgggc ttgacccgct gtcagcgcaa gacggatcgg   13320
tcaaccgtcg gcatcgacaa cagcgtgaat cttggtggtc aaaccgccac gggaacgtcc   13380
catacagcca tcgtcttgat cccgctgttt cccgtcgccg catgttggtg gacgcggaca   13440
caggaactgt caatcatgac gacattctat cgaaagcctt ggaaatcaca ctcagaatat   13500
gatcccagac gtctgcctca cgccatcgta caaagcgatt gtagcaggtt gtacaggaac   13560
cgtatcgatc aggaacgtct gcccagggcg ggcccgtccg gaagcgccac aagatgacat   13620
tgatcacccg cgtcaacgcg cggcacgcga cgcggcttat ttgggaacaa aggactgaac   13680
aacagtccat tcgaaatcgg tgacatcaaa gcggggacgg gttatcagtg gcctccaagt   13740
caagcctcaa tgaatcaaaa tcagaccgat ttgcaaacct gatttatgag tgtgcggcct   13800
aaatgatgaa atcgtccttc tagatcgcct ccgtggtgta gcaacacctc gcagtatcgc   13860
cgtgctgacc ttggccaggg aattgactgg caagggtgct tcacatgac cgctctttg    13920 gccgcgatag atgatttcgt tgctgctttg ggcacgtaga aggagagaag tcatatcgga   13980
gaaattcctc ctggcgcgag agcctgctct atcgcgacgg catcccactg tcgggaacag   14040
accggatcat tcacgaggcg aaagtcgtca acacatgcgt tataggcatc ttcccttgaa   14100
ggatgatctt gttgctgcca atctggaggt gcggcagccg caggcagatg cgatctcagc   14160
gcaacttgcg gcaaaacatc tcactcacct gaaaaccact agcgagtctc gcgatcagac   14220
gaaggccttt tacttaacga cacaatatcc gatgtctgca tcacaggcgt cgctatccca   14280
```

```
gtcaatacta aagcggtgca ggaactaaag attactgatg acttaggcgt gccacgaggc    14340
ctgagacgac gcgcgtagac agttttttga aatcattatc aaagtgatgg cctccgctga    14400
agcctatcac ctctgcgccg gtctgtcgga gagatgggca agcattatta cggtcttcgc    14460
gcccgtacat gcattggacg attgcagggt caatggatct gagatcatcc agaggattgc    14520
cgcccttacc ttccgtttcg agttggagcc agcccctaaa tgagacgaca tagtcgactt    14580
gatgtgacaa tgccaagaga gagatttgct taacccgatt tttttgctca agcgtaagcc    14640
tattgaagct tgccggcatg acgtccgcgc cgaaagaata tcctacaagt aaaacattct    14700
gcacaccgaa atgcttggtg tagacatcga ttatgtgacc aagatcctta gcagtttcgc    14760
ttggggaccg ctccgaccag aaataccgaa gtgaactgac gccaatgaca ggaatccctt    14820
ccgtctgcag ataggtacca tcgatagatc tgctgcctcg cgcgtttcgg tgatgacggt    14880
gaaaacctct gacacatgca gctcccggag acggtcacag cttgtctgta agcggatgcc    14940
gggagcagac aagcccgtca gggcgcgtca gcgggtgttg gcgggtgtcg gggcgcagcc    15000
atgacccagt cacgtagcga tagcggagtg tatactggct taactatgcg gcatcagagc    15060
agattgtact gagagtgcac catatgcggt gtgaaatacc gcacagatgc gtaaggagaa    15120
aataccgcat caggcgctct tccgcttcct cgctcactga ctcgctgcgc tcggtcgttc    15180
ggctgcggcg agcggtatca gctcactcaa aggcggtaat acggttatcc acagaatcag    15240
gggataacgc aggaaagaac atgtgagcaa aaggccagca aaaggccagg aaccgtaaaa    15300
aggccgcgtt gctggcgttt ttccataggc tccgcccccc tgacgagcat cacaaaaatc    15360
gacgctcaag tcagaggtgg cgaaacccga caggactata aagataccag gcgtttcccc    15420
ctggaagctc cctcgtgcgc tctcctgttc cgaccctgcc gcttaccgga tacctgtccg    15480
cctttctccc ttcgggaagc gtggcgcttt ctcatagctc acgctgtagg tatctcagtt    15540
cggtgtaggt cgttcgctcc aagctgggct gtgtgcacga accccccgtt cagcccgacc    15600
gctgcgcctt atccggtaac tatcgtcttg agtccaaccc ggtaagacac gacttatcgc    15660
cactggcagc agccactggt aacaggatta gcagagcgag gtatgtaggc ggtgctacag    15720
agttcttgaa gtggtggcct aactacggct acactagaag gacagtattt ggtatctgcg    15780
ctctgctgaa gccagttacc ttcggaaaaa gagttggtag ctcttgatcc ggcaaacaaa    15840
ccaccgctgg tagcggtggt ttttttgttt gcaagcagca gattacgcgc agaaaaaaag    15900
gatctcaaga agatcctttg atcttttcta cggggtctga cgctcagtgg aacgaaaact    15960
cacgttaagg gattttggtc atgagattat caaaaaggat cttcacctag atccttttaa    16020
attaaaaatg aagttttaaa tcaatctaaa gtatatatga gtaaacttgg tctgacagtt    16080
accaatgctt aatcagtgag gcacctatct cagcgatctg tctatttcgt tcatccatag    16140
ttgcctgact ccccgtcgtg tagataacta cgatacggga gggcttacca tctggcccca    16200
gtgctgcaat gataccgcga gacccacgct caccggctcc agatttatca gcaataaacc    16260
agccagccgg aagggccgag cgcagaagtg gtcctgcaac tttatccgcc tccatccagt    16320
ctattaattg ttgccgggaa gctagagtaa gtagttcgcc agttaatagt ttgcgcaacg    16380
ttgttgccat tgctgcaggg gggggggggg ggggggactt ccattgttca ttccacggac    16440
aaaaacagag aaaggaaacg acagaggcca aaaagcctcg ctttcagcac ctgtcgtttc    16500
ctttcttttc agagggtatt ttaaataaaa acattaagtt atgacgaaga gaacggaaa     16560 cgccttaaac cggaaaattt tcataaatag cgaaaacccg cgaggtcgcc gccccgtaac    16620
ctgtcggatc accggaaagg acccgtaaag tgataatgat tatcatctac atatcacaac    16680
```

```
gtgcgtggag gccatcaaac cacgtcaaat aatcaattat gacgcaggta tcgtattaat   16740
tgatctgcat caacttaacg taaaaacaac ttcagacaat acaaatcagc gacactgaat   16800
acggggcaac ctcatgtccc cccccccccc cccctgcag gcatcgtggt gtcacgctcg    16860
tcgtttggta tggcttcatt cagctccggt tcccaacgat caaggcgagt tacatgatcc    16920
cccatgttgt gcaaaaaagc ggttagctcc ttcggtcctc cgatcgttgt cagaagtaag   16980
ttggccgcag tgttatcact catggttatg gcagcactgc ataattctct tactgtcatg   17040
ccatccgtaa gatgcttttc tgtgactggt gagtactcaa ccaagtcatt ctgagaatag   17100
tgtatgcggc gaccgagttg ctcttgcccg gcgtcaacac gggataatac cgcgccacat   17160
agcagaactt taaaagtgct catcattgga aaacgttctt cggggcgaaa actctcaagg   17220
atcttaccgc tgttgagatc cagttcgatg taacccactc gtgcacccaa ctgatcttca   17280
gcatctttta ctttcaccag cgtttctggg tgagcaaaaa caggaaggca aaatgccgca   17340
aaaaagggaa taagggcgac acggaaatgt tgaatactca tactcttcct ttttcaatat   17400
tattgaagca tttatcaggg ttattgtctc atgagcggat acatatttga atgtatttag   17460
aaaaataaac aaatagggt tccgcgcaca tttccccgaa aagtgccacc tgacgtctaa    17520
gaaaccatta ttatcatgac attaacctat aaaaataggc gtatcacgag gccctttcgt   17580
cttcaagaat tggtcgacga tcttgctgcg ttcggatatt tcgtggagt tcccgccaca    17640 gacccggatt gaaggcgaga tccagcaact cgcgccagat catcctgtga cggaactttg   17700
gcgcgtgatg actggccagg acgtcggccg aaagagcgac aagcagatca cgcttttcga   17760
cagcgtcgga tttgcgatcg aggattttc ggcgctgcgc tacgtccgcg accgcgttga    17820
gggatcaagc cacagcagcc cactcgacct tctagccgac ccagacgagc caagggatct   17880
ttttggaatg ctgctccgtc gtcaggcttt ccgacgtttg ggtggttgaa cagaagtcat   17940
tatcgtacgg aatgccaagc actcccgagg ggaaccctgt ggttggcatg cacatacaaa   18000
tggacgaacg gataaacctt ttcacgccct tttaaatatc cgttattcta ataaacgctc   18060
ttttctctta ggtttacccg ccaatatatc ctgtcaaaca ctgatagttt aaactgaagg   18120
cgggaaacga caatctgatc atgagcggag aattaaggga gtcacgttat gaccccgcc   18180 gatgacgcgg gacaagccgt tttacgtttg gaactgacag aaccgcaacg ttgaaggagc   18240
cactcagcaa gctggtacga ttgtaatacg actcactata gggcgaattg agcgctgttt   18300
aaacgctctt caactggaag agcggttact accggctgga tggcggggcc ttgatcgtgc   18360
accgccggcg tccggataag tgactagggt cacgtgaccc tagtcactta tcgagctagt   18420
taccctatga ggtgacatga agcgctcacg gttactatga cggttagctt cacgactgtt   18480
ggtggcagta gcgtacgact tagctatagt tccggtagat ctgaagttcc tattccgaag   18540
ttcctattct tcaaaaggta taggaacttc ctcgaattgt tgtggtgggg tatagaggtt   18600
tgatataggg ggaactgctg tagagcgtgg agatataggg ggaaagagaa cgctgatgtg   18660
acaagtgagt gagatatagg gggagaaatt taggggaac gccgaacaca gtctaaagaa    18720
gcttgggacc caaagcactc tgttcggggg tttttttttt tgtctttcaa cttttttgctg  18780 taatgttatt caaaataaga aaagcacttg gcatggctaa gaaatagagt tcaacaactg   18840
aacagtacag tgtattatca atggcataaa aaacaaccct tacagcattg ccgtattta    18900 ttgatcaaac attcaactca acactgacga gtggtcttcc accgatcaac ggactaatgc   18960
tgctttgtca gatcaccggt taagtgacta gggtcacgtg accctagtca cttaggttac   19020
```

```
cagagctggt caccttttgtc caccaagatg gaactgcggc cgctcattaa ttaagtcagg   19080
cgcgcctcta gttgaagaca cgttcatgtc ttcatcgtaa gaagacactc agtagtcttc   19140
ggccagaatg gccatctgga ttcagcaggc ataacttcgt ataatgtatg ctatacgaag   19200
ttatctctag aactagtgga tctcgatgtg tagtctacga aagggttaa ccgtctcttc    19260
gtgagaataa ccgtggccta aaataagcc gatgaggata aataaaatgt ggtggtacag    19320
tacttcaaga ggtttactca tcaagaggat gcttttccga tgagctctag tagtacatcg   19380
gacctcacat acctccattg tggtgaaata ttttgtgctc atttagtgat gggtaaattt   19440
tgtttatgtc actctaggtt ttgacatttc agttttgcca ctcttaggtt ttgacaaata   19500
atttccattc cgcggcaaaa gcaaacaat tttattttac ttttaccact cttagctttc    19560
acaatgtatc acaaatgcca ctctagaaat tctgtttatg ccacagaatg tgaaaaaaaa   19620
cactcactta tttgaagcca aggtgttcat ggcatggaaa tgtgacataa agtaacgttc   19680
gtgtataaga aaaattgta ctcctcgtaa caagagacgg aaacatcatg agacaatcgc    19740
gtttggaagg ctttgcatca cctttggatg atgcgcatga atggagtcgt ctgcttgcta   19800
gccttcgcct accgcccact gagtccgggc ggcaactacc atcggcgaac gacccagctg   19860
acctctaccg accggacttg aatgcgctac cttcgtcagc gacgatggcc gcgtacgctg   19920
gcgacgtgcc cccgcatgca tggcggcaca tggcgagctc agaccgtgcg tggctggcta   19980
caaatacgta ccccgtgagt gccctagcta gaaacttaca cctgcaactg cgagagcgag   20040
cgtgtgagtg tagccgagta gatcccccgg tcgccaccat ggcctcctcc gagaacgtca   20100
tcaccgagtt catgcgcttc aaggtgcgca tggaggcac cgtgaacggc cacgagttcg    20160
agatcgaggg cgagggcgag ggccgcccct acgagggcca caacaccgtg aagctgaagg   20220
tgaccaaggg cggccccctg cccttcgcct gggacatcct gtcccccag ttccagtacg    20280
gctccaaggt gtacgtgaag cacccccgcg acatccccga ctacaagaag ctgtccttcc   20340
ccgagggctt caagtgggag cgcgtgatga acttcgagga cggcggcgtg gcgaccgtga   20400
cccaggactc ctccctgcag gacggctgct tcatctacaa ggtgaagttc atcggcgtga   20460
acttcccctc cgacgccccc gtgatgcaga agaagaccat gggctgggag gcctccaccg   20520
agcgcctgta cccccgcgac ggcgtgctga agggcgagac ccacaaggcc ctgaagctga   20580
aggacggcgg ccactacctg gtggagttca gtccatcta catggccaag aagcccgtgc   20640
agctgcccgg ctactactac gtggacgcca agctggacat cacctcccac aacgaggact   20700
acaccatcgt ggagcagtac gagcgcaccg agggccgcca ccacctgttc ctgtagcggc   20760
ccatggatat tcgaacgcgt aggtaccaca tggttaacct agacttgtcc atcttctgga   20820
ttggccaact taattaatgt atgaaataaa aggatgcaca catagtgaca tgctaatcac   20880
tataatgtgg gcatcaaagt tgtgtgttat gtgtaattac tagttatctg aataaaagag   20940
aaagagatca tccatatttc ttatcctaaa tgaatgtcac gtgtctttat aattctttga   21000
tgaaccagat gcatttcatt aaccaaatcc atatacatat aaatattaat catatataat   21060
taatatcaat tgggttagca aaacaaatct agtctaggtg tgttttgcga atgcggccat   21120
aacttcgtat aatgtatgct atacgaagtt atctagaagg ccatttaaat cctgaggatc   21180
tggtcttcct aaggacccgg gatatcgcta tcaactttgt atagaaaagt tgaacgagaa   21240
acgtaaaatg atataaatat caatatatta aattagattt tgcataaaaa acagactaca   21300
taatactgta aaacacaaca tatccagtca ctatggtcga cctgcagact ggctgtgtat   21360
aagggagcct gacatttata ttccccagaa catcaggtta atggcgtttt tgatgtcatt   21420
```

```
ttcgcggtgg ctgagatcag ccacttcttc cccgataacg gagaccggca cactggccat    21480
atcggtggtc atcatgcgcc agctttcatc cccgatatgc accaccgggt aaagttcacg    21540
ggggacttta tctgacagca gacgtgcact ggccaggggg atcaccatcc gtcgcccggg    21600
cgtgtcaata atatcactct gtacatccac aaacagacga taacggctct ctcttttata    21660
ggtgtaaacc ttaaactgca tttcaccagc ccctgttctc gtcggcaaaa gagccgttca    21720
tttcaataaa ccgggcgacc tcagccatcc cttcctgatt ttccgctttc cagcgttcgg    21780
cacgcagacg acgggcttca ttctgcatgg ttgtgcttac cgaaccggag atattgacat    21840
catatatgcc ttgagcaact gatagctgtc gctgtcaact gtcactgtaa tacgctgctt    21900
catagcatac ctcttttttga catacttcgg gtatacatat cagtatatat tcttataccg    21960
caaaaatcag cgcgcaaata cgcatactgt tatctggctt ttagtaagcc ggatcctcta    22020
gattacgccc cgcctgccac tcatcgcagt actgttgtaa ttcattaagc attctgccga    22080
catggaagcc atcacaaacg gcatgatgaa cctgaatcgc cagcggcatc agcaccttgt    22140
cgccttgcgt ataatatttg cccatggtga aacgggggc gaagaagttg tccatattgg    22200
ccacgtttaa atcaaaactg gtgaaactca cccaggggatt ggctgagacg aaaaacatat    22260
tctcaataaa ccctttaggg aaataggcca ggttttcacc gtaacacgcc acatcttgcg    22320
aatatatgtg tagaaactgc cggaaatcgt cgtggtattc actccagagc gatgaaaacg    22380
tttcagtttg ctcatggaaa acggtgtaac aagggtgaac actatcccat atcaccagct    22440 caccgtctt cattgccata cggaattccg gatgagcatt catcaggcgg gcaagaatgt    22500
gaataaaggc cggataaaac ttgtgcttat ttttctttac ggtctttaaa aaggccgtaa    22560
tatccagctg aacggtctgg ttataggtac attgagcaac tgactgaaat gcctcaaaat    22620
gttctttacg atgccattgg gatatatcaa cggtggtata ccagtgatt ttttttctcca    22680 ttttagcttc cttagctcct gaaaatctcg acggatccta actcaaaatc cacacattat    22740
acgagccgga agcataaagt gtaaagcctg gggtgcccta atgcggccgc catagtgact    22800
ggatatgttg tgttttacag tattatgtag tctgtttttt atgcaaaatc taatttaata    22860
tattgatatt tatatcattt tacgtttctc gttcaacttt attatacaaa gttgatagat    22920
atcggaccga ttaaacttta attcggtccg atgcatgtat acgaagttcc tattccgaag    22980
ttcctattct acatagagta taggaacttc acctggtggc gccgctagtg gatccccgg    23040 gctgcagtgc agcgtgaccc ggtcgtgccc ctctctagag ataatgagca ttgcatgtct    23100 aagtata aaaattaccac atatttttttt tgtcacactt gtttgaagtg cagtttatct    23160
atctttatac atatatttaa acttactct acgaataata taatctatag tactacaata    23220
atatcagtgt tttagagaat catataaatg aacagttaga catggtctaa aggacaattg    23280
agtattttga caacaggact ctacagtttt atcttttttag tgtgcatgtg ttctcctttt    23340
tttttgcaaa tagcttcacc tatataatac ttcatccatt ttattagtac atccatttag    23400
ggtttagggt taatggtttt tatagactaa ttttttttagt acatctattt tattctattt    23460
tagcctctaa attaagaaaa ctaaaactct attttagttt ttttatttaa taattttagat    23520 ataaaataga ataaaataaa gtgactaaaa attaaacaaa taccctttaa gaaattaaaa    23580
aaactaagga aacatttttc ttgtttcgag tagataatgc cagcctgtta aacgccgtcg    23640
acgagtctaa cggacaccaa ccagcgaacc agcagcgtcg cgtcgggcca agcgaagcag    23700
acggcacggc atctctgtcg ctgcctctgg acccctctcg agagttccgc tccaccgttg    23760
```

```
gacttgctcc gctgtcggca tccagaaatt gcgtggcgga gcggcagacg tgagccggca    23820
cggcaggcgg cctcctcctc ctctcacggc accggcagct acggggggatt cctttcccac    23880
cgctccttcg cttccccttc ctcgcccgcc gtaataaata gacaccccct ccacaccctc    23940
tttccccaac ctcgtgttgt tcggagcgca cacacacaca accagatctc ccccaaatcc    24000
acccgtcggc acctccgctt caaggtacgc cgctcgtcct ccccccccc cctctctacc     24060
ttctctagat cggcgttccg gtccatgcat ggttagggcc cggtagttct acttctgttc    24120
atgtttgtgt tagatccgtg tttgtgttag atccgtgctg ctagcgttcg tacacggatg    24180
cgacctgtac gtcagacacg ttctgattgc taacttgcca gtgtttctct ttggggaatc    24240
ctgggatggc tctagccgtt ccgcagacgg gatcgatttc atgattttt ttgtttcgtt     24300
gcataggggtt tggtttgccc ttttcctta tttcaatata tgccgtgcac ttgtttgtcg    24360
ggtcatcttt tcatgctttt ttttgtcttg gttgtgatga tgtggtctgg ttgggcggtc    24420
gttctagatc ggagtagaat tctgtttcaa actacctggt ggatttatta attttggatc    24480
tgtatgtgtg tgccatacat attcatagtt acgaattgaa gatgatggat ggaaatatcg    24540
atctaggata ggtatacatg ttgatgcggg ttttactgat gcatatacag agatgctttt    24600
tgttcgcttg gttgtgatga tgtggtgtgg ttgggcggtc gttcattcgt tctagatcgg    24660
agtagaatac tgtttcaaac tacctggtgt atttattaat tttggaactg tatgtgtgtg    24720
tcatacatct tcatagttac gagtttaaga tggatgaaa tatcgatcta ggataggtat     24780
acatgttgat gtgggtttta ctgatgcata tacatgatgg catatgcagc atctattcat    24840
atgctctaac cttgagtacc tatctattat aataaacaag tatgttttat aattattttg    24900
atcttgatat acttggatga tggcatatgc agcagctata tgtggattt tttagccctg      24960
ccttcatacg ctatttattt gcttggtact gtttcttttg tcgatgctca ccctgttgtt    25020
tggtgttact tctgcaggtc gactttaact tagcctagga tccacacgac accatgtccc    25080
ccgagcgccg ccccgtcgag atccgcccgg ccaccgccgc cgacatggcc gccgtgtgcg    25140
acatcgtgaa ccactacatc gagacctcca ccgtgaactt ccgcaccgag ccgcagaccc    25200
cgcaggagtg gatcgacgac ctggagcgcc tccaggaccg ctacccgtgg ctcgtggccg    25260
aggtggaggg cgtggtggcc ggcatcgcct acgccggccc gtggaaggcc cgcaacgcct    25320
acgactggac cgtggagtcc accgtgtacg tgtcccaccg ccaccagcgc ctcggcctcg    25380
gctccaccct ctacacccac ctcctcaaga gcatggaggc ccagggcttc aagtccgtgg    25440
tggccgtgat cggcctcccg aacgaccgt ccgtgcgcct ccacgaggcc ctcggctaca    25500
ccgcccgcgg caccctccgc gccgccggct acaagcacgg cggctggcac gacgtcggct    25560
tctgggcagcg cgacttcgag ctgccggccc cgccgcgccc ggtgcgcccg gtgacgcaga    25620
tctgagtcga aacctagact tgtccatctt ctggattggc caacttaatt aatgtatgaa    25680
ataaaaggat gcacacatag tgacatgcta atcactataa tgtgggcatc aaagttgtgt    25740
gttatgtgta attactagtt atctgaataa aagagaaaga gatcatccat atttcttatc    25800
ctaaatgaat gtcacgtgtc tttataattc tttgatgaac cagatgcatt tcattaacca    25860
aatccatata catataaata ttaatcatat ataattaata tcaattgggt tagcaaaaca    25920
aatctagtct aggtgtgttt tgcgaattgc ggccgctcta gcgtatacga agttcctatt    25980
ccgaagttcc tattctctag aaagtatagg aacttctgat tccgatgact tcgtaggttc    26040
ctagctcaag ccgtcgtgt ccaagcgtca cttacgatta gctaatgatt acggcatcta    26100
ggaccgacta gtaagtgact agggtcacgt gaccctagtc acttatacgt agaattaatt    26160
```

```
cattccgatt aatcgtggcc tcttgctctt caggatgaag agctatgttt aaacgtgcaa   26220
gcgctactag acaattcagt acattaaaaa cgtccgcaat gtgttattaa gttgtctaag   26280
cgtcaatttg tttacaccac aatatatcct gccaccagcc agccaacagc tccccgaccg   26340
gcagctcggc acaaaatcac cactcgatac aggcagccca tcagtccggg acggcgtcag   26400
cgggagagcc gttgtaaggc ggcagacttt gctcatgtta ccgatgctat tcggaagaac   26460
ggcaactaag ctgccgggtt tgaaacacgg atgatctcgc ggagggtagc atgttgattg   26520
taacgatgac agagcgttgc tgcctgtgat caaatatcat ctccctcgca gagatccgaa   26580
ttatcagcct tcttattcat ttctcgctta accgtgacag gctgtcgatc ttgagaacta   26640
tgccgacata ataggaaatc gctggataaa gccgctgagg aagctgagtg gcgctatttc   26700
tttagaagtg aacgttgacg atcgtcgacc gtaccccgat gaattaattc ggacgtacgt   26760
tctgaacaca gctggatact tacttgggcg attgtcatac atgacatcaa caatgtaccc   26820
gtttgtgtaa ccgtctcttg gaggttcgta tgacactagt ggttcccctc agcttgcgac   26880
tagatgttga ggcctaacat tttattagag agcaggctag ttgcttagat acatgatctt   26940
caggccgtta tctgtcaggg caagcgaaaa ttggccattt atgacgacca atgccccgca   27000
gaagctccca tctttgccgc catagacgcc gcgccccccct tttggggtgt agaacatcct   27060
tttgccagat gtggaaaaga agttcgttgt cccattgttg gcaatgacgt agtagccggc   27120
gaaagtgcga gacccatttg cgctatatat aagcctacga tttccgttgc gactattgtc   27180
gtaattggat gaactattat cgtagttgct ctcagagttg tcgtaatttg atggactatt   27240
gtcgtaattg cttatggagt tgtcgtagtt gcttggagaa atgtcgtagt tggatgggga   27300
gtagtcatag ggaagacgag cttcatccac taaaacaatt ggcaggtcag caagtgcctg   27360
ccccgatgcc atcgcaagta cgaggcttag aaccaccttc aacagatcgc gcatagtctt   27420
ccccagctct ctaacgcttg agttaagccg cgccgcgaag cggcgtcggc ttgaacgaat   27480
tgttagacat tatttgccga ctaccttggt gatctcgcct ttcacgtagt gaacaaattc   27540
ttccaactga tctgcgcgcg aggccaagcg atcttcttgt ccaagataag cctgcctagc   27600
ttcaagtatg acgggctgat actgggccgg caggcgctcc attgcccagt cggcagcgac   27660
atccttcggc gcgattttgc cggttactgc gctgtaccaa atgcgggaca acgtaagcac   27720
tacatttcgc tcatcgccag cccagtcggg cggcgagttc catagcgtta aggtttcatt   27780
tagcgcctca aatagatcct gttcaggaac cggatcaaag agttcctccg ccgctggacc   27840
taccaaggca acgctatgtt ctcttgcttt tgtcagcaag atagccagat caatgtcgat   27900
cgtggctggc tcgaagatac ctgcaagaat gtcattgcgc tgccattctc caaattgcag   27960
ttcgcgctta gctggataac gccacggaat gatgtcgtcg tgcacaacaa tggtgacttc   28020
tacagcgcgg agaatctcgc tctctccagg ggaagccgaa gtttccaaaa ggtcgttgat   28080
caaagctcgc cgcgttgttt catcaagcct tacagtcacc gtaaccagca aatcaatatc   28140
actgtgtggc ttcaggccgc catccactgc ggagccgtac aaatgtacgg ccagcaacgt   28200
cggttcgaga tggcgctcga tgacgccaac tacctctgat agttgagtcg atacttcggc   28260
gatcaccgct tccctcatga tgtttaactc ctgaattaag ccgcgccgcg aagcggtgtc   28320
ggcttgaatg aattgttagg cgtcatcctg tgctcccgag aaccagtacc agtacatcgc   28380
tgtttcgttc gagacttgag gtctagtttt atacgtgaac aggtcaatgc cgccgagagt   28440
aaagccacat tttgcgtaca aattgcaggc aggtacattg ttcgtttgtg tctctaatcg   28500
```

```
tatgccaagg agctgtctgc ttagtgccca cttttttcgca aattcgatga gactgtgcgc    28560
gactcctttg cctcggtgcg tgtgcgacac aacaatgtgt tcgatagagg ctagatcgtt    28620
ccatgttgag ttgagttcaa tcttcccgac aagctcttgg tcgatgaatg cgccatagca    28680
agcagagtct tcatcagagt catcatccga gatgtaatcc ttccggtagg ggctcacact    28740
tctggtagat agttcaaagc cttggtcgga taggtgcaca tcgaacactt cacgaacaat    28800
gaaatggttc tcagcatcca atgtttccgc cacctgctca gggatcaccg aaatcttcat    28860
atgacgccta acgcctggca cagcggatcg caaacctggc gcggcttttg cacaaaagg     28920 cgtgacaggt ttgcgaatcc gttgctgcca cttgttaacc cttttgccag atttggtaac    28980
tataatttat gttagaggcg aagtcttggg taaaaactgg cctaaaattg ctggggattt    29040
caggaaagta aacatcacct tccggctcga tgtctattgt agatatatgt agtgtatcta    29100
cttgatcggg ggatctgctg cctcgcgcgt ttcggtgatg acggtgaaaa cctctgacac    29160
atgcagctcc cggagacggt cacagcttgt ctgtaagcgg atgccgggag cagacaagcc    29220
cgtcagggcg cgtcagcggg tgttggcggg tgtcggggcg cagccatgac ccagtcacgt    29280
agcgatagcg gagtgtatac tggcttaact atgcggcatc agagcagatt gtactgagag    29340
tgcaccatat gcggtgtgaa ataccgcaca gatgcgtaag gagaaaatac cgcatcaggc    29400
gctcttccgc ttcctcgctc actgactcgc tgcgctcggt cgttcggctg cggcgagcgg    29460
tatcagctca ctcaaaggcg gtaatacggt tatccacaga atcaggggat aacgcaggaa    29520
agaacatgtg agcaaaaggc cagcaaaagg ccaggaaccg taaaaaggcc gcgttgctgg    29580 cgttttttcca taggctccgc ccccctgacg agcatcacaa aaatcgacgc tcaagtcaga    29640
ggtggcgaaa cccgacagga ctataaagat accaggcgtt tccccctgga agctccctcg    29700
tgcgctctcc tgttccgacc ctgccgctta ccggatacct gtccgccttt ctcccttcgg    29760
gaagcgtggc gctttctcat agctcacgct gtaggtatct cagttcggtg taggtcgttc    29820
gctccaagct gggctgtgtg cacgaacccc ccgttcagcc cgaccgctgc gccttatccg    29880
gtaactatcg tcttgagtcc aacccggtaa gacacgactt atcgccactg gcagcagcca    29940
ctggtaacag gattagcaga gcgaggtatg taggcggtgc tacagagttc ttgaagtggt    30000
ggcctaacta cggctacact agaaggacag tatttggtat ctgcgctctg ctgaagccag    30060
ttaccttcgg aaaaagagtt ggtagctctt gatccggcaa acaaaccacc gctggtagcg    30120
gtggtttttt tgtttgcaag cagcagatta cgcgcagaaa aaaaggatct caagaagatc    30180
ctttgatctt ttctacgggg tctgacgctc agtggaacga aaactcacgt taagggattt    30240
tggtcatgag attatcaaaa aggatcttca cctagatcct ttttaaattaa aaatgaagtt    30300 ttaaatcaat ctaaagtata tatgagtaaa cttggtctga cagttaccaa tgcttaatca    30360
gtgaggcacc tatctcagcg atctgtctat ttcgttcatc catagttgcc tgactccccg    30420
tcgtgtagat aactacgata cgggagggct taccatctgg ccccagtgct gcaatgatac    30480
cgcgagaccc acgctcaccg gctccagatt tatcagcaat aaaccagcca gccggaaggg    30540
ccgagcgcag aagtggtcct gcaactttat ccgcctccat ccagtctatt aattgttgcc    30600
gggaagctag agtaagtagt tcgccagtta atagtttgcg caacgttgtt gccattgctg    30660 caggggggg gggggggggg gacttccatt gttcattcca cggacaaaaa cagagaaagg    30720
aaacgacaga ggccaaaaag cctcgctttc agcacctgtc gtttcctttc ttttcagagg    30780 gtatttttaaa taaaaacatt aagttatgac gaagaagaac ggaaacgcct taaaccgaa     30840 aattttcata aatagcgaaa acccgcgagg tcgccgcccc gtaacctgtc ggatcaccgg    30900
```

```
aaaggacccg taaagtgata atgattatca tctacatatc acaacgtgcg tggaggccat   30960
caaaccacgt caaataatca attatgacgc aggtatcgta ttaattgatc tgcatcaact   31020
taacgtaaaa acaacttcag acaatacaaa tcagcgacac tgaatacggg gcaacctcat   31080 gtccccccccc ccccccccccc tgcaggcatc gtggtgtcac gctcgtcgtt tggtatggct   31140
tcattcagct ccggttccca acgatcaagg cgagttacat gatcccccat gttgtgcaaa   31200
aaagcggtta gctccttcgg tcctccgatc gttgtcagaa gtaagttggc cgcagtgtta   31260
tcactcatgg ttatggcagc actgcataat tctcttactg tcatgccatc cgtaagatgc   31320
ttttctgtga ctggtgagta ctcaaccaag tcattctgag aatagtgtat gcggcgaccg   31380
agttgctctt gcccggcgtc aacacgggat aataccgcgc cacatagcag aactttaaaa   31440
gtgctcatca ttggaaaacg ttcttcgggg cgaaaactct caaggatctt accgctgttg   31500
agatccagtt cgatgtaacc cactcgtgca cccaactgat cttcagcatc ttttactttc   31560
accagcgttt ctgggtgagc aaaaacagga aggcaaaatg ccgcaaaaaa gggaataagg   31620
gcgacacgga aatgttgaat actcatactc ttccttttc aatattattg aagcatttat   31680
cagggttatt gtctcatgag cggatacata tttgaatgta tttagaaaaa taaacaaata   31740
ggggttccgc gcacatttcc ccgaaaagtg ccacctgacg tctaagaaac cattattatc   31800
atgacattaa cctataaaaa taggcgtatc acgaggccct ttcgtcttca agaattcgga   31860
gcttttgcca ttctcaccgg attcagtcgt cactcatggt gatttctcac ttgataacct   31920
tatttttgac gaggggaaat taataggttg tattgatgtt ggacgagtcg gaatcgcaga   31980
ccgataccag gatcttgcca tcctatggaa ctgcctcggt gagttttctc cttcattaca   32040
gaaacggctt tttcaaaaat atggtattga taatcctgat atgaataaat tgcagtttca   32100
tttgatgctc gatgagtttt tctaatcaga attggttaat tggttgtaac actggcagag   32160
cattacgctg acttgacggg acggcggctt tgttgaataa atcgaacttt tgctgagttg   32220
aaggatcaga tcacgcatct tcccgacaac gcagaccgtt ccgtggcaaa gcaaaagttc   32280
aaaatcacca actggtccac ctacaacaaa gctctcatca accgtggctc cctcactttc   32340
tggctggatg atgggcgat tcaggcctgg tatgagtcag caacaccttc ttcacgaggc   32400
agacctcagc gccagaaggc cgccagagag gccgagcgcg gccgtgaggc ttggacgcta   32460
gggcagggca tgaaaagcc cgtagcgggc tgctacgggc gtctgacgcg gtggaaaggg   32520
ggaggggatg ttgtctacat ggctctgctg tagtgagtgg gttgcgctcc ggcagcggtc   32580
ctgatcaatc gtcacccttt ctcggtcctt caacgttcct gacaacgagc ctccttttcg   32640
ccaatccatc gacaatcacc gcgagtccct gctcgaacgc tgcgtccgga ccggcttcgt   32700
cgaaggcgtc tatcgcggcc cgcaacagcg gcgagagcgg agcctgttca acggtgccgc   32760
cgcgctcgcc ggcatcgctg tcgccggcct gctcctcaag cacggcccca acagtgaagt   32820
agctgattgt catcagcgca ttgacggcgt ccccggccga aaaacccgcc tcgcagagga   32880
agcgaagctg cgcgtcggcc gtttccatct gcggtgcgcc cggtcgcgtg ccggcatgga   32940
tgcgcgcgcc atcgcggtag gcgagcagcg cctgcctgaa gctgcgggca ttcccgatca   33000
gaaatgagcg ccagtcgtcg tcggctctcg gcaccgaatg cgtatgattc tccgccagca   33060
tggcttcggc cagtgcgtcg agcagcgccc gcttgttcct gaagtgccag taaagcgccg   33120
gctgctgaac cccaaccgt tccgccagtt tgcgtgtcgt cagaccgtct acgccgacct   33180
cgttcaacag gtccagggcg gcacggatca ctgtattcgg ctgcaacttt gtcatgcttg   33240
```

| | |
|---|---|
| acactttatc actgataaac ataatatgtc caccaactta tcagtgataa agaatccgcg | 33300 |
| cgttcaatcg gaccagcgga ggctggtccg gaggccagac gtgaaaccca acatacccct | 33360 |
| gatcgtaatt ctgagcactg tcgcgctcga cgctgtcggc atcggcctga ttatgccggt | 33420 |
| gctgccgggc ctcctgcgcg atctggttca ctcgaacgac gtcaccgccc actatggcat | 33480 |
| tctgctggcg ctgtatgcgt tggtgcaatt tgcctgcgca cctgtgctgg gcgcgctgtc | 33540 |
| ggatcgtttc gggcggcggc caatcttgct cgtctcgctg gccggcgcca ctgtcgacta | 33600 |
| cgccatcatg gcgacagcgc cttccttg gttctctat atcgggcgga tcgtggccgg | 33660 |
| catcaccggg gcgactgggg cggtagccgg cgcttatatt gccgatatca ctgatggcga | 33720 |
| tgagcgcgcg cggcacttcg gcttcatgag cgcctgtttc gggttcggga tggtcgcggg | 33780 |
| acctgtgctc ggtgggctga tgggcggttt ctcccccac gctccgttct tcgccgcggc | 33840 |
| agccttgaac ggcctcaatt tcctgacggg ctgtttcctt ttgccggagt cgcacaaagg | 33900 |
| cgaacgccgg ccgttacgcc gggaggctct caacccgctc gcttcgttcc ggtgggcccg | 33960 |
| gggcatgacc gtcgtcgccg ccctgatggc ggtcttcttc atcatgcaac ttgtcggaca | 34020 |
| ggtgccggcc gcgctttggg tcattttcgg cgaggatcgc tttcactggg acgcgaccac | 34080 |
| gatcggcatt tcgcttgccg catttggcat tctgcattca ctcgcccagg caatgatcac | 34140 |
| cggccctgta gccgcccggc tcggcgaaag gcgggcactc atgctcggaa tgattgccga | 34200 |
| cggcacaggc tacatcctgc ttgccttcgc gacacgggga tggatggcgt tcccgatcat | 34260 |
| ggtcctgctt gcttcgggtg gcatcggaat gccggcgctg caagcaatgt tgtccaggca | 34320 |
| ggtggatgag gaacgtcagg ggcagctgca aggctcactg gcggcgctca ccagcctgac | 34380 |
| ctcgatcgtc ggaccccctcc tcttcacggc gatctatgcg gcttctataa caacgtggaa | 34440 |
| cgggtgggca tggattgcag gcgctgccct ctacttgctc tgcctgccgg cgctgcgtcg | 34500 |
| cgggctttgg agcggcgcag ggcaacgagc cgatcgctga tcgtggaaac gataggccta | 34560 |
| tgccatgcgg gtcaaggcga cttccggcaa gctatacgcg ccctaggagt gcggttggaa | 34620 |
| cgttggccca gccagatact cccgatcacg agcaggacgc cgatgatttg aagcgcactc | 34680 |
| agcgtctgat ccaagaacaa ccatcctagc aacacgcgg tccccgggct gagaaagccc | 34740 |
| agtaaggaaa caactgtagg ttcgagtcgc gagatccccc ggaaccaaag gaagtaggtt | 34800 |
| aaacccgctc cgatcaggcc gagccacgcc aggccgagaa cattggttcc tgtaggcatc | 34860 |
| gggattggcg gatcaaacac taaagctact ggaacgagca gaagtcctcc ggccgccagt | 34920 |
| tgccaggcgt aaaggtgag cagaggcacg ggaggttgcc acttgcgggt cagcacggtt | 34980 |
| ccgaacgcca tggaaaccgc ccccgccagg cccgctgcga cgccgacagg atctagcgct | 35040 |
| gcgtttggtg tcaacaccaa cagcgccacg cccgcagttc cgcaaatagc ccccaggacc | 35100 |
| gccatcaatc gtatcgggct acctagcaga gcggcagaga tgaacacgac catcagcggc | 35160 |
| tgcacacgcg ctaccgtcgc cgcgaccccg cccggcaggc ggtagaccga aataaacaac | 35220 |
| aagctccaga atagcgaaat attaagtgcg ccgaggatga agatgcgcat ccaccagatt | 35280 |
| cccgttggaa tctgtcggac gatcatcacg agcaataaac ccgccggcaa cgcccgcagc | 35340 |
| agcataccgg cgacccctcg gcctcgctgt tcgggctcca cgaaaacgcc ggacagatgc | 35400 |
| gccttgtgag cgtccttggg gccgtcctcc tgtttgaaga ccgacagccc aatgatctcg | 35460 |
| ccgtcgatgt aggcgccgaa tgccacggca tctcgcaacc gttcagcgaa cgcctccatg | 35520 |
| ggcttttct cctcgtgctc gtaaacggac ccgaacatct ctggagcttt cttcagggcc | 35580 |
| gacaatcgga tctcgcggaa atcctgcacg tcggccgctc caagccgtcg aatctgagcc | 35640 |

```
ttaatcacaa ttgtcaattt taatcctctg tttatcggca gttcgtagag cgcgccgtgc   35700
gtcccgagcg atactgagcg aagcaagtgc gtcgagcagt gcccgcttgt tcctgaaatg   35760
ccagtaaagc gctggctgct gaaccccag ccggaactga ccccacaagg ccctagcgtt    35820
tgcaatgcac caggtcatca ttgacccagg cgtgttccac caggccgctg cctcgcaact   35880
cttcgcaggc ttcgccgacc tgctcgcgcc acttcttcac gcgggtggaa tccgatccgc   35940
acatgaggcg gaaggtttcc agcttgagcg ggtacggctc ccggtgcgag ctgaaatagt   36000
cgaacatccg tcgggccgtc ggcgacagct tgcggtactt ctcccatatg aatttcgtgt   36060
agtggtcgcc agcaaacagc acgacgattt cctcgtcgat caggacctgg caacgggacg   36120
ttttcttgcc acggtccagg acgcggaagc ggtgcagcag cgacaccgat tccaggtgcc   36180
caacgcggtc ggacgtgaag cccatcgccg tcgcctgtag gcgcgacagg cattcctcgg   36240
ccttcgtgta ataccggcca ttgatcgacc agcccaggtc ctggcaaagc tcgtagaacg   36300
tgaaggtgat cggctcgccg ataggggtgc gcttcgcgta ctccaacacc tgctgccaca   36360
ccagttcgtc atcgtcggcc cgcagctcga cgccggtgta ggtgatcttc acgtccttgt   36420
tgacgtggaa aatgaccttg ttttgcagcg cctcgcgcgg gattttcttg ttgcgcgtgg   36480
tgaacagggc agagcgggcc gtgtcgtttg gcatcgctcg catcgtgtcc ggccacggcg   36540
caatatcgaa caaggaaagc tgcatttcct tgatctgctg cttcgtgtgt ttcagcaacg   36600
cggcctgctt ggcctcgctg acctgttttg ccaggtcctc gccggcggtt tttcgcttct   36660
tggtcgtcat agttcctcgc gtgtcgatgg tcatcgactt cgccaaacct gccgcctcct   36720
gttcgagacg acgcgaacgc tccacggcgg ccgatggcgc gggcagggca gggggagcca   36780
gttgcacgct gtcgcgctcg atcttggccg tagcttgctg gaccatcgag ccgacggact   36840
ggaaggtttc gcgggcgca cgcatgacgg tgcggcttgc gatggtttcg gcatcctcgg    36900
cggaaaaccc cgcgtcgatc agttcttgcc tgtatgcctt ccggtcaaac gtccgattca   36960
ttcaccctcc ttgcgggatt gccccgactc acgccgggc aatgtgccct tattcctgat    37020
ttgacccgcc tggtgccttg gtgtccagat aatccacctt atcggcaatg aagtcggtcc   37080
cgtagaccgt ctggccgtcc ttctcgtact tggtattccg aatcttgccc tgcacgaata   37140
ccagcgaccc cttgcccaaa tacttgccgt gggcctcggc ctgagagcca aaacacttga   37200
tgcggaagaa gtcggtgcgc tcctgcttgt cgccggcatc gttgcgccac tcttcattaa   37260
ccgctatatc gaaaattgct tgcggcttgt tagaattgcc atgacgtacc tcggtgtcac   37320
gggtaagatt accgataaac tggaactgat tatggctcat atcgaaagtc tccttgagaa   37380
aggagactct agtttagcta acattggtt ccgctgtcaa gaactttagc ggctaaaatt    37440
ttgcgggccg cgaccaaagg tgcgagggc ggcttccgct gtgtacaacc agatattttt    37500
caccaacatc cttcgtctgc tcgatgagcg gggcatgacg aaacatgagc tgtcggagag   37560 ggcagggggtt tcaatttcgt ttttatcaga cttaaccaac ggtaaggcca cccctcgtt   37620 gaaggtgatg gaggccattg ccgacgccct ggaaactccc ctacctcttc tcctggagtc   37680
caccgacctt gaccgcgagg cactcgcgga gattgcgggt catcctttca agagcagcgt   37740
gccgcccgga tacgaacgca tcagtgtggt tttgccgtca cataaggcgt ttatcgtaaa   37800
gaaatggggc gacgacaccc gaaaaaagct gcgtggaagg ctctgacgcc aagggttagg   37860
gcttgcactt ccttctttag ccgctaaaac ggcccttct ctgcgggccg tcggctcgcg    37920
catcatatcg acatcctcaa cggaagccgt gccgcgaatg gcatcgggcg ggtgcgcttt   37980
```

```
gacagttgtt ttctatcaga acccctacgt cgtgcggttc gattagctgt ttgtcttgca   38040
ggctaaacac tttcggtata tcgtttgcct gtgcgataat gttgctaatg atttgttgcg   38100
taggggttac tgaaaagtga gcgggaaaga agagtttcag accatcaagg agcgggccaa   38160
gcgcaagctg gaacgcgaca tgggtgcgga cctgttggcc gcgctcaacg acccgaaaac   38220
cgttgaagtc atgctcaacg cggacggcaa ggtgtggcac gaacgccttg gcgagccgat   38280
gcggtacatc tgcgacatgc ggcccagcca gtcgcaggcg attatagaaa cggtggccgg   38340
attccacggc aaagaggtca cgcggcattc gcccatcctg gaaggcgagt tccccttgga   38400
tggcagccgc tttgccggcc aattgccgcc ggtcgtggcc gcgccaacct ttgcgatccg   38460
caagcgcgcg gtcgccatct tcacgctgga acagtacgtc gaggcgggca tcatgacccg   38520
cgagcaatac gaggtcatta aaagcgccgt cgcggcgcat cgaaacatcc tcgtcattgg   38580
cggtactggc tcgggcaaga ccacgctcgt caacgcgatc atcaatgaaa tggtcgcctt   38640
caacccgtct gagcgcgtcg tcatcatcga ggacaccggc gaaatccagt gcgccgcaga   38700
gaacgccgtc caataccaca ccagcatcga cgtctcgatg acgctgctgc tcaagacaac   38760
gctgcgtatg cgccccgacc gcatcctggt cggtgaggta cgtggccccg aagcccttga   38820
tctgttgatg gcctggaaca ccgggcatga aggaggtgcc gccaccctgc acgcaaacaa   38880
ccccaaagcg ggcctgagcc ggctcgccat gcttatcagc atgcaccggg attcaccgaa   38940
acccattgag ccgctgattg gcgaggcggt tcatgtggtc gtccatatcg ccaggacccc   39000
tagcggccgt cgagtgcaag aaattctcga agttcttggt tacgagaacg gccagtacat   39060
caccaaaacc ctgtaaggag tatttccaat gacaacggct gttccgttcc gtctgaccat   39120
gaatcgcggc attttgttct accttgccgt gttcttcgtt ctcgctctcg cgttatccgc   39180
gcatccggca atggcctcgg aaggcaccgg cggcagcttg ccatatgaga gctggctgac   39240
gaacctgcgc aactccgtaa ccggcccggt ggccttcgcg ctgtccatca tcggcatcgt   39300
cgtcgccgga ggcgtgctga tcttcggcgg cgaactcaac gccttcttcc gaaccctgat   39360
cttcctggtt ctggtgatgg cgctgctggt cggcgcgcag aacgtgatga gcaccttctt   39420
cggtcgtggt gccgaaatcg cggccctcgg caacggggcg ctgcaccagg tgcaagtcgc   39480
ggcggcggat gccgtgcgtg cggtagcggc tggacggctc gcctaatcat ggctctgcgc   39540
acgatcccca tccgtcgcgc aggcaaccga gaaaacctgt tcatgggtgg tgatcgtgaa   39600
ctggtgatgt tctcgggcct gatggcgttt gcgctgattt tcagcgccca agagctgcgg   39660
gccaccgtgg tcggtctgat cctgtggttc ggggcgctct atgcgttccg aatcatggcg   39720
aaggccgatc cgaagatgcg gttcgtgtac ctgcgtcacc gccggtacaa gccgtattac   39780
ccggcccgct cgaccccgtt ccgcgagaac accaatagcc aagggaagca ataccgatga   39840
tccaagcaat tgcgattgca atcgcgggcc tcggcgcgct tctgttgttc atcctctttg   39900
cccgcatccg cgcggtcgat gccgaactga aactgaaaaa gcatcgttcc aaggacgccg   39960
gcctggccga tctgctcaac tacgccgctg tcgtcgatga cggcgtaatc gtgggcaaga   40020
acggcagctt tatggctgcc tggctgtaca agggcgatga caacgcaagc agcaccgacc   40080
agcagcgcga agtagtgtcc gcccgcatca accaggcccct cgcgggcctg ggaagtgggt   40140
ggatgatcca tgtggacgcc gtgcggcgtc ctgctccgaa ctacgcggag cggggcctgt   40200
cggcgttccc tgaccgtctg acggcagcga ttgaagaaga gcgctcggtc ttgccttgct   40260
cgtcggtgat gtacttcacc agctccgcga agtcgctctt cttgatggag cgcatgggga   40320
cgtgcttggc aatcacgcgc acccccccggc cgttttagcg gctaaaaaag tcatggctct   40380
```

```
gccctcgggc ggaccacgcc catcatgacc ttgccaagct cgtcctgctt ctcttcgatc   40440
ttcgccagca gggcgaggat cgtggcatca ccgaaccgcg ccgtgcgcgg gtcgtcggtg   40500
agccagagtt tcagcaggcc gcccaggcgg cccaggtcgc cattgatgcg ggccagctcg   40560
cggacgtgct catagtccac gacgcccgtg attttgtagc cctggccgac ggccagcagg   40620
taggccgaca ggctcatgcc ggccgccgcc gccttttcct caatcgctct tcgttcgtct   40680
ggaaggcagt acaccttgat aggtgggctg cccttcctgg ttggcttggt ttcatcagcc   40740
atccgcttgc cctcatctgt tacgccggcg gtagccggcc agcctcgcag agcaggattc   40800
ccgttgagca ccgccaggtg cgaataaggg acagtgaaga aggaacaccc gctcgcgggt   40860
gggcctactt cacctatcct gcccggctga cgccgttgga tacaccaagg aaagtctaca   40920 cgaaccettt ggcaaaatcc tgtatatcgt gcgaaaaagg atggatatac cgaaaaaatc   40980
gctataatga ccccgaagca gggttatgca gcggaaaagc gctgcttccc tgctgttttg   41040
tggaatatct accgactgga aacaggcaaa tgcaggaaat tactgaactg aggggacagg   41100
cgagagacga tgccaaagag ctacaccgac gagctggccg agtgggttga atcccgcgcg   41160
gccaagaagc gccggcgtga tgaggctgcg gttgcgttcc tggcggtgag gcggatgtc   41220 gaggcggcgt tagcgtccgg ctatgcgctc gtcaccattt gggagcacat gcgggaaacg   41280
gggaaggtca agttctccta cgagacgttc cgctcgcacg ccaggcggca catcaaggcc   41340
aagcccgccg atgtgcccgc accgcaggcc aaggctgcgg aacccgcgcc ggcacccaag   41400
acgccggagc cacggcggcc gaagcagggg ggcaaggctg aaaagccggc ccccgctgcg   41460
gccccgaccg gcttcacctt caacccaaca ccggacaaaa aggatctact gtaatggcga   41520
aaattcacat ggttttgcag ggcaagggcg gggtcggcaa gtcggccatc gccgcgatca   41580
ttgcgcagta caagatggac aaggggcaga caccettgtg catcgacacc gacccggtga   41640
acgcgacgtt cgagggctac aaggccctga acgtccgccg gctgaacatc atggccggcg   41700
acgaaattaa ctcgcgcaac ttcgacaccc tggtcgagct gattgcgccg accaaggatg   41760
acgtggtgat cgacaacggt gccagctcgt tcgtgcctct gtcgcattac ctcatcagca   41820
accaggtgcc ggctctgctg caagaaatgg ggcatgagct ggtcatccat accgtcgtca   41880
ccggcggcca ggctctcctg gacacggtga gcggcttcgc ccagctcgcc agccagttcc   41940
cggccgaagc gcttttcgtg gtctggctga acccgtattg ggggcctatc gagcatgagg   42000
gcaagagctt tgagcagatg aaggcgtaca cggccaacaa ggcccgcgtg tcgtccatca   42060
tccagattcc ggccctcaag gaagaaacct acggccgcga tttcagcgac atgctgcaag   42120
agcggctgac gttcgaccag gcgctggccg atgaatcgct cacgatcatg acgcggcaac   42180
gcctcaagat cgtgcggcgc ggcctgtttg aacagctcga cgcggcggcc gtgctatgag   42240
cgaccagatt gaagagctga tccgggagat tgcgccaag cacggcatcg ccgtcggccg   42300
cgacgacccg gtgctgatcc tgcataccat caacgcccgg ctcatggccg acagtgcggc   42360
caagcaagag gaaatccttg ccgcgttcaa ggaagagctg gaagggatcg cccatcgttg   42420
gggcgaggac gccaaggcca aagcggagcg gatgctgaac gcggccctgg cggccagcaa   42480
ggacgcaatg gcgaaggtaa tgaaggacag cgccgcgcag gcggccgaag cgatccgcag   42540
ggaaatcgac gacggccttg gccgccagct cgcggccaag gtcgcggacg cgcggcgcgt   42600
ggcgatgatg aacatgatcg ccggcggcat ggtgttgttc gcggccgccc tggtggtgtg   42660
ggcctcgtta tgaatcgcag aggcgcagat gaaaaagccc ggcgttgccg ggctttgttt   42720
```

```
ttgcgttagc tgggcttgtt tgacaggccc aagctctgac tgcgcccgcg ctcgcgctcc   42780
tgggcctgtt tcttctcctg ctcctgcttg cgcatcaggg cctggtgccg tcgggctgct   42840
tcacgcatcg aatcccagtc gccggccagc tcgggatgct ccgcgcgcat cttgcgcgtc   42900
gccagttcct cgatcttggg cgcgtgaatg cccatgcctt ccttgatttc gcgcaccatg   42960
tccagccgcg tgtgcagggt ctgcaagcgg gcttgctgtt gggcctgctg ctgctgccag   43020
gcggcctttg tacgcggcag ggacagcaag ccggggggcat tggactgtag ctgctgcaaa   43080
cgcgcctgct gacggtctac gagctgttct aggcggtcct cgatgcgctc cacctggtca   43140
tgctttgcct gcacgtagag cgcaagggtc tgctggtagg tctgctcgat gggcgcggat   43200
tctaagaggg cctgctgttc cgtctcggcc tcctgggccg cctgtagcaa atcctcgccg   43260
ctgttgccgc tggactgctt tactgccggg gactgctgtt gccctgctcg cgccgtcgtc   43320
gcagttcggc ttgccccac tcgattgact gcttcatttc gagccgcagc gatgcgatct   43380
cggattgcgt caacggacgg ggcagcgcgg aggtgtccgg cttctccttg ggtgagtcgg   43440
tcgatgccat agccaaaggt ttccttccaa aatgcgtcca ttgctggacc gtgtttctca   43500
ttgatgcccg caagcatctt cggcttgacc gccaggtcaa gcgcgccttc atgggcggtc   43560
atgacggacg ccgccatgac cttgccgccg ttgttctcga tgtagccgcg taatgaggca   43620
atggtgccgc ccatcgtcag cgtgtcatcg acaacgatgt acttctggcc ggggatcacc   43680 tcccctcga aagtcgggtt gaacgccagg cgatgatctg aaccggctcc ggttcggggc   43740
accttctccc gctgcacaat gtccgtttcg acctcaaggc caaggcggtc ggccagaacg   43800
accgccatca tggccggaat cttgttgttc cccgccgcct cgacggcgag gactggaacg   43860
atgcggggct tgtcgtcgcc gatcagcgtc ttgagctggg caacagtgtc gtccgaaatc   43920
aggcgctcga ccaaattaag cgccgcttcc gcgtcgccct gcttcgcagc ctggtattca   43980
ggctcgttgg tcaaagaacc aaggtcgccg ttgcgaacca ccttcgggaa gtctccccac   44040
ggtgcgcgct cggctctgct gtagctgctc aagacgcctc ccttttagc cgctaaaact   44100 ctaacgagtg cgcccgcgac tcaacttgac gctttcggca cttacctgtg ccttgccact   44160
tgcgtcatag gtgatgcttt tcgcactccc gatttcaggt actttatcga aatctgaccg   44220
ggcgtgcatt acaaagttct tccccacctg ttggtaaatg ctgccgctat ctgcgtggac   44280
gatgctgccg tcgtggcgct gcgacttatc ggccttttgg gccatataga tgttgtaaat   44340
gccaggtttc agggccccgg ctttatctac ctttctggttc gtccatgcgc cttggttctc   44400
ggtctggaca attctttgcc cattcatgac caggaggcgg tgtttcattg ggtgactcct   44460
gacggttgcc tctggtgtta aacgtgtcct ggtcgcttgc cggctaaaaa aaagccgacc   44520
tcggcagttc gaggccggct ttccctagag ccgggcgcgt caaggttgtt ccatctattt   44580
tagtgaactg cgttcgattt atcagttact ttcctcccgc tttgtgtttc ctcccactcg   44640
tttccgcgtc tagccgaccc ctcaacatag cggcctcttc ttgggctgcc tttgcctctt   44700
gccgcgcttc gtcacgctcg gcttgcaccg tcgtaaagcg ctcggcctgc ctggccgcct   44760
cttgcgccgc caacttcctt tgctcctggt gggcctcggc gtcggcctgc gccttcgctt   44820
tcaccgctgc caactccgtg cgcaaactct ccgcttcgcg cctggtggcg tcgcgctcgc   44880
cgcgaagcgc ctgcatttcc tggttggccg cgtccagggt cttgcggctc tcttctttga   44940
atgcgcgggc gtcctggtga gcgtagtcca gctcggcgcg cagctcctgc gctcgacgct   45000
ccacctcgtc ggcccgctgc gtcgccagcg cggcccgctg ctcggctcct gccagggcgg   45060
tgcgtgcttc ggccagggct tgccgctggc gtgcggccag ctcggccgcc tcggcggcct   45120
```

```
gctgctctag caatgtaacg cgcgcctggg cttcttccag ctcgcgggcc tgcgcctcga    45180
aggcgtcggc cagctccccg cgcacggctt ccaactcgtt gcgctcacga tcccagccgg    45240
cttgcgctgc ctgcaacgat tcattggcaa gggcctgggc ggcttgccag agggcggcca    45300
cggcctggtt gccggcctgc tgcaccgcgt ccggcacctg gactgccagc ggggcggcct    45360
gcgccgtgcg ctggcgtcgc cattcgcgca tgccggcgct ggcgtcgttc atgttgacgc    45420
gggcggcctt acgcactgca tccacggtcg ggaagttctc ccggtcgcct tgctcgaaca    45480
gctcgtccgc agccgcaaaa atgcggtcgc gcgtctcttt gttcagttcc atgttggctc    45540
cggtaattgg taagaataat aatactctta cctaccttat cagcgcaaga gtttagctga    45600
acagttctcg acttaacggc aggttttta gcggctgaag ggcaggcaaa aaaagccccg    45660
cacggtcggc gggggcaaag ggtcagcggg aaggggatta gcgggcgtcg ggcttcttca    45720
tgcgtcgggg ccgcgcttct tgggatggag cacgacgaag cgcgcacgcg catcgtcctc    45780
ggccctatcg gcccgcgtcg cggtcaggaa cttgtcgcgc gctaggtcct ccctggtggg    45840 caccagggc atgaactcgg cctgctcgat gtaggtccac tccatgaccg catcgcagtc    45900
gaggccgcgt tccttcaccg tctcttgcag gtcgcggtac gcccgctcgt tgagcggctg    45960
gtaacgggcc aattggtcgt aaatggctgt cggccatgag cggccttttcc tgttgagcca    46020 gcagccgacg acgaagccgg caatgcaggc ccctggcaca accaggccga cgccggggggc    46080 aggggatggc agcagctcgc caaccaggaa ccccgccgcg atgatgccga tgccggtcaa    46140
ccagcccttg aaactatccg gccccgaaac acccctgcgc attgcctgga tgctgcgccg    46200
gatagcttgc aacatcagga gccgtttctt ttgttcgtca gtcatggtcc gccctcacca    46260
gttgttcgta tcggtgtcgg acgaactgaa atcgcaagag ctgccggtat cggtccagcc    46320
gctgtccgtg tcgctgctgc cgaagcacgg cgaggggtcc gcgaacgccg cagacggcgt    46380
atccggccgc agcgcatcgc ccagcatggc cccggtcagc gagccgccgg ccaggtagcc    46440
cagcatggtg ctgttggtcg ccccggccac cagggccgac gtgacgaaat cgccgtcatt    46500
ccctctggat tgttcgctgc tcggcggggc agtgcgccgc gccggcggcg tcgtggatgg    46560
ctcgggttgg ctggcctgcg acggccggcg aaaggtgcgc agcagctcgt tatcgaccgg    46620
ctgcggcgtc ggggccgccg ccttgcgctg cggtcggtgt tccttcttcg gctcgcgcag    46680
cttgaacagc atgatcgcgg aaaccagcag caacgccgcg cctacgcctc ccgcgatgta    46740
gaacagcatc ggattcattc ttcggtcctc cttgtagcgg aaccgttgtc tgtgcggcgc    46800
gggtggcccg cgccgctgtc tttggggatc agccctcgat gagcgcgacc agtttcacgt    46860
cggcaaggtt cgcctcgaac tcctggccgt cgtcctcgta cttcaaccag gcatagcctt    46920 ccgccggcg ccgacggttg aggataaggc gggcagggcg ctcgtcgtgc tcgacctgga    46980
cgatggcctt tttcagcttg tccgggtccg gctccttcgc gccctttttcc ttggcgtcct    47040 taccgtcctg gtcgccgtcc tcgccgtcct ggccgtcgcc ggcctccgcg tcacgctcgg    47100
catcagtctg gccgttgaag gcatcgacgg tgttgggatc gcggcccttc tcgtccagga    47160
actcgcgcag cagcttgacc gtgccgcgcg tgatttcctg ggtgtcgtcg tcaagccacg    47220
cctcgacttc ctccgggcgc ttcttgaagg ccgtcaccag ctcgttcacc acggtcacgt    47280
cgcgcacgcg gccggtgttg aacgcatcgg cgatcttctc cggcaggtcc agcagcgtga    47340
cgtgctgggt gatgaacgcc ggcgacttgc cgatttcctt ggcgtatcg cctttcttct    47400 tgcccttcgc cagctcgcgg ccaatgaagt cggcaatttc gcgcggggtc agctcgttgc    47460
```

```
gttgcaggtt ctcgataacc tggtcggctt cgttgtagtc gttgtcgatg aacgccggga    47520
tggacttctt gccggcccac ttcgagccac ggtagcggcg ggcgccgtga ttgatgatat    47580
agcggcccgg ctgctcctgg ttctcgcgca ccgaaatggg tgacttcacc ccgcgctctt    47640
tgatcgtggc accgatttcc gcgatgctct ccggggaaaa gccggggttg tcggccgtcc    47700
gcggctgatg cggatcttcg tcgatcaggt ccaggtccag ctcgataggg ccggaaccgc    47760
cctgagacgc cgcaggagcg tccaggaggc tcgacaggtc gccgatgcta tccaacccca    47820
ggccggacgg ctgcgccgcg cctgcggctt cctgagcggc cgcagcggtg ttttcttgg    47880
tggtcttggc ttgagccgca gtcattggga aatctccatc ttcgtgaaca cgtaatcagc    47940
cagggcgcga acctctttcg atgccttgcg cgcggccgtt ttcttgatct tccagaccgg    48000
cacaccggat gcgagggcat cggcgatgct gctgcgcagg ccaacggtgg ccggaatcat    48060
catcttgggg tacgcggcca gcagctcggc ttggtggcgc gcgtggcgcg gattccgcgc    48120
atcgaccttg ctgggcacca tgccaaggaa ttgcagcttg gcgttcttct ggcgcacgtt    48180
cgcaatggtc gtgaccatct tcttgatgcc ctggatgctg tacgcctcaa gctcgatggg    48240
ggacagcaca tagtcggccg cgaagagggc ggccgccagg ccgacgccaa gggtcggggc    48300
cgtgtcgatc aggcacacgt cgaagccttg gttcgccagg gccttgatgt tcgccccgaa    48360
cagctcgcgg gcgtcgtcca gcgacagccg ttcggcgttc gccagtaccg ggttggactc    48420
gatgagggcg aggcgcgcgg cctggccgtc gccggctgcg ggtgcggttt cggtccagcc    48480
gccggcaggg acagcgccga acagcttgct tgcatgcagg ccggtagcaa agtccttgag    48540
cgtgtaggac gcattgccct gggggtccag gtcgatcacg gcaacccgca agccgcgctc    48600
gaaaaagtcg aaggcaagat gcacaagggt cgaagtcttg ccgacgccgc ctttctggtt    48660
ggccgtgacc aaagtttca tcgtttggtt tcctgttttt tcttggcgtc cgcttcccac    48720
ttccggacga tgtacgcctg atgttccggc agaaccgccg ttacccgcgc gtacccctcg    48780
ggcaagttct tgtcctcgaa cgcggcccac acgcgatgca ccgcttgcga cactgcgccc    48840
ctggtcagtc ccagcgacgt tgcgaacgtc gcctgtggct tcccatcgac taagacgccc    48900
cgcgctatct cgatggtctg ctgccccact tccagcccct ggatcgcctc ctggaactgg    48960
cttcggtaa gccgtttctt catggataac acccataatt tgctccgcgc cttggttgaa    49020
catgcggtg acagccgcca gcacatgaga gaagtttagc taaacatttc tgcacgtca    49080
acacctttag ccgctaaaac tcgtccttgg cgtaacaaaa caaagcccg gaaaccgggc    49140
tttcgtctct tgccgcttat ggctctgcac ccggctccat caccaacagg tcgcgcacgc    49200
gcttcactcg gttgcggatc gacactgcca gcccaacaaa gccggttgcc gccgccgcca    49260
ggatcgcgcc gatgatgccg gccacaccgg ccatcgccca ccaggtcgcc gccttccggt    49320
tccattcctg ctggtactgc ttcgcaatgc tggacctcgg ctcaccatag gctgaccgct    49380
cgatggcgta tgccgcttct ccccttggcg taaaacccag cgccgcaggc ggcattgcca    49440
tgctgcccgc cgctttcccg accacgacgc gcgcaccagg cttgcggtcc agaccttcgg    49500
ccacggcgag ctgcgcaagg acataatcag ccgccgactt ggctccacgc gcctcgatca    49560
gctcttgcac tcgcgcgaaa tccttggcct ccacggccgc catgaatcgc gcacgcggcg    49620
aaggctccgc agggccggcg tcgtgatcgc cgccgagaat gcccttcacc aagttcgacg    49680
acacgaaaat catgctgacg gctatcacca tcatgcagac ggatcgcacg aacccgctga    49740
attgaacacg agcacggcac ccgcgaccac tatgccaaga atgcccaagg taaaaattgc    49800
cggccccgcc atgaagtccg tgaatgcccc gacggccgaa gtgaagggca ggccgccacc    49860
```

```
caggccgccg ccctcactgc ccggcacctg gtcgctgaat gtcgatgcca gcacctgcgg    49920
cacgtcaatg cttccgggcg tcgcgctcgg gctgatcgcc catcccgtta ctgccccgat    49980
cccggcaatg gcaaggactg ccagcgctgc cattttgggg gtgaggccgt tcgcggccga    50040
ggggcgcagc ccctgggggg atgggaggcc cgcgttagcg ggccgggagg gttcgagaag    50100
ggggggcacc ccccttcggc gtgcgcggtc acgcgcacag ggcgcagccc tggttaaaaa    50160
caaggtttat aaatattggt ttaaaagcag gttaaaagac aggttagcgg tggccgaaaa    50220
acgggcggaa acccttgcaa atgctggatt ttctgcctgt ggacagcccc tcaaatgtca    50280
ataggtgcgc ccctcatctg tcagcactct gcccctcaag tgtcaaggat cgcgcccctc    50340
atctgtcagt agtcgcgccc ctcaagtgtc aataccgcag ggcacttatc cccaggcttg    50400
tccacatcat ctgtgggaaa ctcgcgtaaa atcaggcgtt ttcgccgatt tgcgaggctg    50460
gccagctcca cgtcgccggc cgaaatcgag cctgcccctc atctgtcaac gccgcgccgg    50520
gtgagtcggc ccctcaagtg tcaacgtccg cccctcatct gtcagtgagg gccaagtttt    50580
ccgcgaggta tccacaacgc cggcggccgc ggtgtctcgc acacggcttc gacggcgttt    50640
ctggcgcgtt tgcagggcca tagacggccg ccagcccagc ggcgagggca accagcccgg    50700
tgagcgtcgg aaaggcgctg gaagcccccgt agcgacgcgg agaggggcga gacaagccaa    50760
gggcgcaggc tcgatgcgca gcacgacata gccggttctc gcaaggacga gaatttccct    50820
gcggtgcccc tcaagtgtca atgaaagttt ccaacgcgag ccattcgcga gagccttgag    50880
tccacgctag atgagagctt tgttgtaggt ggaccagttg gtgatttga acttttgctt     50940
tgccacggaa cggtctgcgt tgtcgggaag atgcgtgatc tgatccttca actcagcaaa    51000
agttcgattt attcaacaaa gccacgttgt gtctcaaaat ctctgatgtt acattgcaca    51060
agataaaaat atatcatcat gaacaataaa actgtctgct tacataaaca gtaatacaag    51120
gggtgttatg agccatattc aacgggaaac gtcttgctcg ac                       51162
```

<210> SEQ ID NO 61
<211> LENGTH: 42
<212> TYPE: DNA
<213> ORGANISM: Artificial Sequence
<220> FEATURE:
<223> OTHER INFORMATION: sense primer for i1

<400> SEQUENCE: 61
ccatgcatac atccaacgcc attcgcttac acctgatatc cc                          42

<210> SEQ ID NO 62
<211> LENGTH: 46
<212> TYPE: DNA
<213> ORGANISM: Artificial Sequence
<220> FEATURE:
<223> OTHER INFORMATION: i1-sense oligonucleotide 2

<400> SEQUENCE: 62
ggactggcgc caggtccgtt cccgtcccag atccgtccat ggcttc                      46

<210> SEQ ID NO 63
<211> LENGTH: 46
<212> TYPE: DNA
<213> ORGANISM: Artificial Sequence
<220> FEATURE:
<223> OTHER INFORMATION: i1-sense oligonucleotide 3

<400> SEQUENCE: 63

```
gtccagatct gacctgtcct gacacaccct cacccggatc tgtccc            46
```

<210> SEQ ID NO 64
<211> LENGTH: 45
<212> TYPE: DNA
<213> ORGANISM: Artificial Sequence
<220> FEATURE:
<223> OTHER INFORMATION: i1-sense oligonucleotide 4

<400> SEQUENCE: 64

```
tccttcccct ctccctgca gctggcgcct tgggatccat tcctg              45
```

<210> SEQ ID NO 65
<211> LENGTH: 42
<212> TYPE: DNA
<213> ORGANISM: Artificial Sequence
<220> FEATURE:
<223> OTHER INFORMATION: i1-antisense oligonucleotide 1

<400> SEQUENCE: 65

```
ggacctggcg ccagtccggg atatcaggtg taagcgaatg gc                42
```

<210> SEQ ID NO 66
<211> LENGTH: 49
<212> TYPE: DNA
<213> ORGANISM: Artificial Sequence
<220> FEATURE:
<223> OTHER INFORMATION: i1-antisenseoligonucleotide 2

<400> SEQUENCE: 66

```
aggacaggtc agatctggac gaagccatgg acggatctgg gacgggaac         49
```

<210> SEQ ID NO 67
<211> LENGTH: 51
<212> TYPE: DNA
<213> ORGANISM: Artificial Sequence
<220> FEATURE:
<223> OTHER INFORMATION: i1-antisense oligonucleotide 3

<400> SEQUENCE: 67

```
ccagctgcag gggagagggg aaggagggac agatccgggt gagggtgtgt c      51
```

<210> SEQ ID NO 68
<211> LENGTH: 44
<212> TYPE: DNA
<213> ORGANISM: Artificial Sequence
<220> FEATURE:
<223> OTHER INFORMATION: i1-antisense oligonucleotide 4

<400> SEQUENCE: 68

```
ggtggaggcg ttgtaagctg gaatcaggaa tggatcccaa ggcg              44
```

<210> SEQ ID NO 69
<211> LENGTH: 48
<212> TYPE: DNA
<213> ORGANISM: Artificial Sequence
<220> FEATURE:
<223> OTHER INFORMATION: i2_flanking sense primer

<400> SEQUENCE: 69

```
ccatcagata tcccggactg gcgccaggtc tgcttcgtcc tcgctagg          48
```

<210> SEQ ID NO 70
<211> LENGTH: 56
<212> TYPE: DNA
<213> ORGANISM: Artificial Sequence
<220> FEATURE:
<223> OTHER INFORMATION: i2_sense oligonucleotide 2

<400> SEQUENCE: 70
tttcatttcg cggtctgttt gtgccgttgg ggctagatcc gggtcgtggt tcaaca      56

<210> SEQ ID NO 71
<211> LENGTH: 44
<212> TYPE: DNA
<213> ORGANISM: Artificial Sequence
<220> FEATURE:
<223> OTHER INFORMATION: i2_sense oligonucleotide 3

<400> SEQUENCE: 71
gatctgcttc gttttggtac agatctgcgt tcgctcgaat cgag      44

<210> SEQ ID NO 72
<211> LENGTH: 43
<212> TYPE: DNA
<213> ORGANISM: Artificial Sequence
<220> FEATURE:
<223> OTHER INFORMATION: i2_sense oligonucleotide 4

<400> SEQUENCE: 72
catgacgttt tcatgtgatt atgcagctgg cgccttggga tcc      43

<210> SEQ ID NO 73
<211> LENGTH: 52
<212> TYPE: DNA
<213> ORGANISM: Artificial Sequence
<220> FEATURE:
<223> OTHER INFORMATION: i2_antisense oligonucleotide 1

<400> SEQUENCE: 73
ggcacaaaca gaccgcgaaa tgaaacctag cgaggacgaa gcagacctgg cg      52

<210> SEQ ID NO 74
<211> LENGTH: 53
<212> TYPE: DNA
<213> ORGANISM: Artificial Sequence
<220> FEATURE:
<223> OTHER INFORMATION: i2_antisense oligonucleotide 2

<400> SEQUENCE: 74
ctgtaccaaa acgaagcaga tctgttgaac cacgacccgg atctagcccc aac      53

<210> SEQ ID NO 75
<211> LENGTH: 45
<212> TYPE: DNA
<213> ORGANISM: Artificial Sequence
<220> FEATURE:
<223> OTHER INFORMATION: i2_antisense oligonucleotide 3

<400> SEQUENCE: 75
cataatcaca tgaaaacgtc atgctcgatt cgagcgaacg cagat      45

<210> SEQ ID NO 76
<211> LENGTH: 41
<212> TYPE: DNA
<213> ORGANISM: Artificial Sequence
<220> FEATURE:
<223> OTHER INFORMATION: i2_antisense flanking primer

<400> SEQUENCE: 76
gtggtaagcg aatgcaggaa tggatcccaa ggcgccagct g      41

<210> SEQ ID NO 77
<211> LENGTH: 37
<212> TYPE: DNA
<213> ORGANISM: Artificial Sequence
<220> FEATURE:
<223> OTHER INFORMATION: i3_sense flanking primer

<400> SEQUENCE: 77
ccatcagtac tcgatatccc ggactggcgc caggtgc                    37

<210> SEQ ID NO 78
<211> LENGTH: 45
<212> TYPE: DNA
<213> ORGANISM: Artificial Sequence
<220> FEATURE:
<223> OTHER INFORMATION: i3_sense oligonucleotide 2

<400> SEQUENCE: 78
gtgcatgcgc acgctctgct tctgcctccc tttcccttttt cctcc          45

<210> SEQ ID NO 79
<211> LENGTH: 50
<212> TYPE: DNA
<213> ORGANISM: Artificial Sequence
<220> FEATURE:
<223> OTHER INFORMATION: i3_sense oligonucleotide 3

<400> SEQUENCE: 79
gaaagaactg aaacggaacg catcttcgct cagctggcgc cttgggatcc      50

<210> SEQ ID NO 80
<211> LENGTH: 39
<212> TYPE: DNA
<213> ORGANISM: Artificial Sequence
<220> FEATURE:
<223> OTHER INFORMATION: i3_antisense oligonucleotide 1

<400> SEQUENCE: 80
tgcgcatgca cgcacctggc gccagtccgg gatatcgag                  39

<210> SEQ ID NO 81
<211> LENGTH: 54
<212> TYPE: DNA
<213> ORGANISM: Artificial Sequence
<220> FEATURE:
<223> OTHER INFORMATION: i3_antisense oligo2

<400> SEQUENCE: 81
cgttccgttt cagttctttc ggaggaaaag ggaaagggag gcagaagcag agcg 54

<210> SEQ ID NO 82
<211> LENGTH: 43
<212> TYPE: DNA
<213> ORGANISM: Artificial Sequence
<220> FEATURE:
<223> OTHER INFORMATION: i3_antisense flanking primer

<400> SEQUENCE: 82
gtcgaggtga tgtggatccc aaggcgccag ctgagcgaag atg             43

<210> SEQ ID NO 83
<211> LENGTH: 50
<212> TYPE: DNA
<213> ORGANISM: Artificial Sequence
<220> FEATURE:
<223> OTHER INFORMATION: i4_sense flanking primer

<400> SEQUENCE: 83
ccatcagata tcccggactg gcgccaggtg cgtcactgtc caggtgcttg         50

<210> SEQ ID NO 84
<211> LENGTH: 50
<212> TYPE: DNA
<213> ORGANISM: Artificial Sequence
<220> FEATURE:
<223> OTHER INFORMATION: i4_s2_sense oligo 3

<400> SEQUENCE: 84
gcttggatca gaatattgtt ggcggtgaca ctgtcttctc tcgatcgatc         50

<210> SEQ ID NO 85
<211> LENGTH: 45
<212> TYPE: DNA
<213> ORGANISM: Artificial Sequence
<220> FEATURE:
<223> OTHER INFORMATION: i4_sense oligonucleotide 3

<400> SEQUENCE: 85
gatcgatgac agctggcgcc ttgggatcca catcaatcac catgc              45

<210> SEQ ID NO 86
<211> LENGTH: 49
<212> TYPE: DNA
<213> ORGANISM: Artificial Sequence
<220> FEATURE:
<223> OTHER INFORMATION: i4_antisense oligonucleotide 1

<400> SEQUENCE: 86
caatattctg atccaagcca agcacctgga cagtgacgca cctggcgcc          49

<210> SEQ ID NO 87
<211> LENGTH: 50
<212> TYPE: DNA
<213> ORGANISM: Artificial Sequence
<220> FEATURE:
<223> OTHER INFORMATION: i4_antisense oligonucleotide 2

<400> SEQUENCE: 87
cgccagctgt catcgatcga tcgatcgaga gaagacagtg tcaccgccaa         50

<210> SEQ ID NO 88
<211> LENGTH: 43
<212> TYPE: DNA
<213> ORGANISM: Artificial Sequence
<220> FEATURE:
<223> OTHER INFORMATION: i4_antisense flanking primer

<400> SEQUENCE: 88
gctggaacga tggaatgcat ggtgattgat gtggatccca agg                43

<210> SEQ ID NO 89
<211> LENGTH: 48
<212> TYPE: DNA
<213> ORGANISM: Artificial Sequence
<220> FEATURE:
<223> OTHER INFORMATION: i5_flanking sense primer

<400> SEQUENCE: 89
ccatcagata tcccggactg gcgccaggtc ggtttccaat ctgttgac           48

<210> SEQ ID NO 90

```
<211> LENGTH: 47
<212> TYPE: DNA
<213> ORGANISM: Artificial Sequence
<220> FEATURE:
<223> OTHER INFORMATION: i5_sense oligonucleotide 2

<400> SEQUENCE: 90
catggatcca cagatcggag cagttctttc atagtactca gcgatct            47

<210> SEQ ID NO 91
<211> LENGTH: 50
<212> TYPE: DNA
<213> ORGANISM: Artificial Sequence
<220> FEATURE:
<223> OTHER INFORMATION: i5_sense oligonucleotide 3

<400> SEQUENCE: 91
gtttgggtcc taaatttcct ttccccggct gttgtttagc tggcgccttg         50

<210> SEQ ID NO 92
<211> LENGTH: 50
<212> TYPE: DNA
<213> ORGANISM: Artificial Sequence
<220> FEATURE:
<223> OTHER INFORMATION: i5_antisense oligonucleotide 1

<400> SEQUENCE: 92
ctccgatctg tggatccatg gtcaacagat tggaaaccga cctggcgcca         50

<210> SEQ ID NO 93
<211> LENGTH: 45
<212> TYPE: DNA
<213> ORGANISM: Artificial Sequence
<220> FEATURE:
<223> OTHER INFORMATION: i5_antisense oligonucleotide 2

<400> SEQUENCE: 93
gaaatttagg acccaaacag atcgctgagt actatgaaag aactg              45

<210> SEQ ID NO 94
<211> LENGTH: 44
<212> TYPE: DNA
<213> ORGANISM: Artificial Sequence
<220> FEATURE:
<223> OTHER INFORMATION: i5_antisense flanking primer

<400> SEQUENCE: 94
cgatgtagat ctcaaggcgc cagctaaaca acagccgggg aaag               44

<210> SEQ ID NO 95
<211> LENGTH: 535
<212> TYPE: DNA
<213> ORGANISM: Zea mays

<400> SEQUENCE: 95
gtccgccttg tttctcctct gtctcttgat ctgactaatc ttggtttatg attcgttgag    60
taattttggg gaaagcttcg tccacagttt ttttcgatg aacagtgccg cagtggcgct    120
gatcttgtat gctatcctgc aatcgtggtg aacttattc ttttatatcc tttactccca    180
tgaaaaggct agtaatcttt ctcgatgtaa catcgtccag cactgctatt accgtgtggt    240
ccatccgaca gtctggctga acacatcata cgatctatgg agcaaaaatc tatcttccct    300
gttctttaat gaaggacgtc attttcatta gtatgatcta ggaatgttgc aacttgcaag    360
gaggcgtttc tttctttgaa tttaactaac tcgttgagtg gccctgtttc tcggacgtaa    420
```

```
ggcctttgct gctccacaca tgtccattcg aattttaccg tgtttagcaa gggcgaaaag    480
tttgcatctt gatgatttag cttgactatg cgattgcttt cctggacccg tgcag         535
```

<210> SEQ ID NO 96
<211> LENGTH: 344
<212> TYPE: DNA
<213> ORGANISM: Zea mays

<400> SEQUENCE: 96

```
gtacagtaca cacacatatg tatatatgta tgatgtatcc cttcgatcga aggcatgcct     60
tggtcgaata actgagtagt cattttatta cgttattttg acaagtcagt agttcatcca    120
tttgtcccat tttttcagct aggaagtttg gttacactgg ccttggtcta ataactgagt    180
agtcatttta ttacgttgtt tcgacaagtc agtagctcat ccatctgtcc catttttttc    240
agctaggaag tttggttaca ctggacttgg tctaataact gagtagtcat tttattacgt    300
tgtttcgaca agtcattagc tcatccatct gtcccatttt tcag                     344
```

<210> SEQ ID NO 97
<211> LENGTH: 1014
<212> TYPE: DNA
<213> ORGANISM: Zea mays

<400> SEQUENCE: 97

```
gtatgcttgc tctcctgttc atctccgtgc taaacctctg tcctctgggt gggttttttgc    60 tgggattttg agctaatctg ctggccgcgg tagaaaagac cgtgtcccct gatgagctca    120
agcgctcgcc ttagccgcgt ccttgtcccc cgccatttct tgcggtttcg ctgtgttccc    180
gtgactcgcc gggtgcgtca tcgcctgaat cttgtctggg ctctgctgac atgttcttgg    240
ctagttgggt ttatagattc ctctgatcta aaaccgtgcc tgtgctgcgc acagaactct    300
cccctgtcct ttcctgtggt tttggttacg tggtggtagt aagctggat ttgcacatgg    360 ataaagttgt tctaagctcc gtggtttgct tgagatcttg ctgttattgc gtgccgtgct    420
cacttctttt gcaatccgag gaatgaattt gtcgtttact cgtttttggtg gattattagc    480 gcgaaaaaaa actcttttttt tttgttcttt tactacgaaa agcatcttct tggattttgc    540
tatcttcttt tactacgaaa aactcttgag tctaggaatt tgaatttgtg atgtccattc    600
ttgcagtgcg ctgtgcttta ttgggaagcc aaatcctatt attttctgcc tctagggtct    660
gaatggaatc agtactattg agacaaaatc aatccaatca agttgatttc tttctttaaa    720
aatattatca cagaactaag tgcttgtgcg gaatcagtac tggcttttgt ttggtggagg    780
atcaatactt gcttttgttt tggggtggca actgttttgc tataagattc catgtgttcc    840
tgttgagatg aatcatatat agtatagctg catactacaa atctgttttt caaatttagg    900
ttgctttggc atgatcaatt ttttttcaga cagtctttct aagtggtagc tcttgatttc    960
ttgttcttct acaactggtg ctgctgaatc ttgaccgtat agctcgaatt gcag          1014
```

<210> SEQ ID NO 98
<211> LENGTH: 1010
<212> TYPE: DNA
<213> ORGANISM: Zea mays

<400> SEQUENCE: 98

```
gtacgccgct cgtcctcccc cccccccct ctctaccttc tctagatcgg cgttccggtc      60
catggttagg gcccggtagt tctacttctg ttcatgtttg tgttagatcc gtgtttgtgt    120
```

```
tagatccgtg ctgctagcgt tcgtacacgg atgcgacctg tacgtcagac acgttctgat      180
tgctaacttg ccagtgtttc tctttgggga atcctgggat ggctctagcc gttccgcaga      240
cgggatcgat ttcatgattt ttttgtttc gttgcatagg gtttggtttg ccctttcct       300 ttatttcaat atatgccgtg cacttgtttg tcgggtcatc ttttcatgct ttttttgtc      360 ttggttgtga tgatgtggtc tggttgggcg gtcgttctag atcggagtag aattctgttt      420
caaactacct ggtggattta ttaattttgg atctgtatgt gtgtgccata catattcata      480
gttacgaatt gaagatgatg gatggaaata tcgatctagg ataggtatac atgttgatgc      540 gggtttact gatgcatata cagagatgct ttttgttcgc ttggttgtga tgatgtggtg      600
tggttgggcg gtcgttcatt cgttctagat cggagtagaa tactgtttca aactacctgg      660
tgtatttatt aattttggaa ctgtatgtgt gtgtcataca tcttcatagt tacgagttta     720
agatggatgg aaatatcgat ctaggatagg tatacatgtt gatgtgggtt ttactgatgc     780
atatacatga tggcatatgc agcatctatt catatgctct aaccttgagt acctatctat     840
tataataaac aagtatgttt tataattatt ttgatcttga tatacttgga tgatggcata     900
tgcagcagct atatgtggat tttttagcc ctgccttcat acgctattta tttgcttggt      960
actgtttctt ttgtcgatgc tcaccctgtt gtttggtgtt acttctgcag                1010
```

<210> SEQ ID NO 99
<211> LENGTH: 8
<212> TYPE: DNA
<213> ORGANISM: Artificial Sequence
<220> FEATURE:
<223> OTHER INFORMATION: motif

<400> SEQUENCE: 99

```
cagatctg                                                                     8
```

<210> SEQ ID NO 100
<211> LENGTH: 5
<212> TYPE: DNA
<213> ORGANISM: Artificial Sequence
<220> FEATURE:
<223> OTHER INFORMATION: 5 bp motif

<400> SEQUENCE: 100

```
atctg                                                                        5
```

<210> SEQ ID NO 101
<211> LENGTH: 867
<212> TYPE: DNA
<213> ORGANISM: Zea mays

<400> SEQUENCE: 101

```
gtatgggtga cgtggtggca ctcgatctgc tgggttcaga tctgattttc ttggtgacgg       60
gatggcttgc cggcgatggt gcaggccgtc cactccaacg accctccgg gcagcttgag      120 gccaccacac agttcaggaa gctgcttct atagttgaga ttgggatctt atgtgcagtt      180
agcattccag atggatagag tttagggtt gagatttggg ccatgctcga ggtattaggc      240
catacccaaa cgtgagggta tggtcagttg tagctgtttc gggcaattgt tgtatacagg     300
acttgacttg tggattgtga gctatcaaaa ttagtcgttg caccctctca ttttcagatt     360
acttaattta ctgtctcgtc agaaaaaaaa caaaccctat cctatggcct gcaacatg       420 catatgacca tgtatgccca aaagttctga aaaaagttat actcctgaaa gcatttgatt     480
tcatgaacca ctattctatt ttttccagta gtgttctgct tgcagctggg gcaattatca     540
```

```
ttgcatccat gtgtgtgttt gcgcatgcat gtgtgtgtta tacattgttt tattgtctta    600
aaatggtata tgcagactat gtgtgtgttt gcgcattagt gtgtgttata cattgtttta    660
ttgtcttaaa aaggtcatgg agagtctgcg tacctctttt catattcttg tacatcgtag    720
atagcagctt tgatatcttg tgggattctt gtatttgttg gtgaatccag atgagtgcat    780
ggtacttctt tcttaattcc cactacaact ttatgtgaaa gttaagtagt aacttgctga    840
ttgagtttcc ataaatttct ctcgtag                                        867
```

<210> SEQ ID NO 102
<211> LENGTH: 847
<212> TYPE: DNA
<213> ORGANISM: Zea mays

<400> SEQUENCE: 102

```
gtgcgaccgg ctcgtattct cttccttgaa aagcatctcc atcaccatct tcgattgttt     60
tctgatctgt cgtcgaggag tgctgcaatt tgcagttgca gggcgttagt actcgaatcg    120
gggtgaagta ctgaagtggc ttaggttagg gttttttttt cgtcagatct gttgctagta    180
ctactaggat ctgaaatttc ctgcacgatt taagctgcca ccatcctgtg ttttaggtgt    240
atcgtggatt tcgtttgtta atactttgcg gcagaaataa caggatgttc cgatcgaatt    300
tggcatctcg tatttgttga tggtcacgcc aattcttgac agattgcgat gtcgtaataa    360
gtcatctgcc gttccgtgac cggtttggat ctggtttgtg tgtggatgaa ctgcgctatc    420
tttgtttctg ttattgtcga ctaggaattg attgaattcg ccttttacta tttcgtgaat    480
caagctctga ttctgtaact tttactcatg ttgttttcat ttcttcggcc tgatccaaaa    540
ttttccagtg gaacgatgct ttcttttgtg ctgtacaact gcaatatttc gtgactcaag    600
ctctgattct gtaaaattta cccatgttgt tcccatttct cagatctgat gcaggaatga    660
cgctttagtt ctagttgtgt ctgtgcaact gtaatacgac tgtactgaaa tttctctctc    720
ctatgaattt gagatgctcg cctgccttct gattcaaata cttattacac taatggcacc    780
tcgcaatcat gttcctttga tcgttttatg atctgaacca cattaaacac ctttctattt    840
cacgcag                                                              847
```

<210> SEQ ID NO 103
<211> LENGTH: 1448
<212> TYPE: DNA
<213> ORGANISM: Zea mays

<400> SEQUENCE: 103

```
gtgaggccgc ccgccggggg ttcctcagat ctggggccga tgctgggtcc gcctagatcc     60
acgcgtttct cggctgctcc ggcgaggatt atgttttttt agtgtccgtc gtttgttaat    120
aggatatgca cacgtttctc taagagtggg tgagatcttt gcgggggggta gaaggtccgg    180 agttttgcta cccgttcgtt tatttagtgg gtttcacgct gatctggtca tctggcggtg    240
aagttcctat tattaggctg cggatgcctg ggtgagctcg aatgccattc tattttttacc    300 ctcttccggg accgtagcaa ctgtctaggt agcacaaaat catcattttg ttaggaccga    360
agcgagtttc aggttgcatg atttttttcgg aatgaagac aaatatctat gtctgtgtgg    420
ggtgggtggg tgggggctcg gtacctctgg ggactaacaa ttggtgtatc ccttccccccc    480 ttcaaacccct tcaaactatg tacttttttta tgatatattt ttgttcacta ctggcaccgt    540
cccaactgtg gattttttttc aagggtggct catgtgatgt gctactgttg ttttgctagt    600
```

```
attcgattca cgggccccaa gtagggctgg caaacaattc cttttttccca cctcttggac    660 gtgtgatgag tgtgggcttt ggcttttggat gcttgtagta gcttagctgg tggatctagg    720
ctttattgaa gttgtctttt aatgcctatc cgtgttcttg ccctgtgtcg gtgctgcagt    780
aaaaggtgta gctttcagtt gacatggccc gatctcgcct ggcgcctttc ttctagacta    840
aaactcggta atggaaggtg cgtgacggat ctgtcacaaa ttgattatgc aaacacgtag    900
caagttaggc agagcaccat ttggtaagta gatctggacc tggaagttcc tgggtggggg    960
ttctctgcca tctgtcaccc acgtgtcgtt tgttcactga cctttgaact tcccatttag   1020
atcagcatgg atggccctag tgctcatcag atacttgtcc gatatgtggg gcttttgttt   1080
taagcgggtc accaatcttt gacccgatgt gcatgtgcta ttttctatga ttgagacggc   1140
gacacaggaa gatgagcact tttgagttaa cctggttggg ggtccatgag ttagctgctt   1200
acctgtgtgg ttgacaaatg gatgttggat gcttcagtct attaatcacc cgttatttat   1260
tttctgatac tgcaaatata aactggacag gttttgacat tctttctgaa tctactattg   1320
taccattgta ttgtacacag tttgaatttg cagcacaata taaccttgtg tggtttata    1380 tttacatcct agtgatccta accatatgat tgacatctaa aaaaaaactc ttgctctttt   1440
atggacag                                                            1448

<210> SEQ ID NO 104
<211> LENGTH: 169
<212> TYPE: DNA
<213> ORGANISM: Zea mays

<400> SEQUENCE: 104
gtccgtgcct ttttctttt cctttcaatt tcacccgcaa aaggttcatt ctttcatcga     60
tctgggtggt tttgaccggg ttctatggcc ctgttcgtcc agatctggtg atttcttggc    120
tgttctttcc atggggtttt gacaaaaaaa aaatcacttg tgatggcag                169

<210> SEQ ID NO 105
<211> LENGTH: 1500
<212> TYPE: DNA
<213> ORGANISM: zea mays

<400> SEQUENCE: 105
atctttttgt gtggagtgac ctgttttcaa gagctccatt gtagagtgac ctgttttgcc     60
aattttctct cggctatgtg aaccatcaaa tatggtaact aacaatatat aaaatataag    120
ataaattgtt gctatggtac atcagatttg tgtggcattg tccatcgcat atgaaacttt    180
ctatgttagg ctgcattcca ttataaagtc atgtctgttt tttacatagg ccgataaata    240 tattttttcat atctgtatcc taaaaggttt taggcttagt aggtctaaaa cagagtatat    300
gaagtgtgat ttcagtgcca tggggtatga ggatggcgat gttagtcttg atgggcaagt    360
ggtacccaag aaagacactt ttcgttactt aggatcaatg cttcaaaagg agggagacat    420
cgaggaggat gtcagtcata gaattaaagt cggatggttg aagtggcgac aagctgcggg    480
tgtcttatgc gaccaccggg tgccacgcaa actaaaaggc aaattctaca ggacagcaat    540
ccggccggct atgttgtatg gagcagaatg ttggcccact aaaagacgac atgtccaaca    600
actaagtgtg gcagagatgc gtatgttgcg ctggatatgt ggccacacaa ggagagatcg    660
agtccggaat gatgatatac gagagagagt aggagtggcg ccaattgagg agaagcttat    720
gcaacatcgc ttgagatggt ttggacatat ccaacgaaga cctgaagagg caccagtgca    780
tatcggaata attaggcgtc ccgaaaatgt gaagagaggt agaggtcgac caactttgac    840
```

```
gtggacagag gctgtgaaga gagacctgaa ggagtggaat aatgacaaag agctcgccgc    900
agataggaag gggtggaagt gtgcaattca cgtgccagaa ccctgattga tagtttcgct    960
tttcctcctt aatcgtttga ccttttcttg tgtccatttt agatcttgct ggtccttgtg   1020
ggttttatct cttttatgtg tttccccgtt tcgttgtttt cggttctcct ttgcctttgt   1080
ttcccttttc tgttctttgg gggttgagct ctgaggtttt catacggggt ttcatctcta   1140 gcctaccca acgtgcttgg gacaaaaagg ctttgttgtt gttgttgttg ttgtatctgt   1200
atcctaaaag gtgagagaga agggttatta agaaaaaccc tcgtcgctgg ccactgaagg   1260
ccgggcccaa tttagaacct agacctgctg ccaccgcact acaagaccga ggcctaaaag   1320
gcccatcagg aggcgcatcg gcgaatgccc caaactaaaa ccctaccccg gcaagtatat   1380
atatcctccc aacctcagtt cttgttccca ttatcacggc ggcggtggcg gagcgtaagg   1440
cgaaggagta gcagcagcag gcggcgccga gtagcggctc cccatctcga gcttgccacc   1500
```

<210> SEQ ID NO 106
<211> LENGTH: 1500
<212> TYPE: DNA
<213> ORGANISM: zea mays

<400> SEQUENCE: 106

```
ataagcgcta ctacttgaga aatgatttta catttcacac aaaatgatgg ttttatgca     60 atcaaactag cacctaaatg taaacaaaac atgcttgtca tgtatctcct ttaagcgcta    120
ttttgagaac tctgttttta caatgaattt atattttctc acataaattt aattcatttt    180
ttcttagaaa aaaaaagaa atccttgag aaaacagagt tcccaaacta gccataaagt     240
tgcacggagt tttcttctag cgagattaca tcaattgttt gaggtacaag tatttcgtat    300
atgccaaatt attagcaccc tagttattta gattcttaaa tatgttttgg ggtaaaaata    360
taacatacca tgttataccc aacttttgtc aaagatttag gagagttttt ttaatcgaac    420 tgatgttta gcgcctaaga attttattgg tacttgtaaa aaaaatgtta acatgccccc    480
attagaatgt aggaaaaaat gggagaaaaa actatgattt caatccctat gaattgattt    540
gttctatagc ctttgttttg ctagaatttg tctgaaaacg taagagtggg ttcgttttca    600
cacgaaaaga tctactcaaa tatcattatt ccttgtttac acccatagtt cattcaacta    660
cctattttat gttaattttt tctgttttca ctcctccaga tatctattct tcttaacttt    720
tttgtttttc accccataac tttgcataga tatttctatc ttatttatgt ttttttctat    780 tgttgactttt tcaatatgtga cattcaaaag aaggttgctg atatttttcc caatcttgca    840
tttaaagagg accatactta aaaagactct agaagctttg agagcatctc taacaatacc    900
ttaaactagt gtctcaaatt aaaatacaag gctgtacgca gaaaaaacta ctccaacaat    960
gcttcatttt ataaaatttg gtcaaaattt ttttagtgca ctctcttata tgtctcaaat   1020
atactacacc acaatgttct gccctataat ctagatttgg ggttttacta ttggagcaga   1080 atatttatt ggtgctctaa atcaaataaa atataaccat tttaaaatta tagggcattt    1140
ttatagatca cgtgttgttg gagatgctct aacaaaacca tttaaaagat gaacgttatc   1200
aatgtaataa tattttgatc tgtagtgttt ataaatatat atacaataat ttttaaaaac   1260
ttataataat atcattattg tatcatcaat ctataaacaa atttaagttt tcattaaaaa   1320
tagtaagtag tctgacattg actttttttt cattcgagaa ggacaaactg gaaagaaat    1380 atagcccagg ggtagttttg ggaaaaaaga tatttggatg ctggcgaatg tgacggccac   1440
```
gtctagtgga agcgcgtata atcgtccct tctttctttc ctcacccgcc cctgatccac    1500

<210> SEQ ID NO 107
<211> LENGTH: 1500
<212> TYPE: DNA
<213> ORGANISM: zea mays

<400> SEQUENCE: 107
cgagcggatg ttgttccggc ccgccaagcg gcaatcagca gctcaggtag tgtctagcca      60
gtgacgcggg gcgcgctact gtatgtgtct cgccgcctcg ctgggggcac ttcgtgtcgg     120
tagtacagga aaaagggaag gagtcgagat cgttcgcttc actgtctgtg tttcgtgtcg     180
gtaggtaccg tatagtgggg gagaagagat cgttcgcatc agtgcttgtg tttcacttag     240
ttgaacgtat acgtatatc gtatttggcc cattgcaaag caaggtgccg gaccaagaca     300
ccatccatcc atttgttgta gtagcaaaac aacagattca tctgtttgga agtcctattt     360
tgagccatac gttctcagtc ccgttgttgg gacgtgggag aatcctaatc ccaaaaatct     420
gcaaccaagt cgggggcta gtgaaggagg agaaatttac tattttgcca ctctcaattt     480
tggctgtctt ttattatgcc atcccgtgtc tatgactggt gggaccgtct gtgtctatga     540
tttgtgggtc cgatggcata ttggcgaagc ccacaaataa taatggcaaa attgccaatg     600
gctcagtgaa agagaggccg agcacagctg accgctgctg cgctgcacaa ggaggctgtg     660
tgcctgcacg tttttttttt ttgcctcagg gctcaggctc tcgcaatttg ggccctaacc     720
aatggacgct aaatcatcgg aaaccgctga ccgcatagca ccagtactgc tgctgttgct     780
gtctgatgaa gcgccctcca gttctccact acggccccta ccccacaccc ctgacaatgc     840
gaccgtttgc ttttatcacc acacaagtat actgaaacac acacacacac acacaaaaag     900
gggttcgctg ctgactttc acctggcact gagagccgta atagcacttc ctgctcctgc     960
agcgtgcaat aatccgcgtt caagggatgg gtaaattggt cggatagatc gcaaatctta    1020
tcagatcgat ctcgtgccaa ggcagccatg ccccaccccc accgcgtttg gtgcgacacg    1080
gtccccagcc gcgcatatga tatgcgtgta cgagtagtcc gcaggttttc tctcgccagc    1140
aacgccatct caggacctgc ggagcaagta tataaagca ctagcgattg ttgtttcacc    1200
cacaagattc caccatcacc acctcatttg ttagcggtaa tacctcgcct ccgttacccc    1260
gtgcttttaa ttccacggga aaccgaaaaa gaagagagag ggaaatgcca gcgaaattgc    1320
atggtggcct cgaaacgccg tccagactcc agagagaacc aggcatggct tcagagagag    1380
agagaaagcg gcgacaaaga accaaacgaa accaaaacaa aaaaaggctt tctttgcaaa    1440
gtcggacgca caaagcgggg agggcgaatt ccgcacgaaa cacgcagacc atatatgccc    1500

<210> SEQ ID NO 108
<211> LENGTH: 1500
<212> TYPE: DNA
<213> ORGANISM: zea mays

<400> SEQUENCE: 108
cccgccctcg tttttcagta aaaaaaatat ggtaatggaa gtgggagaga gttttccaa      60
ctgtttccga tcgttttcat ccctatctat aaacatccac atgagtaggg gaggcggggt     120
ggcgagtgga cgacactgta gccaacctaa ggaccaaagc tttagcctta accattgcac     180
catgtgtcgc ttattgttat atagagtata taaatgtata tagtaacaat ttgaaaatta     240
aaattaaaat catgattgaa taaaaatctc atttaaataa aaaattacat atatgatata     300
tagaattcat aacaatgtac gagtaactaa ctagttctat acttaagcat aaatagaaag     360

```
cgtagcaatg tatgcacact ttgctagtcg gatatttaga tactagttag aagtattaaa    420
tatagtctaa gtataaaact aattatatag atgaggacta acagcaaga cgaacctatt    480 aagtttaagt agtccatggt tcgtccatgt aaaataaata tttgctaata atagattaat    540
tagacttaat agatccatct cgtcgtttag tctttatcta tataattact tttgtagtta    600
gactatattt aattttagta attgacattt aaacatccga tatgatccag acttgatgtt    660
agtcaggaaa accaaacatc cccttaacca tattggtccc aatttttggt gcctttaccc    720
atcaaatgat attcacacaa tcacacatct gggcctaact ttcatcgttg ctgtccacga    780
cggcgacctg gaggcgaggt caattccttg cccaagcat agcttggagc ttgcacgcta    840
agaagaggct ctcgtactct acaaacagta cagcacatac aggtgacaaa acgacacaca    900
tcaaccagcc aaataataaa tgagcttctt catgggcacg gcaagccgac aactaccaac    960
aagatacagg tgacaaaaag aaaacaagag gcccccactc accagtgggt cgtaggcaac   1020
gcacgcggac gcggtccagc gggcgagaag atccccgact gcgcccaaa gaagatacag   1080 gatcaaggat ttttaaccgc agtttttctat tccacgacct tatccacacc agcagattcg   1140
aaattcacgg acaggcccat ggacccggcg aaagccagcg gtggttcagc ccctgacgtg   1200
cgggtcccac tctccagccg caccgcctag agaggcagag gcatcccttc gcgtggaagc   1260
aaacgaggcg tgataaagtg gggctcctcg gtcccggcgt tggccgcatc gacactcgcc   1320
gcgcaccacc accaccgctg cggctcacgg ctacgcagcc cgctctcccg acccccccgt   1380
gccctcctct ttttgctact agcacataga gtttcgcccg aatcgatcgc cgactgactc   1440
cgctagggtt cggcccgatc gccgcttcgt cctcccggct cccgcgggga ccccgccgag   1500

<210> SEQ ID NO 109
<211> LENGTH: 1500
<212> TYPE: DNA
<213> ORGANISM: zea mays

<400> SEQUENCE: 109
ttcgtgtata catttattta tcctatgtac atgcaatgta aatgatacat agtgcatatt     60
gaccttattt ttaacatgta cttctttcaa agcaaaccac ccgcgaagtg tcacaatgca    120
tacatccttc ggtgtcgagg gacctcatca tgaggcccct gccccctaa gtctagcttc    180 caatgtcatt taaggaagaa gatgagtttc gaggcccttta gggcctctga ggttctaccg    240
aacaatctag gttatctttg tctcttagat ccctgcatc agacccctct tggacctcga    300
ccttggagcc cttcaaggtt ctgaagccct cttgagatct atggctctta atgtgggaac    360
ccaagcttct ctcttgacta agtacaagaa tgctccacat tgaggcatac aactagttgt    420
aaccccgggg caagaagtac catgggagta tggtcccata gccacaactg tctctactta    480
agacgaccat gtgatactaa tgttccgaat aaagcttttg cacatcacat taatgtgatg    540
gatgatattg tggtcaagca ggcatatggt agccaccaca aaggatatga agcatacccca   600 aatccactat gaggagtgtg tcgcgtacct atgccacacc taaatgtgct aatttacctg    660
taagcattat aaaatataag caattacacc gtatctgatg gcatggactc gagtacataa    720
ctatgatatg atatatttct cactgccgca agatatgcat attacaatga catgttcaag    780
cgccattgtg gtccgcgtag agtcctcgtc tctaacaaga tgaagtaatc gagcatgttc    840
actacgaacc aacatgtgat cctcctcttc ttcgagctat aaaatattca tccagcttaa    900
atttcaaaat atgtgtgtca gagttaaaaa aatattcgat tcaaatctaa atatcagttc    960
```

```
tgtattcata tcctagaata ttcgaatcta tatttgaatt cagattacaa ggtagtgaat    1020
tgtgacatgt attcgttcct atccgatccg tcgttttgga gcactaggtg cggtcactgt    1080
gacgcgtgga cttggcttcg cccactgcca tcgtggaccc acgtcatcag caagtgtcca    1140
tatccaccac ccgacccgac gaccgcttgc cgtccgatcc gtgtgctccc gagggcaagg    1200
atggcatttc gccacgcgag atattttcg gtggcctgca caggccggca gtgcagcggc     1260
caaaacgagg tcaggtcagt cacgctgggc ccgcctcac gctcccgtcc tgctccgggt     1320
cccaacaaag ccgtccccgg gaggtgctcg tgtgctcgta gcgcggtggc gaccccgatg    1380
ccccgcatat tccactgggc gtccgcgccg tcggatggga tcaggacggc cgcggcggcc    1440
ccgcgctcgg ctataaagac gctgcggggg acgcattccc tctccgtgct ttcttagagg    1500

<210> SEQ ID NO 110
<211> LENGTH: 1500
<212> TYPE: DNA
<213> ORGANISM: zea mays

<400> SEQUENCE: 110
tgcacccatc gatagcagcc tggctcaaca gttgaattgg tggttggggg ctatatatac      60
cctccaacca cctccactcc aaccatccaa gcattcatta ctgcatattc aatacaagag     120
caatagacac cactccaaag acacaattca agtgatcgat ccgctcaaag tctacaattc     180
aactctagcg catttagact tgtgagagga tcatttgtgt tttccttgtt gctcttgttt     240
gcttggttgg ctttcttctt cctcattctt gttctcaaga aacttgtaat caaagcaaga     300
gacaccaagt ttgtaagtgg tccttgcggg gtctaagtga tccggttgat taagagaaa      360 gctcactcgg tctaggtgac cgtttgagag agggaaagag ttgaaagaga cccggtcttt     420
gtgaccacct caacggggac taggttcttt agaaccgaac ttcggtaaaa caaatcattg     480
tgtcatccgc ttttattttc ttggttgatt tgttttcctc tctccccgg actcggattt      540 attctaacgc taacccccggc ttgtagaatt aaatcgtgcg actcaagata tatagaaaaa    600
tttacacgac tgtcgcatgg aaacttttca tggcaccact tgatgtattt cctttcttga    660
tactttcctt ttcattttc aattaaagtt gttactcatt ttatctttac ggacactgag      720
tatacactag gagcaaactt gttagtaact ttatttgttt tgtcatctaa tcatcaaaac     780
cctcaacttg ggggtgattt cacttacaat atgaccaatc tcaactcctt tacgaatgc      840 cgatagacac atattctgga caatcacagt ctcccgtgca aaacgagggt aaacccgtca     900
atttgcgtat ggacgtaccg tccgcacgtg agcacaaacc gtctggtcca acgatcgtcg     960
accccatttt tttgaaccga attactggaa tccgcgtcta agccaccaca tctcatgata    1020
ctatatatta atacagtatt atatttagta tacgatga tatggtaaaa taacatatga      1080
tactatatat taatacagta ttatctttag tatatacgat gatatggtaa ttttagatat    1140
tgtgataaga aactatatag gttggaaata gcctaaggtg aggcgagtac agccccggca    1200
cacaaccaat cacggtgacg ctctaggatt gggccatttg tgtggcact gtagcgaggc     1260 ccagctcggt ccatgagcag cattctggtc ggcttgacag atccatcacg ccatcggcaa    1320
aaatatctgg ctctcgagaa ccctcccggt cccagcgcgg taggcccacc tcgggatcct    1380
tatcctccgg tcggaccgtt gttgcgcgg tcgccgcccg atccgatcat gacggcgccc     1440
gtcacgtccg tcgcgctata aatctgcggg gtagggcttc ctcactccct cgtgctctct    1500

<210> SEQ ID NO 111
<211> LENGTH: 1500
```

```
<212> TYPE: DNA
<213> ORGANISM: zea mays

<400> SEQUENCE: 111
tttggcctcc tctccttcac ggatcaccct tgcagtcgag cgtactctgg ccatctgatg    60
atgaattttt ttgcagtttt tacgaagctg atgttttta cagttttttg acgaagctcc    120
ctcttttgac gaagctaatt aaagatgatg gtttgctcaa gaatgcagtg aaaaagcttc   180
gactatggtt aaattttca acagcacaac actgcaatga caatgaatgt tgtggtaact    240
tcacacctac ctctctgttt tatatagtgc tgcaggtggg aaggtgaatg gccaagttgc   300
ctgcacccgc tgaacagtta cccgcacccg ctgaacggtg gaccactcga cgcttgggag   360
gcgaatcgcc agaccgtgcg tacccgccgc atggtgggcc acctcgtgct tggaatattt   420
taatcgtttc ttgacaacga gctcagggaa ggtgtttttt ggatctacgg cattccgaag   480
ccttggagat ttttcacgga tcaagctcgt tacaaaaaac gatctagcac cgcgaaggag   540
ctattgttgg gagactactt catcgccaaa ggtcctttaa gagaaacat cttcggaaga    600
tcagtacata caacgcgaag gtacatgccg aagctaccat ccagggagct tcggcatagc   660
gacatgcctt gagacgaagg gctgcaccga cttaaagagg aaaagaccaa tcggtccatg   720
ataatttgtg tcatggttgt aactaattgc caaggacata aatgtaattc tgaccgggct   780
gcgtcctgtg cctataaata ggtgaacagt acctctgtac tgttcacgct ggattgtatt   840
cactcgtacg tcacgcttgg accttttgcct tctgtcaagc cgaaggtaca aatacaattc   900
aatgtaattc atgttcattt ataatgatat aaaaaagata tattaatgat gttatataac   960
tattcatttt actcctcatg tttcatatgc ttctttttc attaatatat aatatgatga  1020
tgaaggtacg tgcttcatga ccttcgtctg aagatcatta tatcctatga gaataatga   1080
ttcgaaggac gaagacccct aaccattaat attttatgtt gccttattct taattcgaag  1140
catttaagaa caagttccca acattttcga tacctactca ttatctatta tcaaattcct  1200
tctaactaac gattactaag gtgcacggaa acaaaaatg aaaagtgttt agaggtgaac   1260
gccaacaaca aggggtgaga aaagaaacc gccatgtagt gtgggctgct aggggacggc   1320
cgtgccccca tgtagcccct tatcccctgt gatcggatca tcacaaaata tctttggagc  1380
gcggttgata ttatcactat aattgggggt ttacacgaaa aatcgcacca tctagaggtt  1440
tatgaagcct ccaaaaaat atctaaacaa caactacttc ctagtataaa gtgacagtag  1500

<210> SEQ ID NO 112
<211> LENGTH: 1500
<212> TYPE: DNA
<213> ORGANISM: zea mays

<400> SEQUENCE: 112
atggagtact catgtttaat aagattttc tttataaaga gagccttatt aaaactcaac    60
aggtataaga gttttaaaaa tgatcgtctt cgctcgcctt ctcattccgc tctgtaaatg   120
atcctttggc tctcaagttc caactgattg acgatgggac gttgggataa attccaggag  180
acaacattct aatataatta attactcgca atttaaagga cagagaaaac catgctactt   240
gcttcgatgt ttattttac aaaaattaaa aacatagaga tacagaaaaa tctgaccacg    300
agaattgcta gactctagcg tcacatgaat tgggagttat tgtaagtttt tgggccaagg   360
tgctagcgtg gagagtgagt agagacaagc agcgtgtgtg cttggcaaaa taaaagtttt  420
acttttctt ttgcttctta aaagactgag aggtgcagtg gatgaaatct cggatcttga   480
```

```
caaatgattc gggccttttt gtgttgcttt ttcttttgct tctttaaaga ctttgagagg    540
tgcggtgaag cttgagtgca gtaggtttcg aaaggcacga cttacacgaa aaaatggag     600
aaaagagaa  aacaacaaaa actggagatg cggggtatcg atccccgtac ctctcgcatg    660
ctaagcgagc gctctaccat ctgagctaca tccccttttg ttattattat aaaatagtta    720
atatttggta ataatgagct agactaagtt ggaccatgtt aagaaaaatt cattagccaa    780
ttacttagca tgtgaaaatc atgcgcactg gtgtgagatt tgtaagaggt atataaagta    840
tctatggtct catgatatta gaaagaggac atgaaaaatc aaaggagttt atagtggaaa    900
aaggaggcgg acacaactgc atcgccaaat tcatcacacc tgcatgcaca accctgagtt    960
gagtgagttc cacgtcgtgc tctgtagcat agcagaccct gtggtggtac tacccgtaac   1020
atgttgttgg agatgtctaa agtgttggac aacagtgtgc cctatgcccc tatgtctata   1080
ggatctcgag catctcaacg aaggagacag tcaactaatc gctctactag aagtctagtt   1140
cagccatgat agtaggccca ccatcttacg agtgggacag atgataaagt tgttgcttac   1200
caacatccac gcaaggtcat atcccttgat attgaaaaga tgtcactgac acatgggacc   1260
tgcctgtatc accgagagcg gcaagtatgc aatttgcaat ggcacgatag taatcgacat   1320
taattaaagc aaaaaaatca atgttttttt aaacaaaagg gctaagagcc caagacagac   1380
gacgtagccc aactgaatgc cctcctgcag cccagcccaa cctgtgcgat cgggtcggtc   1440
aagcaaccca ttcgatcggg tcgccttcag acctgacctc tcaaatcaaa ccgggaccgg   1500
```

<210> SEQ ID NO 113
<211> LENGTH: 1500
<212> TYPE: DNA
<213> ORGANISM: zea mays

<400> SEQUENCE: 113

```
agttaagcta acttccgaca aaaaaaattt cgagagccaa actttcgacg ggatggcttt     60
acttccgaga gttagctaa  cttcctagaga tttagggcta acttcctagg gtttaggctc   120
taggaagttc actattttgg tgtagtggga tagatatccc ctaggtccac taaaggaata   180
aaagacctca cgaaaggccc aagggcccaa taactcgtaa ggtcattctt tcgtgggcct   240
ggggtggaac aaccagcaag ggggaacgac atgaggccga ttggtgcaaa cccgagcggc   300
ccacatcgtc gagcgaatga tcgcaacaga gacccgattt tcccgcgcgg gagcccccat   360
gcagcggagc cgtgcgagga taagtcggcg aggatcacgc aggataaact cgagaggttc   420
actatctttt agttacttgt tgttatcata cccacatgtg ttgccccacg gtcgaatata   480
taaggcctag ggggcacccc ttcagaacga tcgaccctat cttacttagc cacccacgta   540
aactctctgt gccttcaatc cagagagccc tcttgtaacc acgctcgtat actcaccagg   600
acgtagggtg ttacgcatct ctaagcggcc cgaacctgta atcttgtcc  actgtctctc   660
gtgcgatcgg cacgaaccat tttgctacag tcgttgacac cgtcctactc ctaaaaacac   720
cttgaggggc aaccccgggt gtgcggtcgg acccaaaaca ccgacaccgg gcccaagggc   780
cggaccgtcc gctcatttg  gtgtccaaca ggtcgccttt taatatattg atcaggtagc   840
tatgaccgaa gaaaatgcac gccctctata tactacctac attcacaaat atatgacaca   900
attgaacttt ttcgaaaact ttgaccactc gttttattca aaatatttac tcaataatgt   960
aaaacttcaa gtaagcacaa attatcttaa gtgataaaac aaatcacaaa aaatgataac  1020
ttattatttt tgaataaga  tgagtgatca agttttttt  aaaagtcaa  cgacgtcata  1080
ttgaacagag ggagtattag agttctatta aatatttata ttatttcatt ataaaagtcg  1140
```

```
gtggctaaag ttcgtatttt gggaacaaat caagttaatt aatttattat ttttccgaaa   1200
gaagcgggta ggacacgaac caaaagcagg tagctacggg accccgcgat tttagcagat   1260
cgcagcaccg gcccgcgcac acccaccaaa cccggcccgc tactgaagtg acgtcactca   1320
agtgtccacg gcccggccca cccagtcata gctaactaca cgacacccac ctgtcttcct   1380
cggctcctcc accccggtcc tctcctgccg cgtcgcgttc gcccctcgca gcggcaact   1440 cccaccgccg ccgcttcgca tccgcccatc tgcttccatc gtctcacgga ggtcgctcac   1500
```

<210> SEQ ID NO 114
<211> LENGTH: 1500
<212> TYPE: DNA
<213> ORGANISM: Zea mays

<400> SEQUENCE: 114

```
gaccggcgtc ccatctggcc agctccgcca gatggacaat gatggcgccc acaagctct     60 atgacgacgg cggctctcag ctctcttacg gaagcagggc gacgtcagca aggactcgac   120
cgctccaaca gctgtccctc cgccaggctc cgtcgctcct ccgacagcca cgacatcacg   180
ccagcaaggt gccaagacct ctccggctgc acattggca tgtacctagg cgctagctc    240 tctctccgct agacacgtag cactctgcta caccccccat tgtacacctg gatcctctcc   300
ttacgactat aaaaggaagg accagggcct tcttagagga ggttggccgc gcggggacga   360
ggacgagaca ggcgctctct tggggccgct cgcttccctc acccgcgtgg acgcttgtaa   420 ccccccctact gcaagcgcac ccgacctggg cgcgggacga acacgaaggc cgcgggatct   480
ccacctctct cacgcccgtc tccggccacc tgcctctcc cccttcgcg ctcacccacg     540 cgctcgaccc atctgggctg gggcacgcag cacactcact cgtcggctcg ggaccccc     600 ggtctcgaaa cgccgacaaa accgtaggaa ataaataact tccgagaggc aactggtagc   660
tctaggaaat aaacataact tcctacggta ttttataaaa gctgtaggaa gttagttttc   720
acatgctgac ccgtgtgttc ggtcaagcga gccactaact tcctagaggc ggccgtagga   780
agttagcatg ggcagctaac ttcctgcggc ctcctctaga aagttaactt ttaattgctg   840
atccgcgggt gtggtcaaat gagccgctaa cttcctacgg cctcctctag aaagttagat   900
ttcagctttt gaccagccaa acgaaaagct cgtgctcaag attacaggaa caatccaaag   960
attacaccaa tcatattaag attggaggat caagaaaagg agaatctaaa tcctaagagc   1020
tagtttgata acctcgtttt tttgacagtt ctctaccgat gttcgcacac gcagcagccc   1080
ttgttgccat tttttctccg cgtcctctgt gccccaggta gggatgctgc cctttataaa   1140
ctttcacctc caactcactc gtatctcctt tcgagagatt ctgatatttt ccatcaacaa   1200
gaaacagatt tgtaaaatta tcatcaggcc acatttcata gacccagctg gacccacaat   1260
ttataaacac agtggtaatt ataacaagaa aacaacattg tgagtggcaa aaatctaatt   1320
gtctcatctc ctttccgttc gccaattcga aatcgaatcc gttccctaat tcgaaatcga   1380
atggggtcgg tcttgtcgtg cgtgcgtggc tgcgcgagcg acttgactgc acccgacccc   1440
cctcctccca gtccccacac actgcacgcc gccgccgggt cctcctaggg tttcgccgcg   1500
```

<210> SEQ ID NO 115
<211> LENGTH: 1500
<212> TYPE: DNA
<213> ORGANISM: Zea mays

<400> SEQUENCE: 115

| | |
|---|---|
| aactggacta gattcgtctc gtcttttaat cttcggctga caaattagtt ttataatccg | 60 |
| actacattta atacccgaaa cggaggttca aacattcgat gggacagggg ctaaatttta | 120 |
| gaggggtgta accaaacacc cccgtagtcc aaaactgcag gttaatgggt ctatgaccta | 180 |
| attttttggg acaccaaaac ataaaaattt ggaaaacaaa tatattctct agactcatag | 240 |
| gaacccctat agattttccc aaattatttt tgattttaa aattcaatct tttgaaccga | 300 |
| aaaaattcaa aattttacac agatcttgat tctgtgcagt gctggtgatg ggaaaaagcg | 360 |
| aaaaaccatc ggtatgtttt tgacaaatat gaaaatggga caaaacaac atgtgtgttt | 420 |
| tttcgaccgt ttccgctttt cttgttttag tcacaatagc tcgttttat ccacatatga | 480 |
| tatctcattt tagataatac atgaacaaat cataattgat tatatcatat ctcaacaaat | 540 |
| taacccgtaa tgaattattt ttctttgata gtcatatgta cattacaata tttcgcttcc | 600 |
| atatgtatgg atgtgatgtt ttaatcgatt gcaacactac ttttattttt atactctatg | 660 |
| tgacaattat ttccgctttt atttacatct tattccgatc tgttatcgat atcgatttgt | 720 |
| tccgtcccgt ttttatctta tttctgatag ttccaattta atcttatttt cgaaataaag | 780 |
| tatgaaaata aaaataagag agattgttac gttcgatccg gttttgaacc ctagctatac | 840 |
| ttgcccgttg ttgcaactgg ccggccattc cataggcggg cacagtcagc actcagcagt | 900 |
| gacagagtgc gcgtgcgaca cacagtttca aatttcaaaa ctgaaacggg cggctataaa | 960 |
| cagaacccgc tgctcccagg agcctcacgc agataaattc acccacatca atggggccca | 1020 |
| aatatttata accatctatt ggtcccacat gttcgtgtca caacatcctc taccgcaggt | 1080 |
| aaagatagcc gtctcgccaa gaccccgagc ccgccggctc cgcgggaccc gccgccagct | 1140 |
| cacacccacc gttgccggcc gctgagccgt tcgaagccaa acggtcgtt aaccacccag | 1200 |
| gctgcgccgt cggctaccat cacgccgtta gccccgaacc agacggcggc taggtcttcc | 1260 |
| gcgccgcgcc gcgccatcac gggccggccg cggccgcctc tcccacgctg cctataaaag | 1320 |
| ccgccgcgag gctgagcagc attatcgctt cagctcggcg tcttcacaaa cgccggcgca | 1380 |
| aactctcgcc cgagcccgac agatcttcaa ttccccattc cgcccaccga tcgaccttca | 1440 |
| cgccagtctc ggtctcttcc gaaggcgtcg cgcgcggttg tttgagagga gaggaggaag | 1500 |

<210> SEQ ID NO 116
<211> LENGTH: 1500
<212> TYPE: DNA
<213> ORGANISM: Zea mays

<400> SEQUENCE: 116

| | |
|---|---|
| atgagctatt atccataaaa ttatctaata ttcattatta ttccataaat tgatcatttt | 60 |
| tgcaaggctc gcgagctgga acgagccggc tcggctcggc tcgctgcaaa acgagctcg | 120 |
| aaacaggagc tcagctcggc tcgtttgagg ctcgcgagcc gctccgagct cgagccggct | 180 |
| cgcgagcctc gagctaattt tccaaccta gccctggcc agtgagctgg gcttccccgt | 240 |
| gagcgtccaa cggctcccct cccccctcac gctcttctcg gtgagagctc tcaccccctc | 300 |
| tccgctaatc agctataata attacaaaat taattttag atttacttag cagataacaa | 360 |
| tatgtattat aacactacaa aaaattgtat aatcatttaa aattccaaaa accgatgtat | 420 |
| aaaagtcaaa taacccaggg ttaaggggac ttgaatagga aaatgattgg atatgaggaa | 480 |
| aaataaggga cagatatttg aggagataga tatttaaata taaatagaaa ttatgaatgt | 540 |
| agggatttag gagggggaat ggttcaaaat agcctaagaa taagagtttg ccacctctct | 600 |
| tgagccatcg tccgctcgct ggcaggagtg gatatatggc catatgggtg tttgttgggg | 660 |

```
tcagttgacc ccgataaaat ttataaatct ttaaataaaa cactaaagtt tgaaaaaaca       720
ttgcatcata taatgaagct gaccctattc cgacatcatt ctttgctaaa ttcgccattg       780
ctcgctcatg cctaaaaaaa gacagagtaa gcacgttggg gggtgcttgg ttcttttagc       840
agcacaggct agcatggtaa ggctgcctaa tcttgctcag cttggccagc aaatataacc       900
atggacaatt taaatagcac aacgacatgc atgtcgtgac tgaaatagta caggaaggcc       960
cacccgtcgg ccagcctcca atcgcagaac gtggtagctt tctccgtccg ctcgccttgc      1020
cagcgcggga gagccgaatt ggccgcccgt ccgcttcaac gacgaggaaa agctagcttg      1080
cccagacaag ttagcttgct aagcaacgca aggttctaaa cacaactagt accaaacacc      1140
ccgtcgctaa tgcagtatcc aagaagatca ttagcttatc caatgctgaa ggcaaatgac      1200
acgtcagtgc aagctcactc acttgatcca gatctttcca tgcctatgcc tataacccta      1260
aataacggag ataagctaaa agatatttat ctcctgggcc cacctgccat cccgggccca      1320
ccgcaccagc aaggcctgca actttcacac ctaacccttc caagttaact gcattcacga      1380
cccacccccc cttcttctct ctcctggcca cctccgtcca ttccacactc cctcctccgg      1440
acgcaccttc cccgctatat aaggcacgcg ccccgagcac aggcgaagag cgtgcagagc      1500

<210> SEQ ID NO 117
<211> LENGTH: 1500
<212> TYPE: DNA
<213> ORGANISM: Zea mays

<400> SEQUENCE: 117
gtctttgagc tgaggtcttc ctgagagaag gtgattgtaa tgtgtgacca tttggatttg        60
atgaagggtc cttatactcc aacatgttgt accattctct gtgcttcctt cttctgcttc       120
ttgttagctg gctcagaact tgaacctccg tgattgggag caccagcttc gtagccgaag       180
gtgtcacaac ttgatcacct tgcgaagcca ttgtcgtggt cgtggaagtg agttctccgg       240
aggtgggcac caatgttggt cacttgttct cgaatgctgt gaattaagaa caaggcaaca       300
cagtcgctag ggattaaaga ccttcgtcct ccgaaacatt gtttcctctt ggattcaatg       360
atcatcggac gaaggccatg aaggacatgc cttcatcata tcataaataa ataaaaatgt       420
aaagagataa atacattgat gattactctt taatacattc atacttgtac tccgtaaaac       480
atgtataaat atcaataaaa ttcacgttat attgatacat tcggcttgct cgaaggtgaa       540
gatgcgagcg agtgattaca attcagcgtg aacagtaggg tgttattgtt catctatttta      600 taggcacgga acgcatccca ggggaaatta cattcacgac cctcaacatt catctagaga       660
caacctagat taacaaggtc tatctggtct tttcttcttc tgcttgactt gaacagaaac       720
taaatggtag ctttgacatt tgactatgtt gattctacat taagtctgtc ttgagaattt       780
tcggcagaaa aaaagtagac ttatgtacca ttttaccgaa gatgtttttg ttgaaaactt       840
ttgtcggaaa agaagacacc caacacttta cgtcgccgcc ataagtcacc agcgtcgtac       900
catgacttat ggcgtctaaa aaagattcaa agaatcatat tacatccttt ataaaaccaa       960
acgtatattc ttttagtaaa aaattaaaat gcaaaaaaaa atggtttccc acagccctag      1020
caaaacacaa tcgccacttc attccacccc ccgtttcgat gatgggtggg acaaaaata      1080 caggggaccca catgtcagtt aaaatctgac catgcatgag tcatggcac ggaatagttc      1140 tttactacta ggcaaccagc acgttgtaca ctgactgtgg ggccaaccgt accttgggtc      1200
cacaagtcac tgtgtgcttg acaacacagc attggcagat ccatgtgtac gttctcagcg      1260
```

| | |
|---|---|
| ccaggaaatt gcggccgtcc tttcctcctt ttccgttaag ccgataatct tcaatgacgc | 1320 |
| acgggtccaa gattagcttg ggcccatatg gcagtgtggg aagctgaatc cggacgcgtg | 1380 |
| acgcgaggtc tcgcgtggtg cggcgggcac tacgtcgtgg atggggaagg ggattaaata | 1440 |
| tcgtcggacg aggcgtggcc aaccccttcc gctcctctcg ccgctttggg ttggggttta | 1500 |

<210> SEQ ID NO 118
<211> LENGTH: 1329
<212> TYPE: DNA
<213> ORGANISM: Zea mays

<400> SEQUENCE: 118

| | |
|---|---|
| gtaactgcga tcatccatcc tcccgcttcc actctcccTt cacctcctct gcttgctagg | 60 |
| tatacgaaca tacgatttat tacgggttat atgggggctt cgattcccag atctggcgat | 120 |
| ctattatcgt agctccgagt cctcgatcta gtaattgtgg gatatgcttg taagaggctc | 180 |
| tgagatgggt tgggttgggt tgggtcgctg tgacgattcc aacagcctcg tttcttaggg | 240 |
| ttggatcttc tcgtggtttc cttttttaatt aaataagtac ctgatgcaga atggtgcgtc | 300 |
| ctattagatg gaaccttgat cttgatgcat ctaaccttga tcttgttcgc tgtgatgatt | 360 |
| ccaacaggct cgtttcttag gcctgttcgt ctggttcgtc agatcagttt cgttgctttt | 420 |
| ggcctcgttg taaggtccat ccagatcgga gtagaatcga atgatttatt atacggtagc | 480 |
| tgctggtctc attagatttg gatctgcatg ggttgaacat atgtattcat aattaatatg | 540 |
| gtgtatacgt actagtttgc tggtcttatt ttttagcct gattgcttct gcctttctgg | 600 |
| caacgcctga tccacgcgtt agctagagtg gattttagtt cctgtttac gcggccacac | 660 |
| ctgccgccta gaaaagctgc agcgagaact ctaattaaat ttggatctac atgtgctagc | 720 |
| atatatgttt gtaattaata tgatggatga atatgtgctt cagagttgag ttcctgttga | 780 |
| tgctgtagtt ctgcctgaat tgttgaggct gtagcttctg cctgattaaa atgcaccgtg | 840 |
| cctatctgtt aaactctagg gtgtgtgatt tagccggtga cggtggttta atatgtgtaa | 900 |
| tttcactgct tatagtaatg caattcacct ttgcttgaac atgcattgtc ttgttgctttt | 960 |
| gttctataca catgcttagc tattatctga tgagcatgca ctgttttgtt ctgtttgata | 1020 |
| tgcatgctca gaaatatgta gatgtgtggc tcctgctcgg ttgttctttta tcatccacct | 1080 |
| gttgaacatg catgttcttg tcgcttatct ttattatata ttaccttcgt tctcgaaatat | 1140 |
| ttgtcgcccg ctagttcatt tttgaactaa accgtgacaa ataaaataga acgtagggag | 1200 |
| tggcatcatg ctgctactgt accttacggt ggcaactaca tcttgagcac gcatatatct | 1260 |
| tatagtgttc cttttctttt cctccttggt ctactgttat atgcttaccT tttttTggtt | 1320 |
| tccttgcag | 1329 |

<210> SEQ ID NO 119
<211> LENGTH: 1076
<212> TYPE: DNA
<213> ORGANISM: Zea mays

<400> SEQUENCE: 119

| | |
|---|---|
| gacggagatc aacgtcccta tttacattat aattaggaaa tgcatccttt gttattaata | 60 |
| aaaacacttt cacttatata tattgttaga tgtaagaaat cattatgggt atattaaaat | 120 |
| aaacatattt gtacaatgat tgatctctta cccaaataat tatttgtttt tattattagc | 180 |
| tagtatacga aaacatcacc acgtacaggt ttgacggatt cccacagaaa cagggatgaa | 240 |
| aaatacttct acatccctgt cccgtttacc catctgagaa agcgggaaat cgggcatagg | 300 |

```
atccattgcc aaagatcgta gggctataac ctaagcgttg caacgaagcg aagcagacgg    360
tggagacgtt gacgcaaagc aatgaacttg aacggcatct ctctcgctgg ccctggcctt    420
ctcgaaggct ctgcgtgggt ccttgcgcag ttgcgccgca gcgggctggc agcatccgga    480
aattgcgtct tgcgtggcgg agcagacact aaggtactat tttacgttct atttagttgg    540
actgtggcgg taaactatga aaaaaactat tgcagactat gagctattaa aaagctaaaa    600
attatttagt gtaaaccact aaaaaccatt aaaaattctt tgatatatat tttcacagtt    660
ttataaaaaa tccactaaaa acaggtcaaa taagctttca attttacact acgaaaaagt    720
cagcttttaa aaaaaactgc ttaaatccag tcctttagtt taattttat cttttaggaa     780 acaaaagcca aaactaaaac caaaccaaac ctacctttaa aaccgatcta ataggaacgc    840
ggtgtttgga acaactagat attaatttta gaggttagac cgccacgaaa gcgtcactgc    900
acacggcatt ccctcccct agcgttatcg tcgcaccata ataaccatc ctctcctcgc      960 ctttccccac atctcatctt cgtctgtgtt cttgggcgta cgcggacaca gccccgatcc   1020
gaatcgtcgt ccttgcgagc ctcgccgatc ccccactccc ctcccctcgc ttcaag       1076

<210> SEQ ID NO 120
<211> LENGTH: 42
<212> TYPE: DNA
<213> ORGANISM: Artificial Sequence
<220> FEATURE:
<223> OTHER INFORMATION: TS2 fwd primer

<400> SEQUENCE: 120
cctccgcttc aagcgatcgc aggtaactgc gatcatccat cc                         42

<210> SEQ ID NO 121
<211> LENGTH: 46
<212> TYPE: DNA
<213> ORGANISM: Artificial Sequence
<220> FEATURE:
<223> OTHER INFORMATION: TS2 rev primer

<400> SEQUENCE: 121
aggctaagtt aaagtcgggt acctgcaagg aaaccaaaaa aaggta                    46

<210> SEQ ID NO 122
<211> LENGTH: 42
<212> TYPE: DNA
<213> ORGANISM: Artificial Sequence
<220> FEATURE:
<223> OTHER INFORMATION: pTS2 fwd primer

<400> SEQUENCE: 122
tcgaagcttg gcgcgccgac ggagatcaac gtccctattt ac                        42

<210> SEQ ID NO 123
<211> LENGTH: 42
<212> TYPE: DNA
<213> ORGANISM: Artificial Sequence
<220> FEATURE:
<223> OTHER INFORMATION: pTS2_TS2 rev primer

<400> SEQUENCE: 123
acaggacgga ccatggctgc aaggaaacca aaaaaggta ag                         42

<210> SEQ ID NO 124
<211> LENGTH: 42
<212> TYPE: DNA
```

```
<213> ORGANISM: Artificial Sequence
<220> FEATURE:
<223> OTHER INFORMATION: pTS2 reverse primer

<400> SEQUENCE: 124
acaggacgga ccatggcctt gaagcgaggg gaggggagtg gg                              42

<210> SEQ ID NO 125
<211> LENGTH: 33
<212> TYPE: DNA
<213> ORGANISM: Artificial Sequence
<220> FEATURE:
<223> OTHER INFORMATION: pTS1 fwd primer

<400> SEQUENCE: 125
cttggcgcgc ctgccacgca aactaaaagg caa                                        33

<210> SEQ ID NO 126
<211> LENGTH: 42
<212> TYPE: DNA
<213> ORGANISM: Artificial Sequence
<220> FEATURE:
<223> OTHER INFORMATION: pTS1 rev primer

<400> SEQUENCE: 126
cctgcgatcg cggtggcaag ctcgagatgg ggagccgcta ct                              42

<210> SEQ ID NO 127
<211> LENGTH: 39
<212> TYPE: DNA
<213> ORGANISM: Artificial Sequence
<220> FEATURE:
<223> OTHER INFORMATION: pTS27 fwd primer

<400> SEQUENCE: 127
tcgaagcttg gcgcgccccg gctataccgc tcccgccct                                  39

<210> SEQ ID NO 128
<211> LENGTH: 42
<212> TYPE: DNA
<213> ORGANISM: Artificial Sequence
<220> FEATURE:
<223> OTHER INFORMATION: pTS27 rev primer

<400> SEQUENCE: 128
ggatgcctca cctgcgatcg caggacgaag cggcgatcgg gc                              42

<210> SEQ ID NO 129
<211> LENGTH: 21
<212> TYPE: DNA
<213> ORGANISM: Artificial Sequence
<220> FEATURE:
<223> OTHER INFORMATION: GUS-F primer

<400> SEQUENCE: 129
cttacgtggc aaaggattcg a                                                     21

<210> SEQ ID NO 130
<211> LENGTH: 20
<212> TYPE: DNA
<213> ORGANISM: Artificial Sequence
<220> FEATURE:
<223> OTHER INFORMATION: GUS-R primer

<400> SEQUENCE: 130
gccccaatcc agtccattaa                                                       20
```

<210> SEQ ID NO 131
<211> LENGTH: 21
<212> TYPE: DNA
<213> ORGANISM: Artificial Sequence
<220> FEATURE:
<223> OTHER INFORMATION: Gr5-F primer

<400> SEQUENCE: 131
ggcagtttgg ttgatgctca t                                              21

<210> SEQ ID NO 132
<211> LENGTH: 26
<212> TYPE: DNA
<213> ORGANISM: Artificial Sequence
<220> FEATURE:
<223> OTHER INFORMATION: Gr5-R primer

<400> SEQUENCE: 132
tgctgtatat ctttgctttg aaccat                                         26

<210> SEQ ID NO 133
<211> LENGTH: 23
<212> TYPE: DNA
<213> ORGANISM: Artificial Sequence
<220> FEATURE:
<223> OTHER INFORMATION: GUS probe

<400> SEQUENCE: 133
aacgtgctga tggtgcacga cca                                            23

<210> SEQ ID NO 134
<211> LENGTH: 17
<212> TYPE: DNA
<213> ORGANISM: Artificial Sequence
<220> FEATURE:
<223> OTHER INFORMATION: Gr5 probe

<400> SEQUENCE: 134
ttgaagtcac aaagcca                                                   17

<210> SEQ ID NO 135
<211> LENGTH: 50976
<212> TYPE: DNA
<213> ORGANISM: Artificial Sequence
<220> FEATURE:
<223> OTHER INFORMATION: vector sequence

<400> SEQUENCE: 135
gtttacccgc caatatatcc tgtcaaacac tgatagttta aactgaaggc gggaaacgac      60
aatctgatca tgagcggaga attaagggag tcacgttatg accccgccg atgacgcggg      120 acaagccgtt ttacgtttgg aactgacaga accgcaacgt tgaaggagcc actcagcaag     180
ctggtacgat tgtaatacga ctcactatag ggcgaattga gcgctgttta aacgctcttc     240
aactggaaga gcggttaccc ggaccggaat tcgagctcgg tacgatatca acaagtttgt     300
acaaaaaagc aggtttaaac ttcgaaacgc gtggaccgaa gcttgcatgc ctgcagtgca     360
gcgtgacccg gtcgtgcccc tctctagaga taatgagcat tgcatgtcta agttataaaa     420
aattaccaca tattttttt gtcacacttg tttgaagtgc agtttatcta tctttataca     480
tatatttaaa ctttactcta cgaataatat aatctatagt actacaataa tatcagtgtt     540
ttagagaatc atataaatga acagttagac atggtctaaa ggacaattga gtattttgac     600

```
aacaggactc tacagtttta tcttttttagt gtgcatgtgt tctccttttt ttttgcaaat      660
agcttcacct atataatact tcatccattt tattagtaca tccatttagg gtttagggtt      720
aatggttttt atagactaat ttttttagta catctatttt attctatttt agcctctaaa      780
ttaagaaaac taaaactcta ttttagttttt tttatttaat aatttagata taaaatagaa     840
taaaataaag tgactaaaaa ttaaacaaat acccctttaag aaattaaaaa aactaaggaa     900
acatttttct tgtttcgagt agataatgcc agcctgttaa acgccgtcga cgagtctaac      960
ggacaccaac cagcgaacca gcagcgtcgc gtcgggccaa gcgaagcaga cggcacggca     1020
tctctgtcgc tgcctctgga cccctctcga gagttccgct ccaccgttgg acttgctccg     1080
ctgtcggcat ccagaaattg cgtggcggag cggcagacgt gagccggcac ggcaggcggc     1140
ctcctcctcc tctcacggca ccggcagcta cggggattc cttttcccacc gctccttcgc     1200 tttcccttcc tcgcccgccg taataaatag acaccccgc cacaccctct ttccccaacc      1260
tcgtgttgtt cggagcgcac acacacacaa ccagatctcc cccaaatcca cccgtcggca     1320
cctccgcttc aaggtacgcc gctcgtcctc ccccccccc cctctctacc ttctctagat      1380
cggcgttccg gtccatggtt agggcccggt agttctactt ctgttcatgt ttgtgttaga     1440
tccgtgtttg tgttagatcc gtgctgctag cgttcgtaca cggatgcgac ctgtacgtca     1500
gacacgttct gattgctaac ttgccagtgt ttctctttgg ggaatcctgg gatggctcta    1560
gccgttccgc agacgggatc gatttcatga ttttttttgt ttcgttgcat agggtttggt    1620
ttgccctttt cctttatttc aatatatgcc gtgcacttgt ttgtcgggtc atcttttcat    1680 gcttttttt gtcttggttg tgatgatgtg gtctggttgg gcggtcgttc tagatcggag     1740
tagaattctg tttcaaacta cctggtggat ttattaattt tggatctgta tgtgtgtgcc    1800
atacatattc atagttacga attgaagatg atggatggaa atatcgatct aggataggta    1860
tacatgttga tgcgggtttt actgatgcat atacagagat gcttttttgtt cgcttggttg    1920 tgatgatgtg gtgtggttgg gcggtcgttc attcgttcta gatcggagta gaatactgtt    1980
tcaaactacc tggtgtattt attaattttg gaactgtatg tgtgtgtcat acatcttcat    2040
agttacgagt ttaagatgga tggaaatatc gatctaggat aggtatacat gttgatgtgg    2100
gttttactga tgcatataca tgatggcata tgcagcatct attcatatgc tctaaccttg    2160
agtacctatc tattataata aacaagtatg ttttataatt attttgatct tgatatactt    2220
ggatgatggc atatgcagca gctatatgtg gattttttta gccctgcctt catacgctat    2280
ttatttgctt ggtactgttt cttttgtcga tgctcaccct gttgtttggt gttacttctg    2340
caggtcgact ctagacagct tcttgtaca aagtggtcga tatcgatcca ccatggtccg    2400
tcctgtagaa accccaaccc gtgaaatcaa aaaactcgac ggcctgtggg cattcagtct    2460
ggatcgcgaa aactgtggaa ttgatcagcg ttggtgggaa agcgcgttac aagaaagccg    2520
ggcaattgct gtgccaggca gttttaacga tcagttcgcc gatgcagata ttcgtaatta    2580
tgcgggcaac gtctggtatc agcgcgaagt ctttataccg aaaggttggg caggccagcg    2640
tatcgtgctg cgtttcgatg cggtcactca ttacggcaaa gtgtgggtca ataatcagga    2700
agtgatggag catcagggcg gctatacgcc atttgaagcc gatgtcacgc cgtatgttat    2760
tgccgggaaa agtgtacgta agtttctgct tctacccttg atatatatat aataattatc    2820
attaattagt agtaatataa tatttcaaat atttttttca aaataaaaga atgtagtata    2880
tagcaattgc ttttctgtag tttataagtg tgtatatttt aatttataac ttttctaata    2940
tatgaccaaa acatggtgat gtgcaggtat caccgtttgt gtgaacaacg aactgaactg    3000
```

```
gcagactatc ccgccgggaa tggtgattac cgacgaaaac ggcaagaaaa agcagtctta    3060
cttccatgat ttctttaact atgccggaat ccatcgcagc gtaatgctct acaccacgcc    3120
gaacacctgg gtggacgata tcaccgtggt gacgcatgtc gcgcaagact gtaaccacgc    3180
gtctgttgac tgccaggtgg tggccaatgg tgatgtcagc gttgaactgc gtgatgcgga    3240
tcaacaggtg gttgcaactg gacaaggcac tagcgggact ttgcaagtgg tgaatccgca    3300
cctctgccaa ccgggtgaag gttatctcta tgaactgtgc gtcacagcca aaagccagac    3360
agagtgtgat atctacccgc ttcgcgtcgg catccggtca gtggcagtga agggccaaca    3420
gttcctgatt aaccacaaac cgttctactt tactggcttt ggtcgtcatg aagatgcgga    3480
cttacgtggc aaaggattcg ataacgtgct gatggtgcac gaccacgcat taatggactg    3540
gattggggcc aactcctacc gtacctcgca ttacccttac gctgaagaga tgctcgactg    3600
ggcagatgaa catggcatcg tggtgattga tgaaactgct gctgtcggct taacctctc    3660 tttaggcatt ggtttcgaag cgggcaacaa gccgaaagaa ctgtacagcg aagaggcagt    3720
caacggggaa actcagcaag cgcacttaca ggcgattaaa gagctgatag cgcgtgacaa    3780
aaaccaccca agcgtggtga tgtggagtat tgccaacgaa ccggataccc gtccgcaagt    3840
gcacgggaat atttcgccac tggcggaagc aacgcgtaaa ctcgacccga cgcgtccgat    3900
cacctgcgtc aatgtaatgt tctgcgacgc tcacaccgat accatcagcg atctctttga    3960
tgtgctgtgc ctgaaccgtt attacggatg gtatgtccaa agcggcgatt tggaaacggc    4020
agagaaggta ctggaaaaag aacttctggc ctggcaggag aaactgcatc agccgattat    4080
catcaccgaa tacggcgtgg atacgttagc cgggctgcac tcaatgtaca ccgacatgtg    4140
gagtgaagag tatcagtgtg catggctgga tatgtatcac cgcgtctttg atcgcgtcag    4200
cgccgtcgtc ggtgaacagg tatggaattt cgccgatttt gcgacctcgc aaggcatatt    4260
gcgcgttggc ggtaacaaga aagggatctt cactcgcgac cgcaaaccga agtcggcggc    4320
ttttctgctg caaaaacgct ggactggcat gaacttcggt gaaaaaccgc agcagggagg    4380
caaacaatga atcaacaact ctcctggcgc accatcgtcg gctacagcct cggtgacgtg    4440
gggcaaccta gacttgtcca tcttctggat tggccaactt aattaatgta tgaaataaaa    4500
ggatgcacac atagtgacat gctaatcact ataatgtggg catcaaagtt gtgtgttatg    4560
tgtaattact agttatctga ataaaagaga agagatcat ccatatttct tatcctaaat    4620
gaatgtcacg tgtctttata attctttgat gaaccagatg catttcatta accaaatcca    4680
tatacatata aatattaatc atatataatt aatatcaatt gggttagcaa acaaatcta    4740 gtctaggtgt gttttgcgaa ttgcggccgc gatctgagct tctagagtcg acctgcaggc    4800
atgcccgcgg atatcgatgg gccccggccg aagcttcggt ccgggtcacc tttgtccacc    4860
aagatggaac tgcggccgct cattaattaa gtcaggcgcg cctctagttg aagacacgtt    4920
catgtcttca tcgtaagaag acactcagta gtcttcggcc agaatggcca tctgattca    4980 gcaggcctag aaggccattt aaatcctgag gatctggtct tcctaaggac ccgggatatc    5040
ggaccgatta aactttaatt cggtccgaag cttgcatgcc tgcagtgcag cgtgacccgg    5100
tcgtgcccct ctctagagat aatgagcatt gcatgtctaa gttataaaaa attaccacat    5160
attttttttg tcacacttgt ttgaagtgca gtttatctat ctttatacat atatttaaac    5220
tttactctac gaataatata atctatagta ctacaataat atcagtgttt tagagaatca    5280
tataaatgaa cagttagaca tggtctaaag gacaattgag tattttgaca acaggactct    5340
```

```
acagttttat cttttagtg tgcatgtgtt ctccttttt tttgcaaata gcttcaccta   5400
tataatactt catccatttt attagtacat ccatttaggg tttagggtta atggttttta   5460
tagactaatt tttttagtac atctatttta ttctatttta gcctctaaat taagaaaact   5520
aaaactctat tttagttttt ttatttaata atttagatat aaaatagaat aaaataaagt   5580
gactaaaaat taaacaaata ccctttaaga aattaaaaaa actaaggaaa cattttcctt   5640
gtttcgagta gataatgcca gcctgttaaa cgccgtcgac gagtctaacg gacaccaacc   5700
agcgaaccag cagcgtcgcg tcgggccaag cgaagcagac ggcacggcat ctctgtcgct   5760
gcctctggac ccctctcgag agttccgctc caccgttgga cttgctccgc tgtcggcatc   5820
cagaaattgc gtggcggagc ggcagacgtg agccggcacg gcaggcggcc tcctcctcct   5880
ctcacggcac cggcagctac gggggattcc tttcccaccg ctccttcgct ttcccttcct   5940
cgcccgccgt aataaataga caccccctcc acacctctt tccccaacct cgtgttgttc   6000
ggagcgcaca cacacacaac cagatctccc ccaaatccac ccgtcggcac ctccgcttca   6060
aggtacgccg ctcgtcctcc ccccccccc tctctacctt ctctagatcg gcgttccggt   6120
ccatggttag ggcccggtag ttctacttct gttcatgttt gtgttagatc cgtgtttgtg   6180
ttagatccgt gctgctagcg ttcgtacacg gatgcgacct gtacgtcaga cacgttctga   6240
ttgctaactt gccagtgttt ctctttgggg aatcctggga tggctctagc cgttccgcag   6300
acgggatcga tttcatgatt tttttgttt cgttgcatag ggtttggttt gcccttttcc   6360
tttatttcaa tatatgccgt gcacttgttt gtcgggtcat cttttcatgc tttttttgt   6420
cttggttgtg atgatgtggt ctggttgggc ggtcgttcta gatcggagta gaattctgtt   6480
tcaaactacc tggtggattt attaattttg gatctgtatg tgtgtgccat acatattcat   6540
agttacgaat tgaagatgat ggatggaaat atcgatctag gataggtata catgttgatg   6600
cgggttttac tgatgcatat acagagatgc ttttttgttcg cttggttgtg atgatgtggt   6660
gtggttgggc ggtcgttcat tcgttctaga tcggagtaga atactgtttc aaactacctg   6720
gtgtatttat taatttgga actgtatgtg tgtgtcatac atcttcatag ttacgagttt   6780
aagatggatg gaaatatcga tctaggatag gtatacatgt tgatgtgggt tttactgatg   6840
catatacatg atggcatatg cagcatctat tcatatgctc taaccttgag tacctatcta   6900
ttataataaa caagtatgtt ttataattat tttgatcttg atatacttgg atgatggcat   6960
atgcagcagc tatatgtgga tttttttagc cctgccttca tacgctattt atttgcttgg   7020
tactgtttct tttgtcgatg ctcaccctgt tgtttggtgt tacttctgca ggtcgaccgc   7080
cggggatcca cacgacacca tggctattga ggttaagcct atcaacgcag aggataccta   7140
tgaccttagg catagagtgc tcagaccaaa ccagcctatc gaagcctgca tgtttgagtc   7200
tgaccttact aggagtgcat ttcaccttgg tggattctac ggaggtaaac tgatttccgt   7260
ggcttcattc caccaagctg agcactctga acttcaaggt aagaagcagt accagcttag   7320
aggtgtggct accttggaag gttatagaga gcagaaggct ggttccagtc tcgtgaaaca   7380
cgctgaagag attctcagaa agagaggtgc tgacatgatc tggtgtaatg ccaggacatc   7440
tgcttcagga tactacagga agttgggatt cagtgagcaa ggagaggtgt tcgatactcc   7500
tccagttgga cctcacatcc tgatgtataa gaggatcaca taagagatct gagtcgaaac   7560
ctagacttgt ccatcttctg gattggccaa cttaattaat gtatgaaata aaaggatgca   7620
cacatagtga catgctaatc actataatgt gggcatcaaa gttgtgtgtt atgtgtaatt   7680
actagttatc tgaataaaag agaaagagat catccatatt tcttatccta aatgaatgtc   7740
```

```
acgtgtcttt ataattcttt gatgaaccag atgcatttca ttaaccaaat ccatatacat    7800
ataaatatta atcatatata attaatatca attgggttag caaaacaaat ctagtctagg    7860
tgtgttttgc gaattgcggc cgccaccgcg gtggagctcg aattcattcc gattaatcgt    7920
ggcctcttgc tcttcaggat gaagagctat gtttaaacgt gcaagcgcta ctagacaatt    7980
cagtacatta aaaacgtccg caatgtgtta ttaagttgtc taagcgtcaa tttgtttaca    8040
ccacaatata tcctgccacc agccagccaa cagctcccg accggcagct cggcacaaaa     8100
tcaccactcg atacaggcag cccatcagtc cgggacggcg tcagcgggag agccgttgta    8160
aggcggcaga ctttgctcat gttaccgatg ctattcggaa gaacggcaac taagctgccg    8220
ggtttgaaac acggatgatc tcgcggaggg tagcatgttg attgtaacga tgacagagcg    8280
ttgctgcctg tgatcaaata tcatctccct cgcagagatc cgaattatca gccttcttat    8340
tcatttctcg cttaaccgtg acaggctgtc gatcttgaga actatgccga cataatagga    8400
aatcgctgga taaagccgct gaggaagctg agtggcgcta tttctttaga agtgaacgtt    8460
gacgatcgtc gaccgtaccc cgatgaatta attcggacgt acgttctgaa cacagctgga    8520
tacttacttg ggcgattgtc atacatgaca tcaacaatgt acccgtttgt gtaaccgtct    8580
cttggaggtt cgtatgacac tagtggttcc cctcagcttg cgactagatg ttgaggccta    8640
acattttatt agagagcagg ctagttgctt agatacatga tcttcaggcc gttatctgtc    8700
agggcaagcg aaaattggcc atttatgacg accaatgccc cgcagaagct cccatctttg    8760
ccgccataga cgccgcgccc ccttttggg gtgtagaaca tccttttgcc agatgtggaa     8820
aagaagttcg ttgtcccatt gttggcaatg acgtagtagc cggcgaaagt gcgagaccca    8880
tttgcgctat atataagcct acgatttccg ttgcgactat tgtcgtaatt ggatgaacta    8940
ttatcgtagt tgctctcaga gttgtcgtaa tttgatggac tattgtcgta attgcttatg    9000
gagttgtcgt agttgcttgg agaaatgtcg tagttggatg gggagtagtc atagggaaga    9060
cgagcttcat ccactaaaac aattggcagg tcagcaagtg cctgccccga tgccatcgca    9120
agtacgaggc ttagaaccac cttcaacaga tcgcgcatag tcttccccag ctctctaacg    9180
cttgagttaa gccgcgccgc gaagcggcgt cggcttgaac gaattgttag acattatttg    9240
ccgactacct tggtgatctc gccttttcacg tagtgaacaa attcttccaa ctgatctgcg    9300
cgcgaggcca agcgatcttc ttgtccaaga taagcctgcc tagcttcaag tatgacgggc    9360
tgatactggg ccggcaggcg ctccattgcc cagtcggcag cgacatcctt cggcgcgatt    9420
ttgccggtta ctgcgctgta ccaaatgcgg gacaacgtaa gcactacatt tcgctcatcg    9480
ccagcccagt cgggcggcga gttccatagc gttaaggttt catttagcgc ctcaaataga    9540
tcctgttcag gaaccggatc aaagagttcc tccgccgctg gacctaccaa ggcaacgcta    9600
tgttctcttg cttttgtcag caagatagcc agatcaatgt cgatcgtggc tggctcgaag    9660
atacctgcaa gaatgtcatt gcgctgccat tctccaaatt gcagttcgcg cttagctgga    9720
taacgccacg gaatgatgtc gtcgtgcaca acaatggtga cttctacagc gcggagaatc    9780
tcgctctctc caggggaagc cgaagtttcc aaaaggtcgt tgatcaaagc tcgccgcgtt    9840
gtttcatcaa gccttacagt caccgtaacc agcaaatcaa tatcactgtg tggcttcagg    9900
ccgccatcca ctgcggagcc gtacaaatgt acggccagca acgtcggttc gagatggcgc    9960
tcgatgacgc caactacctc tgatagttga gtcgatactt cggcgatcac cgcttccctc   10020
atgatgttta actcctgaat taagccgcgc cgcgaagcgg tgtcggcttg aatgaattgt   10080
```

```
taggcgtcat cctgtgctcc cgagaaccag taccagtaca tcgctgtttc gttcgagact   10140
tgaggtctag ttttatacgt gaacaggtca atgccgccga gagtaaagcc acattttgcg   10200
tacaaattgc aggcaggtac attgttcgtt tgtgtctcta atcgtatgcc aaggagctgt   10260
ctgcttagtg cccactttt cgcaaattcg atgagactgt gcgcgactcc tttgcctcgg   10320
tgcgtgtgcg acacaacaat gtgttcgata gaggctagat cgttccatgt tgagttgagt   10380
tcaatcttcc cgacaagctc ttggtcgatg aatgcgccat agcaagcaga gtcttcatca   10440
gagtcatcat ccgagatgta atccttccgg taggggctca cacttctggt agatagttca   10500
aagccttggt cggataggtg cacatcgaac acttcacgaa caatgaaatg gttctcagca   10560
tccaatgttt ccgccacctg ctcagggatc accgaaatct tcatatgacg cctaacgcct   10620
ggcacagcgg atcgcaaacc tggcgcggct tttggcacaa aaggcgtgac aggtttgcga   10680
atccgttgct gccacttgtt aacccttttg ccagatttgg taactataat ttatgttaga   10740
ggcgaagtct tgggtaaaaa ctggcctaaa attgctgggg atttcaggaa agtaaacatc   10800
accttccggc tcgatgtcta ttgtagatat atgtagtgta tctacttgat cggggggatct   10860 gctgcctcgc gcgtttcggt gatgacggta aaaacctctg acacatgcag ctcccggaga   10920
cggtcacagc ttgtctgtaa gcggatgccg ggagcagaca agcccgtcag ggcgcgtcag   10980
cgggtgttgg cgggtgtcgg ggcgcagcca tgacccagtc acgtagcgat agcggagtgt   11040
atactggctt aactatgcgg catcagagca gattgtactg agagtgcacc atatgcggtg   11100
tgaaataccg cacagatgcg taaggagaaa ataccgcatc aggcgctctt ccgcttcctc   11160
gctcactgac tcgctgcgct cggtcgttcg gctgcggcga gcggtatcag ctcactcaaa   11220
ggcggtaata cggttatcca cagaatcagg ggataacgca ggaaagaaca tgtgagcaaa   11280
aggccagcaa aaggccagga accgtaaaaa ggccgcgttg ctggcgtttt tccataggct   11340 ccgccccct gacgagcatc acaaaaatcg acgctcaagt cagaggtggc gaaacccgac   11400
aggactataa agataccagg cgtttccccc tggaagctcc ctcgtgcgct ctcctgttcc   11460
gaccctgccg cttaccggat acctgtccgc ctttctccct tcgggaagcg tggcgctttc   11520
tcatagctca cgctgtaggt atctcagttc ggtgtaggtc gttcgctcca agctgggctg   11580
tgtgcacgaa ccccccgttc agcccgaccg ctgcgcctta tccggtaact atcgtcttga   11640
gtccaacccg gtaagacacg acttatcgcc actggcagca gccactggta acaggattag   11700
cagagcgagg tatgtaggcg gtgctacaga gttcttgaag tggtggccta actacggcta   11760
cactagaagg acagtatttg gtatctgcgc tctgctgaag ccagttacct tcggaaaaag   11820
agttggtagc tcttgatccg gcaaacaaac caccgctggt agcggtggtt ttttttgtttg   11880 caagcagcag attacgcgca gaaaaaaagg atctcaagaa gatcctttga tcttttctac   11940
ggggtctgac gctcagtgga acgaaaactc acgttaaggg attttggtca tgagattatc   12000
aaaaaggatc ttcacctaga tccttttaaa ttaaaaatga agttttaaat caatctaaag   12060
tatatatgag taaacttggt ctgacagtta ccaatgctta atcagtgagg cacctatctc   12120
agcgatctgt ctatttcgtt catccatagt tgcctgactc ccgtcgtgt agataactac   12180 gatacgggag ggcttaccat ctggccccag tgctgcaatg ataccgcgag acccacgctc   12240
accggctcca gatttatcag caataaacca gccagccgga agggccgagc gcagaagtgg   12300
tcctgcaact ttatccgcct ccatccagtc tattaattgt tgccgggaag ctagagtaag   12360
tagttcgcca gttaatagtt tgcgcaacgt tgttgccatt gctgcagggg ggggggggg   12420 gggggacttc cattgttcat tccacggaca aaaacagaga aaggaaacga cagaggccaa   12480
```

```
aaagcctcgc tttcagcacc tgtcgtttcc tttcttttca gagggtattt taaataaaaa   12540
cattaagtta tgacgaagaa gaacggaaac gccttaaacc ggaaaatttt cataaatagc   12600
gaaaacccgc gaggtcgccg ccccgtaacc taacctgtcg gatcaccgga aaggacccgt   12660
aaagtgataa tgattatcat ctacatatca caacgtgcgt ggaggccatc aaaccacgtc   12720
aaataatcaa ttatgacgca ggtatcgtat taattgatct gcatcaactt aacgtaaaaa   12780
caacttcaga caatacaaat cagcgacact gaatacgggg caacctcatg tccccccccc   12840 cccccccct gcaggcatcg tggtgtcacg ctcgtcgttt ggtatggctt cattcagctc   12900
cggttcccaa cgatcaaggc gagttacatg atcccccatg ttgtgcaaaa aagcggttag   12960
ctccttcggt cctccgatcg ttgtcagaag taagttggcc gcagtgttat cactcatggt   13020
tatgcagcca ctgcataatt ctcttactgt catgccatcc gtaagatgct tttctgtgac   13080
tggtgagtac tcaaccaagt cattctgaga atagtgtatg cggcgaccga gttgctcttg   13140
cccggcgtca acacgggata ataccgcgcc acatagcaga actttaaaag tgctcatcat   13200
tggaaaacgt tcttcggggc gaaaactctc aaggatctta ccgctgttga gatccagttc   13260
gatgtaaccc actcgtgcac ccaactgatc ttcagcatct tttactttca ccagcgtttc   13320
tgggtgagca aaaacaggaa ggcaaaatgc cgcaaaaaag ggaataaggg cgacacggaa   13380
atgttgaata ctcatactct tcctttttca atattattga agcatttatc agggttattg   13440
tctcatgagc ggatacatat ttgaatgtat ttagaaaaat aaacaaatag gggttccgcg   13500
cacatttccc cgaaaagtgc cacctgacgt ctaagaaacc attattatca tgacattaac   13560
ctataaaaat aggcgtatca cgaggccctt tcgtcttcaa gaattcggag cttttgccat   13620
tctcaccgga ttcagtcgtc actcatggtg atttctcact tgataacctt atttttgacg   13680
aggggaaatt aataggttgt attgatgttg gacgagtcgg aatcgcagac cgataccagg   13740
atcttgccat cctatggaac tgcctcggtg agttttctcc ttcattacag aaacggcttt   13800
ttcaaaaata tggtattgat aatcctgata tgaataaatt gcagtttcat ttgatgctcg   13860
atgagttttt ctaatcagaa ttggttaatt ggttgtaaca ctggcagagc attacgctga   13920
cttgacggga cggcggcttt gttgaataaa tcgaactttt gctgagttga aggatcagat   13980
cacgcatctt cccgacaacg cagaccgttc cgtggcaaag caaaagttca aaatcaccaa   14040
ctggtccacc tacaacaaag ctctcatcaa ccgtggctcc ctcactttct ggctggatga   14100
tggggcgatt caggcctggt atgagtcagc aacaccttct tcacgaggca gacctcagcg   14160
ccagaaggcc gccagagagg ccgagcgcgg ccgtgaggct tggacgctag gcagggcat   14220 gaaaaagccc gtagcgggct gctacgggcg tctgacgcgg tggaaggggg gagggatgt   14280 tgtctacatg gctctgctgt agtgagtggg ttgcgctccg gcagcggtcc tgatcaatcg   14340
tcaccctttc tcggtccttc aacgttcctg acaacgagcc tccttttcgc caatccatcg   14400
acaatcaccg cgagtccctg ctcgaacgct gcgtccggac cggcttcgtc gaaggcgtct   14460
atcgcggccc gcaacagcgg cgagagcgga gcctgttcaa cggtgccgcc gcgctcgccg   14520
gcatcgctgt cgccggcctg ctcctcaagc acggccccaa cagtgaagta gctgattgtc   14580
atcagcgcat tgacggcgtc cccggccgaa aaacccgcct cgcagaggaa gcgaagctgc   14640
gcgtcggccg tttccatctg cggtgcgccc ggtcgcgtgc cggcatggat gcgcgcgcca   14700
tcgcggtagg cgagcagcgc ctgcctgaag ctgcgggcat tcccgatcag aaatgagcgc   14760
cagtcgtcgt cggctctcgg caccgaatgc gtatgattct ccgccagcat ggcttcggcc   14820
```

```
agtgcgtcga gcagcgcccg cttgttcctg aagtgccagt aaagcgccgg ctgctgaacc    14880
cccaaccgtt ccgccagttt gcgtgtcgtc agaccgtcta cgccgacctc gttcaacagg    14940
tccagggcgg cacggatcac tgtattcggc tgcaactttg tcatgcttga cactttatca    15000
ctgataaaca taatatgtcc accaacttat cagtgataaa gaatccgcgc gttcaatcgg    15060
accagcggag gctggtccgg aggccagacg tgaaacccaa catacccctg atcgtaattc    15120
tgagcactgt cgcgctcgac gctgtcggca tcggcctgat tatgccggtg ctgccgggcc    15180
tcctgcgcga tctggttcac tcgaacgacg tcaccgccca ctatggcatt ctgctggcgc    15240
tgtatgcgtt ggtgcaattt gcctgcgcac ctgtgctggg cgcgctgtcg gatcgtttcg    15300
ggcggcggcc aatcttgctc gtctcgctgg ccggcgccac tgtcgactac gccatcatgg    15360
cgacagcgcc tttcctttgg gttctctata tcgggcggat cgtggccggc atcaccgggg    15420
cgactggggc ggtagccggc gcttatattg ccgatatcac tgatggcgat gagcgcgcgc    15480
ggcacttcgg cttcatgagc gcctgtttcg ggttcgggat ggtcgcggga cctgtgctcg    15540
gtgggctgat gggcggtttc tcccccacg ctccgttctt cgccgcggca gccttgaacg    15600
gcctcaattt cctgacgggc tgtttccttt tgccggagtc gcacaaaggc gaacgccggc    15660
cgttacgccg ggaggctctc aacccgctcg cttcgttccg gtgggccggg gcatgaccg    15720 tcgtcgccgc cctgatggcg gtcttcttca tcatgcaact tgtcggacag gtgccggccg    15780
cgctttgggt cattttcggc gaggatcgct ttcactggga cgcgaccacg atcggcattt    15840
cgcttgccgc atttggcatt ctgcattcac tcgcccaggc aatgatcacc ggccctgtag    15900
ccgcccggct cggcgaaagg cgggcactca tgctcggaat gattgccgac ggcacaggct    15960
acatcctgct tgccttcgcg acacggggat ggatggcgtt cccgatcatg gtcctgcttg    16020
cttcgggtgg catcggaatg ccggcgctgc aagcaatgtt gtccaggcag gtggatgagg    16080
aacgtcaggg gcagctgcaa ggctcactgg cggcgctcac cagcctgacc tcgatcgtcg    16140
gacccctcct cttcacggcg atctatgcgg cttctataac aacgtggaac gggtgggcat    16200
ggattgcagg cgctgccctc tacttgctct gcctgccggc gctgcgtcgc gggctttgga    16260
gcggcgcagg gcaacgagcc gatcgctgat cgtggaaacg ataggcctat gccatgcggg    16320
tcaaggcgac ttccggcaag ctatacgcgc cctaggagtg cggttggaac gttggcccag    16380
ccagatactc ccgatcacga gcaggacgcc gatgatttga agcgcactca gcgtctgatc    16440
caagaacaac catcctagca acacggcggt ccccgggctg agaaagccca gtaaggaaac    16500
aactgtaggt tcgagtcgcg agatcccccg gaaccaaagg aagtaggtta acccgctcc    16560 gatcaggccg agccacgcca ggccgagaac attggttcct gtaggcatcg ggattggcgg    16620
atcaaacact aaagctactg gaacgagcag aagtcctccg gccgccagtt gccaggcggt    16680
aaaggtgagc agaggcacgg gaggttgcca cttgcgggtc agcacggttc cgaacgccat    16740
ggaaaccgcc cccgccaggc ccgctgcgac gccgacagga tctagcgctg cgttggtgt    16800 caacaccaac agcgccacgc ccgcagttcc gcaaatagcc cccaggaccg ccatcaatcg    16860
tatcgggcta cctagcagag cggcagagat gaacacgacc atcagcggct gcacagcgcc    16920
taccgtcgcc gcgaccccgc ccggcaggcg gtagaccgaa ataaacaaca agctccagaa    16980
tagcgaaata ttaagtgcgc cgaggatgaa gatgcgcatc caccagattc ccgttggaat    17040
ctgtcggacg atcatcacga gcaataaacc cgccggcaac gcccgcagca gcataccggc    17100
gacccctcgg cctcgctgtt cgggctccac gaaaacgccg gacagatgcg ccttgtgagc    17160
gtccttgggg ccgtcctcct gtttgaagac cgacagccca atgatctcgc cgtcgatgta    17220
```

```
ggcgccgaat gccacggcat ctcgcaaccg ttcagcgaac gcctccatgg gcttttctc    17280
ctcgtgctcg taaacggacc cgaacatctc tggagctttc ttcagggccg acaatcggat   17340
ctcgcggaaa tcctgcacgt cggccgctcc aagccgtcga atctgagcct taatcacaat   17400
tgtcaatttt aatcctctgt ttatcggcag ttcgtagagc gcgccgtgcg tcccgagcga   17460
tactgagcga agcaagtgcg tcgagcagtg cccgcttgtt cctgaaatgc cagtaaagcg   17520
ctggctgctg aaccccagc cggaactgac cccacaaggc cctagcgttt gcaatgcacc    17580
aggtcatcat tgacccaggc gtgttccacc aggccgctgc ctcgcaactc ttcgcaggct   17640
tcgccgacct gctcgcgcca cttcttcacg cgggtgaat ccgatccgca catgaggcgg    17700
aaggtttcca gcttgagcgg gtacggctcc cggtgcgagc tgaaatagtc gaacatccgt   17760
cgggccgtcg gcgacagctt gcggtacttc tcccatatga atttcgtgta gtggtcgcca   17820
gcaaacagca cgacgatttc ctcgtcgatc aggacctggc aacgggacgt tttcttgcca   17880
cggtccagga cgcggaagcg gtgcagcagc gacaccgatt ccaggtgccc aacgcggtcg   17940
gacgtgaagc ccatcgccgt cgcctgtagg cgcgacaggc attcctcggc cttcgtgtaa   18000
taccggccat tgatcgacca gcccaggtcc tggcaaagct cgtagaacgt gaaggtgatc   18060
ggctcgccga taggggtgcg cttcgcgtac tccaacacct gctgccacac cagttcgtca   18120
tcgtcggccc gcagctcgac gccggtgtag gtgatcttca cgtccttgtt gacgtggaaa   18180
atgaccttgt tttgcagcgc ctcgcgcggg attttcttgt tgcgcgtggt gaacagggca   18240
gagcgggccg tgtcgtttgg catcgctcgc atcgtgtccg gccacggcgc aatatcgaac   18300
aaggaaagct gcatttcctt gatctgctgc ttcgtgtgtt tcagcaacgc ggcctgcttg   18360
gcctcgctga cctgttttgc caggtcctcg ccggcggttt tcgcttctt ggtcgtcata    18420
gttcctcgcg tgtcgatggt catcgacttc gccaaacctg ccgcctcctg ttcgagacga   18480
cgcgaacgct ccacgcggc cgatggcgcg ggcagggcag ggggagccag ttgcacgctg    18540
tcgcgctcga tcttggccgt agcttgctgg accatcgagc cgacggactg gaaggtttcg   18600
cggggcgcac gcatgacggt gcggcttgcg atggtttcgg catcctcggc ggaaaacccc   18660
gcgtcgatca gttcttgcct gtatgccttc cggtcaaacg tccgattcat tcaccctcct   18720
tgcgggattg ccccgactca cgccggggca atgtgcccttt attcctgatt tgacccgcct   18780
ggtgccttgg tgtccagata atccaccttta tcggcaatga agtcggtccc gtagaccgtc   18840
tggccgtcct tctcgtactt ggtattccga atcttgccct gcacgaatac cagcgacccc   18900
ttgcccaaat acttgccgtg ggcctcggcc tgagagccaa acacttgat gcggaagaag    18960
tcggtgcgct cctgcttgtc gccggcatcg ttgcgccact cttcattaac cgctatatcg   19020
aaaattgctt gcggcttgtt agaattgcca tgacgtacct cggtgtcacg ggtaagatta   19080
ccgataaact ggaactgatt atggctcata tcgaaagtct ccttgagaaa ggagactcta   19140
gtttagctaa acattggttc cgctgtcaag aactttagcg gctaaaattt gcgggccgc    19200
gaccaaaggt gcgagggggcg gcttccgctg tgtacaacca gatatttttc accaacatcc   19260
ttcgtctgct cgatgagcgg ggcatgacga aacatgagct gtcggagagg gcaggggttt   19320
caatttcgtt tttatcagac ttaaccaacg gtaaggccaa cccctcgttg aaggtgatgg   19380
aggccattgc cgacgccctg gaaactcccc tacctcttct cctggagtcc accgaccttg   19440
accgcgaggc actcgcggag attgcgggtc atcctttcaa gagcagcgtg ccgcccggat   19500
acgaacgcat cagtgtggtt ttgccgtcac ataaggcgtt tatcgtaaag aaatgggggcg   19560
```

```
acgacacccg aaaaaagctg cgtggaaggc tctgacgcca agggttaggg cttgcacttc    19620
cttctttagc cgctaaaacg gcccctcctc tgcgggccgt cggctcgcgc atcatatcga    19680
catcctcaac ggaagccgtg ccgcgaatgg catcgggcgg gtgcgctttg acagttgttt    19740
tctatcagaa cccctacgtc gtgcggttcg attagctgtt tgtcttgcag gctaaacact    19800
ttcggtatat cgtttgcctg tgcgataatg ttgctaatga tttgttgcgt aggggttact    19860
gaaaagtgag cgggaaagaa gagtttcaga ccatcaagga gcgggccaag cgcaagctgg    19920
aacgcgacat gggtgcggac ctgttggccg cgctcaacga cccgaaaacc gttgaagtca    19980
tgctcaacgc ggacggcaag gtgtggcacg aacgccttgg cgagccgatg cggtacatct    20040
gcgacatgcg gcccagccag tcgcaggcga ttatagaaac ggtggccgga ttccacggca    20100
aagaggtcac gcggcattcg cccatcctgg aaggcgagtt cccccttggat ggcagccgct    20160
ttgccggcca attccgccg gtcgtggccg cgccaacctt tgcgatccgc aagcgcgcgg    20220
tcgccatctt cacgctggaa cagtacgtcg aggcgggcat catgacccgc gagcaatacg    20280
aggtcattaa aagcgccgtc gcggcgcatc gaaacatcct cgtcattggc ggtactggct    20340
cgggcaagac cacgctcgtc aacgcgatca tcaatgaaat ggtcgccttc aacccgtctg    20400
agcgcgtcgt catcatcgag gacaccgcg aaatccagtg cgccgcagag aacgccgtcc    20460
aataccacac cagcatcgac gtctcgatga cgctgctgct caagacaacg ctgcgtatgc    20520
gccccgaccg catcctggtc ggtgaggtac gtggccccga agcccttgat ctgttgatgg    20580
cctggaacac cgggcatgaa ggaggtgccg ccaccctgca cgcaaacaac cccaaagcgg    20640
gcctgagccg gctcgccatg cttatcagca tgcacccgga ttcaccgaaa cccattgagc    20700
cgctgattgg cgaggcggtt catgtggtcg tccatatcgc caggacccct agcggccgtc    20760
gagtgcaaga aattctcgaa gttcttggtt acgagaacgg ccagtacatc accaaaaccc    20820
tgtaaggagt atttccaatg acaacggctg ttccgttccg tctgaccatg aatcgcggca    20880
ttttgttcta ccttgccgtg ttcttcgttc tcgctctcgc gttatccgcg catccggcga    20940
tggcctcgga aggcaccggc ggcagcttgc catatgagag ctggctgacg aacctgcgca    21000
actccgtaac cggcccggtg gccttcgcgc tgtccatcat cggcatcgtc gtcgccggcg    21060
gcgtgctgat cttcggcggc gaactcaacg ccttcttccg aaccctgatc ttcctggttc    21120
tggtgatggc gctgctggtc ggcgcgcaga acgtgatgag caccttcttc ggtcgtggtg    21180
ccgaaatcgc ggccctcggc aacggggcgc tgcaccaggt gcaagtcgcg gcggcggatg    21240
ccgtgcgtgc ggtagcggct ggacggctcg cctaatcatg gctctgcgca cgatccccat    21300
ccgtcgcgca ggcaaccgag aaaacctgtt catgggtggt gatcgtgaac tggtgatgtt    21360
ctcgggcctg atggcgtttg cgctgatttt cagcgcccaa gagctgcggg ccaccgtggt    21420
cggtctgatc ctgtggttcg gggcgctcta tgcgttccga atcatggcga aggccgatcc    21480
gaagatgcgg ttcgtgtacc tgcgtcaccg ccggtacaag ccgtattacc cggcccgctc    21540
gaccccgttc cgcgagaaca ccaatagcca agggaagcaa taccgatgat ccaagcaatt    21600
gcgattgcaa tcgcgggcct cggcgcgctt ctgttgttca tcctctttgc ccgcatccgc    21660
gcggtcgatg ccgaactgaa actgaaaaag catcgttcca aggacgccgg cctggccgat    21720
ctgctcaact acgccgctgt cgtcgatgac ggcgtaatcg tgggcaagaa cggcagcttt    21780
atggctgcct ggctgtacaa gggcgatgac aacgcaagca gcaccgacca gcagcgcgaa    21840
gtagtgtccg cccgcatcaa ccaggccctc gcgggcctgg gaagtgggtg gatgatccat    21900
gtggacgccg tgcggcgtcc tgctccgaac tacgcggagc ggggcctgtc ggcgttccct    21960
```

```
gaccgtctga cggcagcgat tgaagaagag cgctcggtct tgccttgctc gtcggtgatg   22020
tacttcacca gctccgcgaa gtcgctcttc ttgatggagc gcatggggac gtgcttggca   22080
atcacgcgca ccccccggcc gttttagcgg ctaaaaaagt catggctctg ccctcgggcg   22140
gaccacgccc atcatgacct tgccaagctc gtcctgcttc tcttcgatct cgccagcag   22200 ggcgaggatc gtggcatcac cgaaccgcgc cgtgcgcggg tcgtcggtga ccagagttt   22260 cagcaggccg cccaggcggc ccaggtcgcc attgatgcgg ccagctcgc ggacgtgctc   22320 atagtccacg acgcccgtga ttttgtagcc ctggccgacg gccagcaggt aggccgacag   22380
gctcatgccg gccgccgccg ccttttcctc aatcgctctt cgttcgtctg gaaggcagta   22440
caccttgata ggtgggctgc ccttcctggt tggcttggtt tcatcagcca tccgcttgcc   22500
ctcatctgtt acgccggcgg tagccggcca gcctcgcaga gcaggattcc cgttgagcac   22560
cgccaggtgc gaataaggga cagtgaagaa ggaacacccg ctcgcgggtg gcctacttc   22620 acctatcctg cccggctgac gccgttggat acaccaagga aagtctacac gaacccttg   22680 gcaaaatcct gtatatcgtg cgaaaaagga tggatatacc gaaaaaatcg ctataatgac   22740
cccgaagcag ggttatgcag cggaaaagcg ctgcttccct gctgttttgt ggaatatcta   22800
ccgactggaa acaggcaaat gcaggaaatt actgaactga ggggacaggc gagagacgat   22860
gccaaagagc tacaccgacg agctggccga gtgggttgaa tcccgcgcgg ccaagaagcg   22920
ccggcgtgat gaggctgcgg ttgcgttcct ggcggtgagg gcggatgtcg aggcggcgtt   22980
agcgtccggc tatgcgctcg tcaccatttg ggagcacatg cgggaaacgg ggaaggtcaa   23040
gttctcctac gagacgttcc gctcgcacgc caggcggcac atcaaggcca gcccgccga   23100 tgtgcccgca ccgcaggcca aggctgcgga accgcgccg gcacccaaga cgccggagcc   23160
acggcggccg aagcagggg gcaaggctga aaagccggcc cccgctgcgg ccccgaccgg   23220
cttcaccttc aacccaacac cggacaaaaa ggatctactg taatggcgaa aattcacatg   23280
gttttgcagg gcaagggcgg ggtcggcaag tcggccatcg ccgcgatcat tgcgcagtac   23340
aagatggaca aggggcagac acccttgtgc atcgacaccg acccggtgaa cgcgacgttc   23400
gagggctaca aggccctgaa cgtccgccgg ctgaacatca tggccggcga cgaaattaac   23460
tcgcgcaact tcgacaccct ggtcgagctg attgcgccga ccaaggatga cgtggtgatc   23520
gacaacggtc cagctcgtt cgtgcctctg tcgcattacc tcatcagcaa ccaggtgccg   23580
gctctgctgc aagaaatggg gcatgagctg tcatccata ccgtcgtcac cggcggccag   23640
gctctcctga cacggtgag cggcttcgcc cagctcgcca gcagttccc ggccgaagcg   23700 cttttcgtgg tctggctgaa cccgtattgg gggcctatcg agcatgaggg caagagcttt   23760
gagcagatga aggcgtacac ggccaacaag gcccgcgtgt cgtccatcat ccagattccg   23820
gccctcaagg aagaaaccta cggccgcgat ttcagcgaca tgctgcaaga gcggctgacg   23880
ttcgaccagg cgctggccga tgaatcgctc acgatcatga cgcggcaacg cctcaagatc   23940
gtgcggcgcg gcctgtttga acagctcgac gcggcggccg tgctatgagc gaccagattg   24000
aagagctgat ccgggagatt gcggccaagc acggcatcgc cgtcggccgc gacgacccgg   24060
tgctgatcct gcataccatc aacgcccggc tcatggccga cagtgcggcc aagcaagagg   24120
aaatccttgc cgcgttcaag gaagagctgg aagggatcgc ccatcgttgg ggcgaggacg   24180
ccaaggccaa agcggagcgg atgctgaacg cggccctggc ggccagcaag gacgcaatgg   24240
cgaaggtaat gaaggacagc gccgcgcagg cggccgaagc gatccgcagg gaaatcgacg   24300
```

```
acggccttgg ccgccagctc gcggccaagg tcgcggacgc gcggcgcgtg gcgatgatga    24360
acatgatcgc cggcggcatg gtgttgttcg cggccgccct ggtggtgtgg gcctcgttat    24420
gaatcgcaga ggcgcagatg aaaaagcccg gcgttgccgg gctttgtttt tgcgttagct    24480
gggcttgttt gacaggccca agctctgact gcgcccgcgc tcgcgctcct gggcctgttt    24540
cttctcctgc tcctgcttgc gcatcagggc ctggtgccgt cgggctgctt cacgcatcga    24600
atcccagtcg ccggccagct cgggatgctc gcgcgcatc ttgcgcgtcg ccagttcctc     24660
gatcttgggc gcgtgaatgc ccatgccttc cttgatttcg cgcaccatgt ccagccgcgt    24720
gtgcagggtc tgcaagcggg cttgctgttg ggcctgctgc tgctgccagg cggccttttgt   24780
acgcggcagg gacagcaagc cgggggcatt ggactgtagc tgctgcaaac gcgcctgctg    24840
acggtctacg agctgttcta ggcggtcctc gatgcgctcc acctggtcat gctttgcctg    24900
cacgtagagc gcaagggtct gctggtaggt ctgctcgatg ggcgcggatt ctaagagggc    24960
ctgctgttcc gtctcggcct cctgggccgc ctgtagcaaa tcctcgccgc tgttgccgct    25020
ggactgcttt actgccgggg actgctgttg ccctgctcgc gccgtcgtcg cagttcggct    25080
tgcccccact cgattgactg cttcatttcg agccgcagcg atgcgatctc ggattgcgtc    25140
aacgacgggc gcagcgcgga ggtgtccggc ttctccttgg gtgagtcggt cgatgccata    25200
gccaaaggtt tccttccaaa atgcgtccat tgctggaccg tgtttctcat tgatgcccgc    25260
aagcatcttc ggcttgaccg ccaggtcaag gcgccttca tgggcggtca tgacggacgc     25320
cgccatgacc ttgccgccgt tgttctcgat gtagccgcgt aatgaggcaa tggtgccgcc    25380
catcgtcagc gtgtcatcga caacgatgta cttctggccg gggatcacct cccctcgaa     25440
agtcgggttg aacgccaggc gatgatctga accggctccg gttcgggcga ccttctcccg    25500
ctgcacaatg tccgtttcga cctcaaggcc aaggcggtcg gccagaacga ccgccatcat    25560
ggccggaatc ttgttgttcc ccgccgcctc gacggcgagg actggaacga tgcggggctt    25620
gtcgtcgccg atcagcgtct tgagctgggc aacagtgtcg tccgaaatca ggcgctcgac    25680
caaattaagc gccgcttccg cgtcgccctg cttcgcagcc tggtattcag gctcgttggt    25740
caaagaacca aggtcgccgt tgcgaaccac cttcgggaag tctccccacg gtgcgcgctc    25800
ggctctgctg tagctgctca agacgcctcc ctttttagcc gctaaaactc taacgagtgc    25860
gcccgcgact caacttgacg cttttcggcac ttacctgtgc cttgccactt gcgtcatagg    25920
tgatgctttt cgcactcccg atttcaggta ctttatcgaa atctgaccgg gcgtgcatta    25980
caaagttctt ccccacctgt tggtaaatgc tgccgctatc tgcgtggacg atgctgccgt    26040
cgtggcgctg cgacttatcg gccttttggg ccatatagat gttgtaaatg ccaggtttca    26100
gggccccggc tttatctacc ttctggttcg tccatgcgcc ttggttctcg gtctggacaa    26160
ttctttgccc attcatgacc aggaggcggt gtttcattgg gtgactcctg acggttgcct    26220
ctggtgttaa acgtgtcctg gtcgcttgcc ggctaaaaaa aagccgacct cggcagttcg    26280
aggccggctt tccctagagc cgggcgcgtc aaggttgttc catctatttt agtgaactgc    26340
gttcgattta tcagttactt tcctcccgct ttgtgtttcc tcccactcgt ttccgcgtct    26400
agccgacccc tcaacatagc ggcctcttct tgggctgcct ttgcctcttg ccgcgcttcg    26460
tcacgctcgg cttgcaccgt cgtaaagcgc tcggcctgcc tggccgcctc ttgcgccgcc    26520
aacttccttt gctcctggtg ggcctcggcg tcggcctgcg ccttcgcttt caccgctgcc    26580
aactccgtgc gcaaactctc cgcttcgcgc ctggtggcgt cgcgctcgcc gcgaagcgcc    26640
tgcatttcct ggttggccgc gtccagggtc ttgcggctct cttctttgaa tgcgcgggcg    26700
```

```
tcctggtgag cgtagtccag ctcggcgcgc agctcctgcg ctcgacgctc cacctcgtcg   26760
gcccgctgcg tcgccagcgc ggcccgctgc tcggctcctg ccagggcggt gcgtgcttcg   26820
gccagggctt gccgctggcg tgcggccagc tcggccgcct cggcggcctg ctgctctagc   26880
aatgtaacgc gcgcctgggc ttcttccagc tcgcgggcct cgcgcctcgaa ggcgtcggcc   26940 agctccccgc gcacggcttc caactcgttg cgctcacgat cccagccggc ttgcgctgcc   27000
tgcaacgatt cattggcaag ggctgggcg gcttgccaga gggcggccac ggcctggttg   27060
ccggcctgct gcaccgcgtc cggcacctgg actgccagcg gggcggcctg cgccgtgcgc   27120
tggcgtcgcc attcgcgcat gccggcgctg gcgtcgttca tgttgacgcg ggcggcctta   27180
cgcactgcat ccacggtcgg gaagttctcc cggtcgcctt gctcgaacag ctcgtccgca   27240
gccgcaaaaa tgcggtcgcg cgtctctttg ttcagttcca tgttggctcc ggtaattggt   27300
aagaataata atactcttac ctaccttatc agcgcaagag tttagctgaa cagttctcga   27360
cttaacggca ggttttttag cggctgaagg gcaggcaaaa aaagcccgc acggtcggcg   27420 ggggcaaagg gtcagcggga aggggattag cgggcgtcgg gcttcttcat gcgtcgggc   27480 cgcgcttctt gggatggagc acgacgaagc gcgcacgcgc atcgtcctcg gcccctatcgg   27540 cccgcgtcgc ggtcaggaac ttgtcgcgcg ctaggtcctc cctggtgggc accaggggca   27600
tgaactcggc ctgctcgatg taggtccact ccatgaccgc atcgcagtcg aggccgcgtt   27660
ccttcaccgt ctcttgcagg tcgcggtacg cccgctcgtt gagcggctgg taacgggcca   27720
attggtcgta aatggctgtc ggccatgagc ggccttcct gttgagccag cagccgacga   27780
cgaagccggc aatgcaggcc cctggcacaa ccaggccgac gccggggca ggggatggca   27840 gcagctcgcc aaccaggaac cccgccgcga tgatgccgat gccggtcaac cagcccttga   27900
aactatccgg ccccgaaaca cccctgcgca ttgcctggat gctgcgccgg atagcttgca   27960
acatcaggag ccgtttcttt tgttcgtcag tcatggtccg ccctcaccag ttgttcgtat   28020
cggtgtcgga cgaactgaaa tcgcaagagc tgccggtatc ggtccagccg ctgtccgtgt   28080
cgctgctgcc gaagcacggc gaggggtccg cgaacgccgc agacggcgta tccggccgca   28140
gcgcatcgcc cagcatggcc ccggtcagcg agccgccggc caggtagccc agcatggtgc   28200
tgttggtcgc cccggccacc agggccgacg tgacgaaatc gccgtcattc cctctggatt   28260
gttcgctgct cggcggggca gtgcgccgcg ccggcggcgt cgtggatggc tcgggttggc   28320
tggcctgcga cggccggcga aaggtgcgca gcagctcgtt atcgaccggc tgcggcgtcg   28380
gggccgccgc cttgcgctgc ggtcggtgtt ccttcttcgg ctcgcgcagc ttgaacagca   28440
tgatcgcgga aaccagcagc aacgccgcgc ctacgcctcc cgcgatgtag aacagcatcg   28500
gattcattct tcggtcctcc ttgtagcgga accgttgtct gtgcggcgcg ggtggcccgc   28560
gccgctgtct ttggggatca gccctcgatg agcgcgacca gtttcacgtc ggcaaggttc   28620
gcctcgaact cctggccgtc gtcctcgtac ttcaaccagg catagccttc cgccggcggc   28680
cgacggttga ggataaggcg ggcagggcgc tcgtcgtgct cgacctggac gatggccttt   28740
ttcagcttgt ccgggtccgg ctccttcgcg ccctttttcct tggcgtcctt accgtcctgg   28800
tcgccgtcct cgccgtcctg gccgtcgccg gcctccgcgt cacgctcggc atcagtctgg   28860
ccgttgaagg catcgacggt gttgggatcg cggcccttct cgtccaggaa ctcgcgcagc   28920
agcttgaccg tgccgcgcgt gatttcctgg gtgtcgtcgt caagccacgc ctcgacttcc   28980
tccgggcgct tcttgaaggc cgtcaccagc tcgttcacca cggtcacgtc gcgcacgcgg   29040
```

```
ccggtgttga acgcatcggc gatcttctcc ggcaggtcca gcagcgtgac gtgctgggtg   29100
atgaacgccg gcgacttgcc gatttccttg gcgatatcgc ctttcttctt gcccttcgcc   29160
agctcgcggc caatgaagtc ggcaatttcg cgcggggtca gctcgttgcg ttgcaggttc   29220
tcgataacct ggtcggcttc gttgtagtcg ttgtcgatga acgccgggat ggacttcttg   29280
ccggcccact tcgagccacg gtagcggcgg gcgccgtgat tgatgatata gcggcccggc   29340
tgctcctggt tctcgcgcac cgaaatgggt gacttcaccc cgcgctcttt gatcgtggca   29400
ccgatttccg cgatgctctc cggggaaaag ccggggttgt cggccgtccg cggctgatgc   29460
ggatcttcgt cgatcaggtc caggtccagc tcgatagggc cggaaccgcc ctgagacgcc   29520
gcaggagcgt ccaggaggct cgacaggtcg ccgatgctat ccaacccccag gccggacggc  29580
tgcgccgcgc ctgcggcttc ctgagcggcc gcagcgtgtt ttttcttggt ggtcttggct   29640
tgagccgcag tcattgggaa atctccatct tcgtgaacac gtaatcagcc agggcgcgaa   29700
cctctttcga tgccttgcgc gcggccgttt tcttgatctt ccagaccggc acaccggatg   29760
cgagggcatc ggcgatgctg ctgcgcaggc caacggtggc cggaatcatc atcttggggt   29820
acgcggccag cagctcggct tggtggcgcg cgtggcgcgg attccgcgca tcgaccttgc   29880
tgggcaccat gccaaggaat tgcagcttgg cgttcttctg gcgcacgttc gcaatggtcg   29940
tgaccatctt cttgatgccc tggatgctgt acgcctcaag ctcgatgggg gacagcacat   30000
agtcggccgc gaagagggcg gccgccaggc cgacgccaag ggtcggggcc gtgtcgatca   30060
ggcacacgtc gaagccttgg ttcgccaggg ccttgatgtt cgccccgaac agctcgcggg   30120
cgtcgtccag cgacagccgt tcggcgttcg ccagtaccgg gttggactcg atgagggcga   30180
ggcgcgcggc ctggccgtcg ccggctgcgg gtgcggtttc ggtccagccg ccggcaggga   30240
cagcgccgaa cagcttgctt gcatgcaggc cggtagcaaa gtccttgagc gtgtaggacg   30300
cattgccctg ggggtccagg tcgatcacgg caacccgcaa gccgcgctcg aaaaagtcga   30360
aggcaagatg cacaagggtc gaagtcttgc cgacgccgcc tttctggttg gccgtgacca   30420
aagttttcat cgtttggttt cctgtttttt cttggcgtcc gcttcccact tccggacgat   30480
gtacgcctga tgttccggca gaaccgccgt taccgcgcgc tacccctcgg gcaagttctt   30540
gtcctcgaac gcggcccaca cgcgatgcac cgcttgcgac actgcgcccc tggtcagtcc   30600
cagcgacgtt gcgaacgtcg cctgtggctt cccatcgact aagacgcccc gcgctatctc   30660
gatggtctgc tgccccactt ccagcccctg gatcgcctcc tggaactggc tttcggtaag   30720
ccgtttcttc atggataaca cccataattt gctccgcgcc ttggttgaac atagcggtga   30780
cagccgccag cacatgagag aagtttagct aaacatttct cgcacgtcaa caccctttagc 30840
cgctaaaact cgtccttggc gtaacaaaac aaaagcccgg aaaccgggct ttcgtctctt   30900
gccgcttatg gctctgcacc cggctccatc accaacaggt cgcgcacgcg cttcactcgg   30960
ttgcggatcg acactgccag cccaacaaag ccggttgccg ccgccgccag gatcgcgccg   31020
atgatgccgg ccacaccggc catcgcccac caggtcgccg ccttccggtt ccattcctgc   31080
tggtactgct tcgcaatgct ggacctcggc tcaccatagg ctgaccgctc gatggcgtat   31140
gccgcttctc cccttggcgt aaacccagc gccgcaggcg gcattgccat gctgcccgcc    31200
gctttcccga ccacgacgcg cgcaccaggc ttgcggtcca gaccttcggc cacggcgagc   31260
tgcgcaagga cataatcagc cgccgacttg gctccacgcg cctcgatcag ctcttgcact   31320
cgcgcgaaat ccttggcctc cacggccgcc atgaatcgcg cacgcggcga aggctccgca   31380
gggccggcgt cgtgatcgcc gccgagaatg cccttcacca agttcgacga cacgaaaatc   31440
```

```
atgctgacgg ctatcaccat catgcagacg gatcgcacga acccgctgaa ttgaacacga   31500
gcacggcacc cgcgaccact atgccaagaa tgcccaaggt aaaaattgcc ggccccgcca   31560
tgaagtccgt gaatgcccg acggccgaag tgaagggcag gccgccaccc aggccgccgc    31620
cctcactgcc cggcacctgg tcgctgaatg tcgatgccag cacctgcggc acgtcaatgc   31680
ttccgggcgt cgcgctcggg ctgatcgccc atcccgttac tgccccgatc ccggcaatgg   31740
caaggactgc cagcgctgcc attttgggg tgaggccgtt cgcggccgag gggcgcagcc    31800
cctgggggga tgggaggccc gcgttagcgg gccgggaggg ttcgagaagg gggggcaccc   31860
cccttcggcg tgcgcggtca cgcgcacagg gcgcagccct ggttaaaaac aaggtttata   31920
aatattggtt taaaagcagg ttaaaagaca ggttagcggt ggccgaaaaa cgggcggaaa   31980
cccttgcaaa tgctggattt tctgcctgtg dacagcccct caaatgtcaa taggtgcgcc   32040
cctcatctgt cagcactctg cccctcaagt gtcaaggatc gcgcccctca tctgtcagta   32100
gtcgcgcccc tcaagtgtca ataccgcagg gcacttatcc ccaggcttgt ccacatcatc   32160
tgtgggaaac tcgcgtaaaa tcaggcgttt cgccgatttt gcgaggctgg ccagctccac   32220
gtcgccggcc gaaatcgagc ctgccccctca tctgtcaacg ccgcgccggg tgagtcggcc   32280
cctcaagtgt caacgtccgc ccctcatctg tcagtgaggg ccaagttttc cgcgaggtat   32340
ccacaacgcc ggcggccgcg gtgtctcgca cacggcttcg acggcgtttc tggcgcgttt   32400
gcagggccat agacggccgc cagcccagcg gcgagggcaa ccagcccggt gagcgtcgga   32460
aaggcgctgg aagccccgta gcgacgcgga gaggggcgag acaagccaag ggcgcaggct   32520
cgatgcgcag cacgacatag ccggttctcg caaggacgag aatttccctg cggtgccct    32580 caagtgtcaa tgaaagtttc caacgcgagc cattcgcgag agccttgagt ccacgctaga   32640
tgagagcttt gttgtaggtg daccagttgg tgattttgaa cttttgcttt gccacggaac   32700
ggtctgcgtt gtcgggaaga tgcgtgatct gatccttcaa ctcagcaaaa gttcgattta   32760
ttcaacaaag ccacgttgtg tctcaaaatc tctgatgtta cattgcacaa gataaaaata   32820
tatcatcatg aacaataaaa ctgtctgctt acataaacag taatacaagg ggtgttatga   32880
gccatattca acgggaaacg tcttgctcga ctctagagct cgttcctcga ggaacggtac   32940
ctgcggggaa gcttacaata atgtgtgttg ttaagtcttg ttgcctgtca tcgtctgact   33000
gactttcgtc ataaatcccg gcctccgtaa cccagctttg ggcaagctca cggatttgat   33060
ccggcggaac gggaatatcg agatgccggg ctgaacgctg cagttccagc tttcccttc    33120 gggacaggta ctccagctga ttgattatct gctgaagggc cttggttcca cctcctggca   33180
caatgcgaat gattacttga gcgcgatcgg gcatccaatt ttctcccgtc aggtgcgtgg   33240
tcaagtgcta caaggcacct ttcagtaacg agcgaccgtc gatccgtcgc gggatacgg    33300 acaaaatgga gcgcagtagt ccatcgaggg cggcgaaagc ctcgccaaaa gcaatacgtt   33360
catctcgcac agcctccaga tccgatcgag ggtcttcggc gtaggcagat agaagcatgg   33420
atacattgct tgagagtatt ccgatggact gaagtatggc ttccatcttt tctcgtgtgt   33480
ctgcatctat ttcgagaaag cccccgatgc ggcgcaccgc aacgcgaatt gccatactat   33540
ccgaaagtcc cagcaggcgc gcttgatagg aaaaggtttc atactcggcc gatcgcgac    33600 gggcactcac gaccttgaac ccttcaactt tcagggatcg atgctggttg atggtagtct   33660
cactcgacgt ggctctggtg tgttttgaca tagcttcctc caaagaaagc ggaaggtctg   33720
gatactccag cacgaaatgt gcccgggtag acggatggaa gtctagccct gctcaatatg   33780
```

```
aaatcaacag tacatttaca gtcaatactg aatatacttg ctacatttgc aattgtctta   33840
taacgaatgt gaaataaaaa tagtgtaaca acgcttttac tcatcgataa tcacaaaaac   33900
atttatacga acaaaaatac aaatgcactc cggtttcaca ggataggcgg gatcagaata   33960
tgcaactttt gacgttttgt tctttcaaag ggggtgctgg caaaaccacc gcactcatgg   34020
gcctttgcgc tgctttggca aatgacggta aacgagtggc cctctttgat gccgacgaaa   34080
accggcctct gacgcgatgg agagaaaacg ccttacaaag cagtactggg atcctcgctg   34140
tgaagtctat tccgccgacg aaatgcccct tcttgaagca gcctatgaaa atgccgagct   34200
cgaaggattt gattatgcgt tggccgatac gcgtggcggc tcgagcgagc tcaacaacac   34260
aatcatcgct agctcaaacc tgcttctgat ccccaccatg ctaacgccgc tcgacatcga   34320
tgaggcacta tctacctacc gctacgtcat cgagctgctg ttgagtgaaa atttggcaat   34380
tcctacagct gttttgcgcc aacgcgtccc ggtcggccga ttgacaacat cgcaacgcag   34440
gatgtcagag acgctagaga gccttccagt tgtaccgtct cccatgcatg aaagagatgc   34500
atttgccgcg atgaaagaac gcggcatgtt gcatcttaca ttactaaaca cgggaactga   34560
tccgacgatg cgcctcatag agaggaatct tcggattgcg atggaggaag tcgtggtcat   34620
ttcgaaactg atcagcaaaa tcttggaggc ttgaagatgg caattcgcaa gcccgcattg   34680
tcggtcggcg aagcacggcg gcttgctggt gctcgacccg agatccacca tcccaacccg   34740
acacttgttc cccagaagct ggacctccag cacttgcctg aaaaagccga cgagaaagac   34800
cagcaacgtg agcctctcgt cgccgatcac atttacagtc ccgatcgaca acttaagcta   34860
actgtggatg ccccttagtcc acctccgtcc ccgaaaaagc tccaggtttt tctttcagcg   34920
cgaccgcccg cgcctcaagt gtcgaaaaca tatgacaacc tcgttcggca atacagtccc   34980
tcgaagtcgc tacaaatgat tttaaggcgc gcgttggacg atttcgaaag catgctggca   35040
gatggatcat ttcgcgtggc cccgaaaagt tatccgatcc cttcaactac agaaaaatcc   35100
gttctcgttc agacctcacg catgttcccg gttgcgttgc tcgaggtcgc tcgaagtcat   35160
tttgatccgt tggggttgga gaccgctcga gctttcggcc acaagctggc taccgccgcg   35220
ctcgcgtcat tctttgctgg agagaagcca tcgagcaatt ggtgaagagg gacctatcgg   35280
aaccccctcac caaatattga gtgtaggttt gaggccgctg gccgcgtcct cagtcacctt   35340
ttgagccaga taattaagag ccaaatgcaa ttggctcagg ctgccatcgt cccccgtgc   35400
gaaacctgca cgtccgcgtc aaagaaataa ccggcacctc ttgctgtttt tatcagttga   35460
gggcttgacg gatccgcctc aagtttgcgg cgcagccgca aaatgagaac atctatactc   35520
ctgtcgtaaa cctcctcgtc gcgtactcga ctggcaatga gaagttgctc gcgcgataga   35580
acgtcgcggg gtttctctaa aaacgcgagg agaagattga actcacctgc cgtaagtttc   35640
acctcaccgc cagcttcgga catcaagcga cgttgcctga gattaagtgt ccagtcagta   35700
aaacaaaaag accgtcggtc tttggagcgg acaacgttgg ggcgcacgcg caaggcaacc   35760
cgaatgcgtg caagaaactc tctcgtacta acggcttag cgataaaatc acttgctcct   35820
agctcgagtg caacaacttt atccgtctcc tcaaggcggt cgccactgat aattatgatt   35880
ggaatatcag actttgccgc cagatttcga acgatctcaa gcccatcttc acgacctaaa   35940
tttagatcaa caaccacgac atcgaccgtc gcggaagaga gtactctagt gaactgggtg   36000
ctgtcggcta ccgcggtcac tttgaaggcg tggatcgtaa ggtattcgat aataagatgc   36060
cgcatagcga catcgtcatc gataagaaga acgtgtttca acggctcacc tttcaatcta   36120
aaatctgaac ccttgttcac agcgcttgag aaattttcac gtgaaggatg tacaatcatc   36180
```

```
tccagctaaa tgggcagttc gtcagaattg cggctgaccg cggatgacga aaatgcgaac    36240
caagtatttc aattttatga caaaagttct caatcgttgt tacaagtgaa acgcttcgag    36300
gttacagcta ctattgatta aggagatcgc ctatggtctc gccccggcgt cgtgcgtccg    36360
ccgcgagcca gatctcgcct acttcataaa cgtcctcata ggcacggaat ggaatgatga    36420
catcgatcgc cgtagagagc atgtcaatca gtgtgcgatc ttccaagcta gcaccttggg    36480
cgctactttt gacaagggaa aacagtttct tgaatccttg gattggattc gcgccgtgta    36540
ttgttgaaat cgatcccgga tgtcccgaga cgacttcact cagataagcc catgctgcat    36600
cgtcgcgcat ctcgccaagc aatatccggt ccggccgcat acgcagactt gcttggagca    36660
agtgctcggc gctcacagca cccagcccag caccgttctt ggagtagagt agtctaacat    36720
gattatcgtg tggaatgacg agttcgagcg tatcttctat ggtgattagc ctttcctggg    36780
gggggatggc gctgatcaag gtcttgctca ttgttgtctt gccgcttccg gtagggccac    36840
atagcaacat cgtcagtcgg ctgacgacgc atgcgtgcag aaacgcttcc aaatcccgt    36900 tgtcaaaatg ctgaaggata gcttcatcat cctgattttg gcgtttcctt cgtgtctgcc    36960
actggttcca cctcgaagca tcataacggg aggagacttc tttaagacca gaaacacgcg    37020
agcttggccg tcgaatggtc aagctgacgg tgcccgaggg aacggtcggc ggcagacaga    37080
tttgtagtcg ttcaccacca ggaagttcag tggcgcagag ggggttacgt ggtccgacat    37140
cctgctttct cagcgcgccc gctaaaatag cgatatcttc aagatcatca taagagacgg    37200
gcaaaggcat cttggtaaaa atgccggctt ggcgcacaaa tgcctctcca ggtcgattga    37260
tcgcaatttc ttcagtcttc gggtcatcga gccattccaa aatcggcttc agaagaaagc    37320
gtagttgcgg atccacttcc atttacaatg tatcctatct ctaagcggaa atttgaattc    37380
attaagagcg gcggttcctc ccccgcgtgg cgccgccagt caggcggagc tggtaaacac    37440
caaagaaatc gaggtcccgt gctacgaaaa tggaaacggt gtcaccctga ttcttcttca    37500
gggttggcgg tatgttgatg gttgccttaa gggctgtctc agttgtctgc tcaccgttat    37560
tttgaaagct gttgaagctc atcccgccac ccgagctgcc ggcgtaggtg ctagctgcct    37620
ggaaggcgcc ttgaacaaca ctcaagagca tagctccgct aaaacgctgc cagaagtggc    37680
tgtcgaccga gcccggcaat cctgagcgac cgagttcgtc cgcgcttggc gatgttaacg    37740
agatcatcgc atggtcaggt gtctcggcgc gatcccacaa cacaaaaacg cgcccatctc    37800
cctgttgcaa gccacgctgt atttcgccaa caacggtggt gccacgatca agaagcacga    37860
tattgttcgt tgttccacga atatcctgag gcaagacaca ctttacatag cctgccaaat    37920
ttgtgtcgat tgcggtttgc aagatgcacg gaattattgt cccttgcgtt accataaaat    37980
cggggtgcgg caagagcgtg gcgctgctgg gctgcagctc ggtgggtttc atacgtatcg    38040
acaaatcgtt ctcgccggac acttcgccat tcggcaagga gttgtcgtca cgcttgcctt    38100
cttgtcttcg gcccgtgtcg ccctgaatgg cgcgtttgct gacccttga tcgccgctgc    38160 tatatgcaaa aatcggtgtt tcttccggcc gtggctcatg ccgctccggt tcgcccctcg    38220
gcggtagagg agcagcaggc tgaacagcct cttgaaccgc tggaggatcc ggcggcacct    38280
caatcggagc tggatgaaat ggcttggtgt ttgttgcgat caagttgac ggcgatgcgt    38340 tctcattcac cttcttttgg cgcccaccta gccaaatgag gcttaatgat aacgcgagaa    38400
cgacacctcc gacgatcaat ttctgagacc ccgaaagacg ccggcgatgt ttgtcggaga    38460
ccagggatcc agatgcatca acctcatgtg ccgcttgctg actatcgtta ttcatcccctt    38520
```

```
cgcccccttc aggacgcgtt tcacatcggg cctcaccgtg cccgtttgcg gcctttggcc    38580
aacgggatcg taagcggtgt tccagataca tagtactgtg tggccatccc tcagacgcca    38640
acctcgggaa accgaagaaa tctcgacatc gctcccttta actgaatagt tggcaacagc    38700
ttccttgcca tcaggattga tggtgtagat ggagggtatg cgtacattgc ccggaaagtg    38760
gaataccgtc gtaaatccat tgtcgaagac ttcgagtggc aacagcgaac gatcgccttg    38820
ggcgacgtag tgccaattac tgtccgccgc accaagggct gtgacaggct gatccaataa    38880
attctcagct ttccgttgat attgtgcttc cgcgtgtagt ctgtccacaa cagccttctg    38940
ttgtgcctcc cttcgccgag ccgccgcatc gtcggcgggg taggcgaatt ggacgctgta    39000
atagagatcg ggctgctctt tatcgaggtg ggacagagtc ttggaactta tactgaaaac    39060
ataacggcgc atcccggagt cgcttgcggt tagcacgatt actggctgag gcgtgaggac    39120
ctggcttgcc ttgaaaaata gataaatttcc ccgcggtagg gctgctagat cttgctatt    39180
tgaaacggca accgctgtca ccgtttcgtt cgtggcgaat gttacgacca aagtagctcc    39240
aaccgccgtc gagaggcgca ccacttgatc gggattgtaa gccaaataac gcatgcgcgg    39300
atctagcttg cccgccattg gagtgtcttc agcctccgca ccagtcgcag cggcaaataa    39360
acatgctaaa atgaaaagtg cttttctgat catggttcgc tgtggcctac gtttgaaacg    39420
gtatcttccg atgtctgata ggaggtgaca accagacctg ccgggttggt tagtctcaat    39480
ctgccgggca agctggtcac cttttcgtag cgaactgtcg cggtccacgt actcaccaca    39540
ggcattttgc cgtcaacgac gagggtcctt ttatagcgaa tttgctgcgt gcttggagtt    39600
acatcatttg aagcgatgtg ctcgacctcc accctgccgc gtttgccaag aatgacttga    39660
ggcgaactgg gattgggata gttgaagaat tgctggtaat cctggcgcac tgttggggca    39720
ctgaagttcg ataccaggtc gtaggcgtac tgagcggtgt cggcatcata actctcgcgc    39780
aggcgaacgt actcccacaa tgaggcgtta acgacggcct cctcttgagt tgcaggcaat    39840
cgcgagacag acacctcgct gtcaacggtg ccgtccggcc gtatccatag atatacgggc    39900
acaagcctgc tcaacggcac cattgtggct atagcgaacg cttgagcaac atttcccaaa    39960
atcgcgatag ctgcgacagc tgcaatgagt ttggagagac gtcgcgccga tttcgctcgc    40020
gcggtttgaa aggcttctac ttccttatag tgctcggcaa ggctttcgcg cgccactagc    40080
atggcatatt caggccccgt catagcgtcc acccgaattg ccgagctgaa gatctgacgg    40140
agtaggctgc catcgcccca cattcagcgg gaagatcggg cctttgcagc tcgctaatgt    40200
gtcgtttgtc tggcagccgc tcaaagcgac aactaggcac agcaggcaat acttcataga    40260
attctccatt gaggcgaatt tttgcgcgac ctagcctcgc tcaacctgag cgaagcgacg    40320
gtacaagctg ctggcagatt gggttgcgcc gctccagtaa ctgcctccaa tgttgccggc    40380
gatcgccggc aaagcgacaa tgagcgcatc ccctgtcaga aaaacatat cgagttcgta    40440
aagaccaatg atcttggccg cggtcgtacc ggcgaaggtg attacaccaa gcataagggt    40500
gagcgcagtc gcttcggtta ggatgacgat cgttgccacg aggtttaaga ggagaagcaa    40560
gagaccgtag gtgataagtt gcccgatcca cttagctgcg atgtcccgcg tgcgatcaaa    40620
aatatatccg acgaggatca gaggcccgat cgcgagaagc actttcgtga gaattccaac    40680
ggcgtcgtaa actccgaagg cagaccagag cgtgccgtaa aggacccact gtgcccttg    40740
gaaagcaagg atgtcctggt cgttcatcgg accgatttcg gatgcgattt tctgaaaaac    40800
ggcctgggtc acgcgaaca ttgtatccaa ctgtgccgga acagtctgca gaggcaagcc    40860
ggttacacta aactgctgaa caaagtttgg gaccgtcttt tcgaagatgg aaaccacata    40920
```

```
gtcttggtag ttagcctgcc caacaattag agcaacaacg atggtgaccg tgatcacccg    40980
agtgataccg ctacgggtat cgacttcgcc gcgtatgact aaaatacccct gaacaataat    41040 ccaaagagtg acacaggcga tcaatggcgc actcaccgcc tcctggatag tctcaagcat    41100
cgagtccaag cctgtcgtga aggctacatc gaagatcgta tgaatggccg taaacggcgc    41160
cggaatcgtg aaattcatcg attggacctg aacttgactg gtttgtcgca taatgttgga    41220
taaaatgagc tcgcattcgg cgaggatgcg ggcggatgaa caaatcgccc agccttaggg    41280
gagggcacca agatgacag cggtctttg atgctccttg cgttgagcgg ccgcctcttc    41340
cgcctcgtga aggccggcct gcgcggtagt catcgttaat aggcttgtcg cctgtacatt    41400
ttgaatcatt gcgtcatgga tctgcttgag aagcaaacca ttggtcacgg ttgcctgcat    41460
gatattgcga gatcgggaaa gctgagcaga cgtatcagca ttcgccgtca agcgtttgtc    41520
catcgtttcc agattgtcag ccgcaatgcc agcgctgttt gcggaaccgg tgatctgcga    41580
tcgcaacagg tccgcttcag catcactacc cacgactgca cgatctgtat cgctggtgat    41640
cgcacgtgcc gtggtcgaca ttggcattcg cggcgaaaac atttcattgt ctaggtcctt    41700
cgtcgaagga tactgatttt tctggttgag cgaagtcagt agtccagtaa cgccgtaggc    41760
cgacgtcaac atcgtaacca tcgctatagt ctgagtgaga ttctccgcag tcgcgagcgc    41820
agtcgcgagc gtctcagcct ccgttgccgg gtcgctaaca caaactgcg cccgcgcggg    41880 ctgaatatat agaaagctgc aggtcaaaac tgttgcaata agttgcgtcg tcttcatcgt    41940
ttcctacctt atcaatcttc tgcctcgtgg tgacgggcca tgaattcgct gagccagcca    42000
gatgagttgc cttcttgtgc ctcgcgtagt cgagttgcaa agcgcaccgt gttggcacgc    42060
cccgaaagca cggcgacata ttcacgcata tcccgcagat caaattcgca gatgacgctt    42120
ccactttctc gtttaagaag aaacttacgg ctgccgaccg tcatgtcttc acggatcgcc    42180
tgaaattcct tttcggtaca tttcagtcca tcgacataag ccgatcgatc tgcggttggt    42240
gatggataga aaatcttcgt catacattgc gcaaccaagc tggctcctag cggcgattcc    42300
agaacatgct ctggttgctg cgttgccagt attagcatcc cgttgttttt tcgaacggtc    42360
aggaggaatt tgtcgacgac agtcgaaaat ttagggttta acaaataggc gcgaaactca    42420
tcgcagctca tcacaaaacg gcggccgtcg atcatggctc caatccgatg caggagatat    42480
gctgcagcgg gagcgcatac ttcctcgtat tcgagaagat gcgtcatgtc gaagccggta    42540
atcgacggat ctaactttac ttcgtcaact tcgccgtcaa atgcccagcc aagcgcatgg    42600
ccccggcacc agcgttggag ccgcgctcct gcgccttcgg cgggcccatg caacaaaaat    42660
tcacgtaacc ccgcgattga acgcatttgt ggatcaaacg agagctgacg atggatacca    42720
cggaccagac ggcggttctc ttccggagaa atcccacccc gaccatcact ctcgatgaga    42780
gccacgatcc attcgcgcag aaaatcgtgt gaggctgctg tgttttctag gccacgcaac    42840
ggcgccaacc cgctgggtgt gcctctgtga agtgccaaat atgttcctcc tgtggcgcga    42900
accagcaatt cgccaccccg gtccttgtca aagaacacga ccgtacctgc acggtcgacc    42960
atgctctgtt cgagcatggc tagaacaaac atcatgagcg tcgtcttacc cctcccgata    43020
ggcccgaata ttgccgtcat gccaacatcg tgctcatgcg ggatatagtc gaaaggcgtt    43080
ccgccattgg tacgaaatcg ggcaatcgcg ttgccccagt ggcctgagct ggcgccctct    43140
ggaaagtttt cgaaagagac aaaccctgcg aaattgcgtg aagtgattgc ccagggcgt    43200 gtgcgccact taaaattccc cggcaattgg gaccaatagg ccgcttccat accaatacct    43260
```

```
tcttggacaa ccacggcacc tgcatccgcc attcgtgtcc gagcccgcgc gcccctgtcc    43320
ccaagactat tgagatcgtc tgcatagacg caaaggctca aatgatgtga gcccataacg    43380
aattcgttgc tcgcaagtgc gtcctcagcc tcggataatt tgccgatttg agtcacggct    43440
ttatcgccgg aactcagcat ctggctcgat ttgaggctaa gtttcgcgtg cgcttgcggg    43500
cgagtcagga acgaaaaact ctgcgtgaga acaagtggaa atcgaggga tagcagcgcg     43560 ttgagcatgc ccggccgtgt ttttgcaggg tattcgcgaa acgaatagat ggatccaacg    43620
taactgtctt ttggcgttct gatctcgagt cctcgcttgc cgcaaatgac tctgtcggta    43680
taaatcgaag cgccgagtga gccgctgacg accggaaccg gtgtgaaccg accagtcatg    43740
atcaaccgta gcgcttcgcc aatttcggtg aagagcacac cctgcttctc gcggatgcca    43800
agacgatgca ggccatacgc tttaagagag ccagcgacaa catgccaaag atcttccatg    43860
ttcctgatct ggcccgtgag atcgttttcc cttttccgc ttagcttggt gaacctcctc     43920
tttaccttcc ctaaagccgc ctgtgggtag acaatcaacg taaggaagtg ttcattgcgg    43980
aggagttggc cggagagcac gcgctgttca aaagcttcgt tcaggctagc ggcgaaaaca    44040
ctacggaagt gtcgcggcgc cgatgatggc acgtcggcat gacgtacgag gtgagcatat    44100
attgacacat gatcatcagc gatattgcgc aacagcgtgt tgaacgcacg acaacgcgca    44160
ttgcgcattt cagtttcctc aagctcgaat gcaacgccat caattctcgc aatggtcatg    44220
atcgatccgt cttcaagaag gacgatatgg tcgctgaggt ggccaatata agggagatag    44280
atctcaccgg atcttttcggt cgttccactc gcgccgagca tcacaccatt cctctccctc    44340 gtggggggaac cctaattgga tttgggctaa cagtagcgcc cccccaaact gcactatcaa    44400
tgcttcttcc cgcggtccgc aaaaatagca ggacgacgct cgccgcattg tagtctcgct    44460
ccacgatgag ccgggctgca aaccataacg gcacgagaac gacttcgtag agcgggttct    44520
gaacgataac gatgacaaag ccggcgaaca tcatgaataa ccctgccaat gtcagtggca    44580
ccccaagaaa caatgcgggc cgtgtggctg cgaggtaaag ggtcgattct tccaaacgat    44640
cagccatcaa ctaccgccag tgagcgtttg gccgaggaag ctcgcgccaa acatgataac    44700
aatgccgccg acgacgccgg caaccagccc aagcgaagcc cgcccgaaca tccaggagat    44760
cccgatagcg acaatgccga gaacagcgag tgactggccg aacggaccaa ggataaacgt    44820
gcatatattg ttaaccattg tggcggggtc agtgccgcca cccgcagatt gcgctgcggc    44880
gggtccggat gaggaaatgc tccatgcaat tgcaccgcac aagcttgggg cgcagctcga    44940
tatcacgcgc atcatcgcat tcgagagcga gaggcgattt agatgtaaac ggtatctctc    45000
aaagcatcgc atcaatgcgc acctccttag tataagtcga ataagacttg attgtcgtct    45060
gcggatttgc cgttgtcctg gtgtggcggt ggcggagcga ttaaaccgcc agcgccatcc    45120
tcctgcgagc ggcgctgata tgaccccccaa acatcccacg tctcttcgga ttttagcgcc    45180
tcgtgatcgt cttttggagg ctcgattaac gcgggcacca gcgattgagc agctgtttca    45240
acttttcgca cgtagccgtt tgcaaaaccg ccgatgaaat taccggtgtt gtaagcggag    45300
atcgcccgac gaagcgcaaa ttgcttctcg tcaatcgttt cgccgcctgc ataacgactt    45360
ttcagcatgt ttgcagcggc agataatgat gtgcacgcct ggagcgcacc gtcaggtgtc    45420
agaccgagca tagaaaaatt tcgagagttt atttgcatga ggccaacatc cagcgaatgc    45480
cgtgcatcga gacggtgcct gacgacttgg gttgcttggc tgtgatcttg ccagtgaagc    45540
gtttcgccgg tcgtgttgtc atgaatcgct aaaggatcaa agcgactctc cacccttagct   45600 atcgccgcaa gcgtagatgt cgcaactgat ggggcacact tgcgagcaac atggtcaaac    45660
```

```
tcagcagatg agagtggcgt ggcaaggctc gacgaacaga aggagaccat caaggcaaga    45720
gaaagcgacc ccgatctctt aagcatacct tatctcctta gctcgcaact aacaccgcct    45780
ctcccgttgg aagaagtgcg ttgttttatg ttgaagatta tcgggagggt cggttactcg    45840
aaaattttca attgcttctt tatgatttca attgaagcga gaaacctcgc ccggcgtctt    45900
ggaacgcaac atggaccgag aaccgcgcat ccatgactaa gcaaccggat cgacctattc    45960
aggccgcagt tggtcaggtc aggctcagaa cgaaaatgct cggcgaggtt acgctgtctg    46020
taaacccatt cgatgaacgg gaagcttcct tccgattgct cttggcagga atattggccc    46080
atgcctgctt gcgctttgca aatgctctta tcgcgttggt atcatatgcc ttgtccgcca    46140
gcagaaacgc actctaagcg attatttgta aaaatgtttc ggtcatgcgg cggtcatggg    46200
cttgacccgc tgtcagcgca agacggatcg gtcaaccgtc ggcatcgaca acagcgtgaa    46260
tcttggtggt caaaccgcca cgggaacgtc ccatacagcc atcgtcttga tcccgctgtt    46320
tcccgtcgcc gcatgttggt ggacgcggac acaggaactg tcaatcatga cgacattcta    46380
tcgaaagcct tggaaatcac actcagaata tgatcccaga cgtctgcctc acgccatcgt    46440
acaaagcgat tgtagcaggt tgtacaggaa ccgtatcgat caggaacgtc tgcccagggc    46500
gggcccgtcc ggaagcgcca caagatgaca ttgatcaccc gcgtcaacgc gcggcacgcg    46560
acgcggctta tttgggaaca aaggactgaa caacagtcca ttcgaaatcg gtgacatcaa    46620
agcggggacg ggttatcagt ggcctccaag tcaagcctca atgaatcaaa atcagaccga    46680
tttgcaaacc tgatttatga gtgtgcggcc taaatgatga aatcgtcctt ctagatcgcc    46740
tccgtggtgt agcaacacct cgcagtatcg ccgtgctgac cttggccagg gaattgactg    46800
gcaagggtgc tttcacatga ccgctctttt ggccgcgata gatgatttcg ttgctgcttt    46860
gggcacgtag aaggagagaa gtcatatcgg agaaattcct cctggcgcga gagcctgctc    46920
tatcgcgacg gcatcccact gtcgggaaca gaccggatca ttcacgaggc gaaagtcgtc    46980
aacacatgcg ttataggcat cttcccttga aggatgatct tgttgctgcc aatctggagg    47040
tgcggcagcc gcaggcagat gcgatctcag cgcaacttgc ggcaaaacat ctcactcacc    47100
tgaaaaccac tagcgagtct cgccgatcaga cgaaggcctt ttacttaacg acacaatatc    47160
cgatgtctgc atcacaggcg tcgctatccc agtcaatact aaagcggtgc aggaactaaa    47220
gattactgat gacttaggcg tgccacgagg cctgagacga cgcgcgtaga cagttttttg    47280
aaatcattat caaagtgatg gcctccgctg aagcctatca cctctgcgcc ggtctgtcgg    47340
agagatgggc aagcattatt acggtcttcg cgcccgtaca tgcattggac gattgcaggg    47400
tcaatggatc tgagatcatc cagaggattg ccgcccttac cttccgtttc gagttggagc    47460
cagcccctaa atgagacgac atagtcgact tgatgtgaca atgccaagag agagatttgc    47520
ttaacccgat tttttttgctc aagcgtaagc ctattgaagc ttgccggcat gacgtccgcg    47580
ccgaaagaat atcctacaag taaaacattc tgcacaccga aatgcttggt gtagacatcg    47640
attatgtgac caagatcctt agcagtttcg cttggggacc gctccgacca gaaataccga    47700
agtgaactga cgccaatgac aggaatccct tccgtctgca gataggtacc atcgatagat    47760
ctgctgcctc gcgcgtttcg gtgatgacgg tgaaaacctc tgcacacatgc agctcccgga    47820 gacggtcaca gcttgtctgt aagcggatgc cgggagcaga caagcccgtc agggcgcgtc    47880
agcgggtgtt ggcgggtgtc ggggcgcagc catgacccag tcacgtagcg atagcggagt    47940
gtatactggc ttaactatgc ggcatcagag cagattgtac tgagagtgca ccatatgcgg    48000
```

```
tgtgaaatac cgcacagatg cgtaaggaga aaataccgca tcaggcgctc ttccgcttcc   48060
tcgctcactg actcgctgcg ctcggtcgtt cggctgcggc gagcggtatc agctcactca   48120
aaggcggtaa tacggttatc cacagaatca ggggataacg caggaaagaa catgtgagca   48180
aaaggccagc aaaaggccag gaaccgtaaa aaggccgcgt tgctggcgtt tttccatagg   48240
ctccgccccc ctgacgagca tcacaaaaat cgacgctcaa gtcagaggtg gcgaaacccg   48300
acaggactat aaagatacca ggcgtttccc cctggaagct ccctcgtgcg ctctcctgtt   48360
ccgaccctgc cgcttaccgg atacctgtcc gcctttctcc cttcgggaag cgtggcgctt   48420
tctcatagct cacgctgtag gtatctcagt tcggtgtagg tcgttcgctc caagctgggc   48480
tgtgtgcacg aaccccccgt tcagcccgac cgctgcgcct tatccggtaa ctatcgtctt   48540
gagtccaacc cggtaagaca cgacttatcg ccactggcag cagccactgg taacaggatt   48600
agcagagcga ggtatgtagg cggtgctaca gagttcttga agtggtggcc taactacggc   48660
tacactagaa ggacagtatt tggtatctgc gctctgctga agccagttac cttcggaaaa   48720
agagttggta gctcttgatc cggcaaacaa accaccgctg gtagcggtgg tttttttgtt   48780
tgcaagcagc agattacgcg cagaaaaaaa ggatctcaag aagatccttt gatcttttct   48840
acggggtctg acgctcagtg gaacgaaaac tcacgttaag gattttggt catgagatta   48900
tcaaaaagga tcttcaccta gatccttttta aattaaaaat gaagttttaa atcaatctaa   48960
agtatatatg agtaaacttg gtctgacagt taccaatgct taatcagtga ggcacctatc   49020
tcagcgatct gtctatttcg ttcatccata gttgcctgac tccccgtcgt gtagataact   49080
acgatacggg agggcttacc atctggcccc agtgctgcaa tgataccgcg agacccacgc   49140
tcaccggctc cagatttatc agcaataaac cagccagccg aagggccga gcgcagaagt   49200
ggtcctgcaa ctttatccgc ctccatccag tctattaatt gttgccggga agctagagta   49260
agtagttcgc cagttaatag tttgcgcaac gttgttgcca ttgctgcagg ggggggggg   49320
ggggggact tccattgttc attccacgga caaaaacaga gaaggaaac gacagaggcc   49380
aaaaagcctc gctttcagca cctgtcgttt cctttctttt cagagggtat tttaaataaa   49440
aacattaagt tatgacgaag aagaacggaa acgccttaaa ccggaaaatt ttcataaata   49500
gcgaaaaccc gcgaggtcgc cgccccggtc ggatcaccgg aaaggacccg taaagtgata   49560
atgattatca tctacatatc acaacgtgcg tggaggccat caaaccacgt caaataatca   49620
attatgacgc aggtatcgta ttaattgatc tgcatcaact taacgtaaaa acaacttcag   49680
acaatacaaa tcagcgacac tgaatacggg gcaacctcat gtccccccc cccccccc   49740
tgcaggcatc gtggtgtcac gctcgtcgtt tggtatggct tcattcagct ccggttccca   49800
acgatcaagg cgagttacat gatccccccat gttgtgcaaa aaagcggtta gctccttcgg   49860
tcctccgatc gttgtcagaa gtaagttggc cgcagtgtta tcactcatgg ttatggcagc   49920
actgcataat tctcttactg tcatgccatc cgtaagatgc ttttctgtga ctggtgagta   49980
ctcaaccaag tcattctgag aatagtgtat gcggcgaccg agttgctctt gcccggcgtc   50040
aacacgggat aataccgcgc cacatagcag aactttaaaa gtgctcatca ttggaaaacg   50100
ttcttcgggg cgaaaactct caaggatctt accgctgttg agatccagtt cgatgtaacc   50160
cactcgtgca cccaactgat cttcagcatc ttttactttc accagcgttt ctgggtgagc   50220
aaaaacagga aggcaaaatg ccgcaaaaaa gggaataagg gcgacacgga aatgttgaat   50280
actcatactc ttcctttttc aatattattg aagcatttat cagggttatt gtctcatgag   50340
cggatacata tttgaatgta tttagaaaaa taaacaaata ggggttccgc gcacatttcc   50400
```

```
ccgaaaagtg ccacctgacg tctaagaaac cattattatc atgacattaa cctataaaaa    50460
taggcgtatc acgaggccct ttcgtcttca agaattggtc gacgatcttg ctgcgttcgg    50520
atattttcgt ggagttcccg ccacagaccc ggattgaagg cgagatccag caactcgcgc    50580
cagatcatcc tgtgacggaa cttttggcgcg tgatgactgg ccaggacgtc ggccgaaaga    50640
gcgacaagca gatcacgctt ttcgacagcg tcggatttgc gatcgaggat ttttcggcgc    50700
tgcgctacgt ccgcgaccgc gttgagggat caagccacag cagcccactc gaccttctag    50760
ccgacccaga cgagccaagg gatcttttg gaatgctgct ccgtcgtcag gctttccgac    50820
gtttgggtgg ttgaacagaa gtcattatcg tacggaatgc caagcactcc cgaggggaac    50880
cctgtggttg gcatgcacat acaaatggac gaacggataa accttttcac gcccttttaa    50940
atatccgtta ttctaataaa cgctcttttc tcttag                              50976
```

<210> SEQ ID NO 136
<211> LENGTH: 1000
<212> TYPE: DNA
<213> ORGANISM: Zea mays

<400> SEQUENCE: 136

```
tgccacgcaa actaaaaggc aaattctaca ggacagcaat ccggccggct atgttgtatg     60
gagcagaatg ttggcccact aaaagacgac atgtccaaca actaagtgtg cagagatgc    120 gtatgttgcg ctggatatgt ggccacacaa ggagagatcg agtccggaat gatgatatac    180
gagagagagt aggagtggcg ccaattgagg agaagcttat gcaacatcgc ttgagatggt    240
ttggacatat ccaacgaaga cctgaagagg caccagtgca tatcggaata attaggcgtc    300
ccgaaaatgt gaagagagagt agaggtcgac caactttgac gtggacagag gctgtgaaga    360
gagacctgaa ggagtggaat aatgacaaag agctcgccgc agataggaag gggtggaagt    420
gtgcaattca cgtgccagaa ccctgattga tagtttcgct tttcctcctt aatcgtttga    480
ccttttcttg tgtccatttt agatcttgct ggtccttgtg ggttttatct cttttatgtg    540
tttccccgtt tcgttgtttt cggttctcct ttgcctttgt ttcccttttc tgttcttcgg    600
gggttgagct ctgaggtttt catacgggt ttcatctcta gcctacccca acgtgcttgg    660
gacaaaaagg ctttgttgtt gttgttgttg ttgtatctgt atcctaaaag gtgagagaga    720
agggttatta agaaaaaccc tcgtcgctgg ccactgaagg ccgggcccaa tttagaacct    780
agacctgctg ccaccgcact acaagaccga ggcctaaaag gcccatcagg aggcgcatcg    840
gcgaatgccc caaactaaaa ccctacccg gcaagtatat atatcctccc aacctcagtt    900
cttgttccca ttatcacggc ggcggtggcg gagcgtaagg cgaaggagta gcagcagcag    960
gcggcgccga gtagcggctc cccatctcga gcttgccacc                         1000
```

<210> SEQ ID NO 137
<211> LENGTH: 855
<212> TYPE: DNA
<213> ORGANISM: Zea mays

<400> SEQUENCE: 137

```
gtaaggttcc cttccctcct ccctcacac ccctgttcgt gttccttcgg atcggatctc     60
agtggtgatg ttagacgtcc gcggctgcct acgtagtggc attgccgccc gaaaggtttg    120
tttaggtggg gtagatccga aacaggccgg atctggacca tgtccgcggc ggggcggcgg    180
gacttgatcg cgtagctgtc gtgtgcattt ctccctacca gtggcggaat cggcgatgtg    240
```

```
gacctaaggg ctaaggctta tctgctgcct tgaccatttc gtcgctgaca aaaacaaagt    300
gacaatcatg ccgttctctg tttgtttatc tggatcgtta ttacgctgtg aatcctgcga    360
tatgtggcta agtgattttt cttctttttc tgggggcagt ttagcctttg acccagtcct    420
aggtgtggtc actaggactg tgtagcatga tgagtgaggt tgcagcaggc tgattgctag    480
tggacgtttt ttccccaatt tgttaggttt tcacgctcca ggttgtgcaa gtaattttgc    540
tagtgattgt gtgatccatc ttcaacgttg aaccttgttt ttcccctaa aaccccaac     600 aggaaatctt gccccgactt ctattgcaaa aattgtaacg cttagcaccc tgattgactc    660
aattcctgtc actaggcatg ctcggtcaaa agcagatgat ttaccactta gaaactgccc    720
tgcccctgct ttccacatag catttcgaac tttttgacta ctattgacac cccctaact    780 tgccgaacta tttctctctt cagctactat ttacctagtt ataattacat aaatgtttgt    840
gtgtatcttg tgcag                                                    855

<210> SEQ ID NO 138
<211> LENGTH: 884
<212> TYPE: DNA
<213> ORGANISM: Zea mays

<400> SEQUENCE: 138
gtgaggcatc cgatcgattt ttctttcttt ctttactaca ctccttcgcg atatggggac     60
ggcactcggt agtggcgtga ggtgcggtaa atcgcgttag tttagttgta gggtttgatc    120
gcttcggggg ggaccggggg ttgggcttcc cgtgttgaac cgtcaatcgg acgtagtagt    180
agtgcggatt cggggtttga tcgacggaaa gaggggttgt ccgcactctt ggtgtggtta    240
tagggttttg cgatttgttt gtctgtgtag gcccgtttcg tctcggggag tagattttca    300
ttgctactac caatccctat gtgctttggt gaacacgtat tttggtctgt atatggttta    360
aacgtgaaga ctatggtagt gtgagaccat gatttggatc cttttctgtg gcattatagt    420
taaaatcgtg aggatctatc ttttagcgct tagggtattg ttatagacga gatcccctct    480
ttgggctcta aaaatagcaa gaaaaggaca tcttttgggc aagttaacgt cctgtattat    540
tctgaacgag atctgtttac tttcttataa gtttgatgtt ttggtctgga atatggttgc    600
gttcatcgtc caattagtgt gtttgcagta tgtgttggtg tagttcctct gtgggcatttc   660 tgtggcccca gaaatgatag attttaagaa aggtttaggc agaagggggat cttaagtgtt    720 gtccagtaca aagtaacaat ttgtagcact tgtttctttt cttttgtttg actatatgaa    780
atttcggcca tgtaattgtt tcaaaataat aagatcgaat agtgttgcac actacttccc    840
agtcctatgt atacttatca gattttttcct ctttgatatt tcag                    884

<210> SEQ ID NO 139
<211> LENGTH: 1487
<212> TYPE: DNA
<213> ORGANISM: zea mays

<400> SEQUENCE: 139
ccggctatac cgctcccgcc ctcgtttttc agtaaaaaaa atatggtaat ggaagtggga     60
gagagttttt ccaactgttt ccgatcgttt tcatccctat ctataaacat ccacatgagt    120
aggggaggcg gggtggcgag tggacgacac tgtagccaac ctaaggacca aagctttagc    180
cttaaccatt gcaccatgtg tcgcttattg ttatatagag tatataaatg tatatagtaa    240
caatttgaaa attaaaatta aaatcatgat tgaataaaaa tctcatttaa ataaaaaatt    300
acatatatga tatatagaat tcataacaat gtacgagtaa ctaactagtt ctatacttaa    360
```

```
gcataaatag aaagcgtagc aatgtatgca cactttgcta gtcggatatt tagatactag      420
ttagaagtat taaatatagt ctaagtataa aactaattat atagatgagg actaaacagc      480
aagacgaacc tattaagttt aagtagtcca tggttcgtcc atgtaaaata aatatttgct      540
aataatagat taattagact taatagatcc atctcgtcgt ttagtcttta tctatataat      600
tacttttgta gttagactat atttaatttt agtaattgac atttaaacat ccgatatgat      660
ccagacttga tgttagtcag gaaaaccaaa catcccctta accatattgg tcccaatttt      720
tggtgccttt acccatcaaa tgatattcac acaatcacac atctgggcct aactttcatc      780
gttgctgtcc acgacggcga cctggaggcg aggtcaattc cttggcccaa gcatagcttg      840
gagcttgcac gctaagaaga ggctctcgta ctctacaaac agtacagcac atacaggtga      900
caaaacgaca cacatcaacc agccaaataa taatgagctc tcttcatggg cacggcaagc      960
cgacaactac caacaagata caggtgacaa aaagaaaaca agaggccccc actcaccagt     1020
gggtcgtagg caacgcacgc ggacgcggtc cagcgggcga gaagatcccc gacttgcgcc     1080
caaagaagat acaggatcaa ggattttttaa ccgcagtttt ctattccacg accttatcca     1140
caccagcaga ttcgaaattc acggacaggc ccatggaccc ggcgaaagcc agcggtggtt     1200
cagcccctga cgtgcgggtc ccactctcca gccgcaccgc ctagagaggc agaggcatcc     1260
cttcgcgtgg aagcaaacga ggcgtgataa agtggggctc ctcggtcccg gcgttggccg     1320
catcgacact cgccgcgcac caccaccacc gctgcggctc acggctacgc agcccgctct     1380
cccgaccccc ccgtgccctc ctcttttttgc tactagcaca tagagtttcg cccgaatcga     1440
tcgccgactg actccgctag ggttcggccc gatcgccgct tcgtcct                   1487

<210> SEQ ID NO 140
<211> LENGTH: 629
<212> TYPE: DNA
<213> ORGANISM: zea mays

<400> SEQUENCE: 140
atcctctgaa tgtgctgtgt tgagagtttt ttctagttgc tctgcaagga tatagaacaa       60
tgttctaaga ctaccatgtt tttaagtctg cctgatgctt ataattcatg aacgattttt      120
gcagctagct gtaatgtgac tatttatctt atctgcttgt tcaaccctgt tgtcgtgtgt      180
tgattctctg tttcatggtc ttttcactcg acagaaacag ttatttctta agaacttcac      240
cattatattc acagctgtga actatgatat tggaagtctt tggtcatttt tcgttgaact      300
attttgctga aagttttttc cgagaaagat gccagaccgg tctccgatct aagaatggcc      360
ataactgatg agcatcacaa ggtatatatt agttgatcaa atgtctttga gtacatctgt      420
ttgacacagc ttattttttag cttcttcaca tatttaagca tagcttattt ttagcttctt      480
ttaatattta agcagaagtt ttactaaact ggtagcatct ccagcagctt attagttcag      540
ctgactctta gaatgaacta aaagcagcca acaagtataa gctattttttt accagtttct      600 tagataactt gttttttctaa caaatagtg                                       629

<210> SEQ ID NO 141
<211> LENGTH: 607
<212> TYPE: DNA
<213> ORGANISM: zea mays

<400> SEQUENCE: 141
gccatcagtc gttgaagctg ctgctgtatc tgggttatct agtgtctctg ccattgccca       60
```

```
tggatggtgc tgtctttcaa agtatttgta tggtttgtgt cgtgagtcgt gactgagctg      120
gtttcatgga ccagttgtgt tctcgttacc caaaactatc gtgcgaccgc atatggctta      180
atcatgaata aatgttgttt gaatttaaac tattcgctga atattgttgt tttttgtcat      240
gtcagttaat gttactaaat tggttgcctt ctaattttttg tttactggtg tttgtcgcac     300
cttatctttt tactgtatgt ttacttcagg ttctggcagt ctcattttttt gtgactagtt     360 aaaacttaca gctaaaaaaa tgcagttttt cattttcatt tgaagtttga ttagagctat      420
tgataccgga ccatcaggtt aggttagttg tgcatagaat cataaatatt aatcatgttt      480
tctatgaatt aagtcaaact tgaaagtctg gctgaatata gtttctatga atcatattga      540
tatacatgtt tgattatttg ttttgctatt agctatttac tttggtgaat ctatataggc      600
ttatgca                                                                607

<210> SEQ ID NO 142
<211> LENGTH: 646
<212> TYPE: DNA
<213> ORGANISM: zea mays

<400> SEQUENCE: 142
cgcttttagt atggcctcgg aaacatggcc tgcctgttgc tagtagaaag ctagcactgc       60
ccttttggta agggcgtttc aggagcactg tgctggacta tatagagaga tgctcctctg      120
tgactgtgac cacctcacgt tctgcgtact ctgtaatctg gtaggatgcc tgtctctatc      180
atgattcatg aaggacgatt ggtctgtctt tttttttatcg tgctatttat taatcgtgta    240
aatgtactag cgaagggaag gcactggtag ctaggttagc tcgagtccgg atggaatgat      300
aatgctacta atacaaacaa tgccgtagtg tgtgtgtgta tttatcaact cgcgtgtcat      360
cacgtccgtt aagttgccgc tggtatctcc ctccctgtcg gtggcgcgta ttctcggcgc      420
actcctctga accagcatga attcagagca aggtagaggg gcctgtaaac cgtccaccat      480
ctgtctagct gttcttggta gaacacttgc agagattctc agctctctct ctctctctct      540
ctctctctct ctctctctcg tcccgtccta gcggacaagc ggagtggggc tccctcgctc      600
tgtgtcactg cttgctgcat cgctgaaagc ggtagatgcg gcggta                     646

<210> SEQ ID NO 143
<211> LENGTH: 936
<212> TYPE: DNA
<213> ORGANISM: zea mays

<400> SEQUENCE: 143
agatcgtgtg ctatctaagt atatattcgt aaataatgag acggctgtgc cactgcggtg       60
cagccctggt gcgtctcaga gcttgcttat ggtgaactct tcgtgttagg tttcttcctt      120
atatctgtcg tgtctgcggt gtcgatgaac tatctagtat gtggagcgtg tgcgtctcag      180
cagttaccct gccatgccac gtggactggc tgtcgtgcct actgtctgtt accatgtata      240
tatataaaaa atgatgcgtg gaccaatgtt tgatgctggc gctcttgccc tcgtgataat      300
gtattagcgg ttggcttgtt gcttgcttgt cagccccagg taaatcttgc tgcttgcttt      360
gcttgcagaa gcgagcgtct gcacgtacgt aatcaggata actgtatgca gcgatttggt      420
gatatgcact gccagtggag tttgcttcac aaagaatgga atggaacctg gcgaccctac      480
gtggagtttg cgcaccgatg taaggagctg gaggccggct ccgaggacta ttgcttccac      540
ttcctatatg tggcacgctg aagggcaatg ccgtgtttta gttgaaattt ggccagtcc       600 acgagcaatg tggtgtttct actctctgta tctctactaa tattaccaaa atcaaatcct      660
```

```
ctgattatct ctacctgtct ttatcagcca ttggtatttt gggtgtgtgt gtgtttcatc    720
tttatctacg tgcttctgta gaaagatggc aggcaaaatc gtttggggttg tagttgtagg   780 tagtagctac aaagagacga gacttgggag gtgattatct tttgtagagt gaatagcttg    840
aatgaataac cgtttgtgtc tatgtaggac ccactgaata ttcaggagaa aaactgttgt    900
catatattgc gtgctattca agctcgcttc tgcctt                              936
```

<210> SEQ ID NO 144
<211> LENGTH: 16437
<212> TYPE: DNA
<213> ORGANISM: Artificial sequence
<220> FEATURE:
<223> OTHER INFORMATION: Vector sequence

<400> SEQUENCE: 144

```
gtttacccgc caatatatcc tgtcaaacac tgatagttta aactgaaggc gggaaacgac     60
aatctgatca tgagcggaga attaagggag tcacgttatg accccgccg atgacgcggg    120 acaagccgtt ttacgtttgg aactgacaga accgcaacgt tgaaggagcc actcagcaag    180
ctggtacgat tgtaatacga ctcactatag ggcgaattga gcgctgttta aacgctcttc    240
aactggaaga gcggttacca gagctggtca cctttgtcca ccaagatgga actgcggcct    300
cgaagctggc gcgccgtgca gcgtgacccg gtcgtgcccc tctctagaga taatgagcat    360
tgcatgtcta agttataaaa aattaccaca tatttttttt gtcacacttg tttgaagtgc    420
agtttatcta tctttataca tatatttaaa ctttactcta cgaataatat aatctatagt    480
actacaataa tatcagtgtt ttagagaatc atataaatga acagttagac atggtctaaa    540
ggacaattga gtattttgac aacaggactc tacagtttta tcttttttagt gtgcatgtgt    600 tctcctttt ttttgcaaat agcttcacct atataatact tcatccattt tattagtaca    660
tccatttagg gtttagggtt aatggttttt atagactaat ttttttagta catctatttt    720
attctatttt agcctctaaa ttaagaaaac taaaactcta tttttagtttt tttatttaat    780 aatttagata taaaatagaa taaaataaag tgactaaaaa ttaaacaaat accctttaag    840
aaattaaaaa aactaaggaa acatttttct tgtttcgagt agataatgcc agcctgttaa    900
acgccgtcga cgagtctaac ggacaccaac cagcgaacca gcagcgtcgc gtcgggccaa    960
gcgaagcaga cggcacggca tctctgtcgc tgcctctgga cccctctcga gagttccgct   1020
ccaccgttgg acttgctccg ctgtcggcat ccagaaattg cgtggcggag cggcagacgt   1080
gagccggcac ggcaggcggc ctcctcctcc tctcacggca ccggcagcta cggggggattc   1140 cttcccacc gctccttcgc tttcccttcc tcgcccgccg taataaatag cacccctc    1200 cacccctct ttccccaacc tcgtgttgtt cggagcgcac acacacacaa ccagatctcc   1260
cccaaatcca cccgtcggca cctccgcttc aaggtacgcc gctcgtcctc ccccccccc   1320 ctctctacct tctctagatc ggcgttccgg tccatgcatg gttagggccc ggtagttcta   1380
cttctgttca tgtttgtgtt agatccgtgt ttgtgttaga tccgtgctgc tagcgttcgt   1440
acacggatgc gacctgtacg tcagacacgt tctgattgct aacttgccag tgtttctctt   1500
tggggaatcc tgggatggct ctagccgttc cgcagacggg atcgatttca tgatttttt   1560 tgtttcgttg catagggttt ggtttgccct tttcctttat ttcaatatat gccgtgcact   1620
tgtttgtcgg gtcatctttt catgcttttt tttgtcttgg ttgtgatgat gtggtctggt   1680
tgggcggtcg ttctagatcg gagtagaatt ctgtttcaaa ctacctggtg gatttattaa   1740
```

```
ttttggatct gtatgtgtgt gccatacata ttcatagtta cgaattgaag atgatggatg    1800
gaaatatcga tctaggatag gtatacatgt tgatgcgggt tttactgatg catatacaga    1860 gatgctttttt gttcgcttgg ttgtgatgat gtggtgtggt tgggcggtcg ttcattcgtt   1920
ctagatcgga gtagaatact gtttcaaact acctggtgta tttattaatt ttggaactgt    1980
atgtgtgtgt catacatctt catagttacg agtttaagat ggatggaaat atcgatctag    2040
gataggtata catgttgatg tgggttttac tgatgcatat acatgatggc atatgcagca    2100
tctattcata tgctctaacc ttgagtacct atctattata ataaacaagt atgttttata    2160
attattttga tcttgatata cttggatgat ggcatatgca gcagctatat gtggattttt    2220
ttagccctgc cttcatacgc tatttatttg cttggtactg tttcttttgt cgatgctcac    2280
cctgttgttt ggtgttactt ctgcaggtcg actttaactt agcctaggat ccacacgaca    2340
ccatggtccg tcctgtagaa accccaaccc gtgaaatcaa aaaactcgac ggcctgtggg    2400
cattcagtct ggatcgcgaa aactgtggaa ttgatcagcg ttggtgggaa agcgcgttac    2460
aagaaagccg ggcaattgct gtgccaggca gttttaacga tcagttcgcc gatgcagata    2520
ttcgtaatta tgcgggcaac gtctggtatc agcgcgaagt ctttataccg aaaggttggg    2580
caggccagcg tatcgtgctg cgtttcgatg cggtcactca ttacggcaaa gtgtgggtca    2640
ataatcagga agtgatggag catcagggcg gctatacgcc atttgaagcc gatgtcacgc    2700
cgtatgttat tgccgggaaa agtgtacgta agttctgct tctacctttg atatatatat    2760
aataattatc attaattagt agtaatataa tatttcaaat attttttttca aaataaaaga   2820 atgtagtata tagcaattgc ttttctgtag tttataagtg tgtatatttt aatttataac    2880
ttttctaata tatgaccaaa atttgttgat gtgcaggtat caccgtttgt gtgaacaacg    2940
aactgaactg gcagactatc cgccgggaa tggtgattac cgacgaaaac ggcaagaaaa     3000
agcagtctta cttccatgat ttctttaact atgccggaat ccatcgcagc gtaatgctct    3060
acaccacgcc gaacacctgg gtggacgata tcaccgtggt gacgcatgtc gcgcaagact    3120
gtaaccacgc gtctgttgac tggcaggtgg tggccaatgg tgatgtcagc gttgaactgc    3180
gtgatgcgga tcaacaggtg gttgcaactg gacaaggcac tagcgggact ttgcaagtgg    3240
tgaatccgca cctctggcaa ccgggtgaag ttatctcta tgaactgtgc gtcacagcca    3300
aaagccagac agagtgtgat atctacccgc ttcgcgtcgg catccggtca gtggcagtga    3360
agggcgaaca gttcctgatt aaccacaaac cgttctactt tactggcttt ggtcgtcatg    3420
aagatgcgga cttgcgtggc aaaggattcg ataacgtgct gatggtgcac gaccacgcat    3480
taatggactg gattggggcc aactcctacc gtaccctcgca ttacccttac gctgaagaga    3540
tgctcgactg gcagatgaa catggcatcg tggtgattga tgaaactgct gctgtcggct     3600
ttaacctctc tttaggcatt ggtttcgaag cgggcaacaa gccgaaagaa ctgtacagcg    3660
aagaggcagt caacggggaa actcagcaag cgcacttaca ggcgattaaa gagctgatag    3720
cgcgtgacaa aaaccaccca agcgtggtga tgtggagtat tgccaacgaa ccggataccc    3780
gtccgcaagg tgcacgggaa tatttcgcgc cactggcgga agcaacgcgt aaactcgacc    3840
cgacgcgtcc gatcacctgc gtcaatgtaa tgttctgcga cgctcacacc gataccatca    3900
gcgatctctt tgatgtgctg tgcctgaacc gttattacgg atggtatgtc caaagcggcg    3960
atttggaaac ggcagagaag gtactggaaa aagaacttct ggcctggcag gagaaactgc    4020
atcagccgat tatcatcacc gaatacggcg tggatacgtt agccgggctg cactcaatgt    4080
acaccgacat gtggagtgaa gagtatcagt gtgcatggct ggatatgtat caccgcgtct    4140
```

```
ttgatcgcgt cagcgccgtc gtcggtgaac aggtatggaa tttcgccgat tttgcgacct    4200
cgcaaggcat attgcgcgtt ggcggtaaca agaaagggat cttcactcgc gaccgcaaac    4260
cgaagtcggc ggcttttctg ctgcaaaaac gctggactgg catgaacttc ggtgaaaaac    4320
cgcagcaggg aggcaaacaa ggtaccgatc catggcctcc tccgaggacg tcatcaagga    4380
gttcatgcgc ttcaaggtgc gcatggaggg ctccgtgaac ggccacgagt tcgagatcga    4440
gggcgagggc gagggccgcc cctacgaggg cacccagacc gccaagctga aggtgaccaa    4500
gggcggcccc ctgcccttcg cctgggacat cctgtccccc cagttccagt acggctccaa    4560
ggtgtacgtg aagcaccccg ccgacatccc cgactacaag aagctgtcct tccccgaggg    4620
cttcaagtgg gagcgcgtga tgaacttcga ggacggcggc gtggtgaccg tgacccagga    4680
ctcctccctg caggacggct ccttcatcta caaggtgaag ttcatcggcg tgaacttccc    4740
ctccgacggc cccgtaatgc agaagaagac tatgggctgg gaggcctcca ccgagcgcct    4800
gtaccccgc gacggcgtgc tgaagggcga gatccacaag gccctgaagc tgaaggacgg    4860
cggccactac ctggtggagt tcaagtccat ctacatggcc aagaagcccg tgcagctgcc    4920
cggctactac tacgtggact ccaagctgga catcacctcc cacaacgagg actacaccat    4980
cgtggagcag tacgagcgcg ccgagggccg ccaccacctg ttcctgtagg gccggccatc    5040
aacaactctc ctggcgcacc atcgtcggct acagcctcgg tgacgtgggg caacctagac    5100
ttgtccatct tctggattgg ccaacttaat taatgtatga aataaaagga tgcacacata    5160
gtgacatgct aatcactata atgtgggcat caaagttgtg tgttatgtgt aattactagt    5220
tatctgaata aaagagaaag agatcatcca tatttcttat cctaaatgaa tgtcacgtgt    5280
ctttataatt ctttgatgaa ccagatgcat ttcattaacc aaatccatat acatataaat    5340
attaatcata tataattaat atcaattggg ttagcaaaac aaatctagtc taggtgtgtt    5400
ttgcgaattg cggccgcgat ctgagcttct agaggatccc catcgatggg ccccggccga    5460
agcttgcatg cctgcagtgc agcgtgaccc ggtcgtgccc ctctctagag ataatgagca    5520
ttgcatgtct aagttataaa aaattaccac atatttttt tgtcacactt gtttgaagtg    5580
cagtttatct atctttatac atatatttaa actttactct acgaataata taatctatag    5640
tactacaata atatcagtgt tttagagaat catataaatg aacagttaga catggtctaa    5700
aggacaattg agtattttga acaggact ctacagtttt atctttttag tgtgcatgtg    5760
ttctcctttt tttttgcaaa tagcttcacc tatataatac ttcatccatt ttattagtac    5820
atccatttag ggtttagggt taatggtttt tatagactaa ttttttttagt acatctattt    5880
tattctattt tagcctctaa attaagaaaa ctaaaactct attttagttt ttttatttaa    5940
taatttagat ataaaataga ataaaataaa gtgactaaaa attaaacaaa tacccttaa    6000
gaaattaaaa aaactaagga aacatttttc ttgtttcgag tagataatgc cagcctgtta    6060
aacgccgtcg acgagtctaa cggacaccaa ccagcgaacc agcagcgtcg cgtcgggcca    6120
agcgaagcag acggcacggc atctctgtcg ctgcctctgg accctctcg agagttccgc    6180
tccaccgttg gacttgctcc gctgtcggca tccagaaatt gcgtggcgga gcggcagacg    6240
tgagccggca cggcaggcgg cctcctcctc ctctcacggc accggcagct acggggatt    6300
cctttcccac cgctccttcg ctttccttc ctcgcccgcc gtaataaata gacacccct    6360
ccacacccct tttccccaac ctcgtgttgt tcggagcgca cacacacaca accagatctc    6420
ccccaaatcc acccgtcggc acctccgctt caaggtacgc cgctcgtcct cccccccccc    6480
```

```
cctctctacc ttctctagat cggcgttccg gtccatgcat ggttagggcc cggtagttct   6540
acttctgttc atgtttgtgt tagatccgtg tttgtgttag atccgtgctg ctagcgttcg   6600
tacacggatg cgacctgtac gtcagacacg ttctgattgc taacttgcca gtgtttctct   6660
ttggggaatc ctgggatggc tctagccgtt ccgcagacgg gatcgatttc atgatttttt   6720
ttgtttcgtt gcataggggtt tggtttgccc ttttccttta tttcaatata tgccgtgcac   6780
ttgtttgtcg ggtcatcttt tcatgctttt ttttgtcttg gttgtgatga tgtggtctgg   6840
ttgggcggtc gttctagatc ggagtagaat tctgtttcaa actacctggt ggatttatta   6900
attttggatc tgtatgtgtg tgccatacat attcatagtt acgaattgaa gatgatggat   6960
ggaaatatcg atctaggata ggtatacatg ttgatgcggg ttttactgat gcatatacag   7020
agatgctttt tgttcgcttg gttgtgatga tgtggtgtgg ttgggcggtc gttcattcgt   7080
tctagatcgg agtagaatac tgtttcaaac tacctggtgt atttattaat tttgaactg    7140
tatgtgtgtg tcatacatct tcatagttac gagtttaaga tggatggaaa tatcgatcta   7200
ggataggtat acatgttgat gtgggtttta ctgatgcata tacatgatgg catatgcagc   7260
atctattcat atgctctaac cttgagtacc tatctattat aataaacaag tatgttttat   7320
aattattttg atcttgatat acttggatga tggcatatgc agcagctata tgtggatttt   7380
tttagccctg ccttcatacg ctatttattt gcttggtact gtttcttttg tcgatgctca   7440
ccctgttgtt tggtgttact tctgcaggtc gactttaact tagcctagga tccacacgac   7500
accatgtccc ccgagcgccg ccccgtcgag atccgcccgg ccaccgccgc cgacatggcc   7560
gccgtgtgcg acatcgtgaa ccactacatc gagacctcca ccgtgaactt ccgcaccgag   7620
ccgcagaccc cgcaggagtg gatcgacgac ctggagcgcc tccaggaccg ctacccgtgg   7680
ctcgtggccg aggtggaggg cgtggtggcc ggcatcgcct acgccggccc gtggaaggcc   7740
cgcaacgcct acgactggac cgtggagtcc accgtgtacg tgtcccaccg ccaccagcgc   7800
ctcggcctcg gctccaccct ctacacccac ctcctcaaga gcatggaggc ccagggcttc   7860
aagtccgtgg tggccgtgat cggcctcccg aacgaccgt ccgtgcgcct ccacgaggcc    7920
ctcggctaca ccgcccgcgg caccctccgc gccgccggct acaagcacgg cggctggcac   7980
gacgtcggct ctggcagcg cgacttcgag ctgccggccc cgccgcgccc ggtgcgcccg    8040
gtgacgcaga tctgagtcga aacctagact tgtccatctt ctggattggc caacttaatt   8100
aatgtatgaa ataaaaggat gcacacatag tgacatgcta atcactataa tgtgggcatc   8160
aaagttgtgt gttatgtgta attactagtt atctgaataa aagagaaaga gatcatccat   8220
atttcttatc ctaaatgaat gtcacgtgtc tttataattc tttgatgaac cagatgcatt   8280
tcattaacca aatccatata catataaata ttaatcatat ataattaata tcaattgggt   8340
tagcaaaaca aatctagtct aggtgtgttt tgcgaatgcg gccgccaccg cggtggagct   8400
cgaattcatt ccgattaatc gtggcctctt gctcttcagg atgaagagct atgtttaaac   8460
gtgcaagcgc tactagacaa ttcagtacat taaaaacgtc cgcaatgtgt tattaagttg   8520
tctaagcgtc aatttgttta caccacaata tatcctgcca ccagccagcc aacagctccc   8580
cgaccggcag ctcggcacaa aatcaccact cgatacaggc agcccatcag tccgggacgg   8640
cgtcagcggg agagccgttg taaggcggca gactttgctc atgttaccga tgctattcgg   8700
aagaacggca actaagctgc cgggtttgaa acacgatga tctcgcggag ggtagcatgt    8760
tgattgtaac gatgacagag cgttgctgcc tgtgatcaaa tatcatctcc ctcgcagaga   8820
tccgaattat cagccttctt attcatttct cgcttaaccg tgacaggctg tcgatcttga   8880
```

```
gaactatgcc gacataatag gaaatcgctg gataaagccg ctgaggaagc tgagtggcgc   8940
tatttcttta gaagtgaacg ttgacgatcg tcgggcccag gtagaatccg cctgagtcgc   9000
aagggtgact tcgcctatat tggacgacgg cgcgcagagg gcgacctctt tttgggttac   9060
gattgtagga ttatcactaa aacaatacat gaacatattc aaatggcaat ctctctaagg   9120
cattggaaat aaatacaaat aacagttggg tggagttttt cgacctgagg gcgttaacct   9180
tctgttaacc taaaagctct tgcccaaaca gcagaatcgg cgctaattgc cagcggcgga   9240
actttccag tttcgcgaaa aatatcgcca ctggcaagga atgggtttga gatggcgaag    9300
tctgtcctaa aagcagcgcc tgtagttgta gggttgacgg ccttgatgga gcgtcatgcc   9360
gatgccctct cgagccaact tcaagcacat catcttaagg ttttcccgcc gcattccgag   9420
aagggcattc gaacattcgg gccatcgag gcgtccaagc tgctcggcgt tggcgagtca    9480
tatttacggc agaccgcgtc tgagatgcca gagttgaatg ttagcatgag cccgggtggc   9540
aggcgaatgt tctcaattga agatatccat gtgattcgga agtatatgga tcaggtcggc   9600
cgcgggaacc ggcgctacct gccacatcgt cgaggcggcg agcagcttca ggttatctct   9660
gtgatgaatt tcaaaggtgg gtcgggtaag accaccaccg ccgcgcatct ggcgcagtac   9720
ctcgctatgc gcggatatcg agtcttggcc attgatctcg atcctcaagc gagcctttct   9780
gcactctttg ggagccaacc ggagacggac gttggcccga acgaaacgct ctacggcgct   9840
ataaggtatg atgatgagca ggtggcaatc gaacgagtcg tccgagggac ttacattccc   9900
gacctccacc tgattcctgg taaccttgag ctgatggagt ttgaacacga tacgccacgc   9960
gcgctgatga accgcaaaga gggcgacacg ctctttatg gtcgcatcag ccaagtaatt    10020
gaagatatcg cggataacta tgacgtcgtg gtcatcgact gccctcccca gcttgggtat   10080
ctcacgctat ccgcattgac tgcggcgacg tccattcttg tcacggtcca tccgcagatg   10140
ctggatgtga tgtcgatgaa ccagtttctg gcaatgacat cgaaccttt gcgtgaaatc    10200
gagaatgctg gcgccaagtt caagtttaat tggatgcgct atctgataac ccgtttcgaa   10260
ccgagcgacg gaccacagaa ccaaatggta ggttatctgc ggtcgatttt tggcgaaaat   10320
gtcctcaatt ttccgatgct taaaaccacc gcggtttcgg acgctggcct gacaaaccag   10380
actctattcg aagtggagcg tggcctgttc acgcgctcga cctatgatcg agccttggag   10440
gcgatgaacc ccgtcaacga cgagatcgaa acactgatca aaaaagcatg gggtaggccc   10500
acatgagccg gaagcacatc cttggcgtct caactgacgc ccctgagacg tcgcccgccg   10560
acaataggac ggcaaagaac cgctccatgc cgctcctcgg cgtaacaagg aaggagcgcg   10620
atccggcaac gaagctcaca gcgaacattg gtaacgcact gcgagagcaa aacgatcgtc   10680
ttagccgtgc cgaagagatc gagcggcgtc tcgctgaagg tcaggcagtg atagagttgg   10740
atgcctcgtc aatagaaccg tctttcgtgc aggatcgtat gcgaggggac attgacgggc   10800
tccttacttc gatcccggaa caaggacagc aagtcccaat ccttgtgcga ccgcatccga   10860
gccagccggg ccgatatcag gttgccttcg gccaccgccg gctacgcgcc gtttcagaac   10920
tcggacttcc ggtcagagcg gtcgttcgcg aactgacgga cgagcaagtg gtcgtagcac   10980
agggtcagga aaacaatgag cgcgaagatc ttaccttcat cgaaaaggcg cgcttcgcac   11040
atcgcctgaa caggcagttt tctcgagaga ttgtcatcgc cgcgatgtcg atcgacaaga   11100
gcaatttgtc caagatgctt ctgctcgttg acgcctccc ctctgaactg accgatgcta    11160
ttggtgccgc tcctggtgtt ggacggccga gttggcaaca acttgccgag ctgattgaga   11220
```

```
aagtttcttc accggccgac gtggctaaat atgctatgtc ggaggaagtt caagcgctgc   11280
catcggcaga acgattcaag gcggtgatcg ctagtctgaa gcccagtcgg gttgcgcgtg   11340
gacttcccga ggtcatggcc accccagacg gcaccagaat tgcacaggtg acgcagagca   11400
aggccaaact ggaaatcacg attgacagga aggcgacgcc cgattttgcg accttcgtgc   11460
tcgatcatgt gccagcgctg tatcaagcgt accacgctga gaaccaacgg aaacggggag   11520
agtaaaccgc aaaagaaaag agcccccctca acgtcgccgt cgcggaagcc cttctgtctc   11580
tctagcgcga acagaatcgc atttcctcga atcctcgtca agagttttta gcgccgtttt   11640
ggtgagctga tttcctttgc ctgctgaaag gtgaaagatg atgcagacag gaagtgtaac   11700
gacgccattc gggcggcggc caatgacgct tgcgcttgtg cggcgccaga cggcgctggc   11760
cgatatcaaa caaggcaaga cagcggacaa gtggaaggtc tttagagacg cgtccgcggc   11820
tatgaaacta cttggaatcc agtccaacag tcttgccgtc cttgatgcgc tattgagctt   11880
tcacccggaa acggagttgc gtcaggaggc acagctgatc gtcttcccgt cgaatgctca   11940
gcttgccctt cgggcgcatg ggatggctgg cgcgactttg cgtaggcaca tcgccatgct   12000
cgtggagtca ggcttgatcg tccggaagga tagcgccaac ggaaagcgtt acgctcgtaa   12060
ggatggcgct ggtcagatcg agcgcgcgtt tggcttcgat ttgtctccgc ttctcgcgcg   12120
gtccgaagag ctagcgatga tggcacagca ggtgatggcc gatcgagcag cattcaggat   12180
ggccaaagaa agtctgacga tttgccgacg ggacgttcgg aagctaatta cggcagctat   12240
ggaagaggga gcggagggcg actggcaagc tgtcgaggaa gtctatgtgg aacttgtggg   12300
tagaattcca gccgccccga cgcttgctga tgtagagtca attctcgaag agatgtggat   12360
gctccaggaa gagataatca accggttgga aattagagac aattcagaaa ataatagcac   12420
caatgctgcc cagagcgagc agcacataca gaattcaaaa cccgaatccg ttaatgaact   12480
tgaacctcgc tctgaaaagg agcagggcgc taagccgagt gaaatagacc gggcaaggag   12540
cgagccgata aaagcgttcc ccctcgggat gatcctgaaa gcatgcccga ccattggcaa   12600
ttatgggccg agcggtgcgg ttgctagctg gcgtgacctc atgtcggctg cggtggtggt   12660
tcggtctatg ctgggggtca gcccgtcggc ttaccaagac gcgtgtgagg caatgggacc   12720
ggagaatgcg gcagcagcga tggcgtgcat tttggagcga gcgaacttca tcaattcgcc   12780
cgggggctat ctccgagatc tgacacgcg gagcgagctt gggaagtttt cacttggccc   12840
gatgataatg gcgctcttga aggctagcgg gcaggggacg ttgcggtttg gctagaatta   12900
gcgagtatgg agcaggatgg tctgtggtca gctgaccaca gacctaatag gttgaaaaca   12960
tgagcgtttt ttggatgatc gacagaccat ccgattcccg gagtaccaag cgtgctctga   13020
tgggagcgat aacattactc aacaagcacg aaggcccccat gccgatcgtt gatcgtgaag   13080
gagagcctgc tctacatgcg gcggtatttt gccggccgag gcatgtagtc gcggagcact   13140
gcctatttac tgccctaggc acaaacgttg actcttggat cgagctggca gacaaagcaa   13200
taacccacac agaggacgat taatggctga cgaagagatc cagaatccgc cggacggtac   13260
tgctgctgcc gaagttgagc cggctgctcc tagaggtaga agagcaaaga aagcaccagc   13320
cgaaacagcc cgcacgggat cgttcaaatc cgtgaagccg aaaacccgcg gcctcagcaa   13380
ccgagaaaaa ctggagaaga tcggtcaaat cgaagctcag gtcgctggcg gcgcaacctt   13440
gaaggacgcc gttaagatcg tgggtatttc cgttcagacc tattatcaat ggaagagagc   13500
tgcggttcaa cctgtctcac agaatccggc cgtgtctgtt tcagttgacg atgaactcgg   13560
cgagttcatc caactcgagg aggaaaatat gcatggcatg cccgttccat acagaagctg   13620
```

```
ggcgaacaaa cgatgctcgc cttccagaaa accgaggatg cgaaccactt catccggggt   13680
cagcaccacc ggcaagcgcc gcgacggccg aggtcttccg atctcctgaa gccagggcag   13740
atccgtgcac agcaccttgc cgtagaagaa cagcaaggcc gccaatgcct gacgatgcgt   13800
ggagaccgaa accttgcgct cgttcgccag ccaggacaga aatgcctcga cttcgctgct   13860
gcccaaggtt gccgggtgac gcacaccgtg gaaacggatg aaggcacgaa cccagtggac   13920
ataagcctgt tcggttcgta agctgtaatg caagtagcgt atgcgctcac gcaactggtc   13980
cagaaccttg accgaacgca gcggtggtaa cggcgcagtg gcggttttca tggcttgtta   14040
tgactgtttt tttggggtac agtctatgcc tcgggcatcc aagcagcaag cgcgttacgc   14100
cgtgggtcga tgtttgatgt tatggagcag caacgatgtt acgcagcagg gcagtcgccc   14160
taaaacaaag ttaaacatca tgagggaagc ggtgatcgcc gaagtatcga ctcaactatc   14220
agaggtagtt ggcgtcatcg agcgccatct cgaaccgacg ttgctggccg tacatttgta   14280
cggctccgca gtggatggcg gcctgaagcc acacagtgat attgatttgc tggttacggt   14340
gaccgtaagg cttgatgaaa caacgcggcg agctttgatc aacgaccttt tggaaacttc   14400
ggcttcccct ggagagagcg agattctccg cgctgtagaa gtcaccattg ttgtgcacga   14460
cgacatcatt ccgtggcgtt atccagctaa gcgcgaactg caatttggag aatggcagcg   14520
caatgacatt cttgcaggta tcttcgagcc agccacgatc gacattgatc tggctatctt   14580
gctgacaaaa gcaagagaac atagcgttgc cttggtaggt ccagcggcgg aggaactctt   14640
tgatccggtt cctgaacagg atctatttga ggcgctaaat gaaaccttaa cgctatggaa   14700
ctcgccgccc gactgggctg gcgatgagcg aaatgtagtg cttacgttgt cccgcatttg   14760
gtacagcgca gtaaccggca aaatcgcgcc gaaggatgtc gctgccgact gggcaatgga   14820
gcgcctgccg gcccagtatc agcccgtcat acttgaagct agacaggctt atcttggaca   14880
agaagaagat cgcttggcct cgcgcgcaga tcagttggaa gaatttgtcc actacgtgaa   14940
aggcgagatc accaaggtag tcggcaaata atgtctaaca attcgttcaa gccgacgccg   15000
cttcgcggcg cggcttaact caagcgttag atgcactata cgtaaccaac tagtgcgctc   15060
ttccgcttcc tcgctcactg actcgctgcg ctcggtcgtt cggctgcggc gagcggtatc   15120
agctcactca aaggcggtaa tacggttatc cacagaatca ggggataacg caggaaagaa   15180
catgtgagca aaaggccagc aaaaggccag gaaccgtaaa aaggccgcgt tgctggcgtt   15240
tttccatagg ctccgccccc ctgacgagca tcacaaaaat cgacgctcaa gtcagaggtg   15300
gcgaaacccg acaggactat aaagatacca ggcgtttccc cctggaagct ccctcgtgcg   15360
ctctcctgtt ccgaccctgc cgcttaccgg atacctgtcc gcctttctcc cttcgggaag   15420
cgtggcgctt tctcatagct cacgctgtag gtatctcagt tcggtgtagg tcgttcgctc   15480
caagctgggc tgtgtgcacg aaccccccgt tcagcccgac cgctgcgcct tatccggtaa   15540
ctatcgtctt gagtccaacc cggtaagaca cgacttatcg ccactggcag cagccactgg   15600
taacaggatt agcagagcga ggtatgtagg cggtgctaca gagttcttga agtggtggcc   15660
taactacggc tacactagaa ggacagtatt tggtatctgc gctctgctga agccagttac   15720
cttcggaaaa agagttggta gctcttgatc cggcaaacaa accaccgctg gtagcggtgg   15780
tttttttgtt tgcaagcagc agattacgcg cagaaaaaaa ggatctcaag aagatccttt   15840
gatcttttct acgggtctg acgctcagtg gaacgaaaac tcacgttaag ggattttggt   15900
catgagatta tcaaaaagga tcttcaccta gatccttta aattaaaaat gaagcgtacc   15960
```

```
gacgatcttg ctgcgttcgg atattttcgt ggagttcccg ccacagaccc ggattgaagg    16020
cgagatccag caactcgcgc cagatcatcc tgtgacggaa ctttggcgcg tgatgactgg    16080
ccaggacgtc ggccgaaaga gcgacaagca gatcacgctt ttcgacagcg tcggatttgc    16140
gatcgaggat ttttcggcgc tgcgctacgt ccgcgaccgc gttgagggat caagccacag    16200
cagcccactc gaccttctag ccgacccaga cgagccaagg gatcttttg gaatgctgct    16260 ccgtcgtcag gctttccgac gtttgggtgg ttgaacagaa gtcattatcg cacggaatgc    16320
caagcactcc cgaggggaac cctgtggttg gcatgcacat acaaatggac gaacggataa    16380 acctttcac gcccttttaa atatccgatt attctaataa acgctctttt ctcttag       16437

<210> SEQ ID NO 145
<211> LENGTH: 17
<212> TYPE: DNA
<213> ORGANISM: Artificial Sequence
<220> FEATURE:
<223> OTHER INFORMATION: MPSS promiscuous tag

<400> SEQUENCE: 145
gatcaaaaaa aaaaaaa                                                       17

<210> SEQ ID NO 146
<211> LENGTH: 8
<212> TYPE: DNA
<213> ORGANISM: Artificial Sequence
<220> FEATURE:
<223> OTHER INFORMATION: Motif consensus sequence

<400> SEQUENCE: 146 ydratcyg                                                                  8
```

REGULATORY SEQUENCES FOR MODULATING TRANSGENE EXPRESSION IN PLANTS

CROSS REFERENCE TO RELATED APPLICATIONS

This application is a Continuation of U.S. application Ser. No. 14/660,076 filed Mar. 17, 2015, now abandoned, which is a Continuation of U.S. application Ser. No. 13/701,848 filed Dec. 4, 2012, now abandoned, which is a 371 of International Application No. PCT/US11/39691, filed Jun. 9, 2011, now expired, which claims the benefit of U.S. Provisional Application No. 61/372,515 filed Aug. 11, 2010, now expired, and Indian Provisional Application No. 1340/DEL/2010 filed Jun. 9, 2010, now expired, the entire contents of each is herein incorporated by reference.

REFERENCE TO SEQUENCE LISTING SUBMITTED ELECTRONICALLY

The official copy of the sequence listing is submitted electronically via EFS-Web as an ASCII formatted sequence listing with a file named 20150317_BB1787USCNT_SequenceListing.txt created on Mar. 17, 2015 and having a size of 269 kilobytes and is filed concurrently with the specification. The sequence listing contained in this ASCII formatted document is part of the specification and is herein incorporated by reference in its entirety.

FIELD OF INVENTION

The present invention relates to the generation of transgenic plants, particularly to the use of promoter and intron sequences to regulate gene expression in plants.

BACKGROUND

Recent advances in plant genetic engineering have opened new doors to engineer plants to have improved characteristics or traits. These transgenic plants characteristically have recombinant DNA constructs in their genome that have a protein-coding region operably linked to at least one regulatory region that is the promoter. The promoter can be a strong or weak promoter, or a constitutive or tissue-specific promoter. Besides the promoter, the expression level of the gene product can be modulated by other regulatory elements such as introns. Introns are intervening, non-coding sequences that are present in most eukaryotic genes. Introns have been reported to affect the levels of gene expression. This effect is known as Intron Mediated Enhancement (IME) of gene expression (Lu et al., *Mol Genet Genomics* (2008) 279:563-572). Callis et al. (*Genes Dev.* 1987 1:1183-1200) showed that the presence of the first intron from maize alcohol dehydrogenase-1 (Adh1) gene increased the expression levels of transgenes in cultured maize cells up to 100-fold when compared to intronless constructs. Mascarenkas et al. (*Plant Mol. Biol.*, 1990, 15: 913-920) showed that other introns from the maize Adh1 gene could also increase heterologous gene expression in maize protoplasts. Vasil et al. (*Plant Physiol.*, 1989, 91:1575-15790) reported that the constructs containing Shrunken-1 (Sh-1) first intron had much higher expression levels of the reporter gene in plant protoplasts, when compared to the constructs with promoter alone, or to constructs with promoter and Adh-1 first intron. Identifying novel regulatory sequences can lead to finer modulation of gene expression in transgenic plants.

Plant genetic engineering has advanced to introducing multiple traits into commercially important plants, also known as gene stacking. This is accomplished by multigene transformation, where multiple genes are transferred to create a transgenic plant that might express a complex phenotype, or multiple phenotypes. But it is important to modulate or control the expression of each transgene optimally. The regulatory elements such as the promoter and the terminator sequences need to be diverse, to avoid introducing into the same transgenic plant repetitive sequences, which has been correlated with undesirable negative effects on transgene expression and stability (Peremarti et al (2010) *Plant Mol Biol* 73:363-378; Mette et al (1999) *EMBO J* 18:241-248; Mette et al (2000) *EMBO J* 19:5194-5201; Mourrain et al (2007) *Planta* 225:365-379, U.S. Pat. Nos. 7,632,982, 7,491,813, 7,674,950, PCT Application No. PCT/US2009/046968). Therefore it is important to discover and characterize novel regulatory elements that can be used to express heterologous nucleic acids in important crop species. Diverse regulatory regions can be used to control the expression of each transgene optimally.

SUMMARY

The present invention relates to regulatory sequences for modulating gene expression in plants. Recombinant DNA constructs comprising regulatory sequences are provided. Recombinant DNA constructs comprising intron sequences acting as enhancers of gene expression and endogenous promoter and terminator sequences corresponding to these intron sequences are provided.

Another embodiment of the invention is a recombinant DNA construct comprising an intron operably linked to a promoter and a terminator wherein the intron comprises a nucleotide sequence that has at least 95% sequence identity to SEQ ID NO: 4, 8, 13, 19, 52, 53, 56, 57, 58, 101, 102, 103, 104, 118, 137 or 138. In another embodiment, the intron comprises the nucleotide sequence of SEQ ID NO: 4, 8, 13, 19, 52, 53, 56, 57, 58, 101, 102, 103, 104, 118, 137 or 138.

One embodiment of the invention is a recombinant DNA construct comprising an intron operably linked to a promoter and a terminator wherein the promoter comprises a nucleotide sequence that has at least 95% sequence identity to SEQ ID NO: 105-117, 119, 136 or 139. In another embodiment, the promoter comprises the nucleotide sequence of SEQ ID NO: 105-117, 119, 136 or 139.

One embodiment of the invention is a recombinant DNA construct comprising an intron operably linked to a promoter and a terminator wherein the terminator comprises a nucleotide sequence that has at least 95% sequence identity to SEQ ID NOS: 140, 141, 142 or 143. In another embodiment, the terminator comprises the nucleotide sequence of SEQ ID NO: 140, 141, 142 or 143.

One embodiment of the invention is a recombinant DNA construct comprising an intron operably linked to a promoter and a terminator wherein the intron comprises a nucleotide sequence that has at least 95% identity to SEQ ID NOS: 4, 8, 13, 19, 52, 53, 56, 57, 58, 101, 102, 103, 104, 118, 137 or 138; and the promoter comprises a nucleotide sequence that has at least 95% identity to SEQ ID NOS: 105, 106, 107, 108, 109, 110, 111, 112, 113, 114, 115, 116, 117, 119, 136 or 139.

One embodiment of the invention is a recombinant DNA construct comprising an intron operably linked to a promoter and a terminator wherein the intron comprises a nucleotide sequence that has at least 95% identity to SEQ ID NO: 4, 8, 13, 19, 52, 53, 56, 57, 58, 101, 102, 103, 104, 118, 137 or 138; the promoter sequence has at least 95% identity to SEQ ID NO: 105, 106, 107, 108, 109, 110, 111, 112, 113, 114, 115, 116, 117, 119, 136 or 139; and the terminator has at least 95% sequence identity to SEQ ID NO: 140, 141, 142 or 143.

In one embodiment of the current invention, the intron is operably linked to the promoter, and is present downstream of the promoter, in the recombinant DNA constructs described herein. One embodiment of the present invention includes a recombinant DNA construct comprising an intron described in the present invention, operably linked to a promoter and a heterologous polynucleotide, wherein the intron can act as enhancer of expression of the heterologous polynucleotide.

Another embodiment of the invention encompasses a recombinant DNA construct comprising an intron wherein the intron sequence comprises at least one copy of the 8-bp sequence motif of SEQ ID NO: 99; or contains at least one copy of the 8-bp sequence motif of SEQ ID NO: 99 and at least one copy of the 5-bp sequence motif of SEQ ID NO: 100, wherein the intron is capable of enhancing expression of a heterologous polynucleotide in a transgenic plant. The intron sequence can also comprise more than one copy of SEQ ID NO: 99, or can comprise one or more than one copy of SEQ ID NO: 99 and more than one copy of SEQ ID NO: 100.

Another embodiment of this invention is a method to identify novel introns that are useful for enhancing expression of a heterologous polynucleotide in a plant cell, the method comprising the steps of scanning a plurality of introns from plants for presence of SEQ ID NO: 99, selecting a sequence that contains at least one copy of SEQ ID NO: 99, measuring the efficacy of the identified intron to enhance expression of a heterologous polynucleotide in a plant.

Another embodiment of the invention is a method for identifying novel intronic sequences for enhancing transgene expression in monocotyledenous plants by identifying sequences orthologous to SEQ ID NO: 4, 8, 13, 19, 52, 53, 56, 57, 58, 101, 102, 103, 104, 118, 137 or 138; and measuring the enhancing effect of the identified intron on the expression of an operably linked heterologous polynucleotide.

Another embodiment of the current invention includes the promoter and the terminator sequences that are endogenously linked to the introns identified using the methods described in the current invention.

Another embodiment of the current invention is a method for modulating expression of a heterologous polynucleotide in a monocotyledonous plant comprising the steps of: (a) introducing into a regenerable plant cell a recombinant DNA construct comprising a promoter and a heterologous polynucleotide wherein each is operably linked to an intron, wherein the intron comprises either (i) a nucleotide sequence that is orthologous to SEQ ID NO: 4, 8, 13, 19, 52, 53, 56, 57, 58, 101, 102, 103, 104, 118, 137 or 138; or (ii) a nucleotide sequence that contains least one copy of a sequence motif identical to SEQ ID NO: 99; and (b) regenerating a transgenic plant from a regenerable monocotyledonous plant cell after step (a) wherein the transgenic plant comprises the recombinant DNA construct; and (c) obtaining a progeny plant derived from the transgenic plant of step (b), wherein said progeny plant comprises the recombinant DNA construct and exhibits enhanced expression of the heterologous polynucleotide when compared to a plant comprising a corresponding recombinant DNA construct without the intron sequence.

In another embodiment, this invention concerns a vector, cell, plant, or seed comprising a recombinant DNA construct comprising the regulatory sequences described in the present invention.

The invention encompasses regenerated, mature and fertile transgenic plants comprising the recombinant DNA constructs described above, transgenic seeds produced therefrom, T1 and subsequent generations. The transgenic plant cells, tissues, plants, and seeds may comprise at least one recombinant DNA construct of interest.

In one embodiment, the plant comprising the regulatory sequences described in the present invention is a monocotyledenous plant. In another embodiment, the plant comprising the regulatory sequences described in the present invention is a maize plant.

BRIEF DESCRIPTION OF DRAWINGS AND SEQUENCE LISTINGS

The invention can be more fully understood from the following detailed description and the accompanying drawings and Sequence Listing which form a part of this application. The Sequence Listing contains the one letter code for nucleotide sequence characters and the three letter codes for amino acids as defined in conformity with the IUPAC-IUBMB standards described in Nucleic Acids Research 13:3021-3030 (1985) and in the Biochemical Journal 219 (No. 2): 345-373 (1984), which are herein incorporated by reference in their entirety. The symbols and format used for nucleotide and amino acid sequence data comply with the rules set forth in 37 C.F.R. § 1.822.

Figure 1:
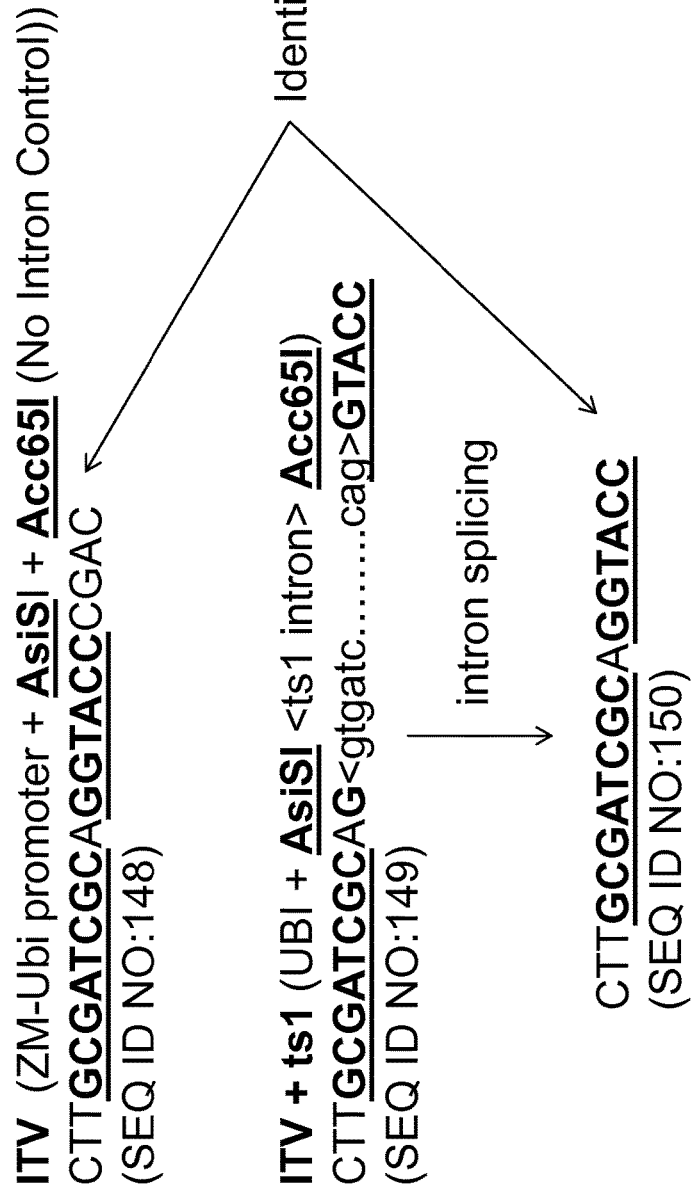
FIG. 1 is a schematic representation of the vector used for testing introns showing the location of restriction sites used to clone introns relative to the maize ubiquitin promoter, as described in Example 2.
Figure 2:
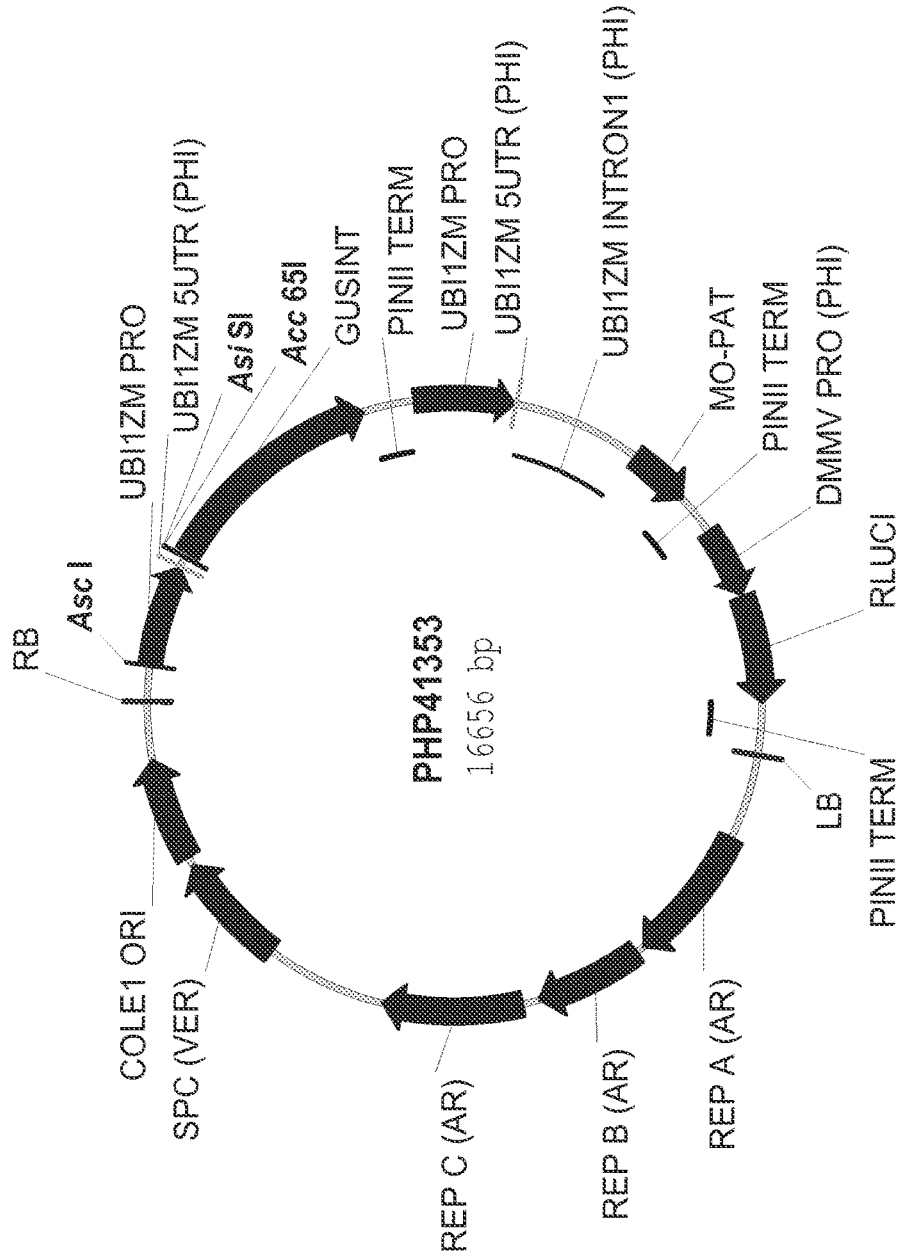
FIG. 2 shows the map of PHP 41353, the ITVUR-2 vector used for testing intron-mediated enhancement of gene expression.

SEQ ID NO: 1 is the sequence of the maize ubiquitin promoter.

SEQ ID NO: 2 is the sequence of the first intron from maize ubiquitin gene.

SEQ ID NO: 3 is the nucleotide sequence of PHP41353, ITVUR-2 vector.

SEQ ID NOS: 4-19 and SEQ ID NOS: 52-58, SEQ ID NO: 118, SEQ ID NOS: 137 and 138 are sequences of introns that were tested to identify expression-enhancing introns, and are described in Table 1 below.

SEQ ID NOS: 105-113, SEQ ID NO: 119 and SEQ ID NOS: 136 and 139 are the sequences of promoters identified for the enhancing introns as described in Example 10 and Example 11, and are described in Table 1 below.

SEQ ID NOS: 140-143 given in Table 1 are the sequences of the endogenous terminators for the introns TS1, TS2, TS13 and TS27, identified as explained in Example 13.

TABLE 1

| SEQ ID NO | Name | Intron/Promoter | Enhancing/Non-Enhancing Intron |
|---|---|---|---|
| 4 | TS1 | Intron | Enhancing |
| 5 | TS4 | Intron | Non-Enhancing |
| 6 | TS5 | Intron | Non-Enhancing |
| 7 | TS6 | Intron | Non-Enhancing |
| 8 | TS7 | Intron | Enhancing* |
| 9 | TS8 | Intron | Non-Enhancing |
| 10 | TS10 | Intron | Non-Enhancing |
| 11 | TS11 | Intron | Non-Enhancing |
| 12 | TS12 | Intron | Non-Enhancing |
| 13 | TS13 | Intron | Enhancing |
| 14 | TS14 | Intron | Non-Enhancing |
| 15 | TS15 | Intron | Non-Enhancing |
| 16 | TS16 | Intron | Non-Enhancing |
| 17 | TS17 | Intron | Non-Enhancing |
| 18 | TS24 | Intron | Non-Enhancing |
| 19 | TS27 | Intron | Enhancing* |
| 52 | i1 | Intron | Enhancing |
| 53 | i2 | Intron | Enhancing |
| 54 | i3 | Intron | Non-Enhancing |
| 55 | i4 | Intron | Non-Enhancing |
| 56 | i5 | Intron | Enhancing |
| 57 | i6 | Intron | Enhancing |
| 58 | i7 | Intron | Enhancing |
| 105 | pTS1 | Promoter | Promoter identified for SEQ ID NO: 4 |
| 106 | pTS7 | Promoter | Promoter identified for SEQ ID NO: 8 |
| 107 | pTS13 | Promoter | Promoter identified for SEQ ID NO: 13 |
| 108 | pTS27 | Promoter | Promoter identified for SEQ ID NO: 19 |
| 109 | pi1 | Promoter | Promoter identified for SEQ ID NO: 52 |
| 110 | pi2 | Promoter | Promoter identified for SEQ ID NO: 53 |
| 111 | pi5 | Promoter | Promoter identified for SEQ ID NO: 56 |

TABLE 1-continued

| SEQ ID NO | Name | Intron/Promoter | Enhancing/Non-Enhancing Intron |
|---|---|---|---|
| 112 | pi6 | Promoter | Promoter identified for SEQ ID NO: 57 |
| 113 | pi7 | Promoter | Promoter identified for SEQ ID NO: 58 |
| 118 | TS2 | Intron | Enhancing |
| 119 | pTS2 | Promoter | Promoter identified for SEQ ID NO: 118 |
| 136 | pTS1v | Promoter | Promoter sequence cloned for SEQ ID NO: 4 |
| 137 | TS7v | Intron | Enhancing |
| 138 | TS27v | Intron | Enhancing |
| 139 | pTS27v | Promoter | Promoter sequence cloned for SEQ ID NO: 19 |
| 140 | tTS1 | Terminator | Terminator identified for SEQ ID NO: 4 |
| 141 | tTS2 | Terminator | Terminator identified for SEQ ID NO: 118 |
| 142 | tTS13 | Terminator | Terminator identified for SEQ ID NO: 13 |
| 143 | tTS27 | Terminator | Terminator identified for SEQ ID NO: 19 |

*based on results from variants

SEQ ID NOS: 20-51 are the primers used for cloning introns as described in Table 2 in Example 3.

SEQ ID NO: 59 is the sequence of the vector PHP38808, used for testing intron-mediated enhancement of gene expression as described in Example 7.

SEQ ID NO: 60 is the sequence of PHP34651, the vector containing GATEWAY® attR recombination sites and a PAT expression cassette used for LR reactions to generate the final expression vectors for introns, as described in Example 7.

SEQ ID NOS: 61-94 are the oligonucleotides used for generating introns by oligonucleotide stacking as described in Table 4 in Example 7.

SEQ ID NO: 95 is the sequence for first intron of adh1 gene.

SEQ ID NO: 96 is the sequence for intron 6 for adh1 gene.

SEQ ID NO: 97 is the sequence for intron 1 for shrunken1 (Sh-1) gene

SEQ ID NO: 98 is the sequence for ubi intron 1 used for computational analyses as described in Example 8.

SEQ ID NO: 99 is the sequence of the 8-bp motif identified as described in Example 8.

SEQ ID NO: 100 is the sequence of the 5-bp motif identified as described in Example 8.

SEQ ID NOS: 101-104 are the intron sequences containing the 8-bp motif (SEQ ID NO: 99), as described in Example 9.

SEQ ID NOS: 114-117 are the promoter sequences identified from the introns of SEQ ID NOS: 101-104 respectively, as described in Examples 9 and 10.

SEQ ID NOS: 120-128 are the sequences of the primers used for cloning the promoters and introns, as described in Table 7.

SEQ ID NOS: 129-134 are the primer and probe sequences for qPCR, as described in Table 9 and Table 10.

SEQ ID NO: 135 is the sequence of the PHP42365 vector that contains ZmUbi promoter and ZmUbi intron.

SEQ ID NO: 144 is the sequence of the PHP49597 vector (terminator test vector or TTV).

SEQ ID NO: 145 corresponds to the nucleotide sequence GATCAAAAAAAAAAAAA of a 'promiscuous' MPSS tags.

SEQ ID NO: 146 corresponds to the nucleotide sequence of a consensus motif sequence, which encompasses variations of the motif sequence given in SEQ ID NO: 99.

The sequence descriptions and Sequence Listing attached hereto comply with the rules governing nucleotide and/or amino acid sequence disclosures in patent applications as set forth in 37 C.F.R. § 1.821-1.825. The Sequence Listing contains the one letter code for nucleotide sequence characters and the three letter codes for amino acids as defined in conformity with the IUPAC-IUBMB standards described in *Nucleic Acids Res.* 13:3021-3030 (1985) and in the *Biochemical J.* 219 (2):345-373 (1984) which are herein incorporated by reference. The symbols and format used for nucleotide and amino acid sequence data comply with the rules set forth in 37 C.F.R. § 1.822.

DETAILED DESCRIPTION OF THE INVENTION

The disclosure of each reference set forth herein is hereby incorporated by reference in its entirety.

As used herein and in the appended claims, the singular forms "a", "an", and "the" include plural reference unless the context clearly dictates otherwise. Thus, for example, reference to "a plant" includes a plurality of such plants, reference to "a cell" includes one or more cells and equivalents thereof known to those skilled in the art, and so forth.

As used herein:

The terms "monocot" and "monocotyledonous plant" are used interchangeably herein. A monocot of the current invention includes the Gramineae.

The terms "dicot" and "dicotyledonous plant" are used interchangeably herein. A dicot of the current invention includes the following families: Brassicaceae, Leguminosae, and Solanaceae.

The terms "full complement" and "full-length complement" are used interchangeably herein, and refer to a complement of a given nucleotide sequence, wherein the complement and the nucleotide sequence consist of the same number of nucleotides and are 100% complementary.

"Transgenic" refers to any cell, cell line, callus, tissue, plant part or plant, the genome of which has been altered by the presence of a heterologous nucleic acid, such as a recombinant DNA construct, including those initial transgenic events as well as those created by sexual crosses or asexual propagation from the initial transgenic event. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

"Genome" as it applies to plant cells encompasses not only chromosomal DNA found within the nucleus, but organelle DNA found within subcellular components (e.g., mitochondrial, plastid) of the cell.

"Plant" includes reference to whole plants, plant organs, plant tissues, seeds and plant cells and progeny of same. Plant cells include, without limitation, cells from seeds, suspension cultures, embryos, meristematic regions, callus tissue, leaves, roots, shoots, gametophytes, sporophytes, pollen, and microspores.

"Progeny" comprises any subsequent generation of a plant.

"Transgenic plant" includes reference to a plant which comprises within its genome a heterologous polynucleotide. For example, the heterologous polynucleotide is stably integrated within the genome such that the polynucleotide is passed on to successive generations. The heterologous polynucleotide may be integrated into the genome alone or as part of a recombinant DNA construct.

"Heterologous" with respect to sequence means a sequence that originates from a foreign species, or, if from the same species, is substantially modified from its native form in composition and/or genomic locus by deliberate human intervention.

"Polynucleotide", "nucleic acid sequence", "nucleotide sequence", or "nucleic acid fragment" are used interchangeably to refer to a polymer of RNA or DNA that is single- or double-stranded, optionally containing synthetic, non-natural or altered nucleotide bases. Nucleotides (usually found in their 5'-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

"Polypeptide", "peptide", "amino acid sequence" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The terms "polypeptide", "peptide", "amino acid sequence", and "protein" are also inclusive of modifications including, but not limited to, glycosylation, lipid attachment, sulfation, gamma-carboxylation of glutamic acid residues, hydroxylation and ADP-ribosylation.

"Messenger RNA (mRNA)" refers to the RNA that is without introns and that can be translated into protein by the cell.

"cDNA" refers to a DNA that is complementary to and synthesized from an mRNA template using the enzyme reverse transcriptase. The cDNA can be single-stranded or converted into the double-stranded form using the Klenow fragment of DNA polymerase I.

An "Expressed Sequence Tag" ("EST") is a DNA sequence derived from a cDNA library and therefore is a sequence which has been transcribed. An EST is typically obtained by a single sequencing pass of a cDNA insert. The sequence of an entire cDNA insert is termed the "Full-Insert Sequence" ("FIS"). A "Contig" sequence is a sequence assembled from two or more sequences that can be selected from, but not limited to, the group consisting of an EST, FIS and PCR sequence. A sequence encoding an entire or functional protein is termed a "Complete Gene Sequence" ("CGS") and can be derived from an FIS or a contig.

"Mature" protein refers to a post-translationally processed polypeptide; i.e., one from which any pre- or pro-peptides present in the primary translation product has been removed.

"Precursor" protein refers to the primary product of translation of mRNA; i.e., with pre- and pro-peptides still present. Pre- and pro-peptides may be and are not limited to intracellular localization signals.

"Isolated" refers to materials, such as nucleic acid molecules and/or proteins, which are substantially free or otherwise removed from components that normally accompany or interact with the materials in a naturally occurring environment. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

"Recombinant" refers to an artificial combination of two otherwise separated segments of sequence, e.g., by chemical synthesis or by the manipulation of isolated segments of nucleic acids by genetic engineering techniques. "Recombinant" also includes reference to a cell or vector, that has been modified by the introduction of a heterologous nucleic acid or a cell derived from a cell so modified, but does not encompass the alteration of the cell or vector by naturally occurring events (e.g., spontaneous mutation, natural transformation/transduction/transposition) such as those occurring without deliberate human intervention.

"Recombinant DNA construct" refers to a combination of nucleic acid fragments that are not normally found together in nature. Accordingly, a recombinant DNA construct may comprise regulatory sequences and coding sequences that are derived from different sources, or regulatory sequences and coding sequences derived from the same source, but arranged in a manner different than that normally found in nature.

The terms "entry clone" and "entry vector" are used interchangeably herein.

The term "insecticidal gene" and "insect resistance gene" are used interchangeably herein.

"Operably linked" refers to the association of nucleic acid fragments in a single fragment so that the function of one is regulated by the other. For example, a promoter is operably linked with a nucleic acid fragment when it is capable of regulating the transcription of that nucleic acid fragment.

"Expression" refers to the production of a functional product. For example, expression of a nucleic acid fragment may refer to transcription of the nucleic acid fragment (e.g., transcription resulting in mRNA or functional RNA) and/or translation of mRNA into a precursor or mature protein.

"Overexpression" refers to the production of a gene product in transgenic organisms that exceeds levels of production in a null segregating (or non-transgenic) organism from the same experiment.

"Phenotype" means the detectable characteristics of a cell or organism.

"Introduced" in the context of inserting a nucleic acid fragment (e.g., a recombinant DNA construct) into a cell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid or mitochondrial DNA), converted into an autonomous replicon, or transiently expressed (e.g., transfected mRNA).

A "transformed cell" is any cell into which a nucleic acid fragment (e.g., a recombinant DNA construct) has been introduced.

"Transformation" as used herein refers to both stable transformation and transient transformation.

"Stable transformation" refers to the introduction of a nucleic acid fragment into a genome of a host organism resulting in genetically stable inheritance. Once stably transformed, the nucleic acid fragment is stably integrated in the genome of the host organism and any subsequent generation.

"Transient transformation" refers to the introduction of a nucleic acid fragment into the nucleus, or DNA-containing organelle, of a host organism resulting in gene expression without genetically stable inheritance.

The term "crossed" or "cross" means the fusion of gametes via pollination to produce progeny (e.g., cells, seeds or plants). The term encompasses both sexual crosses (the pollination of one plant by another) and selfing (self-pollination, e.g., when the pollen and ovule are from the same plant). The term "crossing" refers to the act of fusing gametes via pollination to produce progeny.

A "favorable allele" is the allele at a particular locus that confers, or contributes to, a desirable phenotype, e.g., increased cell wall digestibility, or alternatively, is an allele that allows the identification of plants with decreased cell wall digestibility that can be removed from a breeding program or planting ("counterselection"). A favorable allele of a marker is a marker allele that segregates with the favorable phenotype, or alternatively, segregates with the unfavorable plant phenotype, therefore providing the benefit of identifying plants.

The term "introduced" means providing a nucleic acid (e.g., expression construct) or protein into a cell. Introduced includes reference to the incorporation of a nucleic acid into a eukaryotic or prokaryotic cell where the nucleic acid may be incorporated into the genome of the cell, and includes reference to the transient provision of a nucleic acid or protein to the cell. Introduced includes reference to stable or transient transformation methods, as well as sexually crossing. Thus, "introduced" in the context of inserting a nucleic acid fragment (e.g., a recombinant DNA construct/expression construct) into a cell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid or mitochondrial DNA), converted into an autonomous replicon, or transiently expressed (e.g., transfected mRNA).

Sequence alignments and percent identity calculations may be determined using a variety of comparison methods designed to detect homologous sequences including, but not limited to, the MEGALIGN® program of the LASERGENE® bioinformatics computing suite (DNASTAR® Inc., Madison, Wis.). Unless stated otherwise, multiple alignment of the sequences provided herein were performed using the Clustal V method of alignment (Higgins and Sharp, *CABIOS.* 5:151-153 (1989)) with the default parameters (GAP PENALTY=10, GAP LENGTH PENALTY=10). Default parameters for pairwise alignments and calculation of percent identity of protein sequences using the Clustal V method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences, using the Clustal V program, it is possible to obtain "percent identity" and "divergence" values by viewing the "sequence distances" table on the same program; unless stated otherwise, percent identities and divergences provided and claimed herein were calculated in this manner.

The present invention includes a polynucleotide comprising: (i) a nucleic acid sequence of at least 90%, 91%, 92%, 93%, 94%, 95%, 96%, 97%, 98%, 99%, or 100% sequence identity, based on the Clustal V method of alignment, when compared to SEQ ID NOS: 4, 8, 13, 19, 52, 53, 56, 57, 58, 101-119, 136-143; or (ii) a full complement of the nucleic acid sequence of (i), wherein the polynucleotide acts as a regulator of gene expression in a plant cell.

Standard recombinant DNA and molecular cloning techniques used herein are well known in the art and are described more fully in Sambrook, J., Fritsch, E. F. and Maniatis, T. *Molecular Cloning: A Laboratory Manual*; Cold Spring Harbor Laboratory Press: Cold Spring Harbor, 1989 (hereinafter "Sambrook").

Regulatory Sequences:

A recombinant DNA construct (including a suppression DNA construct) of the present invention may comprise at least one regulatory sequence.

"Regulatory sequences" or "regulatory elements" are used interchangeably and refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to, promoters, translation leader sequences, introns, and polyadenylation recognition sequences. The terms "regulatory sequence" and "regulatory element" are used interchangeably herein.

"Promoter" refers to a nucleic acid fragment capable of controlling transcription of another nucleic acid fragment.

"Promoter functional in a plant" is a promoter capable of controlling transcription in plant cells whether or not its origin is from a plant cell.

"Tissue-specific promoter" and "tissue-preferred promoter" are used interchangeably to refer to a promoter that is expressed predominantly but not necessarily exclusively in one tissue or organ, but that may also be expressed in one specific cell.

"Developmentally regulated promoter" refers to a promoter whose activity is determined by developmental events.

Promoters that cause a gene to be expressed in most cell types at most times are commonly referred to as "constitutive promoters".

High level, constitutive expression of the candidate gene under control of the 35S or UBI promoter may have pleiotropic effects, although candidate gene efficacy may be estimated when driven by a constitutive promoter. Use of tissue-specific and/or stress-specific promoters may eliminate undesirable effects but retain the ability to enhance drought tolerance. This effect has been observed in *Arabidopsis* (Kasuga et al. (1999) *Nature Biotechnol.* 17:287-91).

Suitable constitutive promoters for use in a plant host cell include, but are not limited to, the core promoter of the Rsyn7 promoter and other constitutive promoters disclosed in WO 99/43838 and U.S. Pat. No. 6,072,050; the core CaMV 35S promoter (Odell et al., *Nature* 313:810-812 (1985)); rice actin (McElroy et al., *Plant Cell* 2:163-171 (1990)); ubiquitin (Christensen et al., *Plant Mol. Biol.* 12:619-632 (1989) and Christensen et al., *Plant Mol. Biol.* 18:675-689 (1992)); pEMU (Last et al., *Theor. Appl. Genet.* 81:581-588 (1991)); MAS (Velten et al., *EMBO J.* 3:2723-2730 (1984)); ALS promoter (U.S. Pat. No. 5,659,026), and the like. Other constitutive promoters include, but are not limited to, for example, those discussed in U.S. Pat. Nos. 5,608,149; 5,608,144; 5,604,121; 5,569,597; 5,466,785; 5,399,680; 5,268,463; 5,608,142; and 6,177,611.

In choosing a promoter to use in the methods of the invention, it may be desirable to use a tissue-specific or developmentally regulated promoter.

A tissue-specific or developmentally regulated promoter is a DNA sequence which regulates the expression of a DNA sequence selectively in the cells/tissues of a plant critical to tassel development, seed set, or both, and limits the expression of such a DNA sequence to the period of tassel development or seed maturation in the plant. Any identifiable promoter may be used in the methods of the present invention which causes the desired temporal and spatial expression.

Promoters which are seed or embryo-specific and may be useful in the invention include, but are not limited to, soybean Kunitz trypsin inhibitor (Kti3, Jofuku and Goldberg, *Plant Cell* 1:1079-1093 (1989)), patatin (potato tubers) (Rocha-Sosa, M., et al. (1989) *EMBO J.* 8:23-29), convicilin, vicilin, and legumin (pea cotyledons) (Rerie, W. G., et al. (1991) *Mol. Gen. Genet.* 259:149-157; Newbigin, E. J., et al. (1990) *Planta* 180:461-470; Higgins, T. J. V., et al. (1988) *Plant. Mol. Biol.* 11:683-695), zein (maize endosperm) (Schemthaner, J. P., et al. (1988) *EMBO J.* 7:1249-1255), phaseolin (bean cotyledon) (Segupta-Gopalan, C., et al. (1985) *Proc. Natl. Acad. Sci. U.S.A.* 82:3320-3324), phytohemagglutinin (bean cotyledon) (Voelker, T. et al. (1987) *EMBO J.* 6:3571-3577), B-conglycinin and glycinin (soybean cotyledon) (Chen, Z-L, et al. (1988) *EMBO J.* 7:297-302), glutelin (rice endosperm), hordein (barley endosperm) (Marris, C., et al. (1988) *Plant Mol. Biol.* 10:359-366), glutenin and gliadin (wheat endosperm) (Colot, V., et al. (1987) *EMBO J.* 6:3559-3564), and sporamin (sweet potato tuberous root) (Hattori, T., et al. (1990) *Plant Mol. Biol.* 14:595-604). Promoters of seed-specific genes operably linked to heterologous coding regions in chimeric gene constructions maintain their temporal and spatial expression pattern in transgenic plants. Such examples include, but are not limited to, *Arabidopsis thaliana* 2S seed storage protein gene promoter to express enkephalin peptides in *Arabidopsis* and *Brassica napus* seeds (Vanderkerckhove et al., *Bio/Technology* 7:L929-932 (1989)), bean lectin and bean beta-phaseolin promoters to express luciferase (Riggs et al., *Plant Sci.* 63:47-57 (1989)), and wheat glutenin promoters to express chloramphenicol acetyl transferase (Colot et al., *EMBO J* 6:3559-3564 (1987)).

Inducible promoters selectively express an operably linked DNA sequence in response to the presence of an endogenous or exogenous stimulus, for example by chemical compounds (chemical inducers) or in response to environmental, hormonal, chemical, and/or developmental signals. Inducible or regulated promoters include, but are not limited to, for example, promoters regulated by light, heat, stress, flooding or drought, phytohormones, wounding, or chemicals such as ethanol, jasmonate, salicylic acid, or safeners.

For instance, introns of the present invention can be combined with inducible promoters to enhance their activity without affecting their inducibility characteristics.

A minimal or basal promoter is a polynucleotide molecule that is capable of recruiting and binding the basal transcription machinery. One example of basal transcription machinery in eukaryotic cells is the RNA polymerase II complex and its accessory proteins.

Plant RNA polymerase II promoters, like those of other higher eukaryotes, are comprised of several distinct "cis-acting transcriptional regulatory elements," or simply "cis-elements," each of which appears to confer a different aspect of the overall control of gene expression. Examples of such cis-acting elements include, but are not limited to, such as TATA box and CCAAT or AGGA box. The promoter can roughly be divided in two parts: a proximal part, referred to as the core, and a distal part. The proximal part is believed to be responsible for correctly assembling the RNA polymerase II complex at the right position and for directing a basal level of transcription, and is also referred to as "minimal promoter" or "basal promoter". The distal part of the promoter is believed to contain those elements that regulate the spatio-temporal expression. In addition to the proximal and distal parts, other regulatory regions have also been described, that contain enhancer and/or repressors elements The latter elements can be found from a few kilobase pairs upstream from the transcription start site, in the introns, or even at the 3' side of the genes they regulate (Rombauts, S. et al. (2003) *Plant Physiology* 132:1162-1176, Nikolov and Burley, (1997) *Proc Natl Acad Sci USA* 94: 15-22), Tjian and Maniatis (1994) *Cell* 77: 5-8; Fessele et al., 2002 *Trends Genet* 18: 60-63, Messing et al., (1983) *Genetic Engineering of Plants: an Agricultural Perspective*, Plenum Press, NY, pp 211-227).

When operably linked to a heterologous polynucleotide sequence, a promoter controls the transcription of the linked polynucleotide sequence.

In an embodiment of the present invention, the "cis-acting transcriptional regulatory elements" from the promoter sequence disclosed herein can be operably linked to "cis-acting transcriptional regulatory elements" from any heterologous promoter. Such a chimeric promoter molecule can be engineered to have desired regulatory properties. In an embodiment of this invention a fragment of the disclosed promoter sequence that can act either as a cis-regulatory sequence or a distal-regulatory sequence or as an enhancer sequence or a repressor sequence, may be combined with either a cis-regulatory or a distal regulatory or an enhancer sequence or a repressor sequence or any combination of any of these from a heterologous promoter sequence.

In a related embodiment, a cis-element of the disclosed promoter may confer a particular specificity such as conferring enhanced expression of operably linked polynucleotide molecules in certain tissues and therefore is also capable of regulating transcription of operably linked polynucleotide molecules. Consequently, any fragment, portion, or region of the promoter comprising the polynucleotide sequence shown in SEQ ID NO: 105, 106, 107, 108, 109, 110, 111, 112, 113, 114, 115, 116, 117, 119, 136 or 139 can be used as a regulatory polynucleotide molecule.

Promoter fragments that comprise regulatory elements can be added, for example, fused to the 5' end of, or inserted within, another promoter having its own partial or complete regulatory sequences (Fluhr et al., *Science* 232:1106-1112, 1986; Ellis et al., *EMBO J.* 6:11-16, 1987; Strittmatter and Chua, *Proc. Nat. Acad. Sci. USA* 84:8986-8990, 1987; Poulsen and Chua, *Mol. Gen. Genet.* 214:16-23, 1988; Comai et al., *Plant Mol. Biol.* 15:373-381, 1991; 1987; Aryan et al., *Mol. Gen. Genet.* 225:65-71, 1991).

Cis elements can be identified by a number of techniques, including deletion analysis, i.e., deleting one or more nucleotides from the 5' end or internal to a promoter; DNA binding protein analysis using DNase I footprinting; methylation interference; electrophoresis mobility-shift assays, in vivo genomic footprinting by ligation-mediated PCR; and other conventional assays; or by sequence similarity with known cis element motifs by conventional sequence comparison methods. The fine structure of a cis element can be further studied by mutagenesis (or substitution) of one or more nucleotides or by other conventional methods (see for example, *Methods in Plant Biochemistry and Molecular Biology*, Dashek, ed., CRC Press, 1997, pp. 397-422; and *Methods in Plant Molecular Biology*, Maliga et al., eds., Cold Spring Harbor Press, 1995, pp. 233-300).

Cis elements can be obtained by chemical synthesis or by cloning from promoters that include such elements, and they can be synthesized with additional flanking sequences that contain useful restriction enzyme sites to facilitate subsequent manipulation. Promoter fragments may also comprise other regulatory elements such as enhancer domains, which may further be useful for constructing chimeric molecules.

Methods for construction of chimeric and variant promoters of the present invention include, but are not limited to, combining control elements of different promoters or duplicating portions or regions of a promoter (see for example, U.S. Pat. Nos. 4,990,607; 5,110,732; and 5,097,025). Those of skill in the art are familiar with the standard resource materials that describe specific conditions and procedures for the construction, manipulation, and isolation of macromolecules (e.g., polynucleotide molecules and plasmids), as well as the generation of recombinant organisms and the screening and isolation of polynucleotide molecules.

In an embodiment of the present invention, the promoters disclosed herein can be modified. Those skilled in the art can create promoters that have variations in the polynucleotide sequence. The polynucleotide sequence of the promoters of the present invention as shown in SEQ ID NOS: 105-113, 119, 136 or 139, may be modified or altered to enhance their control characteristics. As one of ordinary skill in the art will appreciate, modification or alteration of the promoter sequence can also be made without substantially affecting the promoter function. The methods are well known to those of skill in the art. Sequences can be modified, for example by insertion, deletion, or replacement of template sequences in a PCR-based DNA modification approach.

The present invention encompasses functional fragments and variants of the promoter sequences disclosed herein.

A "functional fragment" of a regulatory sequence herein is defined as any subset of contiguous nucleotides of any of the regulatory sequences disclosed herein, that can perform the same, or substantially similar function as the full length promoter sequences disclosed herein.

A "functional fragment of a promoter" with substantially similar function to a full length promoter disclosed herein refers to a functional fragment that retains largely the same level of activity as the full length promoter sequence and exhibits the same pattern of expression as the full length promoter sequence.

A "variant promoter", as used herein, is the sequence of the promoter or the sequence of a functional fragment of a promoter containing changes in which one or more nucleotides of the original sequence is deleted, added, and/or substituted, while substantially maintaining promoter function. One or more base pairs can be inserted, deleted, or substituted internally to a promoter. In the case of a promoter fragment, variant promoters can include changes affecting the transcription of a minimal promoter to which it is operably linked. Variant promoters can be produced, for example, by standard DNA mutagenesis techniques or by chemically synthesizing the variant promoter or a portion thereof.

Enhancer sequences refer to the sequences that can increase gene expression. These sequences can be located upstream, within introns or downstream of the transcribed region. The transcribed region is comprised of the exons and the intervening introns, from the promoter to the transcription termination region. The enhancement of gene expression can be through various mechanisms which include, but are not limited to, increasing transcriptional efficiency, stabilization of mature mRNA and translational enhancement.

Recombinant DNA constructs of the present invention may also include other regulatory sequences, including but not limited to, translation leader sequences, introns, and polyadenylation recognition sequences. In another embodiment of the present invention, a recombinant DNA construct of the present invention further comprises an enhancer or silencer.

An "intron" is an intervening sequence in a gene that is transcribed into RNA and then excised in the process of generating the mature mRNA. The term is also used for the excised RNA sequences. An "exon" is a portion of the sequence of a gene that is transcribed and is found in the mature messenger RNA derived from the gene, and is not necessarily a part of the sequence that encodes the final gene product.

Many genes exhibit enhanced expression on inclusion of an intron in the transcribed region, especially when the intron is present within the first 1 kb of the transcription start site. The increase in gene expression by presence of an intron can be at both the mRNA (transcript abundance) and protein levels. The mechanism of this Intron Mediated Enhancement (IME) in plants is not very well known (Rose et al., *Plant Cell*, 20: 543-551(2008) Le-Hir et al, *Trends Biochem Sci.* 28: 215-220 (2003), Buchman and Berg, *Mol. Cell Biol*. (1988) 8:4395-4405; Callis et al., *Genes Dev.* 1(1987):1183-1200).

An "enhancing intron" is an intronic sequence present within the transcribed region of a gene which is capable of enhancing expression of the gene when compared to an intronless version of an otherwise identical gene. An enhancing intronic sequence might also be able to act as an enhancer when located outside the transcribed region of a gene, and can act as a regulator of gene expression independent of position or orientation (Chan et. al. (1999) *Proc. Natl. Acad. Sci.* 96: 4627-4632; Flodby et al. (2007) *Biochem. Biophys. Res. Commun.* 356: 26-31).

Short consensus sequences or motifs can be identified from the intron sequences experimentally identified to be enhancing introns. These motifs can be used to scan and help identify more gene-expression enhancing introns. A motif capable of conferring transgene expression in male reproductive tissue in dicot plants has been described in US application No. US2007/020436.

An 8-bp sequence (SEQ ID NO: 99) and a 5-bp sequence (SEQ ID NO: 100) that can be used for identifying novel enhancing introns have been described in this application. Some variations of the 8-bp sequence can also be useful for identifying enhancing introns. The useful variations from the 8-bp motif (SEQ ID NO: 99) described herein can occur mainly at the first three positions. The last 5 bp of the sequence are highly conserved. Also, the variations from the 8-bp consensus (SEQ ID NO: 99) occur at maximum two out of 8 positions at any one time. In the event of more than 2 bp being different than the consensus, the enhancing intron might have additional copies of either the 5-bp (SEQ ID NO: 100) or the 8-bp motif (SEQ ID NO: 99).

The motif variations can be represented as a consensus motif sequence, Y[R/T]RATCYG (SEQ ID NO: 146). The first position can be any of the two pyrimidine bases, C or T. The second position can be substituted by an A, G or T. The third position can be a purine. The ATC core is the most highly conserved region, and does not exhibit any variability.

An intron sequence can be added to the 5' untranslated region, the protein-coding region or the 3' untranslated region to increase the amount of the mature message that accumulates in the cytosol.

The intron sequences can be operably linked to a promoter. Promoters may be derived in their entirety from a native gene, or be composed of different elements derived from different promoters found in nature, or even comprise synthetic DNA segments.

Sequences orthologous to an intron are sequences that are present in orthologous genes at the same position as the intron in the original gene sequence.

The tissue expression patterns of the genes can be determined using the RNA profile database of the Massively Parallel Signature Sequencing (MPSS™). This proprietary database contains deep RNA profiles of more than 250 libraries and from a broad set of tissue types. The MPSS™ transcript profiling technology is a quantitative expression analysis that typically involves 1-2 million transcripts per cDNA library (Brenner S. et al., (2000). *Nat Biotechnol* 18: 630-634, Brenner S. et al. (2000) *Proc Natl Acad Sci USA* 97: 1665-1670). It produces a 17-base high quality usually gene-specific sequence tag usually captured from the 3'-most DpnII restriction site in the transcript for each expressed gene. The use of this MPSS data including statistical analyses, replications, etc, has been described previously (Guo M et al. (2008) *Plant Mol Biol* 66: 551-563).

IMEter is a word-based discriminator that can do a computational analysis as to whether an intron can act as an enhancer of gene expression or not. The IMeter scoring system is described in Rose, A. B. (2004). Plant J. 40_744-751, and Rose et al (2008) *Plant Cell* 20: 543-551.

"Transcription terminator", "termination sequences", or "terminator" as described herein refer to DNA sequences located downstream of a coding sequence, including polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht, I. L., et al., *Plant Cell* 1:671-680 (1989). A polynucleotide sequence with "terminator activity" refers to a polynucleotide sequence that, when operably linked to the 3' end of a second polynucleotide sequence that is to be expressed, is capable of terminating transcription from the second polynucleotide sequence and facilitating efficient 3' end processing of the messenger RNA resulting in addition of poly A tail. Transcription termination is the process by which RNA synthesis by RNA polymerase is stopped and both the processed messenger RNA and the enzyme are released from the DNA template.

Improper termination of an RNA transcript can affect the stability of the RNA, and hence can affect protein expression. Variability of transgene expression is sometimes attributed to variability of termination efficiency (Bieri et al (2002) *Molecular Breeding* 10: 107-117). As used herein, the terms "bidirectional transcriptional terminator" and "bidirectional terminator" refer to a transcription terminator sequence that has the capability of terminating transcription in both 5' to 3', and 3' to 5' orientations. A single sequence element that acts as a bidirectional transcriptional terminator can terminate transcription from two convergent genes.

The present invention encompasses functional fragments and variants of the terminator sequences disclosed herein.

A "functional fragment of a terminator" with substantially similar function to the full length terminator disclosed herein refers to a functional fragment that retains the ability to terminate transcription largely to the same level as the full length terminator sequence. A recombinant construct comprising a heterologous polynucleotide operably linked to a "functional fragment" of the terminator sequence disclosed herein exhibits levels of heterologous polynucleotide expression substantially similar to a recombinant construct comprising a heterologous polynucleotide operably linked to the full length terminator sequence.

A "variant terminator", as used herein, is the sequence of the terminator or the sequence of a functional fragment of a terminator containing changes in which one or more nucleotides of the original sequence is deleted, added, and/or substituted, while substantially maintaining terminator function. One or more base pairs can be inserted, deleted, or substituted internally to a terminator, without affecting its activity. Fragments and variants can be obtained via methods such as site-directed mutagenesis and synthetic construction.

These terminator functional fragments will comprise at least about 20 contiguous nucleotides, preferably at least about 50 contiguous nucleotides, more preferably at least about 75 contiguous nucleotides, even more preferably at least about 100 contiguous nucleotides of the particular terminator nucleotide sequence disclosed herein. Such fragments may be obtained by use of restriction enzymes to cleave the naturally occurring terminator nucleotide sequences disclosed herein; by synthesizing a nucleotide sequence from the naturally occurring terminator DNA sequence; or may be obtained through the use of PCR technology. See particularly, Mullis et al., *Methods Enzymol.* 155:335-350 (1987), and Higuchi, R. In PCR Technology: Principles and Applications for DNA Amplifications; Erlich, H. A., Ed.; Stockton Press Inc.: New York, 1989. Again, variants of these terminator fragments, such as those resulting from site-directed mutagenesis, are encompassed by the compositions of the present invention.

The terms "substantially similar" and "corresponding substantially" as used herein refer to nucleic acid fragments, particularly regulatory sequences, wherein changes in one or more nucleotide bases do not substantially alter the ability of the regulatory sequence to perform the same function as the corresponding full length sequence disclosed herein. These terms also refer to modifications, including deletions and variants, of the nucleic acid sequences of the instant invention by way of deletion or insertion of one or more nucleotides that do not substantially alter the functional properties of the resulting sequence relative to the initial, unmodified sequence. It is therefore understood, as those skilled in the art will appreciate, that the invention encompasses more than the specific exemplary sequences.

As will be evident to one of skill in the art, any heterologous polynucleotide of interest can be operably linked to the regulatory sequences described in the current invention. Examples of polynucleotides of interest that can be operably linked to the regulatory sequences described in this invention include, but are not limited to, polynucleotides comprising other regulatory elements such as introns, enhancers, promoters, translation leader sequences, protein coding regions such as disease and insect resistance genes, genes conferring nutritional value, genes conferring yield and heterosis increase, genes that confer male and/or female sterility, antifungal, antibacterial or antiviral genes, and the like. Likewise, the regulatory sequences described in the current invention can be used to regulate transcription of any nucleic acid that controls gene expression. Examples of nucleic acids that could be used to control gene expression include, but are not limited to, antisense oligonucleotides, suppression DNA constructs, or nucleic acids encoding transcription factors.

Embodiments of the invention are:

The present invention relates to regulatory sequences for modulating gene expression in plants. Recombinant DNA constructs comprising regulatory sequences are provided. Recombinant DNA constructs comprising intron sequences acting as enhancers of gene expression and endogenous promoter and terminator sequences corresponding to these intron sequences are provided.

Another embodiment of the invention is a recombinant DNA construct comprising an intron operably linked to a promoter and a terminator wherein the intron comprises a nucleotide sequence that has at least 95% sequence identity to SEQ ID NO: 4, 8, 13, 19, 52, 53, 56, 57, 58, 101, 102, 103, 104, 118, 137 or 138. In another embodiment, the intron comprises the nucleotide sequence of SEQ ID NO: 4, 8, 13, 19, 52, 53, 56, 57, 58, 101, 102, 103, 104, 118, 137 or 138.

One embodiment of the invention is a recombinant DNA construct comprising an intron operably linked to a promoter and a terminator wherein the promoter comprises a nucleotide sequence that has at least 95% sequence identity to SEQ ID NO: 105-117, 119, 136 or 139. In another embodiment, the promoter comprises the nucleotide sequence of SEQ ID NO: 105-117, 119, 136 or 139.

One embodiment of the invention is a recombinant DNA construct comprising an intron operably linked to a promoter and a terminator wherein the terminator comprises a nucleotide sequence that has at least 95% sequence identity to SEQ ID NOS: 140, 141, 142 or 143. In another embodiment, the terminator comprises the nucleotide sequence of SEQ ID NO: 140, 141, 142 or 143.

One embodiment of the invention is a recombinant DNA construct comprising an intron operably linked to a promoter and a terminator wherein the intron comprises a nucleotide sequence that has at least 95% identity to SEQ ID NOS: 4, 8, 13, 19, 52, 53, 56, 57, 58, 101, 102, 103, 104, 118, 137 or 138; and the promoter comprises a nucleotide sequence that has at least 95% identity to SEQ ID NOS: 105, 106, 107, 108, 109, 110, 111, 112, 113, 114, 115, 116, 117, 119, 136 or 139.

One embodiment of the invention is a recombinant DNA construct comprising an intron operably linked to a promoter and a terminator wherein the intron comprises a nucleotide sequence that has at least 95% identity to SEQ ID NO: 4, 8, 13, 19, 52, 53, 56, 57, 58, 101, 102, 103, 104, 118, 137 or 138; the promoter sequence has at least 95% identity to SEQ ID NO: 105, 106, 107, 108, 109, 110, 111, 112, 113, 114, 115, 116, 117, 119, 136 or 139; and the terminator has at least 95% sequence identity to SEQ ID NO: 140, 141, 142 or 143.

In one embodiment of the current invention, the intron is operably linked to the promoter, and is present downstream of the promoter, in the recombinant DNA constructs described herein. One embodiment of the present invention includes a recombinant DNA construct comprising an intron described in the present invention, operably linked to a promoter and a heterologous polynucleotide, wherein the intron can act as enhancer of expression of the heterologous polynucleotide.

Another embodiment of the invention encompasses a recombinant DNA construct comprising an intron wherein the intron sequence comprises at least one copy of the 8-bp sequence motif of SEQ ID NO. 99; or contains at least one copy of the 8-bp sequence motif of SEQ ID NO: 99 and at least one copy of the 5-bp sequence motif of SEQ ID NO: 100, wherein the intron is capable of enhancing expression of a heterologous polynucleotide in a transgenic plant. The intron sequence can also comprise more than one copy of SEQ ID NO: 99, or can comprise one or more than one copy of SEQ ID NO: 99 and more than one copy of SEQ ID NO: 100.

Another embodiment of this invention is a method to identify novel introns that are useful for enhancing expression of a heterologous polynucleotide in a plant cell, the method comprising the steps of scanning a plurality of introns from plants for presence of SEQ ID NO: 99, selecting a sequence that contains at least one copy of SEQ ID NO: 99, measuring the efficacy of the identified intron to enhance expression of a heterologous polynucleotide in a plant.

Another embodiment of the invention is a method for identifying novel intronic sequences for enhancing transgene expression in monocotyledenous plants by identifying sequences orthologous to SEQ ID NO: 4, 8, 13, 19, 52, 53, 56, 57, 58, 101, 102, 103, 104, 118, 137 or 138; and measuring the enhancing effect of the identified intron on the expression of an operably linked heterologous polynucleotide.

Another embodiment of the current invention includes the promoter and the terminator sequences that are endogenously linked to the introns identified using the methods described in the current invention.

Another embodiment of the current invention is a method for modulating expression of a heterologous polynucleotide in a monocotyledenous plant comprising the steps of: (a) introducing into a regenerable plant cell a recombinant DNA construct comprising a promoter and a heterologous polynucleotide wherein each is operably linked to an intron, wherein the intron comprises either (i) a nucleotide sequence that is orthologous to SEQ ID NO: 4, 8, 13, 19, 52, 53, 56, 57, 58, 101, 102, 103, 104, 118, 137 or 138; or (ii) a nucleotide sequence that contains least one copy of a sequence motif identical to SEQ ID NO: 99; and; (b) regenerating a transgenic plant from a regenerable monocotyledonous plant cell after step (a) wherein the transgenic plant comprises the recombinant DNA construct; and (c) obtaining a progeny plant derived from the transgenic plant of step (b), wherein said progeny plant comprises the recombinant DNA construct and exhibits enhanced expression of the heterologous polynucleotide when compared to a plant comprising a corresponding recombinant DNA construct without the intron sequence.

In another embodiment, this invention concerns a vector, cell, plant, or seed comprising a recombinant DNA construct comprising the regulatory sequences described in the present invention.

The invention encompasses regenerated, mature and fertile transgenic plants comprising the recombinant DNA constructs described above, transgenic seeds produced therefrom, T1 and subsequent generations. The transgenic plant cells, tissues, plants, and seeds may comprise at least one recombinant DNA construct of interest.

In one embodiment, the plant comprising the regulatory sequences described in the present invention is a monocotyledenous plant. In another embodiment, the plant comprising the regulatory sequences described in the present invention is a maize plant.

EXAMPLES

The present invention is further illustrated in the following Examples, in which parts and percentages are by weight and degrees are Celsius, unless otherwise stated. It should be understood that these examples, while indicating embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Furthermore, various modifications of the invention in addition to those shown and described herein will be apparent to those skilled in the art from the foregoing description. Such modifications are also intended to fall within the scope of the appended claims.

Example 1

Identification of Candidate Gene Expression/Transcript-Enhancing First Introns

Introns that may enhance transcript abundance were sought from among a set of maize genes which (a) had first introns near the N-terminus of the transcript, and (b) had high level transcript abundance. A subset of maize genes were identified whose models were deemed to be complete. This assessment was done using a combination of maize public B73 BAC sequences plus a proprietary EST transcript assembly in an analysis comparing the predicted gene structures and the predicted transcript open reading frames (ORFs) in relation to public reference proteins plus some manual curations. Only full-length transcripts were considered; that is, those with complete protein coding regions. This set did not represent all maize genes, and there was some redundancy in the list.

This set of gene models was then analyzed versus a body of over 250 MPSS mRNA transcript profiling samples produced from a variety of maize tissues and treatments. The MPSS profiling technology produces a 17-bp tag sequence beginning with GATC. These tags were matched to the gene set via the full-length transcript, and those genes which (a) had an MPSS tag matching the plus strand of the transcript, and (b) had a measured expression level of at least 1000 ppm (parts per million) in at least one of the MPSS samples, were retained. In this way a working set of 3131 genes was produced. Using the maize BAC genomic sequence to analyze these 3131 genes, a subset of genes was produced that (a) contained an intron, and (b) contained an intron which was located within the 5'UTR or within the first 300 nucleotides of the ORF. This resulted in a subset of 1185 genes for further consideration.

This set of 1185 candidate genes was then filtered down by a number of criteria. Duplicates were removed. Introns without canonical GT-AG rules were excluded. Genes whose expression was defined by 'promiscuous' MPSS tags, such as GATCAAAAAAAAAAAAA (SEQ ID NO: 145), and also MPSS tags matching repetitive elements, were removed. Genes whose first introns were greater than 2 kb were dropped. In addition, genes whose first introns' GC content were higher than 50% GC and/or the intron T (=U) content was below 25% were removed. In addition, the (Meter score for the first intron had to be positive. The (Meter scoring system is described in Rose, A. B. (2004) *Plant J.* 40:744-751. This resulted in an interim set of remaining 331 candidates. This set was then further manually winnowed down to 86 by positively considering a combinations of factors but chiefly: (a) the breadth of diverse tissue expression and (b) the ratio of the (Meter score to intron length.

This set of 86 introns was one prioritized pool from which introns were drawn for functional testing of whether they enhance transcript abundance. Seventeen of these 86 were tested.

Example 2

Creation of an Intron Testing Vector with Maize Ubiquitin Promoter

Figure 3:
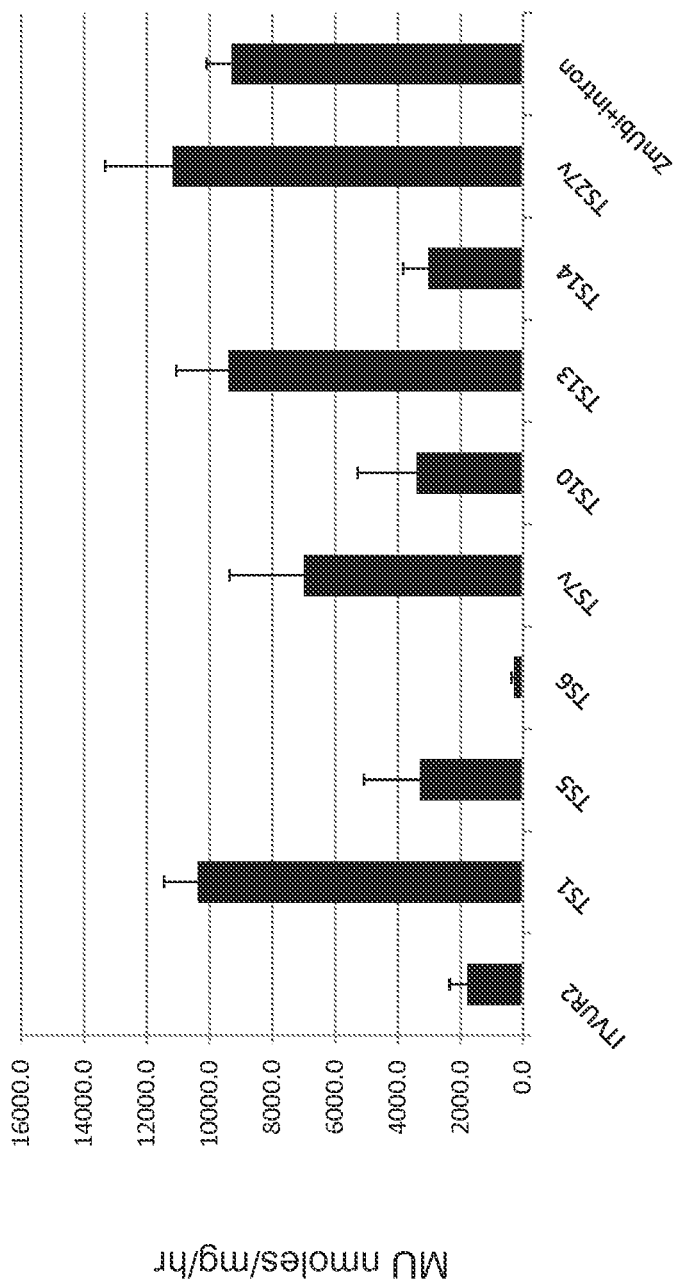
FIG. 3 shows quantitative analysis of GUS reporter gene expression in Maize Embryos infected with the respective constructs.

Maize ubi promoter (SEQ ID NO: 1) along with its intron (SEQ ID NO: 2) in the 5' UTR confers high level constitutive expression in monocot plants (Christensen, A. H., Sharrock, R. A. and Quail, P. H., *Plant Mol. Biol.* 18, 675-89, 1992). This high-level expression is dependent on the first intron in the 5' UTR. Removal of this intron results in a >4-fold reduction in expression measured by transient assays (FIG. 3). We created a plant transformation vector where the maize ubiquitin promoter together with its endogenous intron drives *E. coli* β-glucuronidase (GUS) reporter gene expression. We then replaced the maize ubiquitin intron with two restriction sites, AsiS1 and Acc65I to allow the insertion of novel introns and test their ability to enhance reporter gene expression driven by the ubiquitin promoter (SEQ ID NO: 1) (FIG. 1).

Example 3

Intron Amplification and Cloning

*Zea mays* B73 seeds were germinated in Petri plates and genomic DNA was made from seedling leaf tissue using the QIAGEN® DNEASY® Plant Maxi Kit (QIAGEN® Inc.) according to the manufacturer's instructions. DNA products were amplified with primers shown in Table 2 using genomic DNA as template with PHUSION™ DNA polymerase (New England Biolabs Inc.). The resulting DNA fragments were cloned into the intron testing vector ITVUR-2 (SEQ ID NO: 3), using standard molecular biology techniques (Sambrook et al.) or using INFUSION™ from (Clontech Inc.), and sequenced completely.

TABLE 2

| | Intron | | | |
|---|---|---|---|---|
| Name | SEQ ID NO | Length (nt) | Forward Primer (SEQ ID NO) | Reverse Primer (SEQ ID NO) |
| TS1 | 4 | 814 | 20 | 21 |
| TS4 | 5 | 727 | 22 | 23 |
| TS5 | 6 | 834 | 24 | 25 |
| TS6 | 7 | 982 | 26 | 27 |
| TS7v | 137 | 856 | 28 | 29 |
| TS8 | 9 | 1020 | 30 | 31 |
| TS10 | 10 | 841 | 32 | 33 |
| TS11 | 11 | 1044 | 34 | 35 |
| TS12 | 12 | 648 | 36 | 37 |
| T513 | 13 | 632 | 38 | 39 |
| TS14 | 14 | 1405 | 40 | 41 |
| TS15 | 15 | 1361 | 42 | 43 |
| TS16 | 16 | 703 | 44 | 45 |
| T517 | 17 | 1341 | 46 | 47 |
| T524 | 18 | 1125 | 48 | 49 |
| TS27v | 138 | 884 | 50 | 51 |

All the constructs were mobilized into the *Agrobacterium* strain LBA4404/pSB1 and selected on Spectinomycin and tetracycline. *Agrobacterium* transformants were isolated and the integrity of the plasmid was confirmed by retransforming to *E. coli* or PCR analysis.

Example 4

Transient Transformation and Expression of Intron Constructs in Maize Embryos Infected with *Agrobacterium*

Preparation of *Agrobacterium* Suspension:

*Agrobacterium* was streaked out from −80° C. frozen aliquot onto a plate containing PHI-L medium and was cultured at 28° C. in the dark for 2 days. The PHI-L medium comprises 50 ml Stock Solution A, 50 ml/L stock Solution B, 900 ml Stock Solution C and spectinomycin (Sigma chemicals) was added to a concentration of 50 mg/L in sterile ddH2O (Stock Solution A: K2HPO4 60 g/l, NaH2PO4 20 g/l, pH adjusted to 7.0 w/KOH and autoclaved; stock solution B: NH4Cl 20 g/l, MgSO4.7H2O 6 g/l, KCl 3 g/l, CaCl2 0.2 g/l, FeSO4.7H2O 50 mg/l; stock solution C: glucose 5 g/l, agar 15 g/l (#A-7049, Sigma Chemicals, St. Louis, Mo.) and was autoclaved.

The plate can be stored at 4° C. and used usually for about 1 month. A single colony was picked from the master plate and was streaked onto a plate containing PHI-M medium [Yeast Extract 5 g/l (Difco); Peptone 10 g/l (Difco); NaCl 5 g/l (Hi-Media); agar (Sigma Chemicals) 15 g/l; pH 6.8, containing 50 mg/l spectinomycin] and incubated at 28° C. in the dark for overnight.

Five ml of PHI-A, [CHU (N6) Basal salts (Sigma C-1416) 4 g/l; Erikson's vitamin solution (1000×, Sigma-1511) 1 ml/l; Thiamine.HCl (Sigma) 0.5 mg/l; 2,4-Dichloro phenoxyacetic acid (2,4-D, Sigma) 1.5 mg/l; L-Proline (Sigma) 0.69 g/l; Sucrose (Sigma) 68.5 g/l; Glucose (Sigma) 36 g/l; pH adjusted to 5.2 with KOH] was added to a 14 ml FALCON™ tube in a hood. About 3 full loops (5 mm loop size) *Agrobacterium* was collected from the plate and suspended in the tube, then the tube vortexed to make an even suspension. One ml of the suspension was transferred to a spectrophotometer tube and the OD of the suspension was adjusted to 0.72 at 550 nm by adding either more *Agrobacterium* or more of the same suspension medium, for an *Agrobacterium* concentration of approximately $0.5 \times 10^9$ cfu/ml. The final *Agrobacterium* suspension was aliquoted into 2 ml microcentrifuge tubes, each containing 1 ml of the suspension. The suspension was then used as soon as possible.

Embryo Isolation, Infection and Co-Cultivation:

About 2 ml of the same medium (PHI-A) which is used for the *Agrobacterium* suspension was added into a 2 ml microcentrifuge tube. Immature embryos were isolated from a sterilized ear with a sterile spatula and dropped directly into the medium in the tube. A total of 25 embryos are placed in the tube. The optimal size of the embryos was about 1.7-2.0 mm. The entire medium was drawn off and 1 ml of *Agrobacterium* suspension was added to the embryos and the tube was vortexed for 30 sec. The tube was allowed to stand for 5 min in the hood. The suspension of *Agrobacterium* and embryos was poured into a Petri plate containing co-cultivation medium PHI-B [CHU(N6) Basal salts (Sigma C-1416) 4 g/l; Eriksson's vitamin solution (1000×, Sigma-1511) 1 ml/l; Thiamine.HCl 0.5 mg/l; 2,4-D 1.5 mg/l; L-Proline 0.69 g/l; GELRITE® (Sigma) 3 g/l; Sucrose 30 g/l; pH adjusted to 5.8 with KOH; Post sterilization, Silver nitrate (0.85 mg/l) and acetosyringone (100 mM) were added after cooling the medium to 45° C.]. Any embryos left in the tube were transferred to the plate using a sterile spatula. The *Agrobacterium* suspension was drawn off and the embryos placed axis side down on the media. The plate was sealed with PARAFILM® and was incubated in the dark at 23-25° C. for about 3 days of co-cultivation.

Resting of Co-Cultivated Embryos:

For the resting step, all the embryos were transferred to a new plate containing PHI-C medium [CHU(N6) Basal salts (Sigma C-1416) 4 g/l; Eriksson's vitamin solution (1000×, Sigma-1511) 1 ml/l; Thiamine.HCl 0.5 mg/l; 2,4-D 1.5 mg/l; L-Proline 0.69 g/l; Sucrose 30 g/l; MES buffer (Sigma) 0.5 g/l; agar (Sigma 1-7049) 8 g/l; pH adjusted to 5.8 with KOH; Post sterilization, Silver nitrate (0.85 mg/l) and carbenicillin (100 mg/l) were added after cooling the medium to 45° C.].

The plates were sealed with PARAFILM® and incubated in the dark at 28° C. for 3-5 days.

Histochemical and Fluorometric GUS Analysis:

Transformed embryos were taken for expression analysis after 3 days of resting. Ten embryos for each construct were used for histochemical GUS staining using standard protocols (Janssen and Gardner, *Plant Mol. Biol.* (1989)14:61-72,) and two pools of 5 each were used to do quantitative assays using MUG substrate using standard protocols [Jefferson, R. A., *Nature.* 342:837-838 (1989); Jefferson, R. A., Kavanagh, T. A. & Bevan, M. W. *EMBO J.* 6:3901-3907 (1987)] (FIG. 3). Introns TS1 (SEQ ID NO: 4), TS7v (SEQ ID NO: 137), TS13 (SEQ ID NO: 13) and TS27v (SEQ ID NO: 138) all enhanced the GUS reporter gene expression between 3 to 5 fold when compared to the ubiquitin promoter alone without any intron. The level of enhancement is comparable to that of the maize ubiquitin first intron. Introns TS4, TS5, TS6, TS8, TS10, TS11, TS12, TS14, TS15, TS16, TS17 and TS24 did not enhance expression (Data shown for TS5, TS6, TS10 and TS14 in FIG. 3).

Example 5

Transient Transformation and Expression of Intron Constructs in Rice Calli Via *Agrobacterium*

Preparation of *Agrobacterium* Suspension:

*Agrobacterium* was streaked out from −80° C. frozen aliquot onto a plate containing YEB medium and was cultured at 28° C. in the dark for 2 days. The YEB medium comprises (MgSO4 (Hi-Media) 0.2 g/l; K2HPO4 (Fisher Scientific) 0.5 g/l; Mannitol 10 g/l; NaCl 0.1 g/l; Yeast Extract 0.4 g/l; Agar 15 g/l). *Agrobacterium* cultures harboring the intron constructs were cultured one day prior to rice calli infection in YEB broth. A large swipe of *Agrobacterium* growth was inoculated into 7.5 ml of YEB broth in FALCON™ tubes. Then in the next morning OD of each culture was measured at 550 nm. Cultures were centrifuged at 4000 rpm for 10 minutes. Supernatant was discarded and the pellet was resuspended in PHI-L supplemented with Acetosyringone at 100 µM. Another spin was given to *Agrobacterium* cultures at 4000 rpm for 10 min and the pellets were resuspended in PHI-L supplemented with Acetosyringone at 100 µM and the OD was adjusted to 1.0 by adding either more *Agrobacterium* or more of the same suspension medium, for an *Agrobacterium* concentration of approximately $0.5 \times 10^9$ cfu/ml.

Rice Callus Induction, Infection and Co-Cultivation:

15 to 21 days old Rice calli which were grown on callus induction medium, PHI-R [CHU(N6) Basal salts (Sigma C-1416) 4 g/l; Eriksson's vitamin solution (1000×, Sigma-1511) 1 ml/l; Thiamine.HCl 0.5 mg/l; 2,4-D 2.0 mg/l; L-Proline 0.69 g/l; Casein hydrolysate (Sigma) 300 mg/l; Sucrose (Sigma) 30 g/l; GELRITE® (Sigma) 4 g/l; pH adjusted to 5.8 with KOH]. Coleoptile of the rice calli was removed and calli were spliced to the size of approximately 2 to 3 mm. Spliced calli were transferred to the FALCON™ tubes containing *Agrobacterium* cultures and infected for 15 minutes with gentle intermittent shaking. The liquid *Agrobacterium* culture was decanted and the wet calli were taken out and blotted on sterile WHATMAN® filter paper No 4. Subsequently, the calli were transferred onto co-cultivation medium, PHI-R supplemented with Acetosyringone (Sigma) at 100 µM. The infected calli were co-cultivated in dark at 21° C. for 72 hours.

Resting of Co-Cultivated Rice Calli:

The co-cultivation was terminated by washing in sterile water containing carbenicillin (Sigma, 400 mg/l). Calli were washed with gentle intermittent shaking in the antibiotic solution for 15 minutes. The wet calli were blotted on WHATMAN® filter paper No 4. The dried calli were transferred to resting/callusing medium, PHI-R in which carbenicillin (400 mg/l) was added after cooling the medium to 45° C. after sterilization. The plates were sealed with PARAFILM® and incubated in the dark at 28° C. for 3-5 days.

Figure 4:
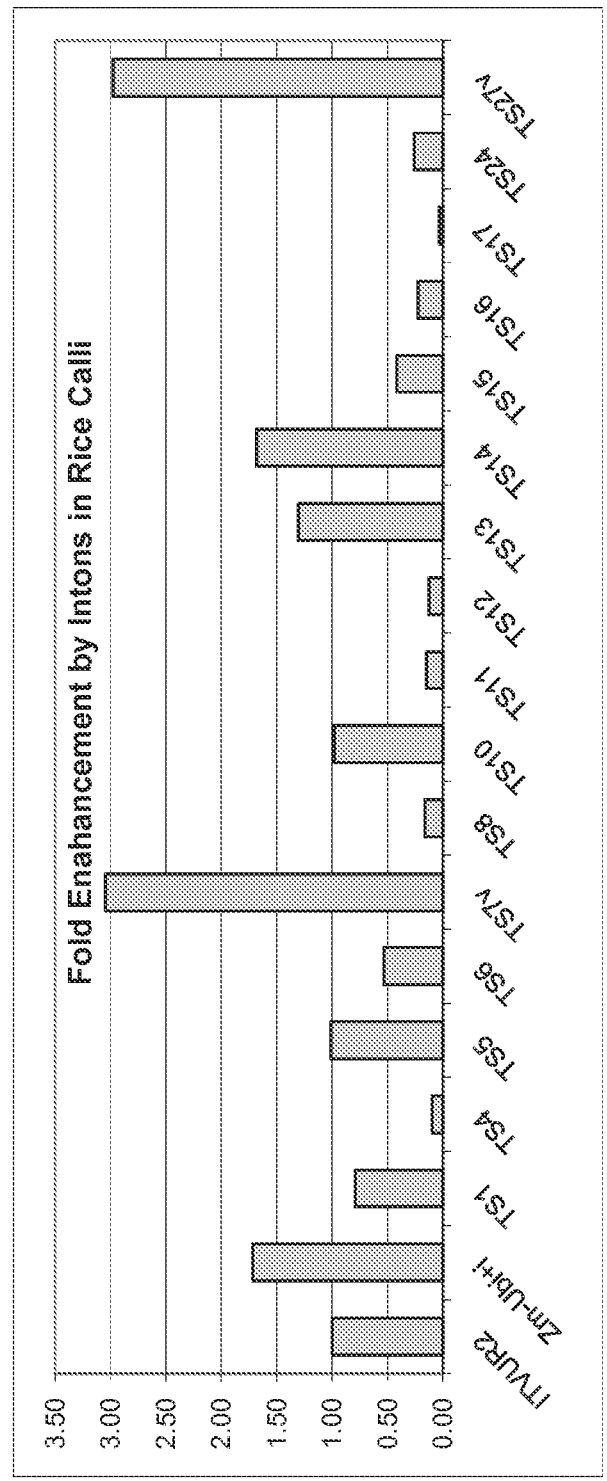
FIG. 4 shows the fold enhancement of GUS reporter gene expression in rice calli infected with intron constructs when compared with the control vector ITVUR-2.

Histochemical and Fluorometric GUS Analysis:

After 3 days, calli were taken for expression analysis. For each construct 20 calli were infected and 8 calli were used for histochemical GUS staining using X-Gluc solution and another eight calli were taken for GUS quantitation using standard protocol (Jefferson et al., *EMBO J.* 6:3901-3907, 1987). TS7v (SEQ ID NO: 137) and TS27v (SEQ ID NO: 138) were able to enhance GUS reporter expression from the maize ubiquitin promoter (SEQ ID NO: 1) (FIG. 4).

Example 6

Description of Constitutive Promoter Selection Via MPSS Samples

Promoter candidates were identified using a set of 241 proprietary expression profiling experiments run on the MPSS (Massively Parallel Signature Sequencing) technology platform provided by Lynx Therapeutics. The 241 samples from corn consisted of various tissue samples spanning most of the range of corn tissues and developmental stages. Each experiment resulted in approximately 20,000 unique sequence tags of 17 bp length from a single tissue sample. Typically these tags could be matched to one or a few transcript sequences from the proprietary "Unicorn" EST assembly set. A query of the MPSS database was performed looking for tags that were observed in 240 or more of the 241 samples. We identified 111 tags that met the criteria and chose 22 that were observed at an expression level of 1 or greater PPM (Parts Per Million tags) in all 241 experiments for further development. 21 of these 22 tags mapped to a single gene based on the transcript set. We took the top 6 candidates from this list and identified the 1500 bp of promoter regions and the first intron, defined as the first intron in the transcript from the 5' end, (i1 (SEQ ID NO: 52), i2 (SEQ ID NO: 53), i3 (SEQ ID NO: 54), i5 (SEQ ID NO: 56), i6 (SEQ ID NO: 57) and i7 (SEQ ID NO: 58). In addition we also included one second intron (i4; SEQ ID NO: 55) to the list. All introns were evaluated for intron-mediated enhancement of expression from CYMV promoter.

Example 7

Enhancement Activity of Introns in Transient Expression System

To determine whether the experimental introns function to enhance promoter activity in plant tissue, transient infiltration assays using the maize suspension cell line, BMS (Black Mexican Sweet), were performed. These *Agrobacterium*-mediated assays, known in the art, provide a rapid screening method to evaluate the enhancement capability of the introns.

The introns were cloned into an expression vector downstream of the Citrus Yellow Mosaic virus promoter and upstream of the coding region of an insecticidal gene described in US2007/0202089 A1. The insecticidal gene acted as a reporter for expression. A vector with no intron between the promoter and coding region was included to provide a baseline control for expression. A vector (SEQ ID NO: 59; PHP38808) with the Adh1 intron1 was also included to provide a comparison for the level of increased expression by each experimental intron. The Adh1 intron has been shown to enhance the expression of foreign genes in plant tissue (Callis et al. (1987) *Genes and Development:* 1183-1200; Kyozuka et al. (1990) *Maydica* 35: 353-357). Each expression vector also contained an expression cassette for phosphinothricin acetyl transferase (PAT).

Transiently transformed BMS cells were evaluated for expression by both northern blot analysis for RNA accumulation and ELISA analysis for protein accumulation. If the experimental introns, particularly introns i1 (SEQ ID NO: 52), i2 (SEQ ID NO: 53), i5 (SEQ ID NO: 56), i6 (SEQ ID NO: 57), and i7 (SEQ ID NO: 58), exhibited intron mediated enhancement of expression, the increased expression would be reflected at both the RNA and protein levels.

Figure 5:
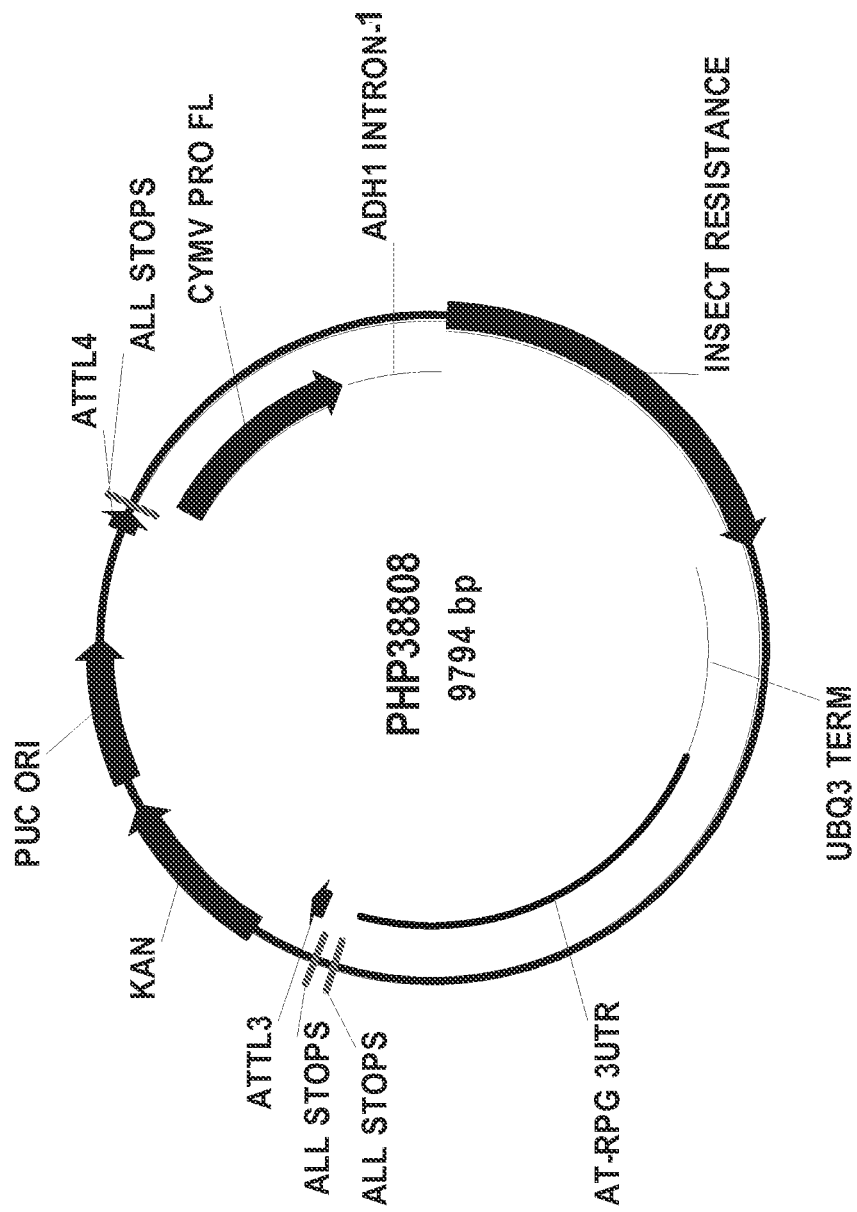
FIG. 5 shows the map of PHP38808, the vector with CYMV promoter and ADH1 intron, used for testing intron-mediated enhancement of gene expression, as described in Example 7.

The ratio of expression for each intron cassette showed that introns i1, i2, i5, i6, and i7 had expression levels that were between 2.3 and 4.8 fold higher than the intronless control (Table 3). These increased expression levels were comparable to the control cassette (SEQ ID NO: 59, PHP38808; FIG. 5) containing the Adh1 intron. The ELISA values were standardized for differences in transformation efficiency between vectors by normalizing against PAT gene expression.

TABLE 3

ELISA Results Indicating Expression Levels of Insecticidal Gene (IG) and PAT in Constructs Containing Experimental Introns

| Intron | IG (ppm) | PAT (ppm) | IG/PAT | Fold difference from no intron |
|---|---|---|---|---|
| none | 38.8 | 179.0 | 0.22 | N/A |
| ADH1 | 104.3 | 117.4 | 0.89 | 4.05 |
| i1 | 98.3 | 136.5 | 0.72 | 3.27 |
| i2 | 118.7 | 154.0 | 0.77 | 3.50 |
| i5 | 115.5 | 108.5 | 1.06 | 4.82 |
| i6 | 107.6 | 209.0 | 0.51 | 2.32 |
| i7 | 104.3 | 117.4 | 0.89 | 4.05 |

Figure 6:
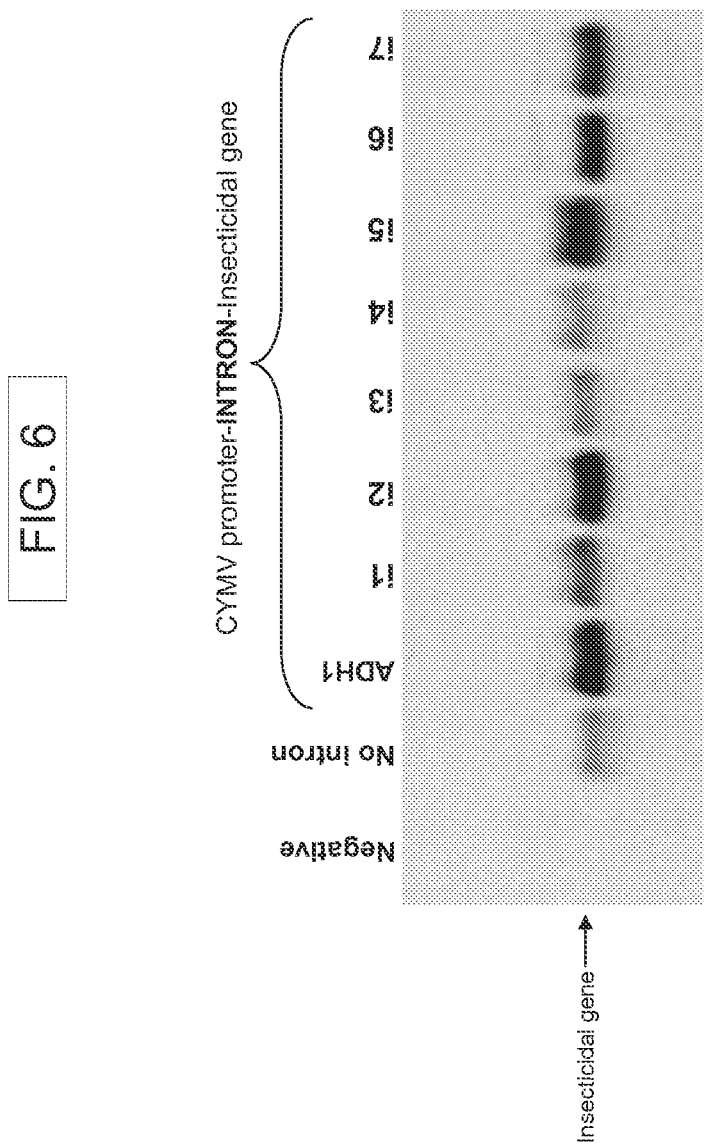
FIG. 6 shows the results of Northern blot of RNA extracted from infiltrated maize tissue culture material and probed with a digoxigenin-labeled DNA probe for the insecticidal gene used. Samples were loaded based on ELISA data to contain equal amounts of PAT.

To determine whether introns i1 (SEQ ID NO: 52), i2 (SEQ ID NO: 53), i5 (SEQ ID NO: 56), i6 (SEQ ID NO: 57), and i7 (SEQ ID NO: 58) resulted in increased mRNA levels, northern blot analysis was performed. RNA amounts for each vector were normalized against PAT expression prior to electrophoresis. The results of the analysis mirrored the ELISA results. Introns i1, i2, i5, i6, and i7 facilitated levels of reporter mRNA accumulation that were above that of the intronless cassette and comparable to the ADH1 cassette (see FIG. 6). These results show that i1, i2, i5, i6, and i7 (SEQ ID NOS: 52-53, 56-58 respectively) display intron-mediated enhancement of expression in this system.

Figure 7:
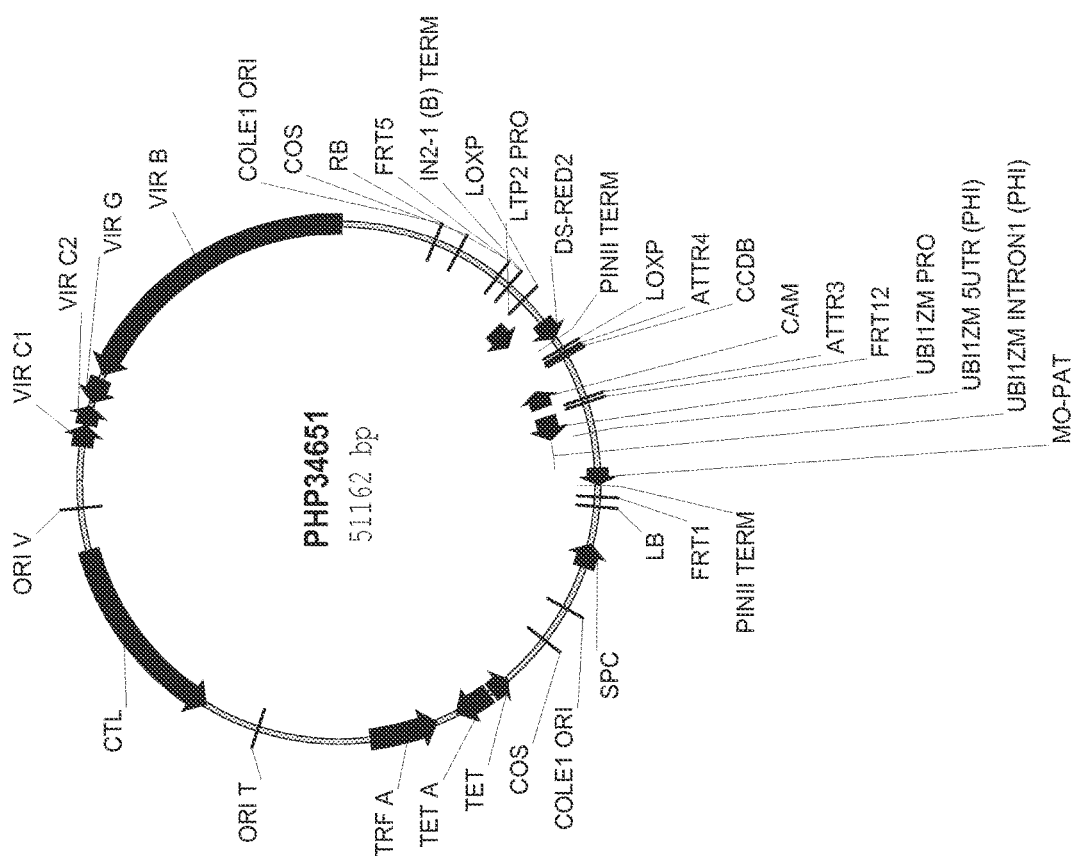
FIG. 7 shows the map of PHP34651, vector containing GATEWAY® attR recombination sites and a PAT expression cassette used for LR reactions to generate the final expression vectors for introns, as described in Example 7.
Figure 8:
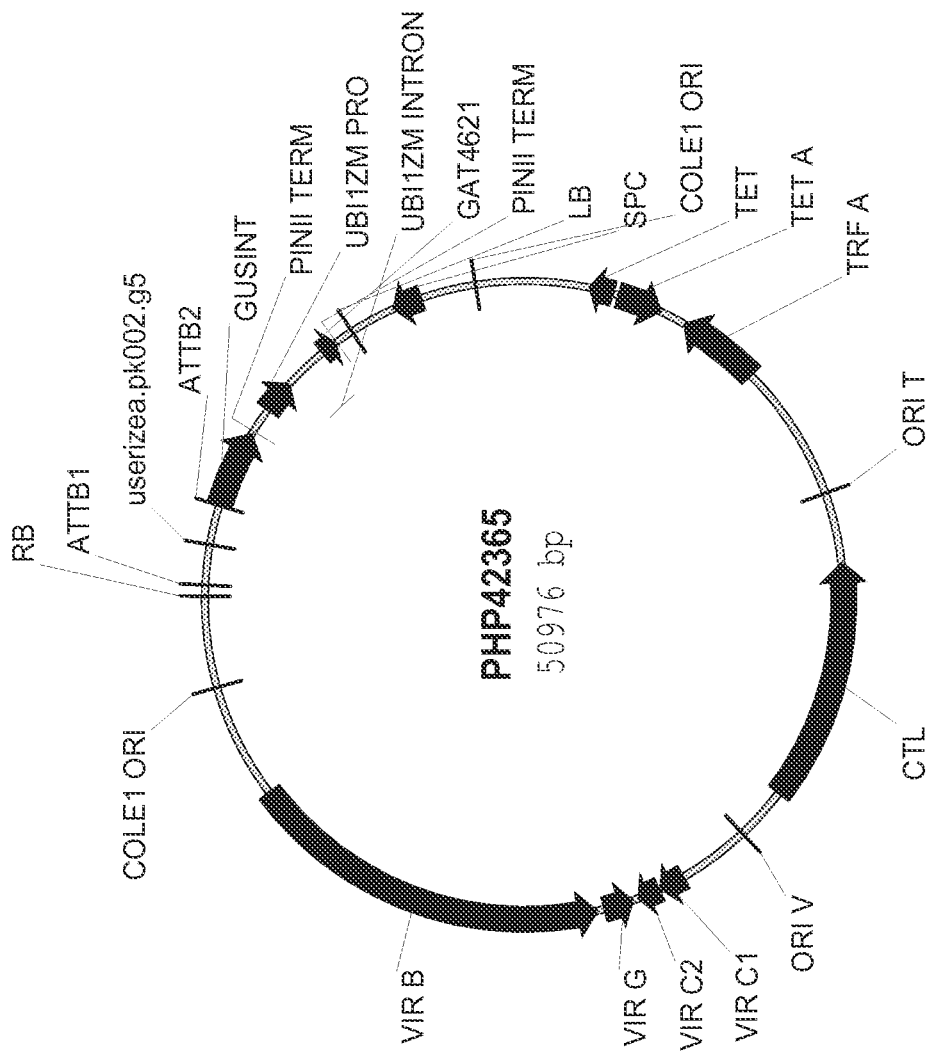
FIG. 8 shows the map of PHP42365, vector containing ZmUbi promoter and ZmUbi intron, for testing in stable transgenic rice plants, as described in Example 11.

Materials and Methods:

Introns i1 (SEQ ID NO: 52), i2 (SEQ ID NO: 53), i3 (SEQ ID NO: 54), i4 (SEQ ID NO: 55) and i5 (SEQ ID NO: 56) were generated using a method known in the art as oligonucleotide stacking. Oligos and primers (Table 4) synthesized by IDT (Integrated DNA Technologies, Inc. Coralville, Iowa) were resuspended in distilled water to a concentration of 100 µM. Equal amounts of each oligonucleotide were mixed to create a total volume of 10 µl. The flanking primers for PCR amplification were also mixed equally to a volume of 10 µl. Two microliters of the oligonucleotide mix and 10 µl of the primer mix were combined for PCR using the HotStart Herculase system from Stratagene. PCR was performed using 10 µl Herculase buffer, 2 µl of 25 nM dNTPs, 1.2 µl of the oligo and primer mixture, 1 µl 100 mM MgSO4, 2 µl DMSO, 1 µl HotStart Herculase enzyme, and 82.8 µl of distilled water. PCR conditions were 96° C. for 3 minutes, then 35 cycles at 94° C. for 30 s, 60° C. for 30 s, and 72° C. for 1 min., followed by 72° C. for 10 min. Reactions were stored at 4° C. Introns i6 and i7 were synthesized by GENEART, Inc., Burlingame, Calif. To clone introns i1 (SEQ ID NO: 52), i2 (SEQ ID NO: 53), i6 (SEQ ID NO: 57), and i7 (SEQ ID NO: 58), the starting product was cut with the restriction enzymes ECoRV (5' end) and BamHI (3' end). Intron i5 (SEQ ID NO: 56), was cut with EcoRV (5' end) and BgIII (3' end). A plasmid containing a cassette (SEQ ID NO: 59, PHP38808; FIG. 5) with the CYMV promoter the ADH1 intron and an insecticidal gene flanked by GATEWAY® (INVITROGEN™) attL recombination sites was cut with EcoRV and BamHI to remove the ADH1 intron and allow the experimental introns to be ligated into the cut plasmid. The resulting vectors (entry vectors, PHP38811, PHP38813, PHP38815, PHP38817, PHP38819, PHP38821, PHP38823 for i1, i2, i3, i4, i5, i6, i7 respectively) were used in LR reactions with a larger plasmid (PHP34651, FIG. 7, SEQ ID NO: 60) containing GATEWAY® attR recombination sites and a PAT expression cassette to generate the final expression vectors (destination vectors PHP38812, PHP38814, PHP38816, PHP38818, PHP38820, PHP38822 and PHP38824 respectively for introns i1, i2, i3, i4, i5, i6, i7, i8 and i9). These vectors were used to transform competent *Agrobacterium tumefaciens* cells, which were then used to transiently transform BMS cells.

TABLE 4

Primers and Oligonucleotides Used for Oligonucleotide Stacking

| Oligo/Primer SEQ ID NO: | (Used for) Intron | Sense/Antisense | Flanking Primer/Oligonucleotide |
|---|---|---|---|
| 61 | i1 | Sense | Flanking Primer |
| 62 | i1 | Sense | Oligonucleotide |
| 63 | i1 | Sense | Oligonucleotide |
| 64 | i1 | Sense | Oligonucleotide |
| 65 | i1 | Antisense | Oligonucleotide |
| 66 | i1 | Antisense | Oligonucleotide |
| 67 | i1 | Antisense | Oligonucleotide |
| 68 | i1 | Antisense | Flanking Primer |
| 69 | i2 | Sense | Flanking Primer |
| 70 | i2 | Sense | Oligonucleotide |
| 71 | i2 | Sense | Oligonucleotide |
| 72 | i2 | Sense | Oligonucleotide |
| 73 | i2 | Antisense | Oligonucleotide |
| 74 | i2 | Antisense | Oligonucleotide |
| 75 | i2 | Antisense | Oligonucleotide |
| 76 | i2 | Antisense | Flanking Primer |
| 77 | i3 | Sense | Flanking Primer |
| 78 | i3 | Sense | Oligonucleotide |
| 79 | i3 | Sense | Oligonucleotide |
| 80 | i3 | Antisense | Oligonucleotide |
| 81 | i3 | Antisense | Oligonucleotide |
| 82 | i3 | Antisense | Flanking Primer |
| 83 | i4 | Sense | Flanking Primer |
| 84 | i4 | Sense | Oligonucleotide |
| 85 | i4 | Sense | Oligonucleotide |
| 86 | i4 | Antisense | Oligonucleotide |
| 87 | i4 | Antisense | Oligonucleotide |
| 88 | i4 | Antisense | Flanking Primer |
| 89 | i5 | Sense | Flanking Primer |
| 90 | i5 | Sense | Oligonucleotide |
| 91 | i5 | Sense | Oligonucleotide |

TABLE 4-continued

Primers and Oligonucleotides Used for Oligonucleotide Stacking

| Oligo/Primer SEQ ID NO: | (Used for) Intron | Sense/ Antisense | Flanking Primer/Oligonucleotide |
|---|---|---|---|
| 92 | i5 | Antisense | Oligonucleotide |
| 93 | i5 | Antisense | Oligonucleotide |
| 94 | i5 | Antisense | Flanking Primer |

RNA was extracted from infiltrated tissue culture material using the QIAGEN® RNA Maxiprep kit. Based on ELISA data for PAT, RNA samples were loaded on an agarose gel (1% Lonza SeaKem LE agarose) to contain equal parts per million of PAT to normalize for variations in transformation efficiency. After electrophoresis, samples on the gel were transferred to a nylon membrane via capillary transfer overnight using the WHATMAN® TurboBlotter system standard protocol. RNA was crosslinked to the membrane by UV light. Prehybridization and hybridization steps were performed following the manufacturer's protocol for Roche DIG Easy Hyb solution (catalog #11603558001). The blot was prehybridized at 50° C. in Roche DIG Easy Hyb solution, then was probed overnight at 50° C. with a mixture of digoxigenin-labeled DNA probes for the insecticidal and PAT gene in Roche DIG Easy Hyb solution. Probes were generated using Roche PCR DIG Probe Synthesis Kit (Roche catalog #11636090910). The blot was washed twice for five minutes each at room temperature in low stringency buffer (2×SSC+0.1% SDS), then washed twice for 15 minutes each at 50° C. in high stringency buffer (0.1×SSC+0.1% SDS).

For detection, the Roche DIG Wash and Block Buffer Set (catalog #11585762001) was used. The membrane was washed for 2 minutes at room temperature in wash buffer, and then blocked in block solution for 30 minutes at room temperature. A 1:10,000 dilution of anti-digoxigenin-AP antibody (Roche catalog #11093274910, 0.75 U/μl) in 50 ml block solution was added to the blot for 30 minutes. The blot was washed twice for 15 minutes each at room temperature in wash buffer, and then equilibrated in 50 ml of detection buffer for 3 minutes. Blot was incubated at room temperature for 5 minutes with 3 ml of CSPD (Roche catalog #1755633001), and then incubated at 37° C. for 10 minutes. Detection was done with film at 37° C.

Example 8

Identification of Unique Motif from Maize First Introns Using the Experimental Dataset of Tested Enhancing Introns Computational analysis was performed to identify unique motifs that were present in the 9 enhancing introns identified as explained in Examples 4 and 7 and Table 1 (TS1, TS7, TS13, TS27, i1, i2, i5, i6, i7 (SEQ ID NOS: 4, 8, 13, 19, 52, 53, 56, 57, and 58 respectively)). The proprietary promoter REAPer tool was adapted to look for possibly conserved motifs. The promoter REAPer tool is a regulatory element identification tool that relies on the conserved word approach. It is described in the U.S. patent application Ser. No. 12/534,471. The introns were searched in both directions using sets of 3-6 introns at a time. When candidates were found, they were used to search all the introns.

The introns were divided into the following categories. "All Enhancing Introns" are the 9 introns (new enhancing introns) described in Table 1 and experimentally shown to be enhancing gene expression (TS1, TS7, TS13, TS27, i1, i2, i5, i6, and i7 (SEQ ID NOS: 4, 8, 13, 19, 52, 53, 56, 57, and 58 respectively), plus four known enhancing introns (Adh1_intron1 (SEQ ID NO: 95), Adh1_intron 6 (SEQ ID NO: 96), Sh-1_intron 1 (SEQ ID NO: 97) and Ubi1ZM_intron (SEQ ID NO: 98) Callis, J. et al (1987) Genes Dev. 1: 1183-1200, Vasil, V. et al (1989) Plant Physiol. 91; 1575-1579, Christensen, A. H. et al (1992) Plant Mol. Biol. 18: 675-689, Jeong, Y.-M. et al (2009) Plant Sci. 176:58-65). The 10 "non-enhancing introns" are 10 introns found not to enhance gene expression in transient maize assays as explained in Examples 4 and 7 and Table 1 (SEQ ID NOS: 5-7, 9, 11, 12, 17, 18, 54, and 55).

The 8-bp sequence CAGATCTG (SEQ ID NO: 99) or its variations were found in all the enhancing introns except TS27. The exact 8-bp sequence CAGATCTG was found in 2 out of the 9 enhancing introns identified (SEQ ID NOS: 52 and 53), but was not found in any of the 10 non-enhancing introns (SEQ ID NOS: 5-79, 11, 12, 17, 18, 54, and 55). A subset of this sequence ATCTG (SEQ ID NO: 100) was also present in 8 out of 9 enhancing introns (SEQ ID NOS: 4, 8, 13, 52, 53, 56, 57 and 58), and was also found to be present in the four known enhancing introns (SEQ ID NOS: 95-98). The frequency of occurrence of these motifs was normalized to the intron length (Table 6).

The variations of the 8-bp sequence CAGATCTG are mainly in the first 3 base pairs. The motif variations can be represented as the consensus sequence, Y[R/T]RATCYG (SEQ ID NO: 146). The first position can be any of the two pyrimidine bases, C or T. The second position can be substituted by an A, G or T and the third position can any purine. The last 5 base pairs of the sequence, that is the sequence ATCTG is highly conserved.

Statistical Analyses of Motif Frequencies:

A number of simple frequency statistics were determined for the introns. The statistics are shown in Tables 5 and 6.

TABLE 5

| Intron Classification | Intron Count | Aggregate Nts | Average Intron Length |
|---|---|---|---|
| All Enhancing Introns | 13 | 7716 | 594 |
| New Enhancing Introns | 9 | 4813 | 535 |
| Other Enhancing Introns | 4 | 2903 | 726 |
| Non-Enhancing Introns | 10 | 7888 | 789 |
| Non-Tested Introns | 1066 | 933097 | 875 |

TABLE 6

| Intron Classification | Total Introns Containing CAGATCTG | Total Introns Containing ATCTG | Frequency Intron Contains CAGATCTG | Frequency Intron Contains ATCTG |
|---|---|---|---|---|
| All Enhancing Introns | 2 | 12 | 0.15 | 0.92 |
| New Enhancing Introns | 2 | 8 | 0.22 | 0.89 |
| Other Enhancing Introns | 0 | 4 | 0.00 | 1.00 |
| Non-Enhancing Introns | 0 | 7 | 0.00 | 0.70 |

TABLE 6-continued

| Intron Classification | | | | |
|---|---|---|---|---|
| Non-Tested Introns | 15 | 502 | 0.01 | 0.47 |
| Ratio All Enhancing/ Non-Enhancing | | 1.71 | | 1.32 |
| Ratio New Enhancing/ Non-Enhancing | | 1.14 | | 1.27 |

| Intron Classification | Total Occurrences CAGATCTG Either Strand | Total Occurrences ATCTG Either Strand | Gross Frequency CAGATCTG | Gross Frequency ATCTG |
|---|---|---|---|---|
| All Enhancing Introns | 6 | 29 | 0.0008 | 0.0038 |
| New Enhancing Introns | 6 | 23 | 0.0012 | 0.0048 |
| Other Enhancing Introns | 0 | 6 | 0 | 0.00207 |
| Non-Enhancing Introns | 0 | 18 | 0 | 0.00228 |
| Non-Tested Introns | 15 | 1391 | 1.6075E−05 | 0.00149 |
| Ratio All Enhancing/ Non-Enhancing | | 1.61 | | 1.647 |
| Ratio New Enhancing/ Non-Enhancing | | 1.28 | | 2.094 |

| Intron Classification | Average Individual Frequency of CAGATCTG/ kb | Average of Individual Intron Frequency of ATCTG/kb | SE Frequency CAGATCTG/ kb | SE Frequency ATCTG/ kb |
|---|---|---|---|---|
| All Enhancing Introns | 0.0036 | 0.0094 | 0.0025 | 0.0004 |
| New Enhancing Introns | 0.0052 | 0.0124 | 0.0035 | 0.0050 |
| Other Enhancing Introns | 0.00000 | 0.00266 | 0.00000 | 0.00107 |
| Non-Enhancing Introns | 0.00000 | 0.00203 | 0.00000 | 0.00057 |
| Non-Tested Introns | 0.00013 | 0.00271 | 0.00005 | 0.00013 |
| Ratio All Enhancing/ Non-Enhancing | | 4.62 | | |
| Ratio New Enhancing/ Non-Enhancing | | 6.10 | | |

SE frequency is standard error of frequency. Gross frequency is simply the total occurrences divided by the aggregate nucleotides of all the introns in the set.

The 'all' 13 enhancing introns have 4.6-fold higher, and the 9 'new' enhancing introns have 6.1-fold higher frequencies of ATCTG relative to the non-enhancing introns on a mean frequency per kb of intron basis (See Tables 5 and 6 above).

Example 9

Identification of Novel Maize Introns with 8-bp Motif

From the initial set of 1085 introns explained in Example 1, 1066 introns that were still not tested experimentally were scanned computationally to identify the ones with the 8-bp motif. Four introns (SEQ ID NOS: 101-104) were found to contain the exact 8-bp motif and these are good candidates for being enhancing introns.

Example 10

Identifying Promoters of Expression-Enhancing Introns

It is likely that the expression enhancing introns from Examples 4, 7 and 9 perform optimally along with their endogenous promoters. To test this 1000 bp-2000 bp of promoter regions upstream of the start codon from the respective genes (SEQ ID NOS: 105-117, SEQ ID NOS: 136 and 139) were identified and these can be tested with the respective introns.

Cloning Endogenous Promoters of Expression Enhancing Introns

We amplified 1000 base pairs region of endogenous promoter, (using the primers given in Table 7) upstream of the start codon of the gene that carries TS1 intron as its first intron and cloned the pTS1v sequence (SEQ ID NO: 136) in ITVUR-2 vector (SEQ ID NO: 3, PHP41353) between AscI-AsiSI restriction sites, followed by the TS1 intron (SEQ ID NO: 4) at AsiSI-Acc65I sites to create an endogenous promoter and intron combination (PHP50061). Similarly, we amplified a 1487 base pair region of endogenous promoter (pTS27v; SEQ ID NO: 139) upstream of the TS27 intron and cloned it in ITVUR-2 vector (SEQ ID NO: 3, PHP41353) at AscI-AsiS1 restriction sites, followed by the TS27v intron (SEQ ID NO: 138) at AsiSI-Acc65I sites to give us an endogenous promoter and intron combination (PHP52322).

Example 11

Cloning and Testing of TS2 Enhancing Intron and Corresponding Endogenous Promoter We tested another intron with potential gene expression enhancing properties. TS2 intron (SEQ ID NO: 118) was cloned into ITVUR-2 vector (SEQ ID NO: 3, PHP41353) using the same procedure as explained in Example 3 to create PHP50062. We created 2 more constructs to test the ability of the endogenous promoter upstream of the start codon of the gene that carries TS2 as its first intron to drive gene expression and ability of TS2 intron to enhance gene expression. We amplified 1077-bp of endogenous TS2 promoter (pTS2; SEQ ID NO: 119), as defined by the sequence upstream of the TS2 intron at the genomic location, and cloned that in ITVUR-2 vector (SEQ ID NO: 3) between AscI and NcoI sites (PHP500063). We also amplified the pTS2 promoter and TS2 intron sequence from the endogenous locus (1077 bp promoter (SEQ ID NO: 118)+1329 bp intron (SEQ ID NO: 119)) and cloned that between AscI and NcoI sites (PHP50111). The primers for these amplifying promoter and intron sequences to make these constructs are given in Table 2 and Table 7.

TABLE 7

| Cloned sequence | | Forward Primer | Reverse Primer |
|---|---|---|---|
| Promoter | Intron | (SEQ ID NO) | (SEQ ID NO) |
| — | TS2 (SEQ ID NO: 118) | 120 | 121 |
| pTS2 (SEQ ID NO: 119) | TS2 (SEQ ID NO: 118) | 122 | 123 |
| pTS2 (SEQ ID NO: 119) | — | 122 | 124 |
| pTS1v (SEQ ID NO: 136) | — | 125 | 126 |
| pTS27v (SEQ ID NO: 139) | — | 127 | 128 |

All the constructs were mobilized into the *Agrobacterium* strain LBA4404/pSB1 and selected on spectinomycin and tetracycline. *Agrobacterium* transformants were isolated and the integrity of the plasmid was confirmed by retransforming to *E. coli* or PCR analysis.

Example 12

Stable Transfection of Rice with Promoter and Intron Sequence Constructs

Transformation and Regeneration of Rice Callus via *Agrobacterium* Infection

*O. sativa* spp. *japonica* rice var. Nipponbare seeds are sterilized in absolute ethanol for 10 minutes then washed 3 times with water and incubated in 70% Sodium hypochlorite [Fisher Scientific-27908] for 30 minutes. The seeds are then washed 5 times with water and dried completely. The dried seeds are inoculated into NB-CL media [CHU(N6) basal salts (PhytoTechnology-C416) 4 g/l; Eriksson's vitamin solution (1000× PhytoTechnology-E330) 1 ml/l; Thiamine HCl (Sigma-T4625) 0.5 mg/l; 2,4-Dichloro phenoxyacetic acid (Sigma-D7299) 2.5 mg/l; BAP (Sigma-B3408) 0.1 mg/l; L-Proline (PhytoTechnology-P698) 2.5 g/l; Casein acid hydrolysate vitamin free (Sigma-C7970) 0.3 g/l; Myo-inositol (Sigma-I3011) 0.1 g/l; Sucrose (Sigma-S5390) 30 g/l; GELRITE® (Sigma-G1101.5000) 3 g/l; pH 5.8) and kept at 28° C. in dark for callus proliferation.

A single *Agrobacterium* colony containing a desired insert with the candidate sequences from a freshly streaked plate can be inoculated in YEB liquid media [Yeast extract (BD Difco-212750) 1 g/l; Peptone (BD Difco-211677) 5 g/l; Beef extract (Amresco-0114) 5 g/l; Sucrose (Sigma-55390) 5 g/l; Magnesium Sulfate (Sigma-M8150) 0.3 g/l at pH-7.0] supplemented with Tetracycline (Sigma-T3383) 5 mg/l, Rifamysin 10 mg/l and Spectinomycin (Sigma-5650) 50 mg/l. The cultures are grown overnight at 28° C. in dark with continuous shaking at 220 rpm. The following day the cultures are adjusted to 0.5 Absorbance at 550 nm in PHI-A(CHU(N6) basal salts (PhytoTechnology-C416) 4 g/l; Eriksson's vitamin solution (1000× PhytoTechnology-E330) 1 ml/l; Thiamine HCl (Sigma-T4625) 0.5 mg/l; 2,4-Dichloro phenoxyacetic acid (Sigma-D7299) 2.5 mg/l, L-Proline (PhytoTechnology-P698) 0.69 mg/l; Sucrose (Sigma-S5390) 68.5 g/l; Glucose-36 g/l (Sigma-G8270); pH 5.8);) media supplemented with 200 µM Acetosyringone (Sigma-D134406) and incubated for 1 hour at 28° C. with continuous shaking at 220 rpm.

17-21 day old proliferating calli are transferred to a sterile culture flask and *Agrobacterium* solution prepared as described above was added to the flask. The suspension is incubated for 20 minutes with gentle shaking every 2 minutes. The *Agrobacterium* suspension is decanted carefully and the calli are placed on WHATMAN filter paper No-4. The calli are immediately transferred to NB-CC medium [NB-CL supplemented with 200 µM Acetosyringone (Sigma-D134406) and incubated at 21° C. for 72 hrs.

Culture Termination and Selection

The co-cultivated Calli are placed in a dry, sterile, culture flask and washed with 1 liter of sterile distilled water containing Cefotaxime (Duchefa-00111.0025) 0.250 g/l and Carbenicillin (Sigma-00109.0025) 0.4 g/l. The washes are repeated 4 times or until the solution appeared clear. The water is decanted carefully and the calli are placed on WHATMAN filter paper No-4 and dried for 30 minutes at room temperature. The dried calli are transferred to NB-RS medium [NB-CL supplemented with Cefotaxime (Duchefa-00111.0025) 0.25 g/l; and Carbenicillin (Sigma-00109.0025) 0.4 g/l and incubated at 28° C. for 4 days.

The calli are then transferred to NB-SB media [NB-RS supplemented with Bialaphos (Meiji Seika K.K., Tokyo, Japan) 5 mg/l and incubated at 28° C. and subcultured into fresh medium every 14 days. After 40-45 days on selection, proliferating, Bialaphos resistant, callus events are easily observable.

Regeneration of Stably Transformed Rice Plants from Transformed Rice Calli

Transformed callus events are transferred to NB-RG media [CHU(N6) basal salts (PhytoTechnology-C416) 4 g/l; N6 vitamins 1000×1 ml {Glycine (Sigma-47126) 2 g/l; Thiamine HCl (Sigma-T4625) 1 g/l; acid; Kinetin (Sigma-K0753) 0.5 mg/l; Casein acid hydrolysate vitamin free (Sigma-C7970) 0.5 g/l; Sucrose (Sigma-S5390) 20 g/l; Sorbitol (Sigma-51876) 30 g/l, pH was adjusted to 5.8 and 4 g/l GELRITE® (Sigma-G1101.5000) was added. Post-sterilization 0.1 ml/l of CuSo4 (100 mM concentration, Sigma-C8027) and 100 ml/l 10× AA Amino acids pH free {Glycine (Sigma-G7126) 75 mg/l; L-Aspartic acid (Sigma-A9256) 2.66 g/l; L-Arginine (Sigma-A5006) 1.74 g/l; L-Glutamine (Sigma-G3126) 8.76 g/l} and incubated at 32° C. in light. After 15-20 days, regenerating plantlets can be transferred to magenta boxes or tubes containing NB-RT media [MS basal salts (PhytoTechnology-M524) 4.33 g/L; B5 vitamins 1 ml/l from 1000× stock {Nicotinic acid (Sigma-G7126) 1 g/l, Thiamine HCl (Sigma-T4625) 10 g/l)}; Myo-inositol (Sigma-I3011) 0.1 g/l; Sucrose (Sigma-55390) 30 g/l; and IBA (Sigma-15386) 0.2 mg/l; pH adjusted to 5.8]. Rooted plants obtained after 10-15 days can be hardened in liquid Y media [1.25 ml each of stocks A-F and water sufficient to make 1000 ml. Composition of individual stock solutions: Stock (A) Ammonium Nitrate (HIMEDIA-RM5657) 9.14 g/l, (B) Sodium hydrogen Phosphate (HIMEDIA-58282) 4.03 g, (C) Potassium Sulphate (HIMEDIA-29658-4B) 7.14 g, (D) Calcium Chloride (HIMEDIA-05080) 8.86 g, (E) Magnesium Sulphate (HIMEDIA-RM683) 3.24 g, (F) (Trace elements) Magnesium chloride tetra hydrate (HIMEDIA-10149) 15 mg, Ammonium Molybdate (HIMEDIA-271974B) 6.74 mg/l, Boric acid (Sigma-136768) 9.34 g/l, Zinc sulphate heptahydrate (Hi-Media-RM695) 0.35 mg/l, Copper Sulphate heptahydrate (HIMEDIA-C8027) 0.31 mg/l, Ferric chloride hexahydrate (Sigma-236489) 0.77 mg/l, Citric acid monohydrate (HIMEDIA-C4540) 0.119 g/l] at 28° C. for 10-15 days before transferring to greenhouse. Leaf samples are collected for histochemical GUS staining with 5-bromo-4-chloro-3-indolyl-β-D-glucuronide (X-Gluc), using standard protocols (Janssen and Gardner, *Plant Mol. Biol.* (1989)14:61-72).

Transgenic plants are analyzed for copy number by southern blotting using standard procedure. All single copy events are transferred to individual pots and further analysis is performed only on these. For all the analysis leaf material from three independent one month old single copy $T_0$ events were taken.

Transgene Copy Number Determination by Quantitative PCR

Transgenic rice plants generated using different constructs were analyzed to determine the transgene copy number using TaqMan-based quantitative real-time PCR (qPCR) analysis. Genomic DNA was isolated from the leaf tissues collected from 10-day old T0 rice plants using the QIAGEN® DNEASY® Plant Maxi Kit (QIAGEN® Inc.) according to the manufacturer's instructions. DNA concentration was adjusted to100 ng/µl and was used as a template for the qPCR reaction to determine the copy number. The copy number analysis was carried out by designing PCR primers and TaqMan probes for the target gene and for the endogenous glutathione reductase 5 (GR5) gene. The endogenous GR5 gene serves as an internal control to normalize the Ct values obtained for the target gene across different samples. In order to determine the relative quantification (RQ) values for the target gene, genomic DNA from known single and two copy calibrators for a given gene were also included in the experiment. Test samples and calibrators were replicated twice for accuracy. Non-transgenic control and no template control were also included in the reaction. The reaction mixture (for a 20 µl reaction volume) comprises 10 µl of 2× TaqMan universal PCR master mix (Applied Biosystems), 0.5 µl of 10 µM PCR primers and 0.5 µl of 10 µM TaqMan probe for both target gene and endogenous gene. Volume was adjusted to 19 µl using sterile Milli Q water and the reaction components were mixed properly and spun down quickly to bring the liquid to bottom of the tube. 19 µl of the reaction mix was added into each well of reaction plate containing 1 µl of genomic DNA to achieve a final volume of 20 µl. The plate was sealed properly using MicroAmp optical adhesive tape (Applied Biosystems) and centrifuged briefly before loading onto the Real time PCR system (7500 Real PCR system, Applied Biosystems). The amplification program used was: 1 cycle each of 50° C. for 2:00 min and 95° C. for 10:00 min followed by 40 repetitions of 95° C. for 15 sec and 58° C. for 1:00 min. After completion of the PCR reaction, the SDS v2.1 software (Applied Biosystems) was used to calculate the RQ values in the test samples with reference to single copy calibrator.

Stable transgenic rice events were generated with the constructs, PHP50063, PHP50111 PHP50062, PHP50061, PHP52322, and PHP42365 as given in Table 8. The primers used for amplifying the cloned promoter and intron sequences for these constructs are given in Table 2 and Table 7.

TABLE 8

Description of Promoter and Intron Elements in Constructs

| Construct | Intron | Promoter |
| --- | --- | --- |
| PHP50063 | — | pTS2 (SEQ ID NO: 119) |
| PHP50111 | TS2 (SEQ ID NO: 118) | pTS2 (SEQ ID NO: 119) |
| PHP50062 | TS2 (SEQ ID NO: 118) | Zm Ubi promoter |
| PHP50061 | TS1 (SEQ ID NO: 4) | pTS1v (SEQ ID NO: 136) |

TABLE 8-continued

Description of Promoter and Intron Elements in Constructs

| Construct | Intron | Promoter |
| --- | --- | --- |
| PHP52322 | TS27v (SEQ ID NO: 138) | pTS27v (SEQ ID NO: 139) |
| PHP42365 | Zm Ubi intron | Zm Ubi promoter |

The stable transgenic rice events generated with these constructs were subjected to TaqMan-based qPCR (quantitative PCR) analysis to determine the transgene copy number as described above. PCR primers and TaqMan probes designed for the GUS reporter gene and for the endogenous GR5 gene are listed in Table 9.

TABLE 9

Primer Sequences for qPCR

| Primer ID | SEQ ID NO: |
| --- | --- |
| GUS F primer | 129 |
| GUS R primer | 130 |
| GR5, F primer | 131 |
| GR5, R primer | 132 |

TABLE 10

Probe Sequences for qPCR

| | SEQ ID NO | Probe | Quencher |
| --- | --- | --- | --- |
| GUS | 133 | Fam | Tamra |
| GR5 | 134 | Vic | MGB |

All single copy events were transferred to individual pots and further analysis was performed on leaf material and panicle collected one month after transplanting in the greenhouse.

Qualitative and Quantitative Analysis of GUS Reporter Gene Expression in Stable Rice Events Both qualitative and quantitative GUS reporter gene expression analyses were carried out in triplicates on at least 5 independent single copy events for each construct. Leaf and panicle samples were collected for histochemical GUS staining with 5-bromo-4-chloro-3-indolyl-6-D-glucuronide (X-Gluc), using standard protocols (Janssen and Gardner, Plant Mol. Biol. (1989)14:61-72) and for quantitative MUG assay using standard protocols (Jefferson, R. A., Nature. 342, 837-8 (1989); Jefferson, R. A., Kavanagh, T. A. & Bevan, M. W., EMBO J. 6, 3901-3907 (1987).

Figure 9:
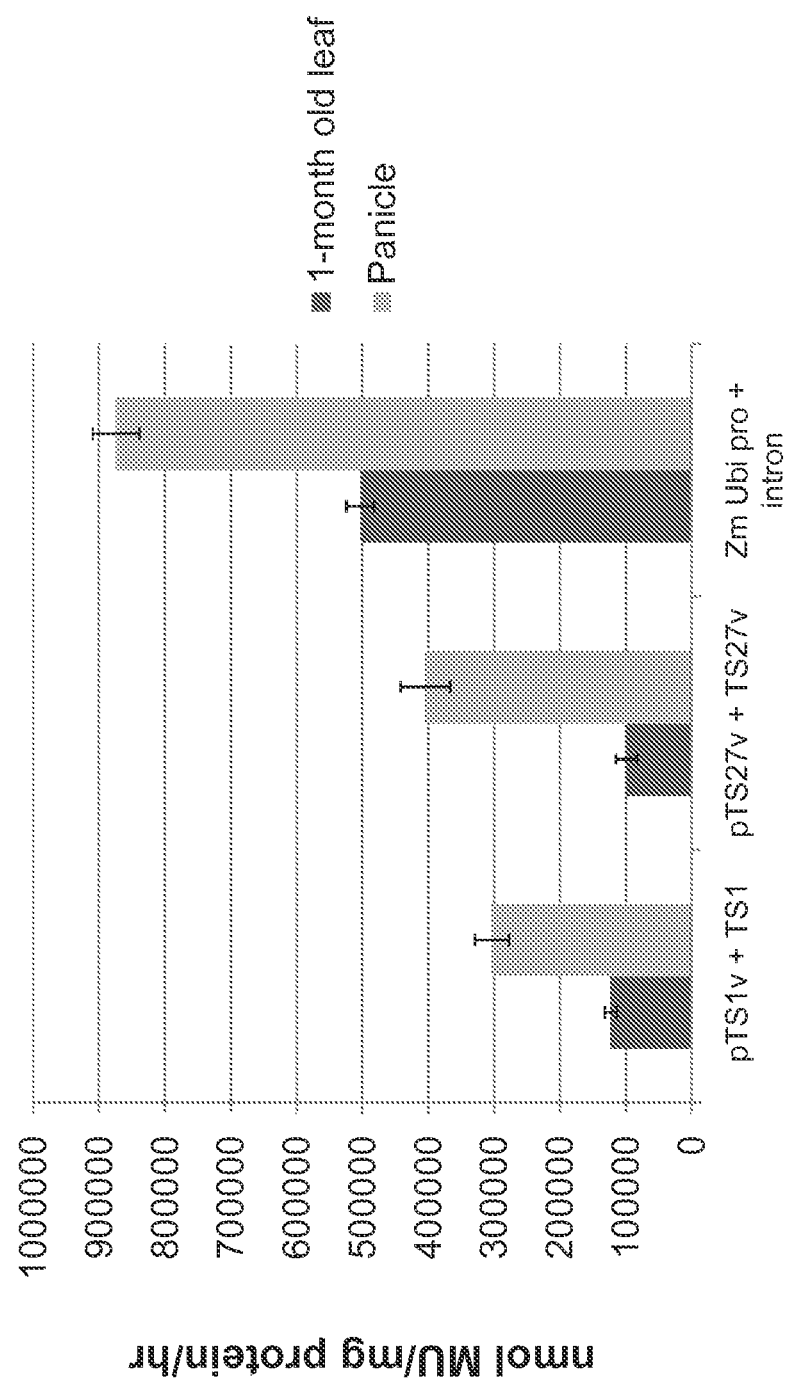
FIG. 9 shows MUG data from stable transgenic lines transformed with different constructs. Data represents the average of 5-8 independent single copy events±SE.

TS1 and TS27v when combined with their respective endogenous promoters (pTS1v+TS1 (PHP50061) and pTS27v+TS27v (PHP52322) were able to drive GUS expression in stable rice transgenic events (FIG. 9).

Figure 10:
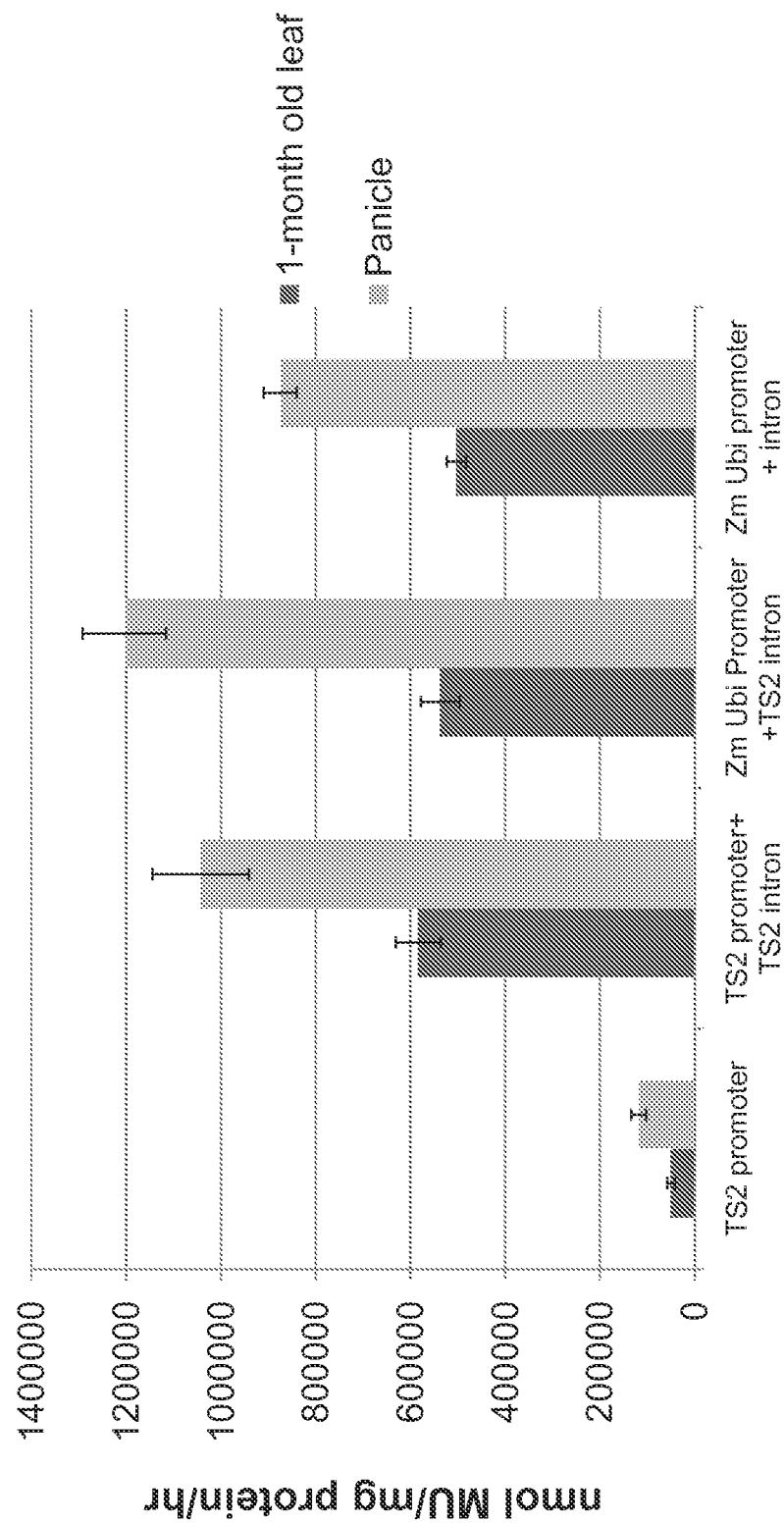
FIG. 10 shows MUG data from stable transgenic lines transformed with different constructs. Data represents the average of 5-8 independent single copy events±SE.

TS2 intron with its endogenous promoter (PHP50111) enhanced the GUS reporter gene expression by 11.6 fold in leaves and 8.9 fold in panicles compared to the TS2 promoter alone (PHP50063) driving the GUS reporter gene expression (FIG. 10) and the values obtained were comparable to the levels observed with maize ubiquitin promoter and intron (PHP42365) driving GUS in transgenic rice plants. There is a slight increase in the GUS reporter gene expression levels when the TS2 intron is cloned with maize Ubiquitin promoter (PHP50062) compared to the data obtained with maize ubiquitin intron cloned with maize ubiquitin promoter (FIG. 10).

Figure 11:
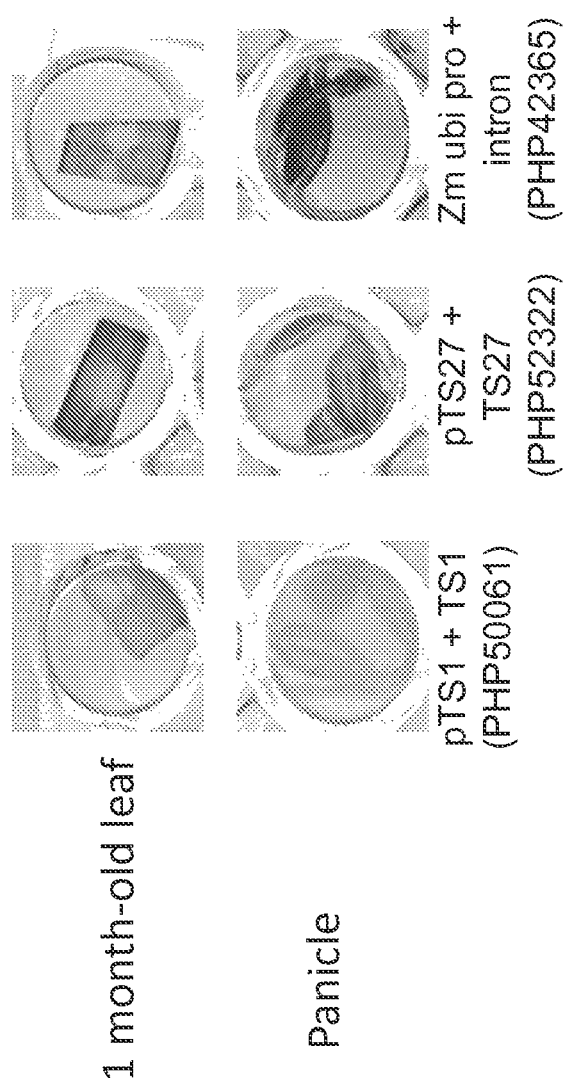
FIG. 11 shows histochemical data from leaves and panicles collected from stable transgenic lines transformed with different constructs. Representative images are shown for each construct analyzed.
Figure 12:
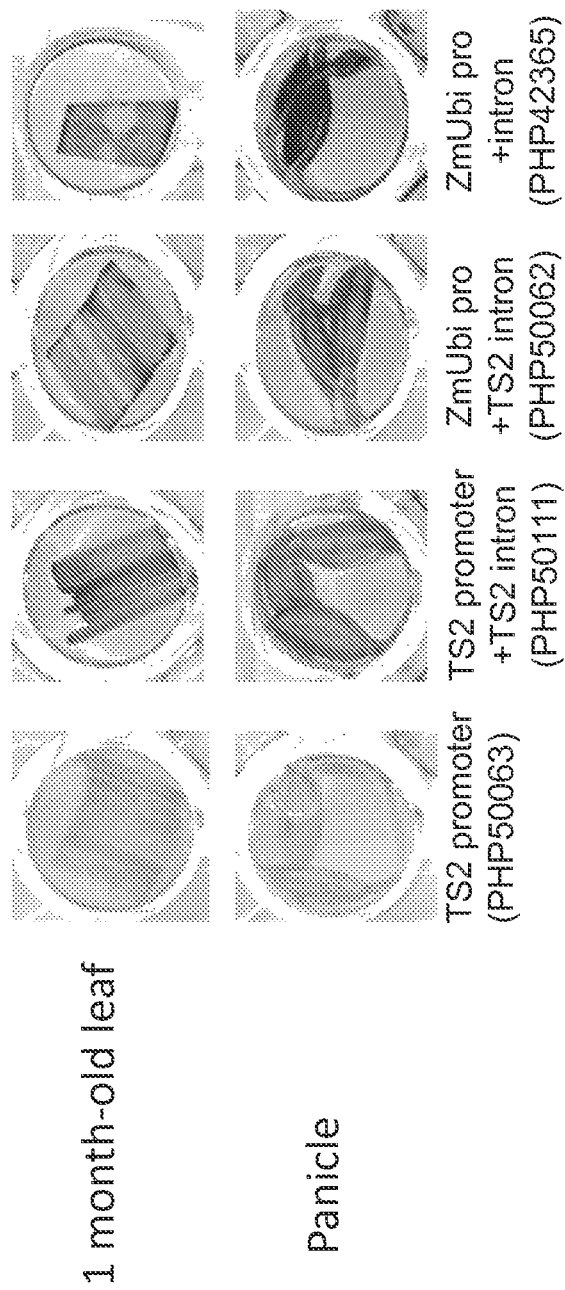
FIG. 12 shows histochemical data from leaves and panicles collected from stable transgenic lines transformed with different constructs. Representative images are shown for each construct analyzed.

GUS histochemical staining data were found to correlate very well with the quantitative GUS assay in all events. Representative images are shown in FIG. 10 and FIG. 11.

Example 13

Identification of Novel Terminator Sequences

Transcription terminators for the 4 genes comprising the expression enhancing introns TS1, TS2, TS13 and TS27v (SEQ ID NOS: 4, 118, 13 and 138 respectively) were identified, and were called tTS1 (SEQ ID NO: 140), tTS2 (SEQ ID NO: 141), tTS13 (SEQ ID NO: 142) and tTS27 (SEQ ID NO: 143). Terminator sequences were defined as 500-900 bp of sequence downstream of the translational stop codon of the respective genes.

Example 14

Amplification and Cloning of Terminator Sequences

Figure 13:
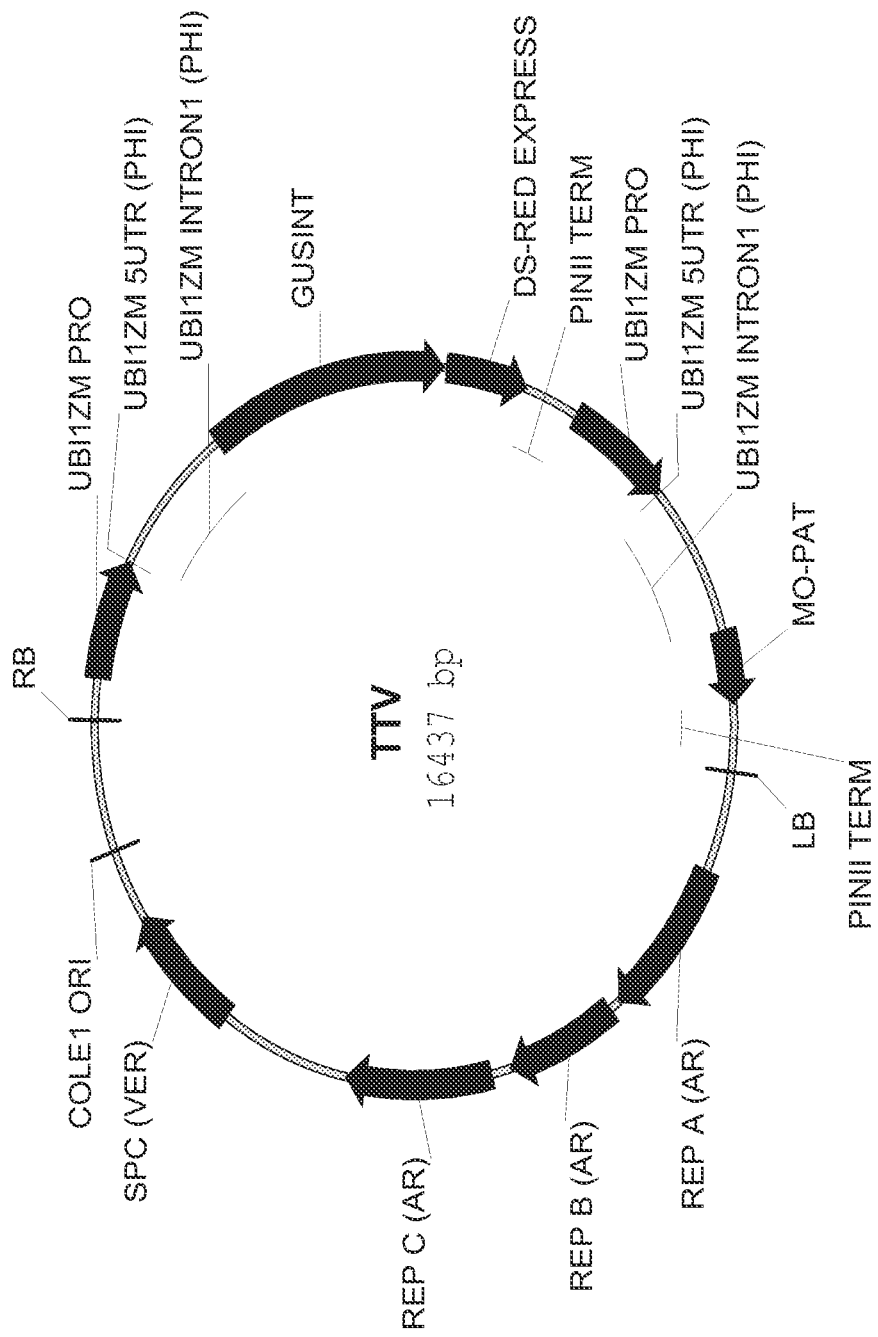
FIG. 13 is the schematic representation of the PHP49597 vector (terminator test vector).

We constructed a terminator test vector (TTV) (PHP49597-FIG. 13; SEQ ID NO: 144) carrying GUS (β-glucuronidase) reporter gene driven by the Maize Ubiquitin promoter using standard molecular biology techniques (Sambrook et al.). A promoterless Ds-RED coding sequence was included downstream of the GUS gene for measurement of transcription downstream of the cloned test terminator sequences (read-through transcripts). The Ds-Red sequence was followed by a PinII terminator to enable termination and polyadenlylation of all transcripts, so we could detect them by reverse-transcription-PCR (RT-PCR) using oligo dT primer. The Terminator test vector also carried a monocot-optimized Phosphinothricin acetyl transferase (MOPAT) gene as a plant selectable marker.

Candidate terminator sequences can be amplified from maize genomic DNA. The resulting DNA fragments can be cloned into the terminator test vector at Acc65I restriction site using IN-FUSION™ cloning (Clontech Inc.). All constructs will be transformed into *Agrobacterium* (LBA4404/pSB1)

Example 15

Rice Transformation with Candidate Terminator Sequences

The candidate maize terminator sequences tTS1, tTS2, tTS13 and tTS27 (SEQ ID NOS:140-143 respectively) will be tested for their ability to function as transcription terminators in stable rice transgenic plants generated by *Agrobacterium* mediated transformation as described in Example 12.

Example 16

Testing of Candidate Rice Terminator Sequences in Stably Transformed Rice Tissues ReverseTranscriptase-PCR (RT-PCR) and GUS assays can be done from stably transformed rice plant tissues, to test the ability of candidate maize terminator sequences tTS1, tTS2, tTS13 and tTS27 (SEQ ID NOS: 140-143 respectively) to prevent transcription read-through and to compare GUS expression Reverse Transcription PCR (RT-PCR) to Determine Transcription Read-Through RNA will be extracted from leaf tissue from multiple independent T0 events for each construct. cDNA can be synthesized using SuperScript® III First-Strand Synthesis System from Invitrogen. The level of GUS gene and read-through transcripts will be assayed using specific primers within GUS gene and DS-Red respectively. Transcript levels can also be measured by quantitative RT-PCR using primers and probes within GUS and DS-Red sequences.

Histochemical and Fluorometric GUS Analysis

Tissue samples from each independent stably transformed rice line can be stained for histochemical GUS analysis, with 5-bromo-4-chloro-3-indolyl-β-D-glucuronide (X-Gluc), using standard protocols (Janssen and Gardner, *Plant Mol. Biol.* (1989)14:61-72,). Tissue samples can also be used for quantitative MUG assay using standard protocols [Jefferson, R. A., Nature. 342:837-838 (1989); Jefferson, R. A., Kavanagh, T. A. & Bevan, M. W. *EMBO J.* 6:3901-3907 (1987)].

We claim:

1. A recombinant DNA construct comprising an intron operably linked to a promoter, a heterologous polynucleotide and a terminator wherein the intron comprises a nucleotide sequence that has at least 96% sequence identity to SEQ ID NO: 8, or 137.

2. The recombinant DNA construct of claim 1, wherein the intron comprises the nucleotide sequence of SEQ ID NO: 8, or 137.

3. The recombinant DNA construct of claim 1, wherein the intron enhances expression of the heterologous polynucleotide in a plant.

4. A plant comprising the recombinant DNA construct of claim 3.

5. A seed comprising the recombinant DNA construct of claim 3.

6. A method for modulating transgene expression in a plant comprising the steps of:

(a) introducing into a regenerable plant cell the recombinant DNA construct of claim 1;

(b) regenerating a transgenic plant from the regenerable plant cell after step (a) wherein the transgenic plant comprises the recombinant DNA construct; and (c) obtaining a progeny plant derived from the transgenic plant of step (b), wherein the progeny plant comprises the recombinant DNA construct and exhibits enhanced transgene expression when compared to a plant comprising in its genome the recombinant DNA construct without the corresponding intron sequence.

7. The method of claim 6 wherein said plant is a monocot.

8. The recombinant DNA construct of claim 1, wherein said promoter is a constitutive promoter, a tissue-preferred promoter, an inducible promoter, or a developmentally regulated promoter.

* * * * *